(12) United States Patent
Bersot et al.

(10) Patent No.: US 10,214,507 B2
(45) Date of Patent: Feb. 26, 2019

(54) CARBAZOLE-CONTAINING AMIDES, CARBAMATES, AND UREAS AS CRYPTOCHROME MODULATORS

(71) Applicant: Reset Therapeutics, Inc., South San Francisco, CA (US)

(72) Inventors: Ross Bersot, Orinda, CA (US); Paul Humphries, Santa Clara, CA (US)

(73) Assignee: Reset Therapeutics, Inc., San Jose, CA (US)

( * ) Notice: Subject to any disclaimer, the term of this patent is extended or adjusted under 35 U.S.C. 154(b) by 0 days.

(21) Appl. No.: 15/985,168

(22) Filed: May 21, 2018

(65) Prior Publication Data

US 2018/0334446 A1 Nov. 22, 2018

Related U.S. Application Data

(63) Continuation of application No. 14/679,846, filed on Apr. 6, 2015, now Pat. No. 10,005,759.

(60) Provisional application No. 61/976,350, filed on Apr. 7, 2014.

(51) Int. Cl.
| | |
|---|---|
| *C07D 401/06* | (2006.01) |
| *C07D 413/02* | (2006.01) |
| *C07D 403/02* | (2006.01) |
| *C07D 209/52* | (2006.01) |
| *C12Q 1/6883* | (2018.01) |
| *A61K 31/5377* | (2006.01) |
| *C07D 413/06* | (2006.01) |
| *A61K 31/403* | (2006.01) |
| *A61K 31/513* | (2006.01) |
| *C07D 403/06* | (2006.01) |
| *A61K 45/06* | (2006.01) |
| *A61K 31/454* | (2006.01) |

(52) U.S. Cl.
CPC .......... *C07D 401/06* (2013.01); *A61K 31/403* (2013.01); *A61K 31/454* (2013.01); *A61K 31/513* (2013.01); *A61K 31/5377* (2013.01); *A61K 45/06* (2013.01); *C07D 209/52* (2013.01); *C07D 403/06* (2013.01); *C07D 413/06* (2013.01); *C12Q 1/6883* (2013.01); *C12Q 2600/118* (2013.01); *Y10T 436/143333* (2015.01)

(58) Field of Classification Search
CPC ... C07D 401/06; C07D 403/02; C07D 413/02
See application file for complete search history.

(56) References Cited

U.S. PATENT DOCUMENTS

| | | | |
|---|---|---|---|
| 4,105,776 A | 8/1978 | Ondetti et al. | |
| 4,230,767 A | 10/1980 | Isaka et al. | |
| 4,231,938 A | 11/1980 | Monaghan | |
| 4,233,402 A | 11/1980 | Maggio | |
| 4,275,149 A | 6/1981 | Litman | |
| 4,276,890 A | 7/1981 | Fichera | |
| 4,302,386 A | 11/1981 | Stevens | |
| 4,316,906 A | 2/1982 | Ondetti | |
| 4,325,952 A | 4/1982 | Silvestrini | |
| 4,337,201 A | 6/1982 | Petrillo, Jr. | |
| 4,344,949 A | 8/1982 | Hoefle et al. | |
| 4,346,227 A | 8/1982 | Terahara et al. | |
| 4,374,829 A | 2/1983 | Harris et al. | |
| 4,376,110 A | 3/1983 | David | |
| 4,410,520 A | 10/1983 | Watthey | |
| 4,444,784 A | 4/1984 | Hoffman et al. | |

(Continued)

FOREIGN PATENT DOCUMENTS

| | | |
|---|---|---|
| EP | 0 253 310 B1 | 1/1988 |
| RU | 2382770 C2 | 5/2008 |

(Continued)

OTHER PUBLICATIONS

Akashi, M. et. al., "Noninvasive method for assessing the human circadian clock using hair follicle cells", *Proc. Natl. Acad. Sci. USA*, (2010) 107(35): 15643-15648.

(Continued)

*Primary Examiner* — Nyeemah A Grazier
(74) *Attorney, Agent, or Firm* — Cooley LLP; Ivor R. Elrifi; Christina K. Stock

(57) ABSTRACT

The subject matter herein is directed to carbazole-containing amide, carbamate, and urea derivatives and pharmaceutically acceptable salts or hydrates thereof of structural formula I wherein the variable $R_1$, $R_2$, $R_3$, $R_4$, $R_5$, $R_6$, $R_7$, A, D, E, G, J, L, M, Q, a, and b are accordingly described. Also provided are pharmaceutical compositions containing the compounds of formula I to treat a Cry-mediated disease or disorder, such as diabetes, complications associated with diabetes, Cushing's syndrome, NASH, NAFLD, asthma, and COPD.

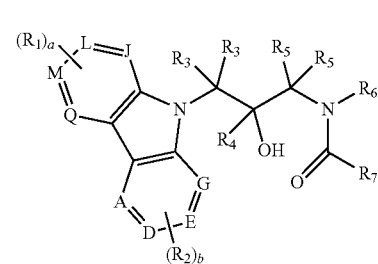

22 Claims, 18 Drawing Sheets

(56) References Cited

U.S. PATENT DOCUMENTS

| | | | |
|---|---|---|---|
| 4,508,729 A | 4/1985 | Vincent et al. |
| 4,512,924 A | 4/1985 | Attwood et al. |
| 4,587,258 A | 5/1986 | Gold et al. |
| 4,659,678 A | 4/1987 | Forrest et al. |
| 4,727,022 A | 2/1988 | Skold et al. |
| 4,739,073 A | 4/1988 | Kathawala |
| 4,772,684 A | 9/1988 | Brunck et al. |
| 4,780,401 A | 10/1988 | Heusser et al. |
| 4,786,653 A | 11/1988 | Golwyn |
| 4,788,189 A | 11/1988 | Glazer |
| 4,816,463 A | 3/1989 | Blankley et al. |
| 4,845,079 A | 7/1989 | Luly et al. |
| 4,885,292 A | 12/1989 | Ryono et al. |
| 4,894,437 A | 1/1990 | Tenbrink |
| 4,980,283 A | 12/1990 | Huang et al. |
| 5,034,512 A | 7/1991 | Hudspeth et al. |
| 5,036,053 A | 7/1991 | Himmelsbach et al. |
| 5,036,054 A | 7/1991 | Kaltenbronn et al. |
| 5,055,466 A | 10/1991 | Weller, III et al. |
| 5,063,207 A | 11/1991 | Doherty et al. |
| 5,063,208 A | 11/1991 | Rosenberg et al. |
| 5,064,825 A | 11/1991 | Chakravarty et al. |
| 5,064,965 A | 11/1991 | Ocain et al. |
| 5,066,643 A | 11/1991 | Abeles et al. |
| 5,071,837 A | 12/1991 | Doherty et al. |
| 5,073,566 A | 12/1991 | Lifer et al. |
| 5,075,451 A | 12/1991 | Ocain et al. |
| 5,081,127 A | 1/1992 | Carini et al. |
| 5,085,992 A | 2/1992 | Chen et al. |
| 5,087,634 A | 2/1992 | Reitz |
| 5,089,471 A | 2/1992 | Hanson et al. |
| 5,095,006 A | 3/1992 | Bender et al. |
| 5,095,119 A | 3/1992 | Ocain et al. |
| 5,098,924 A | 3/1992 | Poss |
| 5,104,869 A | 4/1992 | Albright et al. |
| 5,106,835 A | 4/1992 | Albright et al. |
| 5,114,937 A | 5/1992 | Hamby |
| 5,116,835 A | 5/1992 | Ruger |
| 5,273,995 A | 12/1993 | Roth |
| 5,474,995 A | 12/1995 | Ducharme et al. |
| 5,521,213 A | 5/1996 | Prasit et al. |
| 5,536,752 A | 7/1996 | Ducharme et al. |
| 5,550,142 A | 8/1996 | Ducharme et al. |
| 5,552,422 A | 9/1996 | Gauthier et al. |
| 5,604,253 A | 2/1997 | Lau et al. |
| 5,604,260 A | 2/1997 | Guay |
| 5,639,780 A | 6/1997 | Lau et al. |
| 5,643,933 A | 7/1997 | Talley et al. |
| 5,677,318 A | 10/1997 | Lau |
| 5,691,374 A | 11/1997 | Black et al. |
| 5,698,584 A | 12/1997 | Black |
| 5,710,140 A | 1/1998 | Ducharme et al. |
| 5,723,591 A | 3/1998 | Livak et al. |
| 5,733,909 A | 3/1998 | Black et al. |
| 5,744,305 A | 4/1998 | Fodor |
| 5,750,015 A | 5/1998 | Soane et al. |
| 5,789,413 A | 8/1998 | Black et al. |
| 5,801,155 A | 9/1998 | Kutyavin et al. |
| 5,817,700 A | 10/1998 | Dube et al. |
| 5,849,943 A | 12/1998 | Atkinson et al. |
| 5,861,419 A | 1/1999 | Dube et al. |
| 5,922,742 A | 7/1999 | Black et al. |
| 5,925,631 A | 7/1999 | Black et al. |
| 6,084,102 A | 7/2000 | Kutyavin et al. |
| 7,776,905 B2 | 8/2010 | Hadida Ruah et al. |
| 8,604,074 B2 | 12/2013 | McKnight et al. |
| 8,642,660 B2 | 2/2014 | Goldfarb |
| 9,265,772 B2 * | 2/2016 | Bersot .................. A61K 31/403 |
| 9,357,781 B2 | 6/2016 | Woods et al. |
| 9,775,845 B2 * | 10/2017 | Bersot .................. A61K 31/403 |
| 2002/0138208 A1 | 9/2002 | Paulse et al. |
| 2002/0193950 A1 | 12/2002 | Gavin et al. |
| 2003/0004402 A1 | 1/2003 | Hitt et al. |
| 2003/0055615 A1 | 3/2003 | Zhang et al. |
| 2009/0163545 A1 | 6/2009 | Goldfarb |
| 2011/0003836 A1 | 1/2011 | McKnight et al. |
| 2012/0022096 A1 | 1/2012 | McKnight et al. |
| 2013/0040977 A1 | 2/2013 | McKnight et al. |
| 2013/0303524 A1 | 11/2013 | Bersot et al. |
| 2014/0142107 A1 | 5/2014 | Kaufman et al. |
| 2014/0329674 A1 | 11/2014 | Woods et al. |
| 2014/0343018 A1 | 11/2014 | McKnight et al. |
| 2015/0094307 A1 | 4/2015 | Schmidt et al. |
| 2016/0200732 A1 | 7/2016 | Bersot et al. |
| 2018/0071306 A1 * | 3/2018 | Bersot .................. A61K 31/403 |

FOREIGN PATENT DOCUMENTS

| | | |
|---|---|---|
| RU | 2497807 C2 | 11/2012 |
| WO | WO 1995/000501 A2 | 1/1995 |
| WO | WO 1995/018799 A1 | 7/1995 |
| WO | WO 98/32438 A1 | 7/1998 |
| WO | WO 2001/007654 A1 | 2/2001 |
| WO | WO 0131580 A2 | 5/2001 |
| WO | WO 2003/105759 A2 | 12/2003 |
| WO | WO 2004/056456 A1 | 7/2004 |
| WO | WO 2004/088309 A2 | 10/2004 |
| WO | WO 2006/023590 A1 | 3/2006 |
| WO | WO 2008/073956 A2 | 6/2008 |
| WO | WO 2012/009372 A2 | 1/2012 |
| WO | WO 2013/170186 A1 | 11/2013 |
| WO | WO 2014031125 A1 | 2/2014 |
| WO | WO 2014/039515 A2 | 3/2014 |
| WO | WO 2015/157182 A1 | 10/2015 |

OTHER PUBLICATIONS

Amat, M. et al., "Access to enantiopure 4-substituted 1,5-aminoalcohols from phenylglycinol-derived δ-lactams: synthesis of Haliclona alkaloids", *J. Org. Chem.* (2014), 79(6): 2792-2802.

Balakin et al. "Property-Based Design of GPCR-Targeted Library." *J. Chem. Inf. Comput. Sci.* 42.6(2002):1332-1342.

Barker, A. et al., "Association of genetic Loci with glucose levels in childhood and adolescence: a meta-analysis of over 6,000 children", *Diabetes* (2011), 60: 1805-1812.

Bjarnason, G.A. et al., "Circadian expression of clock genes in human oral mucosa and skin: association with specific cell-cycle phases", *Am. J. Pathol.* (2001), 158(5): 1793-1801.

Bravo, R. D. et al. "An Efficient Synthesis of 3,4-Dihydro-1H-2,3-Benzothiazine 2,2-Dioxides Using Amberlyst 15 and Amberlyst XN 1010", *Synthetic Commmunications*, 2002, 32, 3675.

Boden, G. et al., "Disruption of circadian insulin secretion is associated with reduced glucose uptake in first-degree relatives of patients with type 2 diabetes", *Diabetes* (1999), 48(11): 2182-2188.

Bugge, A. et al, "Rev-erbα and Rev-erbβ coordinately protect the circadian clock and normal metabolic function", *Genes Dev.* (2012), 26: 657-667.

Choi et al. "1,3-Diphenyl-1H-pryazole Derivatives as a New Series of Potent PPARγ Partial Agonists." *Bioorganic and Medical Chemistry*, 18(2010): 8315-8323.

Chun et al., "Identification and validation of cryptochrome inhibitors that modulate the molecular circadian Clock", *ACS Chemical Biology* (2014), 9(3): 703-710.

Database accession No. 1222876-06-3, Database Registry Online, XP002739832, Chemical Abstracts Service, May 13, 2010, 1 page.

de Filippis, A. et al., "Palladium-catalyzed a-arylation of N-protected 2-piperidinones", *Tetrahedron* (2004), 60(43): 9757-9767.

DiRocco, D. A. et al., "Catalytic Asymmetric Intermolecular Stetter Reaction of Heterocyclic Aldehydes with Nitroalkenes: Backbone Fluorination Improves Selectivity", *J. Am. Chem. Soc.* (2009), 131(31): 10872-10874.

Dupuis, J. et al., "New genetic loci implicated in fasting glucose homeostasis and their impact on type 2 diabetes risk", *Nat. Genet.* (2010), 42(2): 105-116.

Dupuis et al. "Erratum: New Genetic Loci Implicated in Fasting Glucose Homeostasis and Their Impact on Type 2 Diabetes Risk." *Nat. Genet.* 42(2010):464.

Eckel-Mahan, K. L. et al. "Reprogramming of the Circadian Clock by Nutritional Challenge" *Cell* (2013) 155:1464-1478.

(56) References Cited

OTHER PUBLICATIONS

Eisen and Brown, "DNA arrays for analysis of gene expression", *Methods Enzymol.* (1999), 303: 179-205.
Ekins and Chu, "Microarrays: their origins and applications", *Trends in Biotechnology* (1999), 17: 217-218.
Green, C. B. et al., "The meter of metabolism", *Cell* (2008), 134(5): 728-742.
Harris et al., "Synthesis of 3S-Pyrrolidinol from L-Glutamic Acid", *Synthetic Communications* (1986), 16(14): 1815-1822.
Hatori et al. "CRY Links the Circadian Clock and CREB-Mediated Gluconeogenesis." *Cell Res.* 20(2010): 1285-1288.
Hirota et al., "Identification of Small Molecule Activators of Cryptochrome", *Science* (2012), 337(6098): 1094-1097.
Jain, "Statistical Pattern Recognition: A Review", *IEEE Transactions on Pattern Analysis and Machine Intelligence* (2000), 22(1): 4-37.
Jungblut and Thiede, "Protein identification from 2-DE gels by MALDI mass spectrometry", *Mass Spectr. Rev.* (1997), 16(3): 145-162.
Kim et al., "Highly Improved Copper-Mediated Michael Addition of Ethyl Bromodifluoroacetate in the Presence of Protic Additive", *Synthesis* (2012), 44(20): 3165-3170, and Supporting Information, 25 pages.
Lamia, K. A. et al, "Physiological significance of a peripheral tissue circadian clock", *Proc. Natl. Acad. Sci. USA* (2008), 105(39): 15172-15177.
Lamia, K. A. et al., "Cryptochromes mediate rhythmic repression of the glucocorticoid receptor", *Nature* (2011), 480(7378): 552-556.
Liu, C. et al., "Variants in GLIS3 and CRY2 are associated with type 2 diabetes and impaired fasting glucose in Chinese Hans", *PLoS One* (2011), 6(6): e21464, 6 pages.
Macmillan et al. "Development of Proneurogenic, Neuroprotective Small Molecules." *J. Am. Chem. Soc.* 133.5(2011):1428-1437.
Marcheva, B. et al., "Disruption of the clock components CLOCK and BMAL1 leads to hypoinsulinaemia and diabetes", *Nature* (2010), 466(7306): 627-631.
Mohawk, J. A. et al. "Central and peripheral circadian clocks in mammals", *Ann. Rev. Neurosci.* (2012), 35: 445-462.
Molette, J. et al., "Identification and Optimization of an Aminoalcohol-Carbazole Series with Antimalarial Properties", *ACS Med Chem. Lett.* (2013), 4(11): 1037-1041.
Nakamura C. E. et al. "Metabolic engineering for the microbial production of 1,3-propanediol" *Current Opinion in Biotechnology*, 2003, 14, pp. 454-459.
Niesen et al., "The use of differential scanning fluorimetry to detect ligand interactions that.promote protein stability", *Nature Protocols* (2007), 2(9): 2212-2221.
Oikawa et al., "Reductive opening of α-methylspiroketals", *Tetrahedron* (1995), 51(22): 6237-6254.
Panda, S. et al., "Coordinated transcription of key pathways in the mouse by the circadian clock", *Cell* (2002), 109: 307-320.
Pantoliano et al., "High-density miniaturized thermal shift assays as a general strategy for drug discovery", *Journal of Biomolecular Screening* (2001), 6(6): 429-440.
Patani, et al., "Bioisosterism: A Rational Approach in Drug Design", *Chem Rev.* (1996), 96(8): 3147-3176.
Polonsky, K. S. et al., "Abnormal patterns of insulin secretion in non-insulin-dependent diabetes mellitus", *N. Engl. J. Med.* (1988), 318: 1231-1239.
PubChem CID: 2054503, Create Date: Jul. 14, 2005.
PubChem CID: 2054505, Create Date: Jul. 14, 2005.
PubChem CID: 4130908, Create Date: Sep. 13, 2005.
Rey, G. et al., "Genome-wide and phase-specific DNA-binding rhythms of BMAL1 control circadian output functions in mouse liver", PLoS Biol. (2011), 9(2): e1000595, 18 pages.
Scheer, F. A. et al., "Adverse metabolic and cardiovascular consequences of circadian misalignment", *Proc. Natl. Acad. Sci. USA* (2009), 106(11): 4453-4458.
Shoemaker, D. D. et al., "Experimental annotation of the human genome using microarray technology", *Nature* (2001), 409(6822): 922-927.
Spiegel, K. et al., "Impact of sleep debt on metabolic and endocrine function", *Lancet* (1999), 354(9188): 1435-1439.
Spiegel, K. et al., "Sleep loss: a novel risk factor for insulin resistance and Type 2 diabetes", *J. Appl. Physiol.* (2005), 99: 2008-2019.
Stamenkovich, J. A. et al., "Regulation of core clock genes in human islets", *Metabolism* (2012), 61(7): 978-985.
STN registry CAS No. 694499-58-6, entered STN Jun. 17, 2004.
STN registry, CAS No. 865611-93-4, entered STN Oct. 19, 2005.
STN registry, CAS 429656-46-2, entered STN Jun. 13, 2002.
STN registry, CAS 429650-83-9, entered STN Jun. 13, 2002.
STN registry, CAS 309928-48-1, entered STN Dec. 20, 2000.
Tahira, K. et al., "Obesity alters the expression profile of clock genes in peripheral blood mononuclear cells", Arch. Med. Sci. 2011, 7(6): 933-940.
Takahashi, J. S. et al., "The genetics of mammalian circadian order and disorder: implications for physiology and disease", *Nat. Rev. Genet.* (2008), 9(10): 764-775.
Takeuchi, H. et al. "Enhancement of the dissolution rate of a poorly water-soluble drug(tolbutamide) by a spray-drying solvent deposition method and disintegrants", *J. Pharm. Pharmacol.* 1987, 39, 769-773.
Turek, F. W. et al., "Obesity and metabolic syndrome in circadian Clock mutant mice", *Science* (2005), 308(5724): 1043-1045.
Wirth, U. et al., "Post-translational modification detection using metastable ions in reflector matrix-assisted laser desorption/ionization-time of flight mass spectrometry", *Proteomics* (2002), 2(10): 1445-1451.
Wong et al., "Nonpeptide angiotensin II receptor antagonists. I. Pharmacological characterization of 2-n-butyl-4-chloro-1-(2-chlorobenzyl)imidazole-5-acetic acid, sodium salt (S-8307)", *J. Pharmacol. Exp. Ther.* (1988), 247(1): 1-7.
Yin, L. et al., "Rev-erbalpha, a heme sensor that coordinates Metabolic and circadian pathways", *Science* (2007), 318(5857): 1786-1789.
Zhang and Kay, "Clocks not winding down: unravelling circadian networks", *Nat. Rev. Mol. Cell. Biol.* (2010), 11: 764-776.
Zhang, E. E. et al., "Cryptochrome mediates circadian regulation of cAMP signaling and hepatic gluconeogenesis", *Nat. Med.* (2010), 16(10): 1152-1156.
Zhang, E. E. et al., "A genome-wide RNAi screen for modifiers of the circadian clock in human cells", *Cell* (2009), 139(1): 199-210.

\* cited by examiner

Fasted plasma glucose

Fasted plasma insulin

A: Vehicle sc + Vehicle po
B: Cortisone 30 mg/kg sc + Vehicle po
C: Cortisone 30 mg/kg sc + Compound 72 50 mg/kg po
D: Cortisone 30 mg/kg sc + Mifepristone 30 mg/kg po ☐ A: Vehicle sc + Vehicle po
■ B: Cortisone 30 mg/kg sc + Vehicle po
▨ C: Cortisone 30 mg/kg sc + Compound 72 50 mg/kg po
▥ D: Cortisone 30 mg/kg sc + Mifepristone 30 mg/kg po

CARBAZOLE-CONTAINING AMIDES, CARBAMATES, AND UREAS AS CRYPTOCHROME MODULATORS

RELATED APPLICATIONS

This application is a continuation of U.S. application Ser. No. 14/679,846, filed on Apr. 6, 2015, now U.S. Pat. No. 10,005,759, which claims priority to U.S. Provisional Application No. 61/976,350 filed on Apr. 7, 2014, the entirety of each of which is herein incorporated by reference.

TECHNICAL FIELD

The subject matter disclosed herein relates to, inter alia, carbazole-containing amide, carbamate, and urea derivatives, pharmaceutical compositions containing these compounds, methods for their use in treating cryptochrome-mediated diseases or disorders, and processes for their production. Also provided are methods of diagnosing, detecting, or monitoring the progression of cryptochrome-dependent diseases in subjects receiving the compounds and compositions disclosed herein.

BACKGROUND

The circadian clock is an intrinsic time-keeping mechanism that controls the daily rhythms of many physiological processes, such as sleep/wake behavior, body temperature, hormone secretion, and metabolism (Takahashi, J. S. et al. *Nat. Rev. Genet.* 2008, 9, 764; Green, C. B. et al. *Cell,* 2008, 134, 728; Zhang, E. E. et al. *Nat. Rev. Mol. Cell. Biol.* 2010, 11, 764). Circadian rhythms are generated in a cell-autonomous manner through transcriptional regulatory networks of clock genes. In the core feedback loop, the transcription factors CLOCK and BMAL1 activate expression of Period (Per1 and Per2) and Cryptochrome (Cry1 and Cry2) genes. After translation and nuclear localization, PER and CRY proteins inhibit the function of CLOCK-BMAL1, resulting in sustained rhythmic gene expression. Many physiological pathways are under the control of the circadian clock (Panda, S. et al. *Cell,* 2002, 109, 307), including direct regulation of numerous hepatic processes (Rey, G. et al. *PLoS Biol.* 2011, 9, e1000595; Bugge, A. et al. *Genes Dev.* 2012, 26, 657).

Circadian desynchrony has been associated with impaired insulin sensitivity (Spiegel, K. et al. *J. Appl. Physiol.* 2005, 99, 2008; Spiegel, K. et al. *Lancet,* 1999, 354, 1435), decreased leptin levels and results in hyperglycemia, hyperinsulinemia and postprandial glucose responses comparable to those of a prediabetic state (Scheer, F. A. et al. *Proc. Natl. Acad. Sci. USA,* 2009, 106, 4453). Several genome-wide association studies led to the discovery that Cry2 may be important in the regulation of mammalian glucose levels (Dupuis, J. et al. *Nat. Genet.* 2010, 42, 105; Liu, C. et al. *PLoS One,* 2011, 6, e21464; Barker, A. et al. *Diabetes,* 2011, 60, 1805).

Glucose concentrations in the blood are highly rhythmic because of changes in insulin sensitivity and insulin secretory capacity of the endocrine pancreas (Polonsky, K. S. et al. *N. Engl. J. Med.* 1988, 318, 1231). Clock$^{\Delta19}$ mutant mice develop age-dependent hyperglycemia and these animals also develop susceptibility to diet-induced obesity, have inappropriately low concentrations of insulin (Turek, F. W. et al. *Science,* 2005, 308, 1043) and display a steeper drop in blood sugar in response to treatment with insulin, indicating that these animals have enhanced insulin sensitivity, thereby masking their β-cell deficiency (Marcheva, B. et al. *Nature,* 2010, 466, 627). Liver-specific deletion of Bmal1 in mice results in impaired glucose tolerance and increased insulin sensitivity (Lamia, K. A. et al. *Proc. Natl. Acad. Sci. USA,* 2008, 105, 15172). Individuals with type 2 diabetes, and even their first-degree relatives not yet affected with the disease, display altered rhythmicity in glucose tolerance (Boden, G. et al. *Diabetes,* 1999, 48, 2182). Also, Per2, Per3, and Cry2 expression is significantly lower in humans with type 2 diabetes versus humans without the disease (Stamenkovich, J. A. et al. *Metabolism,* 2012, 61, 978). The gluconeogenic genes phosphoenol pyruvate carboxykinase (Pck1) and glucose 6-phosphatase (G6pc) are controlled by CRY and the Bmal1 gene regulator REV-ERB (Zhang, E. E. et al. *Nat. Med.* 2010, 16, 1152; Lamia, K. A. et al. *Nature,* 2011, 480, 552; Yin, L. et al. *Science,* 2007, 318, 1786). Gluconeogenesis is tightly controlled by multiple signaling mechanisms and moreover, studies in mice have revealed that modulation of Cry1 and Cry2 can perturb gluconeogenesis and regulate blood sugar levels (Zhang, E. E. et al. *Nat. Med.* 2010, 16, 1152).

In a monotherapeutic or combination therapy context, new and established oral antidiabetic agents have non-uniform and limited effectiveness. Oral antidiabetic therapies suffer from poor or limited glycemic control, or poor patient compliance due to unacceptable side effects, such as edema, weight gain, or even more serious complications like hypoglycemia. Metformin, a substituted biguanide, can cause diarrhea and gastrointestinal discomfort. Finally, edema, weight gain, and in some cases, hepatotoxicity and cardiotoxicity, have been linked to the administration of some thiazolidine-2,4-dione antidiabetic agents (e.g. Rosiglitazone and Pioglitazone). Combination therapy using two or more of the above agents is common, but generally only leads to incremental improvements in glycemic control.

Cry1 and Cry2 also interact with the glucocorticoid receptor (GR) to globally alter the transcriptional response to glucocorticoids (Lamia, K. A. et al. *Nature,* 2011, 480, 552). Loss of Cry1 and/or Cry2 results in glucose intolerance and constitutively high levels of circulating corticosterone, suggesting reduced suppression of the hypothalamic-pituitary-adrenal axis coupled with increased glucocorticoid transactivation in the liver. Genomically, Cry1 and Cry2 associate with a glucocorticoid response element in the Pck1 promoter in a hormone-dependent manner, and dexamethasone-induced transcription of the Pck1 gene was strikingly increased in cryptochrome-deficient livers. This suggests that the undesirable metabolic side effects of glucocorticoids (e.g. hyperglycemia, insulin resistance and suppression of adrenal function) used to suppress inflammation may be alleviated by combining them with agents that can stabilize Cry1 and/or Cry2.

SUMMARY

The subject matter herein relates to cryptochrome (Cry) modulating compounds, pharmaceutical compositions containing the Cry modulating compounds and methods of treating Cry-related diseases or disorders, such as, e.g. diabetes, obesity, metabolic syndrome, Cushing's syndrome and glaucoma, by administration of Cry modulating compounds.

In one aspect, the subject matter disclosed herein is directed to a compound of formula I:

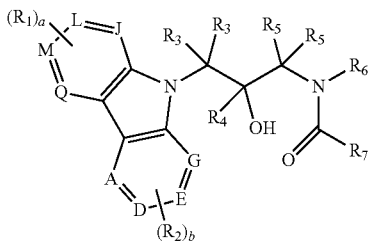

or a pharmaceutically acceptable salt or hydrate thereof, wherein:

each of A, D, E, G, J, L, M, and Q is independently N or C;

each of $R_1$ and $R_2$, when A, D, E, G, J, L, M, and Q is C, is independently selected from H, halo, cyano, nitro, —$CF_3$, —$CHF_2$, —$CH_2F$, trifluoromethoxy, azido, hydroxyl, ($C_1$-$C_6$)alkoxy, ($C_1$-$C_6$)alkyl, ($C_2$-$C_6$)alkenyl, ($C_2$-$C_6$)alkynyl, —(C=O)—$R_8$, —(C=O)—O—$R_8$, —O—(C=O)—$R_8$, —$NR_8$(C=O)—$R_{10}$, —(C=O)—$NR_8R_9$, —$NR_8R_9$, —$NR_8OR_9$, —S(O)$_c$$NR_8R_9$, —S(O)$_d$($C_1$-$C_8$)alkyl, —O—SO$_2$—$R_8$, $NR_8$—S(O)$_c$, —(CR$_8R_9$)$_d$(3-10)-membered cycloalkyl, —(CR$_8R_9$)$_e$($C_6$-$C_{10}$)aryl, —(CR$_8R_9$)$_e$(4-10)-membered heterocyclyl, —(CR$_8R_9$)$_f$(C=O)(CR$_8R_9$)$_e$($C_6$-$C_{10}$)aryl, —(CR$_8R_9$)$_f$(C=O)(CR$_8R_9$)$_e$(4-10)-membered heterocyclyl, —(CR$_8R_9$)$_e$O(CR$_8R_9$)$_f$($C_6$-$C_{10}$)aryl, —(CR$_8R_9$)$_e$O(CR$_8R_9$)$_f$(4-10)-membered heterocyclyl, —(CR$_8R_9$)$_f$S(O)$_d$(CR$_8R_9$)$_e$($C_6$-$C_{10}$)aryl, and —(CR$_8R_9$)$_f$S(O)$_d$(CR$_8R_9$)$_e$(4-10)-membered heterocyclyl;

each of $R_3$ and $R_5$ is independently selected from H, cyano, —$CF_3$, —$CHF_2$, —$CH_2F$, ($C_1$-$C_6$)alkyl, ($C_2$-$C_6$)alkenyl, ($C_2$-$C_6$)alkynyl, —(C=O)—$R_8$, —(C=O)—O—$R_8$, —(C=O)—$NR_8R_9$, —S(O)$_c$$NR_8R_9$, —S(O)$_d$($C_1$-$C_8$)alkyl, —(CR$_8R_9$)$_d$(3-10)-membered cycloalkyl, —(CR$_8R_9$)$_e$($C_6$-$C_{10}$)aryl, —(CR$_8R_9$)$_e$(4-10)-membered heterocyclyl, —(CR$_8R_9$)$_f$(C=O)(CR$_8R_9$)$_e$($C_6$-$C_{10}$)aryl, (CR$_8R_9$)$_f$(C=O)(CR$_8R_9$)$_e$(4-10)-membered heterocyclyl, —(CR$_8R_9$)$_e$O(CR$_8R_9$)$_f$($C_6$-$C_{10}$)aryl, —(CR$_8R_9$)$_e$O(CR$_8R_9$)$_f$(4-10)-membered heterocyclyl, —(CR$_8R_9$)$_f$S(O)$_d$(CR$_8R_9$)$_e$($C_6$-$C_{10}$)aryl, and —(CR$_8R_9$)$_f$S(O)$_d$(CR$_8R_9$)$_e$(4-10)-membered heterocyclyl;

wherein each of the $R_3$ groups are optionally linked to each other as a 4-12 membered mono- or bicyclic ring;

wherein each of the $R_5$ groups are optionally linked to each other as a 4-12 membered mono- or bicyclic ring;

$R_4$ is H, —$CF_3$, —$CHF_2$, —$CH_2F$, ($C_1$-$C_6$)alkyl, ($C_2$-$C_6$)alkenyl, ($C_2$-$C_6$)alkynyl, —(C=O)—$R_8$, —(C=O)—O—$R_8$, —(C=O)—$NR_8R_9$, —(CR$_8R_9$)$_d$(3-10)-membered cycloalkyl, —(CR$_8R_9$)$_e$($C_6$-$C_{10}$)aryl, —(CR$_8R_9$)$_e$(4-10)-membered heterocyclyl, —(CR$_8R_9$)$_f$(C=O)(CR$_8R_9$)$_e$($C_6$-$C_{10}$)aryl, (CR$_8R_9$)$_f$(C=O)(CR$_8R_9$)$_e$(4-10)-membered heterocyclyl, —(CR$_8R_9$)$_e$O(CR$_8R_9$)$_f$($C_6$-$C_{10}$)aryl, —(CR$_8R_9$)$_e$O(CR$_8R_9$)$_f$(4-10)-membered heterocyclyl, —CR$_8R_9$)$_f$S(O)$_d$(CR$_8R_9$)$_e$($C_6$-$C_{10}$)aryl, and —(CR$_8R_9$)$_f$S(O)$_d$(CR$_8R_9$)$_e$(4-10)-membered heterocyclyl;

wherein $R_6$ and $R_7$ are linked to each other as a 4-12 membered mono- or bicyclic ring;

each of $R_8$, $R_9$ and $R_{10}$ are independently selected from H, ($C_1$-$C_6$)alkyl, —(CR$_{11}R_{12}$)$_e$(3-10)-membered cycloalkyl, —(CR$_{11}R_{12}$)$_g$($C_6$-$C_{10}$)aryl, and —(CR$_{11}R_{12}$)$_g$(4-10)-membered heterocyclyl;

any carbon atoms of the ($C_1$-$C_6$)alkyl, the (3-10)-membered cycloalkyl, the ($C_6$-$C_{10}$)aryl and the (4-10)-membered heterocyclyl of the foregoing $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$ are independently optionally substituted with 1 to 3 $R_{14}$ substituents each independently selected from halo, cyano, nitro, —$CF_3$, —$CHF_2$, —$CH_2F$, trifluoromethoxy, azido, hydroxyl, —O—$R_{15}$, ($C_1$-$C_6$)alkoxy, ($C_1$-$C_6$)alkyl, ($C_2$-$C_6$)alkenyl, ($C_2$-$C_6$)alkynyl, —(C=O)—$R_{11}$, —(C=O)—$R_{15}$, —(C=O)—O—$R_{11}$, —(C=O)—O—$R_{15}$, —O—(C=O)—$R_{11}$, —O—(C=O)—$R_{15}$, —NR11(C=O)—$R_{13}$, —(C=O)—$NR_{11}R_{12}$, —(C=O)—$NR_{11}R_{15}$, —$NR_{11}R_{12}$, —$NR_{11}R_{15}$, —$NR_{11}OR_{12}$, —$NR_{11}OR_{15}$, —S(O)$_c$$NR_{11}R_{12}$, —S(O)$_c$$NR_{11}R_{15}$, —S(O)$_d$($C_1$-$C_6$)alkyl, —S(O)$_d$$R_{15}$, —O—SO$_2$—$R_{11}$, —O—SO$_2$—$R_{15}$, —$NR_{11}$—S(O)$_c$, —$NR_{15}$—S(O)$_c$, —(CR$_{11}R_{12}$)$_e$(3-10)-membered cycloalkyl, —(CR$_{11}R_{12}$)$_e$($C_6$-$C_{10}$)aryl, —(CR$_{11}R_{12}$)$_e$(4-10)-membered heterocyclyl, —(CR$_{11}R_{12}$)$_f$(C=O)(CR$_{11}R_{12}$)$_e$($C_6$-$C_{10}$)aryl, —(CR$_{11}R_{12}$)$_f$(C=O)(CR$_{11}R_{12}$)$_e$(4-10)-membered heterocyclyl, —(CR$_{11}R_{12}$)$_e$O(CR$_{11}R_{12}$)$_f$($C_6$-$C_{10}$)aryl, —(CR$_{11}R_{12}$)$_e$O(CR$_{11}R_{12}$)$_f$(4-10)-membered heterocyclyl, —(CR$_{11}R_{12}$)$_f$S(O)$_d$(CR$_{11}R_{12}$)$_e$($C_6$-$C_{10}$)aryl, and —(CR$_{11}R_{12}$)$_f$S(O)$_d$(CR$_{11}R_{12}$)$_e$(4-10)-membered heterocyclyl;

any carbon atoms of the ($C_1$-$C_6$)alkyl, the (3-10)-membered cycloalkyl, the ($C_6$-$C_{10}$)aryl and the (4-10)-membered heterocyclyl of the foregoing $R_{14}$ are independently optionally substituted with 1 to 3 $R_{16}$ substituents each independently selected from halo, cyano, nitro, —$CF_3$, —$CHF_2$, —$CH_2F$, trifluoromethoxy, azido, (CH$_2$)$_e$OH, ($C_1$-$C_6$)alkoxy, ($C_1$-$C_6$)alkyl, ($C_2$-$C_6$)alkenyl, ($C_2$-$C_6$)alkynyl, —(C=O)—$R_{11}$, —(C=O)—$R_{15}$, —(C=O)—O—$R_{11}$, —(C=O)—O—$R_{15}$, —O—(C=O)—$R_{11}$, —O—(C=O)—$R_{15}$, —NR$_{11}$(C=O)—$R_{13}$, —(C=O)—$NR_{11}R_{12}$, —$NR_{11}R_{12}$, and —$NR_{11}R_{15}$;

any nitrogen atoms of the (4-10)-membered heterocyclyl of the foregoing $R_1$, $R_2$, $R_3$, $R_4$, $R_8$, $R_6$, $R_7$, $R_8$, $R_9$, $R_{10}$, $R_{14}$, and $R_{15}$ are independently optionally substituted with ($C_1$-$C_6$)alkyl, ($C_2$-$C_6$)alkenyl, ($C_2$-$C_6$)alkynyl, —(C=O)—$R_{11}$, —(C=O)—O—$R_{11}$, —(C=O)—$NR_{11}R_{12}$, —(CR$_{11}R_{12}$)$_e$(3-10)-membered cycloalkyl, —(CR$_{11}R_{12}$)$_e$($C_6$-$C_{10}$)aryl, —(CR$_{11}R_{12}$)$_e$(4-10)-membered heterocyclyl, —(CR$_{11}R_{12}$)$_f$(C=O)(CR$_{11}R_{12}$)$_e$($C_6$-$C_{10}$)aryl, or —(CR$_{11}R_{12}$)$_f$(C=O)(CR$_{11}R_{12}$)$_e$(4-10)-membered heterocyclyl;

each $R_{11}$, $R_{12}$, and $R_{13}$ are independently H or ($C_1$-$C_6$)alkyl;

$R_{15}$ is —(CR$_{11}R_{12}$)$_e$(3-10)-membered cycloalkyl, —(CR$_{11}R_{12}$)$_e$($C_6$-$C_{10}$)aryl, or —(CR$_{11}R_{12}$)$_e$(4-10)-membered heterocyclyl;

a and b are each independently 1, 2, 3, or 4;

c is 1 or 2;

d is 0, 1, or 2; and e, f, and g are each independently 0, 1, 2, 3, 4, or 5.

In some embodiments, each of A, D, E, G, J, L, M, and Q are C; each of $R_1$ and $R_2$ is independently selected from H or halo; $R_4$ is H or ($C_1$-$C_6$)alkyl, $R_3$ and $R_5$ are H; $R_6$ and $R_7$ are linked to each other as a 4-12 membered mono- or bicyclic amide ring; $R_8$, $R_9$, $R_{10}$, $R_{11}$, $R_{12}$, $R_{13}$, $R_{14}$, $R_{15}$, $R_{16}$, a, b, c, d, e, and f are as defined herein.

In other embodiments, each of A, D, E, G, J, L, M, and Q are C; each of $R_1$ and $R_2$ is independently selected from H or halo; $R_4$ is H or ($C_1$-$C_6$)alkyl, $R_3$ and $R_5$ are H; $R_6$ and $R_7$ are linked to each other as a 4-12 membered mono- or bicyclic urea ring; $R_8$, $R_9$, $R_{10}$, $R_{11}$, $R_{12}$, $R_{13}$, $R_{14}$, $R_{15}$, $R_{16}$, a, b, c, d, e, and f are as defined herein.

In some embodiments, the compound of formula I is a single enantiomer bearing an (R)-configuration at C-3, wherein each of A, D, E, G, J, L, M, and Q are C; each of $R_1$ and $R_2$ is independently selected from H or halo; $R_4$ is H or ($C_1$-$C_6$)alkyl, $R_3$ and $R_5$ are H; $R_6$ and $R_7$ are linked to each other as a 4-12 membered mono- or bicyclic amide ring; $R_8$, $R_9$, $R_{10}$, $R_{11}$, $R_{12}$, $R_{13}$, $R_{14}$, $R_{15}$, $R_{16}$, a, b, c, d, e, and f are as defined herein.

In other embodiments of the subject matter disclosed herein, the compound of formula I is a single enantiomer bearing an (R)-configuration at C-3, wherein each of A, D, E, G, J, L, M, and Q are C; each of $R_1$ and $R_2$ is independently selected from H or halo; $R_4$ is H or ($C_1$-$C_6$)alkyl, $R_3$ and $R_5$ are H; $R_6$ and $R_7$ are linked to each other as a 4-12 membered mono- or bicyclic urea ring; $R_8$, $R_9$, $R_{10}$, $R_{11}$, $R_{12}$, $R_{13}$, $R_{14}$, $R_{15}$, $R_{16}$, a, b, c, d, e, and fare as defined herein.

Other embodiments of the subject matter described herein are compounds selected from the group consisting of:
1-(3-(3,6-difluoro-9H-carbazol-9-yl)-2-hydroxypropyl)-3-fluoropyrrolidin-2-one;
2-(3-(3,6-difluoro-9H-carbazol-9-yl)-2-hydroxypropyl)-2-azabicyclo[2.2.1]heptan-3-one; 1-(3-(3,6-difluoro-9H-carbazol-9-yl)-2-hydroxypropyl)imidazolidin-2-one;
(1R,4S)-2-((R)-3-(3,6-difluoro-9H-carbazol-9-yl)-2-hydroxypropyl)-2-azabicyclo[2.2.1]heptan-3-one;
(R)-1-(3-(3,6-difluoro-9H-carbazol-9-yl)-2-hydroxypropyl) imidazolidin-2-one;
(R)-1-((R)-3-(3,6-difluoro-9H-carbazol-9-yl)-2-hydroxypropyl)-3-fluoropyrrolidin-2-one;
(S)-1-((S)-3-(9H-carbazol-9-yl)-2-hydroxy-2-methylpropyl)-3-fluoropyrrolidin-2-one;
(R)-1-((R)-3-(9H-carbazol-9-yl)-2-hydroxypropyl)-4-methylimidazolidin-2-one; or a
pharmaceutically acceptable salt or hydrate thereof.

In another aspect, the compounds described herein modulate Cry1 or Cry2. Modulation of Cry1 or Cry2 includes any one of the following: binding to Cry1 or Cry2; inhibiting modification of Cry1 or Cry2; altering Cry1 or Cry2 localization; increasing or decreasing Cry1 or Cry2 stabilization; increasing or decreasing the binding between Cry1 or Cry2 to a target; increasing or decreasing Cry1 or Cry2 activity; and increasing or decreasing activity of a Cry1 or Cry2 target. Targets of Cry1 and/or Cry2 include, but are not limited to, Per1, Per2, glucocorticoid receptor (GR), CLOCK, BMAL1, or a CLOCK-BMAL1 promoter sequence.

In another aspect, the subject matter described herein provides a pharmaceutical composition comprising a compound of formula I, or a pharmaceutically acceptable salt or hydrate thereof, and a pharmaceutically acceptable carrier, adjuvant, or diluent. In some embodiments, the pharmaceutical composition further comprises one or more additional therapeutic agents. Examples of additional therapeutic agents include, but are not limited to, DPP-IV inhibitors such as sitagliptin, alogliptin, vildagliptin, saxagliptin and linagliptin; GLP-1 agonists such as exenatide, liraglutide and albiglutide; SGLT2 inhibitors such as canagliflozin, ertugliflozin, and dapagliflozin); metformin; and sulfonylureas such as glyburide. Other examples of additional therapeutic agents includes Signifor®, ketoconazole, metyrapone, mitotane, etomidate, Korlym®, epidermal growth factor inhibitors, the aldosterone synthase/11β-hydroxylase inhibitor LCI699, and kevoketoconazole (COR-003).

In other aspects, a method of treating a Cry-mediated disease or disorder in a subject is provided, by administering to the subject a therapeutically effective amount of the pharmaceutical composition described herein. In a further aspect, the present invention provides a method for alleviating a symptom of a Cry-mediated disease or disorder in a subject, by administering to the subject a therapeutically effective amount of the pharmaceutical composition described herein. The disease or disorder may be selected from the group consisting of diabetes, diabetic complications, such as diabetic neuropathy, diabetic retinopathy, diabetic nephropathy, cataract formation, glaucoma, diabetic angiopathy, atherosclerosis; nonalcoholic steatohepatitis (NASH); non-alcoholic fatty liver disease (NAFLD); asthma; chronic obstructive pulmonary disease (COPD); metabolic syndrome; insulin resistance syndrome; obesity; glaucoma; Cushing's syndrome; psychotic depression; Alzheimer's disease; neuropathic pain; drug abuse; osteoporosis; cancer; macular degeneration; and myopathy.

Any of the methods described herein can also involve the administration of one or more additional therapeutic agents to the subject. Examples of additional therapeutic agents include, but are not limited to, DPP-IV inhibitors such as sitagliptin, alogliptin, vildagliptin, saxagliptin and linagliptin; GLP-1 agonists such as exenatide, liraglutide and albiglutide; SGLT2 inhibitors such as canagliflozin, ertugliflozin, and dapagliflozin); metformin; sulfonylureas, such as glyburide; Signifor®; ketoconazole; metyrapone; mitotane; etomidate; Korlym®; epidermal growth factor inhibitors; the aldosterone synthase/11β-hydroxylase inhibitor LCI699; and kevoketoconazole (COR-003)

In another aspect, a method of monitoring progression or prognosis of a Cry-mediated disease or disorder in a subject is provided, involving measuring an effective amount of one or more cryptochromes or cryptochrome-regulated genes in a first sample from the subject at a first period of time; measuring an effective amount of one or more cryptochromes or cryptochrome-regulated genes in a second sample from the subject at a second period of time; and comparing the amount of the one or more cryptochromes or cryptochrome-regulated genes detected in the first sample to the amount of the one or more cryptochromes or cryptochrome-regulated genes detected in the second sample, or to a reference value. Examples of cryptochrome-regulated genes include genes that contain an E-box sequence in their promoter. Such genes include, but are not limited to Dbp, Rev-erb alpha, Rev-erb beta, Ror alpha, Ror beta, Ror gamma, Per1, Per2, Per3, Cry1, Cry2, Pck1, G6Pc, Avp, Vip, Cck, SP (substance P), AA-Nat, PK2 (Prokinectin 2), c-Myc, MyoD and Nampt.

In some embodiments, the monitoring comprises evaluating changes in the risk of developing the Cry-mediated disease or disorder in the subject.

The optimal time for dosing in humans is expected to be the evening, corresponding to the peak of human Cry expression and the end of the active (daytime) period.

The subject may comprise one who has been previously treated for the Cry-mediated disease or disorder, one who has not been previously treated for the Cry-mediated disease or disorder, or one who has not been previously diagnosed with the Cry-mediated disease or disorder. The sample can be whole blood, serum, plasma, blood cells, endothelial cells, tissue biopsies, lymphatic fluid, ascites fluid, interstitial fluid, bone marrow, cerebrospinal fluid (CSF), seminal fluid, saliva, mucous, sputum, sweat, or urine.

In some embodiments, the first sample is taken from the subject prior to being treated for the Cry-mediated disease or disorder and the second sample is taken from the subject after being treated for the Cry-mediated disease or disorder. In other embodiments, the subject is treated with the pharmaceutical composition containing the compounds of formula I disclosed herein. In certain embodiments, the monitoring further comprises selecting a treatment for the subject and/or monitoring the effectiveness of a treatment for the Cry-mediated disease or disorder, wherein the treatment for the Cry-mediated disease or disorder comprises surgical intervention, administration of the pharmaceutical composition as defined herein alone or in combination with one or more additional therapeutic agents, surgical intervention following or preceded by administration of the pharmaceutical composition provided herein or in combination with one or more additional therapeutic agents, or taking no further action.

In other embodiments, the reference value comprises an index value, a value derived from one or more Cry-mediated disease or disorder risk prediction algorithms, a value derived from a subject not having a Cry-mediated disease or disorder, or a value derived from a subject diagnosed with a Cry-mediated disease or disorder. In some embodiments, the measuring comprises detecting the presence or absence of the one or more cryptochromes, quantifying the amount of the one or more cryptochromes, qualifying the type of the one or more cryptochromes, and assessing the ability of one or more cryptochromes to bind to a target. The target may be Per1, Per2, or a CLOCK-BMAL1 promoter sequence.

As disclosed herein, the Cry-mediated disease or disorder may be selected from the group consisting of diabetes, diabetic complications such as diabetic neuropathy, diabetic retinopathy, diabetic nephropathy, cataract formation, glaucoma, diabetic angiopathy, atherosclerosis; nonalcoholic steatohepatitis (NASH); non-alcoholic fatty liver disease (NAFLD); asthma; chronic obstructive pulmonary disease (COPD); metabolic syndrome; insulin resistance syndrome; obesity; glaucoma; Cushing's syndrome; psychotic depression; Alzheimer's disease; neuropathic pain; drug abuse; osteoporosis; cancer; macular degeneration; and myopathy.

In one embodiment, in the compounds of formula I disclosed herein, A, D, E, G, J, L, M, and Q are carbon. In another embodiment, in the compounds of formula I, $R_1$ and $R_2$ are hydrogen. In still other embodiments, in the compounds of formula I, $R_1$ and $R_2$ are fluorine and a and b are 1. In further embodiments, in the compounds of formula I, $R_3$ and $R_5$ are hydrogen. In another embodiment, in the compounds of formula I, $R_3$, $R_4$, and $R_5$ are hydrogen. In some embodiments, in the compounds of formula I, $R_6$ and $R_7$ are linked to form an optionally substituted monocyclic ring.

In other embodiments, in the compounds of formula I, $R_6$ and $R_7$ are linked to form an optionally substituted fused bicyclic ring, an optionally substituted bridged bicyclic ring, an optionally substituted spiro bicyclic ring, an optionally substituted pyrrolidinone ring, an optionally substituted imidazolidinone ring, an optionally substituted piperidinone ring, and/or an optionally substituted pyrimidinone ring. Likewise, in any of these embodiments, the ring formed by $R_6$ and $R_7$ can be substituted exclusively with fluorine, methyl groups, ethyl groups, isopropyl groups, $C_3$-6 cycloalkanes, or phenyl groups.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from the following detailed description and claims.

BRIEF DESCRIPTION OF THE DRAWINGS

FIG. 2A and FIG. 2B), G6Pc (Glucose 6-phosphatase catalytic subunit; FIG. 2C and FIG. 2D) at six hour intervals over 24 hours in the livers of C57Bl/6J DIO (FIG. 2A and FIG. 2C) or Balb/c (FIG. 2B and FIG. 2D) mice treated with vehicle ($H_2O$) or Compound 72. Transcript levels were determined by RT-qPCR and compared to vehicle at ZT8 with the dark period shaded. The mRNA levels from Compound 72-treated for each time point was compared to vehicle by T-test: * <0.05,  <0.01, * <0.001, **** <0.0001.

FIG. 8A) Fasting blood glucose levels; FIG. 8B) oral glucose tolerance test (OGTT); FIG. 8C) glucose AUC.

FIG. 9A) Insulin levels before (at 0 h) and after glucose load (at 2 h); FIG. 9B) Homeostatic model assessment estimated insulin resistance (HOMA-IR).

FIG. 11A) Fasting blood glucose levels; FIG. 11B) OGTT; FIG. 11C) glucose AUC.

FIG. 12A) Insulin levels before (at 0 h) and after glucose load (at 2 h); FIG. 12B) Homeostatic model assessment estimated insulin resistance (HOMA-IR).

FIG. 14A) Fasting blood glucose levels; FIG. 14B) OGTT; FIG. 14C) glucose AUC.

FIG. 15A) Insulin levels before (at 0 h) and after glucose load (at 2 h); FIG. 15B) Homeostatic model assessment estimated insulin resistance (HOMA-IR).

FIG. 17A) Fasting blood glucose levels; FIG. 17B) OGTT; FIG. 17C) glucose AUC.

FIG. 18A) Insulin levels before (at 0 h) and after glucose load (at 2 h); FIG. 18B) Homeostatic model assessment estimated insulin resistance (HOMA-IR).

(FIG. 19A) Fasted plasma glucose levels and (FIG. 19B) fasted plasma insulin levels.

FIG. 22A) Fasting blood glucose levels; FIG. 22B) OGTT; FIG. 22C) glucose AUC.

DETAILED DESCRIPTION

Figure 1A:
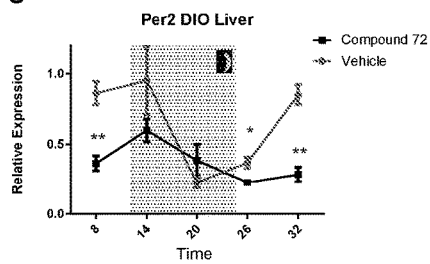
FIGS. 1A-H are a series of graphs showing core clock gene expression in mice after administration of Compound 72. mRNA expression of core clock genes Per2 (FIG. 1A and FIG. 1B), Bmal1 (FIG. 1C and FIG. 1D), Cry1 (FIG. 1E and FIG. 1F), and Cry2 (FIG. 1G and FIG. 1H) was measured in six hour intervals over 24 hours in the livers of C57Bl/6J DIO (FIG. 1A, FIG. 1C, FIG. 1E, FIG. 1G) or Balb/c (FIG. 1B, FIG. 1D, FIG. 1F, FIG. 1H) mice treated with vehicle ($H_2O$) or Compound 72. Transcript levels were determined by RT-qPCR and compared to vehicle at ZT8 with the dark period shaded. The mRNA levels from Compound 72-treated for each time point was compared to vehicle by T-test: * <0.05,  <0.01, * <0.001, **** <0.0001.

Each of the applications and patents cited in this text, as well as each document or reference cited in each of the applications and patents (including during the prosecution of each issued patent; "application cited documents"), and each of the U.S. and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference. Documents incorporated by reference into this text may be employed in the practice of the invention. The features, structures, or characteristics described throughout this specification may be combined in any suitable manner in one or more embodiments. For example, the usage of the phrases "exemplary embodiments," "example embodiments," "some embodiments," or other similar language, throughout this specification refers to the fact that a particular feature, structure, or characteristic described in connection with an embodiment may be included in at least one embodiment described herein. Thus, appearances of the phrases "exemplary embodiments," "example embodiments," "in some embodiments," "in other embodiments," or other similar language, throughout this specification do not necessarily all refer to the same group of embodiments, and the described features, structures, or characteristics can be combined in any suitable manner in one or more embodiments.

To facilitate the understanding of this disclosure, a number of terms are defined below. Terms defined herein have meanings as commonly understood by a person of ordinary skill in the areas relevant to the subject matter described herein. Terms such as "a", "an" and "the" are not intended to refer to only a singular entity, but include the general class of which a specific example may be used for illustration. The terminology herein is used to describe specific embodiments of the subject matter described herein, but their usage does not delimit the subject matter, except as outlined in the claims.

As used herein, the terms "comprising", "including", or "having" are used in their open, non-limiting sense.

The term "halo", as used herein, unless otherwise indicated, means fluoro, chloro, bromo, or iodo.

The term "alkyl", as used herein, unless otherwise indicated, includes saturated monovalent hydrocarbon radicals having straight or branched moieties.

The term "alkenyl", as used herein, represents monovalent straight or branched chain groups of, unless otherwise specified, from 2 to 6 carbons containing one or more carbon-carbon double bonds and is exemplified by ethenyl, 1-propenyl, 2-propenyl, 2-methyl-1-propenyl, 1-butenyl, 2-butenyl, and the like.

The term "alkynyl", as used herein, represents monovalent straight or branched chain groups of from two to six carbon atoms containing a carbon-carbon triple bond and is exemplified by ethynyl, 1-propynyl, and the like.

The term "alkoxy", as used herein, unless otherwise indicated, includes O-alkyl groups wherein alkyl is as defined above.

The term "Me" means methyl, and "Et" means ethyl.

The term "cycloalkyl", as used herein, unless otherwise indicated, refers to a non-aromatic, saturated or partially saturated, monocyclic or fused, spiro or unfused bicyclic or tricyclic hydrocarbon referred to herein containing a total of from 3 to 10 carbon atoms. Illustrative examples of cycloalkyl are derived from, but not limited to, the following:

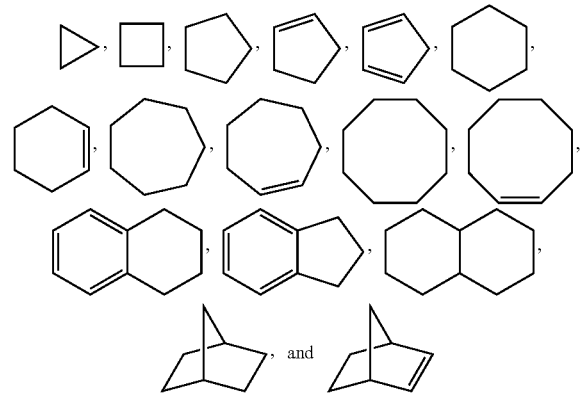

The term "aryl", as used herein, unless otherwise indicated, includes an organic radical derived from an aromatic hydrocarbon by removal of one hydrogen, such as phenyl or naphthyl.

The term "(4-12)-membered heterocyclyl", as used herein, unless otherwise indicated, includes aromatic and non-aromatic heterocyclic groups containing one to four heteroatoms each selected from O, S, and N, wherein each heterocyclic group has from 4-12 atoms, in its ring system, and with the proviso that the ring of said group does not contain two adjacent O or S atoms. Non-aromatic heterocyclic groups include groups having only 3 atoms in their ring system, but aromatic heterocyclic groups must have at least 5 atoms in their ring system. The heterocyclic groups include benzo-fused ring systems. An example of a 3 membered heterocyclic group is aziridine, an example of a 4 membered ring heterocyclic group is azetidinyl (derived from azetidine). An example of a 5 membered heterocyclic group is thiazolyl, an example of a 7 membered ring is azepinyl, and an example of a 10 membered heterocyclic group is quinolinyl. Example of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, traizinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthridinyl, and furopyridinyl. The foregoing groups, as derived from the lists above, may be C-attached or N-attached where such is possible. For instance, a group derived from pyrrole may be pyrrol-1-yl (N-attached) or pyrrol-3-yl (C-attached). Further, a group derived from imidazole may be imidazole-1-yl (N-attached) or imidazole-3-yl (C-attached). The 4-12 membered heterocyclic may be optionally substituted on any ring carbon, sulfur, or nitrogen atom(s) by one or two oxo, per ring. An example of a heterocyclic group wherein 2 ring atoms are substituted with oxo moieties is 1,1-dioxo-thiomorpholinyl. Other illustrative example of 4-12 membered heterocyclic are derived from, but not limited to, the following:

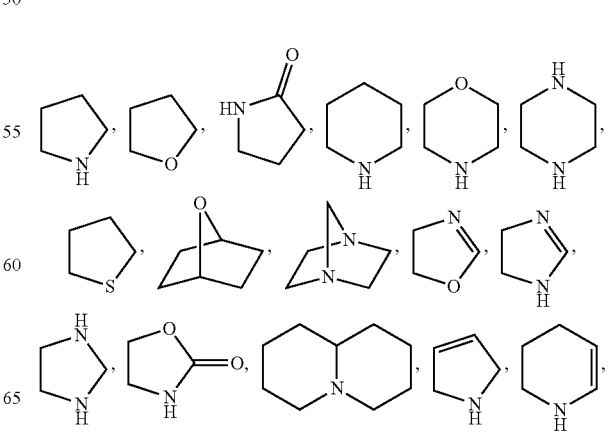

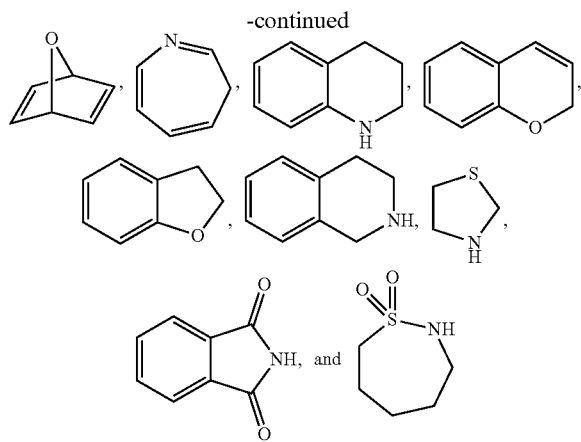

The term "substituted", as used herein, means that any one or more hydrogen atoms on the designated atom is replaced with a selection from the indicated groups, provided that the designated atom's normal valency is not exceeded, and that the substitution results in a stable compound. When a substituent is keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). Non-limiting examples of such groups include, without limitation, H, CH$_3$, NO$_2$, SO$_2$N(CH$_3$)$_2$, SO$_2$N((CH$_3$)SO$_2$), COOH, COOCH$_3$, CO(N(CH$_3$)), alkyl, alkenyl, alkynyl, aryl, aralkyl, cycloalkyl, heterocyclyl, alkylaryl, heteroaryl, heterocycloalkyl, alkoxy (i.e., methoxy, ethoxy, etc), alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, trifluoromethyl, pentafluoroethyl, halogen (i.e., chloro, fluoro, bromo, iodo), cyano, thio, amido, ether, ester, hydroxyl, hydroxyalkyl, saturated or unsaturated fatty acids, azido, phosphonamido, sulfonamido, lactam, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, guanidino, sulfhydryl, alkylthio, arylthio, thiocarboxylate, sulfates, alkylsulfinyl, sulfonato, sulfamoyl, sulfonamido, nitro, cyano, azido, etc.

The subject matter disclosed herein provides carbazole-containing sulfonamide compounds that modulate one or more cryptochrome molecules. These compounds have the general structure set forth in formula I:

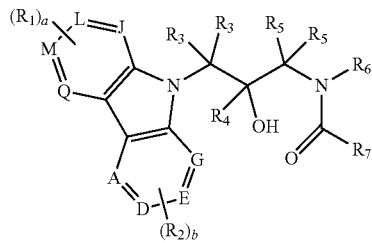

or a pharmaceutically acceptable salt or hydrate thereof, wherein
each of A, D, E, G, J, L, M, and Q is independently N or C;
each of R$_1$ and R$_2$, when A, D, E, G, J, L, M, and Q is C, is independently selected from H, halo, cyano, nitro, —CF$_3$, —CHF$_2$, —CH$_2$F, trifluoromethoxy, azido, hydroxyl, (C$_1$-C$_6$)alkoxy, (C$_1$-C$_6$)alkyl, (C$_2$-C$_6$)alkenyl, (C$_2$-C$_6$)alkynyl, —(C=O)—R$_8$, —(C=O)—O—R$_8$, —O—(C=O)—R$_8$, —NR$_8$(C=O)—R$_{10}$, —(C=O)—NR$_8$R$_9$, —NR$_8$R$_9$, —NR$_8$OR$_9$, —S(O)$_c$NR$_8$R$_9$, —S(O)$_d$(C$_1$-C$_8$)alkyl, —O—SO$_2$—R$_8$, NR$_8$—S(O)$_c$, —(CR$_8$R$_9$)$_d$(3-10)-membered cycloalkyl, —(CR$_8$R$_9$)$_e$(C$_6$-C$_{10}$)aryl, —(CR$_8$R$_9$)$_e$(4-10)-membered heterocyclyl, —(CR$_8$R$_9$)$_f$(C=O)(CR$_8$R$_9$)$_e$(C$_6$-C$_{10}$)aryl, —(CR$_8$R$_9$)$_f$(C=O)(CR$_8$R$_9$)$_e$(4-10)-membered heterocyclyl, —(CR$_8$R$_9$)$_e$O(CR$_8$R$_9$)$_f$(C$_6$-C$_{10}$)aryl, —(CR$_8$R$_9$)$_e$O(CR$_8$R$_9$)$_f$(4-10)-membered heterocyclyl, —(CR$_8$R$_9$)$_f$S(O)$_d$(CR$_8$R$_9$)$_e$(C$_6$-C$_{10}$)aryl, and —(CR$_8$R$_9$)$_f$S(O)$_d$(CR$_8$R$_9$)$_e$(4-10)-membered heterocyclyl;

each of R$_3$ and R$_5$ is independently selected from H, cyano, —CF$_3$, —CHF$_2$, —CH$_2$F, (C$_1$-C$_6$)alkyl, (C$_2$-C$_6$)alkenyl, (C$_2$-C$_6$)alkynyl, —(C=O)—R$_8$, —(C=O)—O—R$_8$, —(C=O)—NR$_8$R$_9$, —S(O)$_c$NR$_8$R$_9$, —S(O)$_d$(C$_1$-C$_8$)alkyl, —(CR$_8$R$_9$)$_d$(3-10)-membered cycloalkyl, —(CR$_8$R$_9$)$_e$(C$_6$-C$_{10}$)aryl, —(CR$_8$R$_9$)$_e$(4-10)-membered heterocyclyl, —(CR$_8$R$_9$)$_f$(C=O)(CR$_8$R$_9$)$_e$(C$_6$-C$_{10}$)aryl, (CR$_8$R$_9$)$_f$(C=O)(CR$_8$R$_9$)$_e$(4-10)-membered heterocyclyl, —(CR$_8$R$_9$)$_e$O(CR$_8$R$_9$)$_f$(C$_6$-C$_{10}$)aryl, —(CR$_8$R$_9$)$_e$O(CR$_8$R$_9$)$_f$(4-10)-membered heterocyclyl, —(CR$_8$R$_9$)$_f$S(O)$_d$(CR$_8$R$_9$)$_e$(C$_6$-C$_{10}$)aryl, and —(CR$_8$R$_9$)$_f$S(O)$_d$(CR$_8$R$_9$)$_e$(4-10)-membered heterocyclyl;

each of the R$_3$ groups are optionally linked to each other as a 4-12 membered mono- or bicyclic ring;
each of the R$_5$ groups are optionally linked to each other as a 4-12 membered mono- or bicyclic ring;
R$_4$ is H, —CF$_3$, —CHF$_2$, —CH$_2$F, (C$_1$-C$_6$)alkyl, (C$_2$-C$_6$)alkenyl, (C$_2$-C$_6$)alkynyl, —(C=O)—R$_8$, —(C=O)—O—R$_8$, —(C=O)—NR$_8$R$_9$, —(CR$_8$R$_9$)$_d$(3-10)-membered cycloalkyl, —(CR$_8$R$_9$)$_e$(C$_6$-C$_{10}$)aryl, —(CR$_8$R$_9$)$_e$(4-10)-membered heterocyclyl, —(CR$_8$R$_9$)$_f$(C=O)(CR$_8$R$_9$)$_e$(C$_6$-C$_{10}$)aryl, (CR$_8$R$_9$)$_f$(C=O)(CR$_8$R$_9$)$_e$(4-10)-membered heterocyclyl, —(CR$_8$R$_9$)$_e$O(CR$_8$R$_9$)$_f$(C$_6$-C$_{10}$)aryl, —(CR$_8$R$_9$)$_e$O(CR$_8$R$_9$)$_f$(4-10)-membered heterocyclyl, —(CR$_8$R$_9$)$_f$S(O)$_d$(CR$_8$R$_9$)$_e$(C$_6$-C$_{10}$)aryl, and —(CR$_8$R$_9$)$_f$S(O)$_d$(CR$_8$R$_9$)$_e$(4-10)-membered heterocyclyl;

wherein R$_6$ and R$_7$ are linked to each other as a 4-12 membered mono- or bicyclic ring; each of R$_8$, R$_9$ and R$_{10}$ are independently selected from H, (C$_1$-C$_6$)alkyl, —(CR$_{11}$R$_{12}$)$_e$(3-10)-membered cycloalkyl, —(CR$_{11}$R$_{12}$)$_g$(C$_6$-C$_{10}$)aryl, and —(CR$_{11}$R$_{12}$)$_g$(4-10)-membered heterocyclyl;

any carbon atoms of the (C$_1$-C$_6$)alkyl, the (3-10)-membered cycloalkyl, the (C$_6$-C$_{10}$)aryl and the (4-10)-membered heterocyclyl of the foregoing R$_1$, R$_2$, R$_3$, R$_4$, R$_5$, R$_6$, R$_7$, R$_8$, R$_9$, R$_{10}$, R$_{11}$, R$_{12}$, R$_{13}$, R$_{14}$, R$_{15}$, and R$_{16}$ are independently optionally substituted with 1 to 3 R$_{14}$ substituents each independently selected from halo, cyano, nitro, —CF$_3$, —CHF$_2$, —CH$_2$F, trifluoromethoxy, azido, hydroxyl, —O—R$_{15}$, (C$_1$-C$_6$)alkoxy, (C$_1$-C$_6$)alkyl, (C$_2$-C$_6$)alkenyl, (C$_2$-C$_6$)alkynyl, —(C=O)—R$_{11}$, —(C=O)—R$_{15}$, —(C=O)—O—R$_{11}$, —(C=O)—O—R$_{15}$, —O—(C=O)—R$_{11}$, —O—(C=O)—R$_{15}$, —NR$_{11}$(C=O)—R$_{13}$, —(C=O)—NR$_{11}$R$_{12}$, —(C=O)—NR$_{11}$R$_{15}$, —NR$_{11}$R$_{12}$, —NR$_{11}$R$_{15}$, —NR$_{11}$OR$_{12}$, —NR$_{11}$OR$_{15}$, —S(O)$_c$NR$_{11}$R$_{12}$, —S(O)$_c$NR$_{11}$R$_{15}$, —S(O)$_d$(C$_1$-C$_6$)alkyl, —S(O)$_d$R$_{15}$, —O—SO$_2$—R$_{11}$, —O—SO$_2$—R$_{15}$, —NR$_{11}$—S(O)$_c$, —NR$_{15}$—S(O)$_c$, —(CR$_{11}$R$_{12}$)$_e$(3-10)-membered cycloalkyl, —(CR$_{11}$R$_{12}$)$_e$(C$_6$-C$_{10}$)aryl, —(CR$_{11}$R$_{12}$)$_e$(4-

10)-membered heterocyclyl, —(CR$_{11}$R$_{12}$)$_f$(C=O)(CR$_{11}$R$_{12}$)$_e$(C$_6$-C$_{10}$)aryl, —(CR$_{11}$R$_{12}$)$_f$(C=O)(CR$_{11}$R$_{12}$)$_e$(4-10)-membered heterocyclyl, —(CR$_{11}$R$_{12}$)$_e$O(CR$_{11}$R$_{12}$)$_f$(C$_6$-C$_{10}$)aryl, —(CR$_{11}$R$_{12}$)$_e$O(CR$_{11}$R$_{12}$)$_f$(4-10)-membered heterocyclyl, —(CR$_{11}$R$_{12}$)$_f$S(O)$_d$(CR$_{11}$R$_{12}$)$_e$(C$_6$-C$_{10}$)aryl, and —(CR$_{11}$R$_{12}$)$_f$S(O)$_d$(CR$_{11}$R$_{12}$)$_e$(4-10)-membered heterocyclyl;

any carbon atoms of the (C$_1$-C$_6$)alkyl, the (3-10)-membered cycloalkyl, the (C$_6$-C$_{10}$)aryl and the (4-10)-membered heterocyclyl of the foregoing R$_{14}$ are independently optionally substituted with 1 to 3 R$_{16}$ substituents each independently selected from halo, cyano, nitro, —CF$_3$, —CHF$_2$, —CH$_2$F, trifluoromethoxy, azido, (CH$_2$)$_e$OH, (C$_1$-C$_6$) alkoxy, (C$_1$-C$_6$)alkyl, (C$_2$-C$_6$)alkenyl, (C$_2$-C$_6$)alkynyl, —(C=O)—R$_{11}$, —(C=O)—R$_{15}$, —(C=O)—O—R$_{11}$, —(C=O)—O—R$_{15}$, —O—(C=O)—R$_{11}$, —O—(C=O)—R$_{15}$, —NR$_{11}$(C=O)—R$_{13}$, —(C=O)—NR$_{11}$R$_{12}$, —NR$_{11}$R$_{12}$, and —NR$_{11}$R$_{15}$;

any nitrogen atoms of the (4-10)-membered heterocyclyl of the foregoing R$_1$, R$_2$, R$_3$, R$_4$, R$_8$, R$_6$, R$_7$, R$_8$, R$_9$, R$_{10}$, R$_{14}$, and R$_{15}$ are independently optionally substituted with (C$_1$-C$_6$)alkyl, (C$_2$-C$_6$)alkenyl, (C$_2$-C$_6$)alkynyl, —(C=O)—R$_{11}$, —(C=O)—O—R$_{11}$, —(C=O)—NR$_{11}$R$_{12}$, —(CR$_{11}$R$_{12}$)$_e$(3-10)-membered cycloalkyl, —(CR$_{11}$R$_{12}$)$_e$(C$_6$-C$_{10}$)aryl, —(CR$_{11}$R$_{12}$)$_e$(4-10)-membered heterocyclyl, —(CR$_{11}$R$_{12}$)$_f$(C=O)(CR$_{11}$R$_{12}$)$_e$(C$_6$-C$_{10}$)aryl, or —(CR$_{11}$R$_{12}$)$_f$(C=O)(CR$_{11}$R$_{12}$)$_e$(4-10)-membered heterocyclyl;

each R$_{11}$, R$_{12}$, and R$_{13}$ are independently H or (C$_1$-C$_6$) alkyl;

R$_{15}$ is —(CR$_{11}$R$_{12}$)$_e$(3-10)-membered cycloalkyl, —(CR$_{11}$R$_{12}$)$_e$(C$_6$-C$_{10}$)aryl, or —(CR$_{11}$R$_{12}$)$_e$(4-10)-membered heterocyclyl;

a and b are each independently 1, 2, 3, or 4;

c is 1 or 2;

d is 0, 1, or 2; and e, f, and g are each independently 0, 1, 2, 3, 4, or 5.

In exemplary embodiments of the compounds of formula I, each of A, D, E, G, J, L, M, and Q are C; each of R$_1$ and R$_2$ is independently selected from H or halo; R$_4$ is H or (C$_1$-C$_6$)alkyl, R$_3$ and R$_5$ are H; R$_6$ and R$_7$ are linked to each other as a 4-12 membered mono- or bicyclic amide ring; R$_8$, R$_9$, R$_{10}$, R$_{11}$, R$_{12}$, R$_{13}$, R$_{14}$, R$_{15}$, R$_{16}$, a, b, c, d, e, and f are as defined herein.

In some embodiments, each of A, D, E, G, J, L, M, and Q are C; each of R$_1$ and R$_2$ is independently selected from H or halo; R$_4$ is H or (C$_1$-C$_6$)alkyl, R$_3$ and R$_5$ are H; R$_6$ and R$_7$ are linked to each other as a 4-12 membered mono- or bicyclic urea ring; R$_8$, R$_9$, R$_{10}$, R$_{11}$, R$_{12}$, R$_{13}$, R$_{14}$, R$_{15}$, R$_{16}$, a, b, c, d, e, and f are as defined herein.

In some embodiments of the subject matter disclosed herein, the compound of formula I is the single enantiomer bearing an (R)-configuration at C-3, wherein each of A, D, E, G, J, L, M, and Q are C; each of R$_1$ and R$_2$ is independently selected from H or halo; R$_4$ is H or (C$_1$-C$_6$)alkyl, R$_3$ and R$_5$ are H; R$_6$ and R$_7$ are linked to each other as a 4-12 membered mono- or bicyclic amide ring; R$_8$, R$_9$, R$_{10}$, R$_{11}$, R$_{12}$, R$_{13}$, R$_{14}$, R$_{15}$, R$_{16}$, a, b, c, d, e, and f are as defined herein.

In other embodiments, the compound of formula I is a single enantiomer bearing an (S)-configuration at C-3, wherein each of A, D, E, G, J, L, M, and Q are C; each of R$_1$ and R$_2$ is independently selected from H or halo; R$_4$ is H or (C$_1$-C$_6$)alkyl, R$_3$ and R$_5$ are H; R$_6$ and R$_7$ are linked to each other as a 4-12 membered mono- or bicyclic urea ring; R$_8$, R$_9$, R$_{10}$, R$_{11}$, R$_{12}$, R$_{13}$, R$_{14}$, R$_{15}$, R$_{16}$, a, b, c, d, e, and f are as defined herein.

In certain embodiments, the compound may be selected from the group consisting of:

1-(3-(3,6-difluoro-9H-carbazol-9-yl)-2-hydroxypropyl)-3-fluoropyrrolidin-2-one;

2-(3-(3,6-difluoro-9H-carbazol-9-yl)-2-hydroxypropyl)-2-azabicyclo[2.2.1]heptan-3-one;

1-(3-(3,6-difluoro-9H-carbazol-9-yl)-2-hydroxypropyl)imidazolidin-2-one;

(1R,4S)-2-((R)-3-(3,6-difluoro-9H-carbazol-9-yl)-2-hydroxypropyl)-2-azabicyclo[2.2.1]heptan-3-one;

(R)-1-(3-(3,6-difluoro-9H-carbazol-9-yl)-2-hydroxypropyl)imidazolidin-2-one;

(R)-1-((R)-3-(3,6-difluoro-9H-carbazol-9-yl)-2-hydroxypropyl)-3-fluoropyrrolidin-2-one;

(S)-1-((S)-3-(9H-carbazol-9-yl)-2-hydroxy-2-methylpropyl)-3-fluoropyrrolidin-2-one;

(R)-1-((R)-3-(9H-carbazol-9-yl)-2-hydroxypropyl)-4-methylimidazolidin-2-one; or a pharmaceutically acceptable salt or hydrate thereof.

The term "pharmaceutically acceptable" as used herein, refers to a material, such as a carrier or diluent, which does not abrogate the biological activity or properties of the compounds described herein, and is relatively nontoxic, i.e., the material may be administered to an individual without causing undesirable biological effects or interacting in a deleterious manner with any of the components of the composition in which it is contained.

The term "pharmaceutically acceptable salt" as used herein, refers to salts that retain the biological effectiveness of the free acids and bases of the specified compound and that are not biologically or otherwise undesirable. Pharmaceutically acceptable salts of the compounds of formula I include the acid addition and base salts thereof. Suitable acid addition salts are formed from acids which form non-toxic salts. Examples include acetate, adipate, arabogalactanesulfonate, ascorbate, aspartate, benzoate, besylate, bicarbonate/carbonate, bisulfate/sulfate, borate, camsylate, cholate, citrate, edisylate, estolate, esylate, formate, fumarate, galacturonate, gluceptate, gluconate, glucuronate, glutamate, hexafluorophosphate, hibenzate, hippurate, hydrochloride/chloride, hydrobromide/bromide, hydroiodide/iodide, 3-hydroxy-2-naphthoate, 1-hydroxy-2-naphthoate, isethionate, lactate, lactobionate, malate, maleate, malonate, mandelate, mesylate, methylsulfate, mucate, napadisylate, naphthalate, 2-napsylate, nicotinate, nitrate, oleate, orotate, oxalate, plamitate, pamoate, phosphate/hydrogen phosphate/dihydrogen phosphate, saccharate, salicylate, stearate, succinate, sulfosalicylate, tartrate, tosylate, trifluoroacetate, and tryptophanate salts.

Suitable base salts are formed from bases which form non-toxic salts. Examples include adenine, aluminum, 2-amino-2-methylpropan-1-ol, arginine, benethamine, benzathine, calcium, choline, cytosine, diethylamine, diolamine, epolamine, erbumine, ethylenediamine, glucosamine, glycine, guanidine, guanine, hydrabamine, lysine, magnesium, meglumine, morpholine, nicotinamide, olamine, omithine, piperazine, potassium, procaine, proline, pyridoxine, serine, silver, sodium, trolamine, tromethamine, tyrosine, valine and zinc salts. For a review on suitable salts, see "Handbook of Pharmaceutical Salts: Properties, Selection, and Use" by Stahl and Wermuth (Wiley-VCH, Weinheim, Germany, 2002).

A pharmaceutically acceptable salt of a compound of formula I may be readily prepared by mixing together solutions of the compound of formula I and the desired acid or base, as appropriate. The salt may precipitate from solution and be collected by filtration or may be recovered by evaporation of the solvent. The degree of ionization in the salt may vary from completely ionized to almost non-ionized.

The compounds of Formula I may also exist in various crystalline forms, known as polymorphs. Polymorphs include the different crystal packing arrangements of the same elemental composition of a compound. Polymorphs may have different X-ray diffraction patterns, infrared spectra, melting points, density, hardness, crystal shape, optical and electrical properties, stability, solvates and solubility. Various factors such as the recrystallization solvent, rate of crystallization, and storage temperature may cause a single crystal form to dominate.

A "solvate" is intended to mean a pharmaceutically acceptable solvate form of a specified compound that retains the biological effectiveness of such compound. Examples of solvates include compounds of the invention in combination with water, isopropanol, ethanol, methanol, dimethylsulfoxide, ethyl acetate, acetic acid, or ethanolamine. The term "hydrate" refers to a solvate where the solvent is water. The term "alcoholate" refers to a solvate where the solvent is an alcohol. Hydrates are formed by the combination of one or more molecules of water with one molecule of the substance in which the water retains its molecular state as $H_2O$. Non-limiting examples of hydrates include monohydrates, dihydrates, etc.

The compounds of the invention include compounds of formula I as defined herein, polymorphs, prodrugs, and isomers, thereof (including optical, geometric, and tautomeric isomers) as well as isotopically-labeled compounds of formula I.

The compounds of the present invention may be administered as prodrugs. Thus certain derivatives of compounds of formula I which may have little or no pharmacological activity themselves can, when administered into or onto the body, be converted into compounds of formula I having the desired activity, for example, by hydrolytic cleavage. Such derivatives are referred to as 'prodrugs'. Further information on the use of prodrugs may be found in "Pro-drugs as Novel Delivery Systems, Vol. 14, ACS Symposium Series (T. Higuchi and W. Stella) and "Bioreversible Carriers in Drug Design", Pergamon Press, 1987 (Ed. E. B. Roche, American Pharmaceutical Association). Prodrugs can, for example, be produced by replacing appropriate functionalities present in the compounds of formula I with certain moieties known to those skilled in the art is 'pro-moieties' as described, for example, in "Design of Prodrugs" by H. Bundgaard (Elsevier, 1985).

Some examples of such prodrugs include where the compound of formula I contains a carboxylic acid functionality (—$CO_2H$), an ester thereof, for example, replacement of the hydrogen with ($C_1$-$C_8$)alkyl; where the compound of formula I contains an alcohol functionality (—OH), an ether thereof, for example, replacement of the hydrogen with ($C_1$-$C_5$)alkanoyloxymethyl; and where the compound of formula I contains a secondary amino functionality (—NHR where R is not H), an amide thereof, for example, replacement of one hydrogen with ($C_1$-$C_{10}$)alkanoyl. Further examples of replacement groups in accordance with the foregoing examples and examples of other prodrug types are known to those of ordinary skill in the art.

Compounds of formula I contain one or more asymmetric carbon atoms. It is to be understood that all the enantiomers and/or diastereomers corresponding to the compounds of formula I can be prepared by analogous methods. All optical isomers and stereoisomers of the compounds of formula I, and mixtures thereof, are considered to be within the scope of the invention. With respect to the compounds of formula I, the invention includes the use of a racemate, one or more enantiomeric forms, one or more diastereomeric forms, or mixtures thereof. The compounds of formula I may also exist as tautomers. This invention relates to the use of all such tautomers and mixtures thereof.

Certain functional groups contained within the compounds of the present invention can be substituted for bioisosteric groups, that is, groups which have similar spatial or electronic requirements to the parent group, but exhibit differing or improved physicochemical or other properties. Suitable examples are well known to those of skill in the art, and include, but are not limited to moieties described in Patini, et al. Chem Rev. 1996, 96, 3147-3176 and references cited therein.

Included within the scope of the claimed compounds of formula I are pharmaceutically acceptable acid addition or base salts wherein the counterion is optically active, for example, D-lactate or L-lysine, or racemic, for example, DL-tartrate or DL-arginine. Cis/trans isomers may be separated by conventional techniques well known to those skilled in the art, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula I contains an acidic or basic moiety, an acid or base such as tartaric acid or 1-phenylethylamine. The resulting diastereomeric mixture may be separated by chromatography and/or fractional crystallization and the diastereomers converted to the corresponding pure enantiomers and/or diastereomers by means well known to a skilled person. The chiral compounds of the invention (and chiral precursors thereof) may be obtained in enantiomerically- and/or diastereomerically-enriched form using chromatography, typically HPLC, on an asymmetric resin with a mobile phase consisting of a hydrocarbon, typically heptane or hexane, containing from 0 to 50% isopropanol, typically 2 to 20%, and from 0 to 5% of an alkylamine, typically 0.1% diethylamine. Concentration of the eluate affords the enriched mixture. Mixtures of enantiomers and/or diastereomers may be separated by conventional techniques known to those skilled in the art. See, for example, "Stereochemistry of Organic Compounds" by E. L. Eliel (Wiley, New York, 1994).

The compounds of formula I may be isotopically-labeled, wherein one or more atoms are replaced by atoms having the same atomic number, but an atomic mass or mass number different from the atomic mass or mass number usually found in nature. Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorous, such as $^{32}P$, and sulfur, such as $^{35}S$. Certain isotopically-labeled compounds of formula I, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of formula I can be generally prepared by conventional techniques known to those skilled in the art or by processes analogous to those described in the accompanying Examples and Preparations using appropriate isotopically-labeled reagents in place of the non-labeled reagent previously employed.

The compounds of the present invention modulate Cry1 and/or Cry2. As used herein, "modulating" refers to increasing, decreasing, or altering Cry1 and Cry2 function, activity or intrinsic characteristics. Modulation of Cry1 or Cry2 includes any one of the following: binding to Cry1 or Cry2; inhibiting modification of Cry1 or Cry2; altering Cry1 or Cry2 localization; increasing or decreasing Cry1 or Cry2 stabilization; increasing or decreasing the binding between Cry1 or Cry2 to a target; increasing or decreasing Cry1 or Cry2 activity; and increasing or decreasing activity of a Cry1 or Cry2 target.

Modulation of Cry1 and Cry2 includes binding of a compound of the present invention to Cry1 and/or Cry2, either through direct interaction or indirect interaction. In some aspects, a compound of the present invention may bind to a complex containing Cry1 and/or Cry2. Methods for detecting interaction between small molecules and proteins are known in the art, for example, immunoprecipitation techniques, chromatography, and various array formats.

Intrinsic characteristics of Cry1 and Cry2, such as post-translational modification, stability, or localization, may be altered by the compounds of the present invention. Post-translational modification of Cry1 and Cry2 may play a critical role in determining the activity, stability, or cellular localization of Cry1 and Cry2. Some studies have shown that phosphorylation may alter Cry1 and Cry2 stability. Compounds of the present invention may prevent or increase post-translational modification of Cry1 and Cry2, for example, phosphorylation, ubiquitination, acetylation, glycosylation, ribosylation, or sumoylation.

Methods for detecting post-translational modification of Cry1 or Cry2 can be readily performed by one skilled in the art. Such methods of detection include western blot and radioimmunoassays. Cry1 and Cry2 localize to the nucleus under particular conditions, for example, upon heterodimerization with Per1 and Per2. Once within the nucleus, Cry1 and Cry2 play a role in disrupting the nuclear CLOCK-BMAL1 complex from initiating transcription, thereby downregulating circadian rhythm genes in a negative feedback loop that is crucial for maintaining circadian oscillations. Localization of proteins can be readily determined by one in the art, for example, by immunofluorescence, sub-cellular fractionation and western blot assays. Downregulation of Cry1 and Cry2 is also critical for circadian oscillations, and is mediated at the transcriptional and protein level. Cry1 and Cry2 stability can be measured by methods known in the art, as well as those presented in Examples 5-8.

Cry1 and Cry2 activity, as used herein, includes the binding between Cry1 or Cry2 to a target and the activity of a downstream Cry1 or Cry2 target. Compounds of the present invention may increase or decrease the binding between Cry1 or Cry2 to a target. Targets that bind to Cry1 and/or Cry2 are known in the art, and include Per1, Per2, glucocorticoid receptor, the CLOCK-BMAL1 promoter sequence, and the VEGF promoter sequence. Other targets include genes for which expression is modulated by Cry1 or Cry2, including genes that contain an E-box sequence in their promoter. Such genes include, without limitation, Dbp, Rev-erb alpha, Rev-erb beta, Ror alpha, Ror beta, Ror gamma, Per1, Per2, Per3, Cry1, Cry2, Pck1, G6Pc, Avp, Vip, Cck, SP (substance P), AA-Nat, PK2 (Prokinectin 2), c-Myc, MyoD and Nampt. Cry1 and Cry2 targets referenced herein also include those targets that have yet to be identified.

Binding between Cry1 or Cry2 and targets can be determined by, for example, immunoprecipitation, yeast two-hybrid, affinity chromatography. Downstream activity of Cry1 or Cry2 targets comprises CLOCK-BMAL1-mediated transcription, binding of Cry1 or Cry2 to the CLOCK-BMAL-1 promoter, binding of Cry1 or Cry2 to the VEGF promoter, Per1 or Per2 localization or stability, CLOCK-BMAL1 dimerization, expression of CLOCK-BMAL1 target genes, such as Cry1, Cry2, Per1, Per2, Rev-erb α and β, Rora, TIM proteins, and VEGF. Methods for detecting promoter activity can be determined by chromatin immunoprecipitation, electrophoretic mobility shift assay, or promoter-luciferase assays as described in Examples 3 and 4. Methods for determining expression of target genes include gene expression analysis and microarrays, which can be readily performed by one ordinarily skilled in the art.

In some embodiments, methods or assays for determining putative efficacy may be useful to identify particular compounds of those described herein that are suitable for treating or alleviating a symptom of a Cry-mediated disease or disorder. In one aspect, the concentration of the compound to induce a response halfway between the baseline and maximum after a specified exposure time (referred to herein as the $EC_{50}$ value or concentration) can be determined in an in vitro assay that measures the effect of the compound on core clock gene expression. Luciferase reporters operably linked to core clock gene promoter sequences (i.e., Per1, Per2, Cry1, Cry2 or Bmal1) are introduced into cells (i.e., transfection, transduction, infection) that are treated with the compounds of the present invention, and the luminescence (or clock gene-driven expression) is measured over time. Specifically, the period, amplitude, and phase of the luminescence compared to expected expression correlating to the circadian rhythm is determined. The $EC_{50}$ value for a compound can be calculated using methods readily available to the skilled person in the art. An example of such an assay is described herein in Example 3. The $EC_{50}$ values are useful for assessing the potency of the compounds of the present invention.

In other aspect, the compounds of the present invention with increased efficacy can be determined by in vivo assay. The compounds are administered to a subject (i.e., a mouse model) for a period of time. A biological sample is isolated from the subject, and the concentration levels of the compound present in the biological sample is measured. The biological sample is, for example, whole blood or any fraction thereof (i.e., serum or plasma), or a tissue, such as a tissue that is affected by a Cry-mediated disease or disorder. The concentration detected in the sample of the treated subject is compared to the $EC_{50}$ concentration value for the same compound, as tested in a relevant in vitro assay (as described above and in Example 3). Compounds with a measured compound concentration in vivo greater than the determined EC50 value are preferred compounds of the present invention. These preferred compounds may demonstrate increased efficacy for treating or alleviating a symptom of a Cry-mediated disease or disorder.

In other aspects of the subject matter disclosed herein, a pharmaceutical composition is provided, comprising the compound according to formula I and a pharmaceutically acceptable carrier, adjuvant or diluent. Methods of preparing various pharmaceutical compositions with a specific amount of active compound are known, or will be apparent, to those skilled in the art. In addition, those of ordinary skill in the art are familiar with formulation and administration techniques. Such topics will be discussed, e.g. in Goodman and Gilman's "The Pharmaceutical Basis of Therapeutics", current edition, Pergamon Press; and "Remington's Pharmaceutical Sciences", current edition, Mack Publishing, Co., Easton, Pa. These techniques can be employed in appropriate aspects and embodiments of the methods and compositions described herein. Pharmaceutical compositions are preferably manufactured under GMP conditions. The following examples are provided for illustrative purposes only and are not meant to serve as limitations of the present invention.

Because the compounds described herein are intended for use in pharmaceutical compositions, it will readily be understood that they are each preferably provided in substantially pure form, for example at least 50% pure, at least 55% pure, at least 60% pure, at least 65% pure, at least 70% pure, at least 75% pure, at least 80% pure, at least 85%, at least 90% pure, at least 95% pure, at least 96% pure, at least 97% pure, at least 98% pure, or at least 99% pure. Percentages as provided herein are on a weight for weight basis. Impure preparations of the compounds may be used for preparing the more pure forms used in the pharmaceutical compositions; these less pure preparations of the compounds should contain at least 1%, more suitably at least 5%, e.g. 10 to 49% of a compound of the Formula I.

The compounds of Formula I may be provided in suitable topical, oral, nasal, ocular, mucosal, rectal, vaginal, and parenteral pharmaceutical formulations for use in the treatment of Cry mediated diseases. The compounds of the present invention may be administered orally as tablets or capsules, as oily or aqueous suspensions, lozenges, troches, powders, granules, emulsions, syrups or elixirs. The compositions for oral use may include one or more agents for flavoring, sweetening, coloring and preserving in order to produce pharmaceutically elegant and palatable preparations. Tablets may contain pharmaceutically acceptable excipients, carriers, diluents, and adjuvants as an aid in the manufacture of such tablets. As is conventional in the art, these tablets may be coated with a pharmaceutically acceptable enteric coating, such as glyceryl monostearate or glyceryl distearate, to delay disintegration and absorption in the gastrointestinal tract to provide a sustained action over a longer period. The dissolution rate of poorly water-soluble compounds may be enhances by the use of spray-dried dispersion, such as those described by Takeuchi, H. et al. J. Pharm. Pharmacol. 1987, 39, 769-773.

Formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, such as peanut oil, liquid paraffin or olive oil.

Aqueous suspensions normally contain active ingredients in admixture with excipients suitable for the manufacture of an aqueous suspension. Such excipients may be a suspending agent, such as Kolliphor, sodium carboxymethyl cellulose, methyl cellulose, hydroxypropylmethyl cellulose, sodium alginate, polyvinylpyrrolidone, gum tragancanth and gum acacia; a dispersing or wetting agent that may be a naturally occurring phosphatide such as lecithin, a condensation product of ethylene oxide and a long chain fatty acid, for example polyoxyethylene stearate, a condensation product of ethylene oxide and a long chain aliphatic alcohol such as heptadecaethyleneoxycetanol, a condensation product of ethylene oxide and a partial ester derived from a fatty acid and hexitol such as polyoxyethylene sorbitol monooleate or a fatty acid hexitol anhydrides such as polyoxyethylene sorbitan monooleate.

The pharmaceutical compositions may be in the form of a sterile injectable aqueous or oleaginous suspension. This suspension may be formulated according to known methods as aqueous isotonic solutions or suspensions, and suppositories can be prepared from fatty emulsions or suspensions. The compositions can be sterilized and/or contain adjuvants, such as preserving, stabilizing, wetting or emulsifying agents, solution promoters, salts for regulating the osmotic pressure and/or buffers. In addition, they can also contain other therapeutically valuable substances. The sterile injectable preparation may also be formulated as a suspension in a non-toxin parenterally-acceptable diluent or solvent, for example as a solution in 1,3-butanediol. Among the acceptable vehicles and solvents that may be employed are water, Ringers solution and isotonic sodium chloride solution. For this purpose any bland fixed oil may be employed including synthetic mono- or diglycerides. In addition fatty acids such as oleic acid find use in the preparation of injectables.

The compounds of formula I may also be administered in the form of suppositories for rectal administration of the drug. These compositions can be prepared by mixing the drug with a suitable non-irritating excipient that is solid at about 25° C., but liquid at rectal temperature and will therefore melt in the rectum to release the drug. Such materials include cocoa butter and other glycerides.

For topical or transdermal use preparations, for example, creams, ointments, jellies solutions or suspensions containing the compounds of the present invention are employed. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations and iontophoresis devices can also be used. Suitable formulations for topical application, e.g., to the skin and eyes, are preferably aqueous solutions, ointments, creams or gels well-known in the art. Such can contain solubilizers, stabilizers, tonicity enhancing agents, buffers and preservatives.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

The compounds of formula I may also be prepared in the form of liposome delivery systems such as small unilamellar vesicles, large unilamellar vesicles and multimellar vesicles. Liposomes can be formed from a variety of phospholipids, such as cholesterol, stearylamine or phosphatidylcholines.

Suitable extended release form of the either active pharmaceutical ingredient or both may be a matrix tablet or capsule composition. Suitable matrix forming materials include, for example, waxes (e.g., carnauba, bees wax, paraffin wax, ceresine, shellac wax, fatty acids, and fatty alcohols), oils, hardened oils or fats (e.g., hardened rapeseed oil, castor oil, beef tallow, palm oil, and soya bean oil), and polymers (e.g., hydroxypropyl cellulose, polyvinylpyrrolidone, hydroxypropyl methyl cellulose, and polyethylene glycol). Other suitable matrix tableting materials are microcrystalline cellulose, powdered cellulose, hydroxypropyl cellulose, ethyl cellulose, with other carriers, and fillers. Tablets may also contain granulates, coated powders, or pellets. Tablets may also be multi-layered. Multi-layered tablets are especially preferred when the active ingredients have markedly different pharmacokinetic profiles. Optionally, the finished tablet may be coated or uncoated.

The coating composition typically contains an insoluble matrix polymer (approximately 15-85% by weight of the coating composition) and a water soluble material (e.g., approximately 15-85% by weight of the coating composition). Optionally an enteric polymer (approximately 1 to 99% by weight of the coating composition) may be used or included. Suitable water soluble materials include polymers such as polyethylene glycol, hydroxypropyl cellulose, hydroxypropyl methyl cellulose, polyvinylpyrrolidone, polyvinyl alcohol, and monomeric materials such as sugars (e.g., lactose, sucrose, fructose, mannitol and the like), salts (e.g., sodium chloride, potassium chloride and the like), organic acids (e.g., fumaric acid, succinic acid, lactic acid, and tartaric acid), and mixtures thereof. Suitable enteric polymers include hydroxypropyl methyl cellulose, acetate succinate, hydroxypropyl methyl cellulose, phthalate, polyvinyl acetate phthalate, cellulose acetate phthalate, cellulose acetate trimellitate, shellac, zein, and polymethacrylates containing carboxyl groups.

The coating composition may be plasticized according to the properties of the coating blend such as the glass transition temperature of the main component or mixture of components or the solvent used for applying the coating compositions. Suitable plasticizers may be added from 0 to 50% by weight of the coating composition and include, for example, diethyl phthalate, citrate esters, polyethylene glycol, glycerol, acetylated glycerides, acetylated citrate esters, dibutylsebacate, and castor oil. If desired, the coating composition may include a filler. The amount of the filler may be 1% to approximately 99% by weight based on the total weight of the coating composition and may be an insoluble material such as silicon dioxide, titanium dioxide, talc, kaolin, alumina, starch, powdered cellulose, MCC, or polacrilin potassium. The coating composition may be applied as a solution or latex in organic solvents or aqueous solvents or mixtures thereof. If solutions are applied, the solvent may be present in amounts from approximate by 25-99% by weight based on the total weight of dissolved solids. Suitable solvents are water, lower alcohol, lower chlorinated hydrocarbons, ketones, or mixtures thereof. If latexes are applied, the solvent is present in amounts from approximately 25-97% by weight based on the quantity of polymeric material in the latex. The solvent may be predominantly water.

Dosage levels of the compounds of the present invention are of the order of about 0.5 mg/kg body weight to about 100 mg/kg body weight, or any increment in between. A preferred dosage rate is between about 30 mg/kg body weight to about 100 mg/kg body weight. The total daily dose may be administered in single or divided doses. Suitable therapeutic doses of the compounds of formula I may be in the range of 1 microgram (µg) to 1000 milligrams (mg) per kilogram body weight of the recipient per day, and any increment in between, such as, e.g., 1, 2, 3, 5, 10, 25, 50, 75, 100, 200, 300, 400, 500, 600, 700, 800, 900, or 1000 µg (1 mg); 2, 3, 5, 10, 25, 50, 75, 100, 200, 300, 400, 500, 600, 700, 800, 900 or 1000 mg. It will be understood, however, that specific dose level for any particular patient will depend upon a number of factors including the activity of the particular compound being administered, the age, body weight, general health, sex, diet, time of administration, route of administration, rate of excretion, drug combination and the severity of the particular disease undergoing therapy.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the therapeutic agent and the particular therapeutic or prophylactic effect to be achieved, and (b) the limitations inherent in the art of compounding such an active compound for the treatment of sensitivity in individuals. Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can be temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

In some embodiments, the compounds and compositions described herein are administered to a subject around bed time or sleep time at night. Preferably, the compounds and compositions described herein are administered to the subject within 6 hours, 5 hours, 4 hours, 3 hours, 120 minutes, 90 minutes, 60 minutes, 45 minutes, 30 minutes, 25 minutes, 20 minutes, 15 minutes, 10 minutes, 5 minutes, or immediately before or after bed time. Preferably, the compounds and compositions of the present invention are administered to the subject within 2 hours to immediately before bed time. "Bed time", as used herein, refers to the time of night at which a subject goes to bed with the intention of resting or falling asleep.

In other embodiments, the compounds and compositions described herein may be administered with or without food. When the compounds or compositions are administered with food, it may be preferable to administer the compounds or compositions within 4 hours before or after a meal, such as breakfast, lunch, dinner or a snack. For example, the compounds or compositions of the present invention are administered within 6 hours, within 5 hours, within 4 hours, within 3 hours, within 120 minutes, within 90 minutes, within 60 minutes, within 45 minutes, within 30 minutes, within 25 minutes, within 20 minutes, within 15 minutes, within 10 minutes, within 5 minutes, or immediately before or after a meal. Preferably, the compounds and compositions of the present invention are administered to the subject within 4 hours, within 3 hours, within 120 minutes, within 90 minutes, or within 60 minutes after dinner.

In another aspect of the subject matter disclosed herein, a method of treating a Cry-mediated disease or disorder is provided, comprising administering a therapeutically effective amount of a compound according to formula I as described in any of the preceding embodiments herein. A preferred embodiment of the present invention is the method of treating a Cry-mediated disease or disorder wherein the disease or disorder characterized by abnormal levels of Cry is selected from the group consisting of diabetes, complications associated with diabetes, metabolic syndrome, insulin resistance syndrome, obesity, glaucoma, Cushing's syndrome, inflammatory disorders, mitochondrial disorders, Friedrich's ataxia, psychotic depression, Alzheimer's disease, neuropathic pain, drug abuse, osteoporosis, cancer, macular degeneration, and myopathy. Particularly preferred Cry-mediated diseases or disorders treated by the compounds disclosed herein include diabetes, diabetic complications such as diabetic neuropathy, diabetic retinopathy, diabetic nephropathy, cataract formation, glaucoma, diabetic angiopathy, atherosclerosis; nonalcoholic steatohepatitis (NASH); non-alcoholic fatty liver disease (NAFLD); asthma; and chronic obstructive pulmonary disease (COPD).

The terms "administer," "administering", "administration," and the like, as used herein, refer to the methods that may be used to enable delivery of compounds or compositions to the desired site of biological action. These methods include, but are not limited to, oral, parenteral, topical, mucosal, ocular, ophthalmic, vaginal, and rectal administration. Those of skill in the art are familiar with administration techniques that can be employed with the compounds and methods described herein, e.g., as discussed in Goodman and Gilman, The Pharmacological Basis of Therapeutics, current ed.; Pergamon; and Remington's, Pharmaceutical Sciences (current edition), Mack Publishing Co., Easton, Pa. As used herein, "parenteral administration" of a pharmaceutical composition includes any route of administration characterized by physical breaching of a tissue of a subject and administration of the pharmaceutical composition through the breach of the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, and intrasternal injection, and kidney dialytic infusion techniques.

A "subject" in the context of the present invention is preferably a mammal. The mammal can be a human, non-human primate, mouse, rat, dog, cat, horse, or cow, but are not limited to these examples. Mammals other than humans can be advantageously used as subjects that represent animal models of a Cry-mediated disease or disorder, such as ob/ob mice. A subject can be male or female. A subject can be one who has been previously diagnosed or identified as having a Cry-mediated disease or disorder, and optionally has already undergone, or is undergoing, a therapeutic intervention or treatment for the disease or disorder. Alternatively, a subject can also be one who has not been previously diagnosed as having a Cry-mediated disease or disorder. For example, a subject can be one who exhibits one or more risk factors for a Cry-mediated disease or disorder, or a subject who does not exhibit risk factors for a Cry-mediated disease or disorder, or a subject who is asymptomatic for a Cry-mediated disease or disorder. A subject can also be one who is suffering from or at risk of developing a Cry-mediated disease or disorder, or who is suffering from or at risk of developing a recurrence of a Cry-mediated disease or disorder. A subject can also be one who has been previously treated for a Cry-mediated disease or disorder, whether by administration of the compounds and compositions disclosed herein, either alone or in combination with other therapeutic agents, surgery, or any combination of the foregoing. The term "subject" and "patient", as used herein, may be used interchangeably.

A "Cry-mediated disease or disorder" may include, without limitation, diabetes (including, without limitation, insulin-dependent "Type I" diabetes, non-insulin dependent "Type II" diabetes, gestational diabetes, and diabetes-related complications like diabetic neuropathy, diabetic retinopathy, diabetic cardiomyopathy, diabetic nephropathy, periodontal disease, and diabetic ketoacidosis), metabolic syndrome, insulin resistance syndrome, obesity, glaucoma, Cushing's syndrome, psychotic depression, Alzheimer's disease, neuropathic pain, drug abuse, osteoporosis, cancer, macular degeneration, and myopathy.

The term "treating", "treat", or "treatment" as used herein includes preventative (e.g. prophylactic), palliative, adjuvant, and curative treatment. For example, the treatment of type 2 diabetes, as used herein means that a patient having type 2 diabetes or at risk of having type 2 diabetes can be treated according to the methods described herein. For patients undergoing preventative treatment, a resulting reduction in the incidence of the disease state being preventively treated is the measurable outcome of the preventative treatment.

The term "alleviating" or "alleviate" as used herein describes a process by which the severity of a sign or symptom of a disorder is decreased, reduced, or inhibited. Importantly, a symptom can be alleviated without being eliminated. In a preferred embodiment, the administration of pharmaceutical compositions of the invention leads to the elimination of a symptom, however, elimination is not required. Therapeutically effective amounts of the compounds or pharmaceutical compositions described herein are expected to decrease the severity of a symptom.

As used herein the term "symptom" is defined as an indication of disease, illness, injury, or that something is not right in the body. Symptoms are felt or noticed by the individual experiencing the symptom, but may not easily be noticed by others. Others are defined by health-care or clinical professionals.

The term "metabolic syndrome", as used herein, unless otherwise indicated means psoriasis, diabetes mellitus, wound healing, inflammation, neurodegenerative diseases, galactosemia, maple syrup urine disease, phenylketonuria, hypersarcosinemia, thymine uraciluria, sulfinuria, isovaleric academia, saccharopurinuria, 4-hydroxybutyric aciduria, glucose-6-phosphate dehydrogenase deficiency, and pyruvate dehydrogenase deficiency.

The term "obesity" or "obese", as used herein, refers generally to individuals who are at least about 20-30% over the average weight for his/her age, sex and height. Technically, "obese" is defined, for males, as individuals whose body mass index is greater than 27.8 $kg/m^2$, and for females, as individuals whose body mass index is greater than 27.3 $kg/m^2$. Those of skill in the art readily recognize that the invention method is not limited to those who fall within the above criteria. Indeed, the method of the invention can also be advantageously practiced by individuals who fall outside of these traditional criteria, for example, by those who may be prone to obesity.

The term "inflammatory disorders", as used herein, refers to disorders such as asthma, chronic obstructive pulmonary disease (COPD), rheumatoid arthritis, ankylosing spondylitis, psoriatic arthritis, psoriasis, chondrocalcinosis, gout, inflammatory bowel disease, ulcerative colitis, Crohn's disease, fibromyalgia, and cachexia.

The term "Cushing's syndrome", as used herein, refers to a constellation of signs and symptoms resulting from prolonged exposure to elevated levels of cortisol. Cushing's syndrome may result from endogenous or exogenous causes. Causes of endogenous Cushing's syndrome include pituitary tumors (also called Cushing's disease), adrenal tumors, and ectopic secretion of adrenocorticotropic hormone (ACTH) and/or corticotropin-releasing hormone (CRH) from other tumors (including, but not limited to, small cell lung cancer). Exogenous (or iatrogenic) Cushing's syndrome results from use of corticosteroids for the treatment of a variety of disorders, including inflammatory disorders including, but not limited to, asthma, psoriasis and rheumatoid arthritis.

The term "mitochondrial diseases", as used herein, refers to diseases such as mitochondrial encephalomyopathy, lactic acidosis, and stroke-like episodes (MELAS), myoclonic epilepsy with ragged-red fibers (MERRF), Kearns-Sayre syndrome, chronic progressive external ophthalmoplegia, Leber's hereditary optic neuropathy, Leigh syndrome, diabetes, deafness, neurogenic muscle weakness, ataxia, and retinitis pigmentosa (NARP), and myoneurogenic gastrointestinal encephalopathy.

The term "cancer", as used herein, refers to disorders and diseases characterized by uncontrolled cell growth and/or proliferation, and include benign and malignant cancers, hyperproliferative disorders and diseases, and metastases. Examples of particularly preferred cancers include solid tumor cancers or epithelial cancers, including but not limited to: lung cancer; brain cancer; pancreatic cancer; head and neck cancer (e.g., squamous cell carcinoma); breast cancer; colorectal cancer; liver cancer; stomach cancer; kidney cancer; ovarian cancer; prostate cancer; or an adenocarcinoma. Other cancers are those with increased VEGF expression, increased angiogenesis, or hypoxic tumors.

The phrase "therapeutically effective amount", as used herein, refers to the amount of drug or pharmaceutical agent that will elicit the biological or medical response of a tissue, system, animal, or human that is being sought by a researcher, veterinarian, medical doctor or other.

The phrase "amount . . . effective to lower blood glucose levels", as used herein, refers to levels of compound sufficient to provide circulating concentrations high enough to accomplish the desired effect. Such a concentration typically falls in the range of about 10 nM up to 2 µM; with concentrations in the range of about 100 nM up to 500 nM being preferred. As noted previously, since the activity of different compounds which fall within the definition of formula I as set forth above may vary considerably, and since individual subjects may present a wide variation in severity of symptoms, it is up to the practitioner to determine a subject's response to treatment and vary the dosages accordingly.

The phrase "insulin resistance", as used herein, refers to the reduced sensitivity to the actions of insulin in the whole body or individual tissues, such as skeletal muscle tissue, myocardial tissue, fat tissue or liver tissue. Insulin resistance occurs in many individuals with or without diabetes mellitus.

The phrase "insulin resistance syndrome", as used herein, refers to the cluster of manifestations that include insulin resistance, hyperinsulinemia, non-insulin dependent diabetes mellits (NIDDM), arterial hypertension, central (visceral) obesity, and dyslipidemia.

The compounds of the present invention may also be useful in the treatment of other metabolic disorders associated with impaired glucose utilization and insulin resistance including major late-stage complications of NIDDM, such as diabetic angiopathy, atherosclerosis, non-alcoholic steatohepatitis (NASH), non-alcoholic fatty liver disease (NAFLD), diabetic nephropathy, diabetic neuropathy, and diabetic ocular complications such as retinopathy, cataract formation and glaucoma, and many other complications linked to NIDDM, including dyslipidemia, glucocorticoid-induced insulin resistance, polycystic ovarian syndrome, obesity, hyperglycemia, hyperlipidemia, hypercholesteremia, hypertriglyceridemia, hyperinsulinemia, and hypertension. Brief descriptions of these conditions are available in any medical dictionary, for instance, "Stedman's Medical Dictionary" (Xth Ed.).

Compounds and compositions disclosed herein can be administered in therapeutically effective amounts in combination with one or more additional therapeutic agents as defined herein. For example, synergistic effects can occur with other substances used in the treatment of Cry-mediated diseases or disorders. Where the compounds of the invention are administered in conjunction with other therapies, dosages of the co-administered compounds will of course vary depending on the type of co-drug employed, on the specific drug employed, on the condition being treated and so forth.

As used herein, the terms "combination treatment", "combination therapy", "combined treatment" or "combinatorial treatment", used interchangeably, refer to a treatment of an individual with at least two different therapeutic agents. The terms "co-administration" or "combined administration" or the like as utilized herein are meant to encompass administration of the selected therapeutic agents to a single subject, and are intended to include treatment regimens in which the agents are not necessarily administered by the same route of administration or at the same time. The combination treatments described herein are intended to provide the beneficial effect from the co-action of the compounds and compositions disclosed herein and one or more additional therapeutic agents. The beneficial effect of the combination includes, but is not limited to, pharmacokinetic or pharmacodynamic co-action resulting from the combination of the compounds disclosed herein and the therapeutic agents. Administration of these therapeutic agents in combination typically is carried out over a defined time period (usually minutes, hours, days or weeks depending upon the combination selected). In some embodiments, the compounds of the present invention are administered in combination with one or more additional therapeutic agent in a simultaneous or sequential manner. When administered simultaneously, the compound(s) of the present invention may be administered in, for example, the same capsule as that of an additional therapeutic agent. Alternatively, the compound of the present invention and the additional therapeutic agent are encompassed in separate compositions (i.e., capsules) that are to be administered at the same time. When administered sequentially, the compound(s) of the present invention may be administered prior to or after the administration of the additional therapeutic agent. The term "pharmaceutical combination" means a product that results from the mixing or combining of more than one active ingredient and includes both fixed and non-fixed combinations of the active ingredients. A "fixed combination" means that the active ingredients, e.g. a compound as disclosed herein and an additional therapeutic agent, are both administered to a patient simultaneously in the form of a single entity or dosage. A "non-fixed combination" means that the active ingredients, e.g. a compound as disclosed herein and an additional therapeutic agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Therapeutic agents for treating diabetes, metabolic syndrome, obesity, insulin resistance syndrome, diabetic complications or cancer include, without limitation of the following, insulin, hypoglycemic agents, anti-diabetic agents, anti-inflammatory agents, lipid reducing agents, anti-hypertensives such as calcium channel blockers, 0-adrenergic receptor blockers, cyclooxygenase-2 inhibitors, angiotensin system inhibitors, ACE inhibitors, renin inhibitors, chemotherapeutic agents, radiotherapy, hormone-modulating agents, immunomodulating agents, anti-angiogenic agents, together with other common risk factor modifying agents.

Insulin includes rapid acting forms, such as Insulin lispro rDNA origin: HUMALOG (1.5 mL, 10 mL, Eli Lilly and Company, Indianapolis, Ind.), Insulin Injection (Regular Insulin) form beef and pork (regular ILETIN I, Eli Lilly], human: rDNA: HUMULIN R (Eli Lilly), NOVOLIN R (Novo Nordisk), Semisynthetic: VELOSULIN Human (Novo Nordisk), rDNA Human, Buffered: VELOSULIN BR, pork: regular Insulin (Novo Nordisk), purified pork: Pork Regular ILETIN II (Eli Lilly), Regular Purified Pork Insulin (Novo Nordisk), and Regular (Concentrated) ILETIN II U-500 (500 units/mL, Eli Lilly); intermediate-acting forms such as Insulin Zinc Suspension, beef and pork: LENTE ILETIN G I (Eli Lilly), Human, rDNA: HUMULIN L (Eli Lilly), NOVOLIN L (Novo Nordisk), purified pork: LENTE ILETIN II (Eli Lilly), Isophane Insulin Suspension (NPH): beef and pork: NPH ILETIN I (Eli Lilly), Human, rDNA: HUMULIN N (Eli Lilly), Novolin N (Novo Nordisk), purified pork: Pork NPH Iletin II (Eli Lilly), NPH-N (Novo Nordisk); and long-acting forms such as Insulin zinc suspension, extended (ULTRALENTE, Eli Lilly), human, rDNA: HUMULIN U (Eli Lilly).

Hypoglycemic agents include, without limitation, sulfonylureas: Acetohexamide (Dymelor), Chlorpropamide (Diabinese), Tolbutamide (Orinase); second-generation sulfonylureas: Glipizide (Glucotrol, Glucotrol XL), Glyburide (Diabeta; Micronase), Glynase), Glimepiride (Amaryl); Biguanides: Metformin (Glucophage); α-glucosidase inhibitors: Acarbose (Precose), Miglitol (Glyset), Thiazolidinediones: Rosiglitazone (Avandia), Pioglitazone (Actos), Troglitazone (Rezulin); Meglitinides: Repaglinide (Prandin); and other hypoglycemics such as Acarbose; Buformin; Butoxamine Hydrochloride; Camiglibose; Ciglitazone; Englitazone Sodium; Darglitazone Sodium; Etoformin Hydrochloride; Gliamilide; Glibomuride; Glicetanile Gliclazide Sodium; Gliflumide; Glucagon; Glyhexamide; Glymidine Sodium; Glyoctamide; Glyparamide; Linogliride; Linogliride Fumarate; Methyl Palmoxirate; Palmoxirate Sodium; Pirogliride Tartrate; Proinsulin Human; Seglitide Acetate; Tolazamide; Tolpyrramide; Zopolrestat.

Anti-diabetic agents include, without limitation, dipeptidyl peptidase IV inhibitors such as sitagliptin, alogliptin, vildagliptin, saxagliptin, linagilptin, anagliptin, teneligliptin, gemigliptin, dutogliptin, or any other gliptins currently in development, berberine and lupeol; and GLP-1 agonists such as exenatide, liraglutide, albiglutide, taspogenitde, and AVE0010.

Anti-inflammatory agents include Alclofenac; Alclometasone Dipropionate; Algestone Acetonide; α-Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Salycilates; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Glucocorticoids; Zomepirac Sodium. An important anti-inflammatory agent is aspirin.

Other anti-inflammatory agents are cytokine inhibitors including cytokine antagonists (e.g., IL-6 receptor antagonists), aza-alkyl lysophospholipids (AALP), and Tumor Necrosis Factor-α (TNF-α) inhibitors, such as anti-TNF-α antibodies, soluble TNF receptor, TNF-α, antisense nucleic acid molecules, multivalent guanylhydrazone (CNI-1493), N-acetylcysteine, pentoxiphylline, oxpentifylline, carbocyclic nucleoside analogues, small molecule S9a, RP 55778 (a TNF-α synthesis inhibitor), Dexanabinol (HU-211), MDL 201,449A (9-[(1R,3R)-trans-cyclopentan-3-ol] adenine, and trichodimerol (BMS-182123). Other TNF-α inhibitors include Etanercept (ENBREL, Immunex, Seattle) and Infliximab (REMICADE, Centocor, Malvern, Pa.).

Lipid reducing agents include gemfibrozil, cholystyramine, colestipol, nicotinic acid, and HMG-CoA reductase inhibitors. HMG-CoA reductase inhibitors useful for administration, or co-administration with other agents according to the invention include, but are not limited to, simvastatin (U.S. Pat. No. 4,444,784), lovastatin (U.S. Pat. No. 4,231,938), pravastatin sodium (U.S. Pat. No. 4,346,227), fluvastatin (U.S. Pat. No. 4,739,073), atorvastatin (U.S. Pat. No. 5,273,995), and cerivastatin.

Calcium channel blockers include dihydropyridines, such as nifedipine, phenyl alkyl amines, such as verapamil, and benzothiazepines, such as diltiazem. Other calcium channel blockers include, but are not limited to, amrinone, amlodipine, bencyclane, felodipine, fendiline, flunarizine, isradipine, nicardipine, nimodipine, perhexilene, gallopamil, tiapamil and tiapamil analogues (such as 1993RO-11-2933), phenytoin, barbiturates, and the peptides dynorphin, omega-conotoxin, and omega-agatoxin, and the like and/or pharmaceutically acceptable salts thereof.

β-adrenergic receptor blocking agents include, but are not limited to, atenolol, acebutolol, alprenolol, befunolol, betaxolol, bunitrolol, carteolol, celiprolol, hedroxalol, indenolol, labetalol, levobunolol, mepindolol, methypranol, metindol, metoprolol, metrizoranolol, oxprenolol, pindolol, propranolol, practolol, practolol, sotalolnadolol, tiprenolol, tomalolol, timolol, bupranolol, penbutolol, trimepranol, 2-(3-(1,1-dimethylethyl)-amino-2-hydroxypropoxy)-3-pyridenecarbonitrilHCl, 1-butylamino-3-(2,5-dichlorophenoxy)-2-propanol, 1-isopropylamino-3-(4-(2-cyclopropylmethoxyethyl)phenoxy)-2-propanol, 3-isopropylamino-1-(7-methylindan-4-yloxy)-2-butanol, 2-(3-t-butylamino-2-hydroxy-propylthio)-4-(5-carbamoyl-2-thienyl)thiazol, 7-(2-hydroxy-3-t-butylaminpropoxy)phthalide. The above-identified compounds can be used as isomeric mixtures, or in their respective levorotating or dextrorotating form.

A number of selective COX-2 inhibitors are known in the art and include, but are not limited to, COX-2 inhibitors described in U.S. Pat. No. 5,474,995; U.S. Pat. No. 5,521,213; U.S. Pat. No. 5,536,752; U.S. Pat. No. 5,550,142; U.S. Pat. No. 5,552,422; U.S. Pat. No. 5,604,253; U.S. Pat. No. 5,604,260; U.S. Pat. No. 5,639,780; U.S. Pat. No. 5,677,318; U.S. Pat. No. 5,691,374; U.S. Pat. No. 5,698,584; U.S. Pat. No. 5,710,140; U.S. Pat. No. 5,733,909; U.S. Pat. No. 5,789,413; U.S. Pat. No. 5,817,700; U.S. Pat. No. 5,849,943; U.S. Pat. No. 5,861,419; U.S. Pat. No. 5,922,742; U.S. Pat. No. 5,925,631; and U.S. Pat. No. 5,643,933. A number of the above-identified COX-2 inhibitors are prodrugs of selective COX-2 inhibitors, and include those described in WO 95/00501, WO 95/18799, and U.S. Pat. No. 5,474,995, issued Dec. 12, 1995.

Examples of angiotensin II antagonists include: peptidic compounds (e.g., saralasin, [(San1)(Val5)(Ala8)] angiotensin-(1-8) octapeptide and related analogs); N-substituted imidazole-2-one (U.S. Pat. No. 5,087,634); imidazole acetate derivatives including 2-N-butyl-4-chloro-1-(2-chlorobenzile) imidazole-5-acetic acid (see Long et al., J. Pharmacol. Exp. Ther. 247(1), 1-7 (1988)); 4,5,6,7-tetrahydro-1H-imidazo[4,5-c] pyridine-6-carboxylic acid and analog derivatives (U.S. Pat. No. 4,816,463); N2-tetrazole 0-glucuronide analogs (U.S. Pat. No. 5,085,992); substituted pyrroles, pyrazoles, and tryazoles (U.S. Pat. No. 5,081,127); phenol and heterocyclic derivatives such as 1,3-imidazoles (U.S. Pat. No. 5,073,566); imidazo-fused 7-member ring heterocycles (U.S. Pat. No. 5,064,825); peptides (e.g., U.S. Pat. No. 4,772,684); antibodies to angiotensin II (e.g., U.S. Pat. No. 4,302,386); and aralkyl imidazole compounds such as biphenyl-methyl substituted imidazoles (e.g., EP 253,310, Jan. 20, 1988); ES8891 (N-morpholinoacetyl-(1-naphthyl)-L-alany-1-(4, thiazolyl)-L-alanyl (35,45)-4-amino-3-hydroxy-5-cyclo-hexapentanoyl-N-hexylamide, Sankyo Company, Ltd., Tokyo, Japan); SKF108566 (E-α-2-[2-butyl-1-(carboxy phenyl) methyl] 1H-imidazole-5-yl[methylane]-2-thiophenepropanoic acid, Smith Kline Beecham Pharmaceuticals, Pa.); Losartan (DUP753/MK954, DuPont Merck Pharmaceutical Company); Remikirin (RO42-5892, F. Hoffman LaRoche AG); A2 agonists (Marion Merrill Dow) and certain non-peptide heterocycles (G. D. Searle and Company).

Angiotensin converting enzyme (ACE) inhibitors include amino acids and derivatives thereof, peptides, including di- and tri-peptides and antibodies to ACE which intervene in the renin-angiotensin system by inhibiting the activity of ACE thereby reducing or eliminating the formation of pressor substance angiotensin II. Other ACE inhibitors include acylmercapto and mercaptoalkanoyl prolines such as captopril (U.S. Pat. No. 4,105,776) and zofenopril (U.S. Pat. No. 4,316,906), carboxyalkyl dipeptides such as enalapril (U.S. Pat. No. 4,374,829), lisinopril (U.S. Pat. No. 4,374,829), quinapril (U.S. Pat. No. 4,344,949), ramipril (U.S. Pat. No. 4,587,258), and perindopril (U.S. Pat. No. 4,508,729), carboxyalkyl dipeptide mimics such as cilazapril (U.S. Pat. No. 4,512,924) and benazapril (U.S. Pat. No. 4,410,520), phosphinylalkanoyl prolines such as fosinopril (U.S. Pat. No. 4,337,201) and trandolopril.

Renin inhibitors include amino acids and derivatives thereof, peptides and derivatives thereof, and antibodies to renin. Other rennin inhibitors include urea derivatives of peptides (U.S. Pat. No. 5,116,835); amino acids connected by nonpeptide bonds (U.S. Pat. No. 5,114,937); di- and tri-peptide derivatives (U.S. Pat. No. 5,106,835); amino acids and derivatives thereof (U.S. Pat. Nos. 5,104,869 and 5,095,119); diol sulfonamides and sulfinyls (U.S. Pat. No. 5,098,924); modified peptides (U.S. Pat. No. 5,095,006); peptidyl 3-aminoacyl aminodiol carbamates (U.S. Pat. No. 5,089,471); pyrolimidazolones (U.S. Pat. No. 5,075,451); fluorine and chlorine statine or statone containing peptides (U.S. Pat. No. 5,066,643); peptidyl amino diols (U.S. Pat. Nos. 5,063,208 and 4,845,079); N-morpholino derivatives (U.S. Pat. No. 5,055,466); pepstatin derivatives (U.S. Pat. No. 4,980,283); N-heterocyclic alcohols (U.S. Pat. No. 4,885,292); monoclonal antibodies to renin (U.S. Pat. No. 4,780,401); and a variety of other peptides and analogs thereof (U.S. Pat. Nos. 5,071,837, 5,064,965, 5,063,207, 5,036,054, 5,036,053, 5,034,512, and 4,894,437).

Other therapeutic agents useful in treating diabetes and related disorders include, but are not limited to, lipase inhibitors such as cetilistat (ATL-962); synthetic amylin analogs such as Symlin pramlintide with or without recombinant leptin; sodium-glucose cotransporter 2 (SGLT2) inhibitors like sergliflozin (869682; KGT-1251), YM543, canagliflozin, ertugliflozin, dapagliflozin, GlaxoSmithKline molecule 189075, and Sanofi-Aventis molecule AVE2268; dual adipose triglyceride lipase and PI3 kinase activators like Adyvia (ID 1101); antagonists of neuropeptide Y2, Y4, and Y5 receptors like Nastech molecule PYY3-36, synthetic analog of human hormones PYY3-36 and pancreatic polypeptide (7TM molecule TM30338); Shionogi molecule S-2367; cannabinoid CB1 receptor antagonists such as rimonabant (Acomplia), taranabant, CP-945,598, Solvay molecule SLV319, *Vernalis* molecule V24343; hormones like oleoyl-estrone; inhibitors of serotonin, dopamine, and norepinephrine (also known in the art as triple monoamine reuptake inhibitors) like tesofensine (Neurosearch molecule NS2330); inhibitors of norepinephrine and dopamine reuptake, like Contrave (bupropion plus opioid antagonist naltrexone) and Excalia (bupropion plus anticonvulsant zonisaminde); inhibitors of 11β-hydroxysteroid dehydrogenase type 1 (11b-HSD1) like Incyte molecule INCB13739; inhibitors of cortisol synthesis such as ketoconazole (DiObex molecule DIO-902); inhibitors of gluconeogenesis such as Metabasis/Daiichi molecule CS-917; glucokinase activators like Roche molecule R1440; antisense inhibitors of protein tyrosine phosphatase-1B such as ISIS 113715; as well as other agents like NicOx molecule NCX 4016; injections of gastrin and epidermal growth factor (EGF) analogs such as Islet Neogenesis Therapy (E1-I.N.T.); betahistine (Obecure molecule OBE101); bile acid sequestrants (e.g., cholestyramine and colestipol), vitamin $B_3$ (also known as nicotinic acid, or niacin), vitamin $B_6$ (pyridoxine), vitamin $B_{12}$ (cyanocobalamin), fibric acid derivatives (e.g., gemfibrozil, clofibrate, fenofibrate and benzafibrate), probucol, nitroglycerin, and inhibitors of cholesterol absorption (e.g., β-sitosterol and acylCoA-cholesterol acyltransferase (ACAT) inhibitors such as melinamide), HMG-CoA synthase inhibitors, squalene epoxidase inhibitors and squalene synthetase inhibitors.

Examples of agents used to treat Cushing's syndrome include, without limitation, neuromodulators (Signifor® (pasireotide), cabergoline); adrenal steroidogenesis inhibitors (ketoconazole, metyrapone, mitotane, etomidate); and nuclear receptor modulators (Korlym® (mifepristone), retinoic acid). Other agents include, without limitation, epidermal growth factor receptor inhibitors (for example, gefitinib), the aldosterone synthase/11β-hydroxylase inhibitor LCI699, and levoketoconazole (COR-003).

Examples of analgesic agents frequently used to treat pain, including neuropathic pain, include, without limitation, opioid or non-opioid analgesic agents. Suitable opioid analgesic agents include, but are not limited to, morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone and propoxyphene. Suitable nonopioid analgesic agents include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam and sulindac.

Examples of therapeutic agents frequently used to treat glaucoma include cholinergic agonists (e.g., pilocarpine and carbachol), cholinesterase inhibitors (e.g., physostigmine, neostigmine, demacarium, echothiophate iodide and isofluorophate), carbonic anhydrase inhibitors (e.g., acetazolamide, dichlorphenamide, methazolamide, ethoxzolamide and dorzolamide), non-selective adrenergic agonists (e.g., epinephrine and dipivefrin), $\alpha_2$-selecteive adrenergic agonists (e.g., apraclonidine and brimonidine), β-blockers (e.g., timolol, betazolol, levobunolol, carteolol and metipranolol), prostaglandin analogs (e.g., latanoprost) and osmotic diuretics (e.g., glycerin, mannitol and isosorbide); corticosteroids, such as beclomethasone, methylprednisolone, betamethasone, prednisone, prenisolone, dexamethasone, fluticasone and hydrocortisone, and corticosteroid analogs such as budesonide.

Examples of therapeutic agents frequently used to treat Alzheimer's disease include β-secretase inhibitors or γ-secretase inhibitors; glycine transport inhibitors, tau phosphorylation inhibitors; blockers of Aβ oligomer formation; p25/CDK5 inhibitors; HMG-CoA reductase inhibitors; PPARγ agonists, such as pioglitazone and rosiglitazone; NK1/NK3 receptor antagonists; NSAID's including ibuprofen; vitamin E; anti-amyloid antibodies, including anti-amyloid humanized monoclonal antibodies; COX-2 inhibitors; anti-inflammatory compounds, such as (R)-flurbiprofen; CB-1 receptor antagonists or CB-1 receptor inverse agonists; antibiotics such as doxycycline and rifampin; N-methyl-D-aspartate (NMDA) receptor antagonists, such as memantine and neramexane; NR2B antagonists; androgen receptor modulators; acetylcholinesterase inhibitors such as galantamine, rivastigmine, donepezil, and tacrine; mGluR5 modulators; growth hormone secretagogues such as ibutamoren, ibutamoren mesylate, and capromorelin; histamine $H_3$ antagonists; AMPA agonists; PDE IV inhibitors; GABAA inverse agonists; GABAA a5 receptor ligands; GABAB receptor ligands; potassium channel blockers; neuronal nicotinic agonists; P-450 inhibitors, such as ritonavir.

Examples of therapeutic agents frequently used to treat affective disorders such as depression include, without limitation, amitriptyline, amitriptyline oxide, desipramine, dibenzepin, dosulepin, doxepin, chloroimipramine, imipramine, nortriptyline, mianserin, maprotiline, trimipramine, CP-122721, elzasonan, PD-171729, MK-869, DOV-216303, DOV-21947, licarbazepine, amfebutamone, radafaxine, vilazodone, GSK-679769, GW-597599, NS-2359, GSK-876008, pramipexole, duloxetine, atomoxetine, LY-628535, desvenlafaxine, escitalopram, LU-AA21004, saredutant, SR-58611, SSR-149415, SSR-146977, moclobemide, R-673, R-1204, BMS-469458, DPC-368, Org-34517, Org-34850, inhibitors of the CRH receptors, ONO-2333Ms, NBI-876008, AAG-561, NBI-34041, DPC-368, PD-171729, SSR-125543, viloxazine, trazodone, nefazodone, mirtazapine, venlafaxine, reboxetine, tranylcypromine, brofaromine, moclobemide, citalopram, escitalopram, paroxetine, fluoxetine, fluvoxamine, sertraline, *Hypericum* (St. John's Wort), alprazolam, clonazepam, diazepam, lorazepam, halazepam, chlordiazepoxide, and other drugs such as buspirone, clonidine, pagoclone, risperidone, olanzapine, quetiapine, ziprasidone, celecoxib, piroxicam, parecoxib, valdecoxib, PMI-001, PH-686464, SC-58236, etoricoxib, rofecoxib, L-776967, lumiracoxib, GW-406381, GW-644784, meloxicam, SVT-2016, PAC-10649, CS-706, LAS-34475, cimicoxib, A-183827.0, or nimesulide.

Examples of therapeutic agents frequently used to treat addiction and drug abuse include, without limitation, phenelzine, phenylalkylhydrazine (U.S. Pat. No. 4,786,653), disulfiram ("Antabuse"), 2-imino-5-phenyl-4-oxazolidinone, α-methyl-para-tyrosine or fusaric acid, piperazine derivatives (U.S. Pat. No. 4,325,952), clonidine in conjunction with a tricyclic antidepressant drug (U.S. Pat. No. 4,788,189), γ-pyrones such as maltol or ethyl maltol (U.S. Pat. No. 4,276,890), acamprosate, gabapentin, vigabatrin, baclofen, N-acetylcysteine, nocaine, modanafil, paroxetine, bupropion, mirtazapine, topiramate, ondansetron, varenicline, antagonists of opioid receptors such as naltrexone, naloxone, nalmephine, antaxone, L-α-acetyl methadol, pentazocine, butorphanol, nalbuphine, buprenorphine, and methadone.

Examples of therapeutic agents frequently used in osteoporosis treatments, and may modulate bone mineral content include, but are not limited to, bisphosphonates such as alendronate (Fosamax®), risedronate (Actonel®), etidronate (Didronel®), pamidronate, tiludronate (Skelid®), clodronate (Bonefos®; Loron®), neridronate, olpadronate, zoledronate (Zometa®), and ibandronate (Boniva®), selective estrogen-receptor modulators (SERMs) such as raloxifene (Evista®), arzoxifene, clomifene, bazedoxifene, lasofoxifene, ormeloxifene, tamoxifen, and toremifine, anabolic therapies such as teriparatide (Forteo®; recombinant parathyroid hormone), and strontium ranelate, and recombinant peptide fragments of parathyroid hormone, estrogen/progesterone replacement therapies, monoclonal antibodies, inhibitors of receptor activator of nuclear factor kB ligand (RANKL) such as denosumab, osteoprotegerin and Pepstatin A, inhibitors of cathepsin K such as but not limited to OST-4077 (furan-2-carboxylic acid-(1-{1-[4-fluoro-2-(2-oxo-pyrrolidin-1-yl)-phenyl]-3-oxo-piperidin-3-ylcarbamoyl}-cyclohexyl)-amide), leupeptin, Cbz-Phe-Ala-CHN2, Cbz-Leu-Leu-Leu-aldehyde, cystatin, irreversible cysteine protease inhibitors like peptide halomethylketones, peptide diazomethylketones, and epoxides, quiescent irreversible cysteine protease inhibitors such as acyloxymethylketones, azapeptides, Michael acceptors like peptide vinyl esters, sulfones and sulfonates, reversible cysteine protease inhibitors such as peptide aldehydes, a-ketoesters and a-ketoamides, peptide methyl ketones and hydroxyl, alkyloxy, aryloxy, alkylthio, and arylthio derivatives thereof, 1,3-bis-(acylamino)-2-propanones, 1,3-bis-(acylhydrazino)-carbonyls, acylamino-pyrazolones, piperidinones, and thiazone-carbonyl-hydrazides, antagonists of integrin Avb3 (also known in the art as vitronectin), calcilytic compounds (Ca2+ receptor antagonists which increase the secretion of PTH), calcitonin (MiacalcinO), nitrates including but not limited to isosorbide mononitrate (ISMO) or nitroglycerin ointment (NTG), and dietary supplements such as calcium and vitamin D, and combinations thereof.

Another embodiment of the present invention is a method of identifying patients in need of treatment based on measuring clock gene (e.g. Cry1 and Cry2) expression levels in samples taken from a subject (Bjarnason, G. A. et al. *Am. J. Pathol.* 2001, 158, 1793; Akashi, M. et. al. *Proc. Natl. Acad. Sci. USA,* 2010, 107, 15643). Rhythmic mRNA expression profiles for human clock genes, including Cry1 and Cry2, measured in samples from a subject indicate a circadian clock is present in peripheral tissues (Mohawk, J. A. et al. *Ann. Rev. Neurosci.* 2012, Epub ahead of print). Expression of circadian clock related genes in these samples has been demonstrated to vary during the day. Furthermore, clock gene (e.g. Cry1 and Cry2) expression patterns in peripheral blood mononuclear cells are altered in humans by diseases such as obesity (Tahira, K. et al. *Arch. Med. Sci.* 2011, 7, 933). Changes in clock gene (e.g. Cry1 and Cry2) expression in peripheral mononuclear blood cells can be correlated with serum leptin, adiponectin, insulin and hsCRP levels, plasma lipid, glucose, melatonin and cortisol levels and, in animals, expression of clock genes (e.g. Cry1 and Cry2) in tissues including liver, adipose, pancreas and skeletal muscle. By contacting samples taken from a subject treated with a compound of formula I and measuring rhythmic mRNA or protein expression profiles, patients in need of treatment may be identified and pharmacological activity can be assessed. In other embodiments, the activities of one or more cryptochromes may be assessed, for example, the ability of cryptochromes to bind to a target such as Per1, Per2, glucocorticoid receptor (GR), or a promoter sequence containing Cry recognition sites, such as, e.g., the CLOCK-BMAL1 promoter.

Accordingly, one aspect of the subject matter disclosed herein relates to a method of monitoring progression or prognosis of a Cry-mediated disease or disorder in a subject, comprising measuring an effective amount of one or more cryptochromes in a first sample from the subject at a first period of time; measuring an effective amount of one or more cryptochromes in a second sample from the subject at a second period of time; and comparing the amount of the one or more cryptochromes detected in the first sample to the amount of the one or more cryptochromes detected in the second sample, or to a reference value.

"Diagnosis", "diagnose", "prognose" or "prognosis" is not limited to a definitive or near definitive determination that an individual has a disease, but also includes determining that an individual has an increased likelihood of having or developing the disease, compared to healthy individuals or to the general population.

As used herein, "expression" and "expression levels" include but are not limited to one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

A "formula," "algorithm," or "model" is any mathematical equation, algorithmic, analytical or programmed process, or statistical technique that takes one or more continuous or categorical inputs (herein called "parameters") and calculates an output value, sometimes referred to as an "index" or "index value." Non-limiting examples of "algorithms" include sums, ratios, and regression operators, such as coefficients or exponents, value transformations and normalizations (including, without limitation, those normalization schemes based on clinical parameters, such as gender, age, body mass index, or ethnicity), rules and guidelines, statistical classification models, and neural networks trained on historical populations. Of particular use in measuring Cry as defined herein are linear and non-linear equations and statistical classification analyses to "correlate" the relationship between levels of Cry detected in a subject sample and the subject's risk of developing a Cry-mediated disease or disorder.

"Measuring" or "measurement" means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's clinical parameters. Measurement or measuring may also involve qualifying the type or identifying the substance. Measurement or measuring may also involve the ability of one or more Cry to bind to a target, wherein the target may be period genes or proteins Per1 and Per2, glucocorticoid receptor (GR), or the promoter region of the CLOCK-BMAL1 gene. Measurement of Cry may be used to diagnose, detect, or identify a Cry-mediated disease or disorder in a subject, to monitor the progression or prognosis of a Cry-mediated disease or disorder in a subject, to predict the recurrence of a Cry-mediated disease or disorder in a subject, or to classify a subject as having a low risk or a high risk of developing a Cry-mediated disease or disorder or a recurrence of a Cry-mediated disease or disorder.

"Risk" in the context of the present invention relates to the probability that an event will occur over a specific time period, as in the development of Cry-mediated disease or disorder, and can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used (odds are according to the formula p/(1−p) where p is the probability of event and (1−p) is the probability of no event) to no-conversion. Alternative continuous measures which may be assessed in the context of the present invention include time to development of a Cry-mediated disease or disorder, or progression to a different stage of a Cry-mediated disease or disorder, including progression or development of a Cry-mediated disease or disorder and therapeutic conversion risk reduction ratios.

"Risk evaluation," or "evaluation of risk" in the context of the subject matter disclosed herein encompasses making a prediction of the probability, odds, or likelihood that an event or disease state may occur, the rate of occurrence of the event or conversion from one disease state to another, i.e., from a "normal" condition to an at-risk condition for developing a Cry-mediated disease or disorder, or from an at-risk condition to a Cry-mediated disease or disorder, or development of recurrent disease or disorder. Risk evaluation can also comprise prediction of other indices of Cry-mediated disease or disorder, either in absolute or relative terms in reference to a previously measured population. The methods of the present invention may be used to make continuous or categorical measurements of the risk of conversion to a Cry-mediated disease or disorder, thus diagnosing and defining the risk spectrum of a category of subjects defined as at risk for developing the disease or disorder. In the categorical scenario, the invention can be used to discriminate between normal and at-risk subject cohorts. In other embodiments, the present invention may be used so as to discriminate at-risk conditions from disease conditions, or disease conditions from normal.

A "sample" as used herein is a biological sample isolated from a subject and can include, by way of example and not limitation, whole blood, serum, plasma, blood cells, endothelial cells, tissue biopsies, lymphatic fluid, ascites fluid, interstitial fluid (also known as "extracellular fluid" and encompasses the fluid found in spaces between cells, including, inter alia, gingival crevicular fluid), bone marrow, seminal fluid, cerebrospinal fluid (CSF), saliva, mucous, sputum, sweat, urine, or any other secretion, excretion, or other bodily fluids.

By "statistically significant", it is meant that the alteration is greater than what might be expected to happen by chance alone (which could be a "false positive"). Statistical significance can be determined by any method known in the art. Commonly used measures of significance include the p-value, which presents the probability of obtaining a result at least as extreme as a given data point, assuming the data point was the result of chance alone. A result is often considered highly significant at a p-value of 0.05 or less.

The risk of a Cry-mediated disease or disorder can be detected by measuring an "effective amount" of one or more cryptochromes in a sample (e.g., a subject derived sample), and comparing the effective amounts to reference values, often utilizing mathematical algorithms or formulae in order to combine information from results of multiple individuals into a single measurement. Subjects identified as having an increased risk of a Cry-mediated disease or disorder can optionally be selected to receive treatment regimens or therapeutic interventions, such as administration of the compounds of formula I as defined herein as monotherapy or in combination with one or more additional therapeutic agents, or implementation of surgical interventions (which may follow or precede administration of the compounds of formula I, alone or in combination with additional therapeutic agents or other therapies).

The methods for detecting these cryptochromes in a sample have many applications. For example, one or more cryptochromes can be measured to aid diagnosis or prognosis of a Cry-mediated disease or disorder. In another example, the methods for detection of the cryptochromes can be used to monitor responses in a subject to treatment of a Cry-mediated disease or disorder. In another example, the methods can be used to assay for and to identify compounds that modulate expression of cryptochromes in vivo or in vitro.

The present invention may be used to make continuous or categorical measurements of the risk of conversion to a Cry-mediated disease or disorder, thus diagnosing and defining the risk spectrum of a category of subjects defined as being at-risk for developing the disease or disorder. In the categorical scenario, the methods of the present invention can be used to discriminate between normal and at-risk subject cohorts. In other embodiments, the present invention may be used so as to discriminate at-risk from disease, or disease from normal. Such differing use may require different combinations in individual panel or profile, mathematical algorithm, and/or cut-off points, but be subject to the same aforementioned measurements of accuracy for the intended use.

Identifying the at-risk subject enables the selection and initiation of various therapeutic interventions or treatment regimens in order to delay, reduce, or prevent that subject's conversion to a Cry-mediated disease or disorder. Levels of an effective amount of cryptochrome proteins, nucleic acids, polymorphisms, metabolites, or other analytes also allows for the course of treatment to be monitored. In this method, a biological sample can be provided from a subject undergoing treatment regimens, e.g., therapeutic treatments, for a Cry-mediated disease or disorder. Such treatment regimens can include, but are not limited to, surgical intervention and treatment with therapeutic agents used in subjects diagnosed or identified with a Cry-mediated disease or disorder, for example, the compounds of formula I described herein. If desired, biological samples are obtained from the subject at various time points before, during, or after treatment. For example, determining the disease status by comparison of a subject's cryptochrome profile to a reference cryptochrome profile can be repeated more than once, wherein the subject's profile can be obtained from a separate sample taken each time the method is repeated. Samples may be taken from the subject at defined time intervals, such as, e.g., 4 hours, 8 hours, 12 hours, 24 hours, 48 hours, 72 hours, or any suitable time interval as would be performed by those skilled in the art.

Differences in the genetic makeup of subjects can result in differences in their relative abilities to metabolize various drugs, which may modulate the symptoms or risk factors of a Cry-mediated disease or disorder. Subjects that have a Cry-mediated disease or disorder, or are at risk for developing a Cry-mediated disease or disorder can vary in age, ethnicity, and other parameters. Accordingly, measuring effective amounts of one or more cryptochromes as defined herein, both alone and together in combination with known genetic factors for drug metabolism, allow for a pre-determined level of predictability that a putative therapeutic or prophylactic to be tested in a selected subject will be suitable for treating or preventing a Cry-mediated disease or disorder in the subject.

To identify therapeutic agents or drugs that are appropriate for a specific subject, a test sample from the subject can also be exposed to a therapeutic agent or a drug, and the level or activity of one or more of cryptochrome proteins, nucleic acids, polymorphisms, splice variants, metabolites or other analytes can be determined. Other genes or proteins that are affected or which directly or indirectly bind to one or more cryptochromes (e.g., Per1, Per2, GR, CLOCK-BMAL1 promoter, etc.) may also be measured. The level of one or more cryptochromes can be compared to sample derived from the subject before and after subject management for a Cry-mediated disease or disorder, e.g., treatment or exposure to a therapeutic agent or a drug, or can be compared to samples derived from one or more subjects who have shown improvements in risk factors as a result of such treatment or exposure.

Nucleic acids may be obtained from the samples in many ways known to one of skill in the art, for example, extraction methods, including e.g., solvent extraction, affinity purification and centrifugation. Selective precipitation can also purify nucleic acids. Chromatography methods may also be utilized including, gel filtration, ion exchange, selective adsorption, or affinity binding. The nucleic acids may be, for example, RNA, DNA or may be synthesized into cDNA. The nucleic acids may be detected using microarray techniques that are well known in the art, for example, Affymetrix arrays followed by multidimensional scaling techniques. See R. Ekins, R. and Chu, F. W. (1999) Trends Biotechnol. 17: 217-218; D. D. Shoemaker, et al., (2001) Nature 409 (6822): 922-927 and U.S. Pat. No. 5,750,015.

If desired, the sample can be prepared to enhance detectability of one or more cryptochromes by, for example, pre-fractionation. Methods of pre-fractionation include, for example, Cibacron blue agarose chromatography, size exclusion chromatography, ion exchange chromatography, heparin chromatography, lectin chromatography, affinity chromatography, single stranded DNA affinity chromatography, sequential extraction, gel electrophoresis and liquid chromatography. The analytes also may be modified prior to detection. A sample can be pre-fractionated by removing proteins that are present in a high quantity or that may interfere with the detection of molecules of interest in a sample. For example, in a blood serum sample, serum albumin is present in a high quantity and may obscure the analysis of one or more cryptochromes. Thus, a blood serum sample can be pre-fractionated by removing serum albumin using, for example, a substrate that comprises adsorbents that specifically bind serum albumin, an affinity column or anti-serum albumin antibodies can be used.

In other embodiments, molecules of interest in a sample can be separated by high-resolution electrophoresis, e.g., one or two-dimensional gel electrophoresis. A fraction can be isolated and further analyzed by gas phase ion spectrometry. Preferably, two-dimensional gel electrophoresis is used to generate two-dimensional array of spots, including one or more cryptochromes. See, e.g., Jungblut and Thiede, (1997) Mass Spectr. Rev. 16: 145-162. The two-dimensional gel electrophoresis can be performed using methods known in the art. See, e.g., Deutscher ed., Methods in Enzymology vol. 182. Typically, a sample may be separated by, e.g., isoelectric focusing, during which one or more cryptochromes in a sample are separated in a pH gradient until they reach a spot where their net charge is zero (i.e., isoelectric point). This first separation step results in one-dimensional array. The molecules in one-dimensional array are further separated using a technique generally distinct from that used in the first separation step. For example, in the second dimension, molecules of interest separated by isoelectric focusing are further separated using a polyacrylamide gel, such as polyacrylamide gel electrophoresis in the presence of sodium dodecyl sulfate (SDS-PAGE). SDS-PAGE gel allows further separation based on molecular mass. Typically, two-dimensional gel electrophoresis can separate chemically different molecules of interest in the molecular mass range from 1000-200,000 Da within complex mixtures.

Molecules of interest in the two-dimensional array can be detected using any suitable methods known in the art. For example, molecules of interest in a gel can be labeled or stained (e.g., Coomassie Blue or silver staining). If gel electrophoresis generates spots that correspond to the molecular weight of one or more cryptochromes of the invention, the spot can be excised and further analyzed by, for example, gas phase ion spectrometry, mass spectrometry, or high performance liquid chromatography. Alternatively, the gel containing molecules of interest can be transferred to an inert membrane by applying an electric field. Then a spot on the membrane that approximately corresponds to the molecular weight of a molecule of interest can be analyzed by e.g., gas phase ion spectrometry, mass spectrometry, or HPLC.

Optionally, a molecule of interest can be modified before analysis to improve its resolution or to determine its identity. For example, the sample may be subject to proteolytic digestion before analysis. Any protease can be used. Proteases, such as trypsin, that are likely to cleave proteins into a discrete number of fragments are particularly useful. The fragments that result from digestion may function as a fingerprint for the molecules of interest, thereby enabling their indirect detection. This is particularly useful where there are molecules of interest with similar molecular masses that might be confused for the preferred molecule, i.e., cryptochromes, in question. Also, proteolytic fragmentation is useful for high molecular weight molecules because smaller molecules are more easily resolved by mass spectrometry. In another example, molecules can be modified to improve detection resolution. For instance, neuraminidase can be used to remove terminal sialic acid residues from glycoproteins to improve binding to an anionic adsorbent (e.g., cationic exchange arrays) and to improve detection resolution. In another example, the molecules can be modified by the attachment of a tag of particular molecular weight that specifically binds to another molecular entity, further distinguishing them. Optionally, after detecting such modified molecules of interest, the identity of the molecules can be further determined by matching the physical and chemical characteristics of the modified versions in a protein database (e.g., SwissProt).

Once captured on a substrate, e.g., biochip or antibody, any suitable method, such as those described herein as well as other methods known in the art, can be used to measure one or more cryptochromes in a sample. The actual measurement of levels or amounts of the such molecules can be determined using any method known in the art. These methods include, without limitation, mass spectrometry (e.g., laser desorption/ionization mass spectrometry), fluorescence (e.g. sandwich immunoassay), surface plasmon resonance, ellipsometry and atomic force microscopy. Methods may further include, by one or more of microarrays, PCR methods, mass spectrometry (including, for example, and without limitation, ESI-MS, ESI-MS/MS, ESI-MS/(MS)n, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS)n, atmospheric pressure photoionization mass spectrometry (APPI-MS), APPI-MS/MS, and APPI-(MS)n, quadrupole mass spectrometry, Fourier transform mass spectrometry (FTMS), and ion trap mass spectrometry), nucleic acid chips, Northern blot hybridization, TMA, SDA, NASBA, PCR, real time PCR, reverse transcriptase PCR, real time reverse transcriptase PCR, in situ PCR, chromatographic separation coupled with mass spectrometry, protein capture using immobilized antibodies or by traditional immunoassays. See for example, U.S. Pat. Nos. 5,723,591; 5,801,155 and 6,084,102 and Higuchi, 1992 and 1993. PCR assays may be done, for example, in a multi-well plate formats or in chips, such as the BioTrove OPEN ARRAY Chips (BioTrove, Woburn, Mass.).

For example, sequences within the sequence database entries corresponding to cryptochromes can be used to construct probes for detecting RNA sequences in, e.g., Northern blot hybridization analyses or methods which specifically, and, preferably, quantitatively amplify specific nucleic acid sequences. As another example, the sequences can be used to construct primers which specifically or selectively hybridize to cryptochrome sequences and which are used to amplifying such sequences in, e.g., amplification-based detection methods such as reverse-transcription based polymerase chain reaction (RT-PCR), e.g., quantitative real-time RT-PCR. When alterations in gene expression are associated with gene amplification, deletion, polymorphisms, and mutations, sequence comparisons in test and reference populations can be made by comparing relative amounts of the examined DNA sequences in subject and reference cell populations. As used herein, the term "specifically (or selectively) hybridizes" when referring to a nucleic acid, refers to a binding reaction that is determinative of the presence of the nucleic acid in a heterogeneous population of nucleic acids. Thus, under designated assay conditions, the specified nucleic acid probe (including inhibitory nucleic acids) may bind or hybridize to a particular nucleic acid of interest at least two times the background and do not substantially bind or hybridize in a significant amount to other nucleic acids present in the sample.

Levels of cryptochromes can also be determined by immunoassay. The antibody may be monoclonal, polyclonal, chimeric, or a fragment of the foregoing, as discussed in detail herein, and the step of detecting the reaction product may be carried out with any suitable immunoassay. The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologies. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to a cryptochrome from specific species such as rat, mouse, or human can be selected to obtain only those polyclonal antibodies that are specifically immunoreactive with that cryptochrome and not with other proteins, except for polymorphic variants and alleles of the cryptochrome. This selection may be achieved by subtracting out antibodies that cross-react with cryptochromes from other species.

Immunoassays carried out in accordance with the present invention may be homogeneous assays or heterogeneous assays. In a homogeneous assay the immunological reaction usually involves the specific antibody (e.g., anti-cryptochrome protein antibody), a labeled analyte, and the sample of interest. The signal arising from the label is modified, directly or indirectly, upon the binding of the antibody to the labeled analyte. Both the immunological reaction and detection of the extent thereof can be carried out in a homogeneous solution. Immunochemical labels which may be employed include free radicals, radioisotopes, fluorescent dyes, enzymes, bacteriophages, or coenzymes.

In a heterogeneous assay approach, the reagents are usually the sample, the antibody, and means for producing a detectable signal. Samples as described above may be used. The antibody can be immobilized on a support, such as a bead (such as protein A and protein G agarose beads), plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the sample. Means for producing a detectable signal include the use of detectable labels. Exemplary detectable labels include magnetic beads (e.g., DYNABEADS™), fluorescent dyes, enzymes (e.g., horse radish peroxide, alkaline phosphatase and others commonly used in an ELISA), radiolabels (e.g., $^{35}S$, $^{125}I$, $^{131}I$) and fluorescent labels (e.g., fluorescein, Alexa, green fluorescent protein, rhodamine) and colorimetric labels such as colloidal gold or colored glass or plastic beads in accordance with known techniques.

Alternatively, the molecule of interest in the sample can be detected using an indirect assay, wherein, for example, a second, labeled antibody is used to detect bound cryptochrome-specific antibody, and/or in a competition or inhibition assay wherein, for example, a monoclonal antibody which binds to a distinct epitope of the cryptochrome is incubated simultaneously with the mixture. For example, if the antigen to be detected contains a second binding site, an antibody which binds to that site can be conjugated to a detectable group and added to the liquid phase reaction solution before the separation step. The presence of the detectable label on the solid support indicates the presence of the antigen in the test sample. Methods for measuring the amount or the presence of antibody-antigen complexes include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and non-confocal), imaging methods and non-imaging methods. Electrochemical methods include voltammetry and amperometry methods. Radio frequency methods include multipolar resonance spectroscopy. Examples of suitable immunoassays include, but are not limited to immunoblotting (e.g., Western blotting, slot blot assay), immunoprecipitation, immunofluorescence methods, chemiluminescence methods, electrochemiluminescence (ECL) or enzyme-linked immunoassays, e.g., enzyme-linked immunosorbent assay (ELISA) and radioimmunoassay (RIA). See generally E. Maggio, Enzyme-Immunoassay, (1980) (CRC Press, Inc., Boca Raton, Fla.); see also U.S. Pat. Nos. 4,727,022; 4,659, 678; 4,376,110; 4,275,149; 4,233,402; and 4,230,767. These methods are also described in, e.g., Methods in Cell Biology: Antibodies in *Cell* Biology, volume 37 (Asai, ed. 1993);

Basic and Clinical Immunology (Stites & Terr, eds., 7th ed. 1991); and Harlow & Lane, supra. All of these are incorporated by reference herein.

Immunoassays can be used to determine presence or absence of one or more cryptochromes in a sample as well as the quantity in a sample. The amount of an antibody-marker complex can be determined by comparing to a standard. A standard can be, e.g., a known compound or another protein known to be present in a sample. As noted above, the test amount of the one or more cryptochromes need not be measured in absolute units, as long as the unit of measurement can be compared to a control.

Proteins frequently exist in a sample in a plurality of different forms characterized by a detectably different mass. These forms can result from either, or both, of pre- and post-translational modification. Pre-translational modified forms include allelic variants, slice variants and RNA editing forms. Post-translationally modified forms include forms resulting from proteolytic cleavage (e.g., fragments of a parent protein), glycosylation, phosphorylation, lipidation, oxidation, methylation, cystinylation, sulphonation and acetylation. Antibodies can also be useful for detecting post-translational modifications of proteins, polypeptides, mutations, and polymorphisms, such as tyrosine phosphorylation, threonine phosphorylation, serine phosphorylation, glycosylation (e.g., O-GlcNAc). Such antibodies specifically detect the phosphorylated amino acids in a protein or proteins of interest, and can be used in immunoblotting, immunofluorescence, and ELISA assays described herein. These antibodies are well-known to those skilled in the art, and commercially available. Post-translational modifications can also be determined using metastable ions in reflector matrix-assisted laser desorption ionization-time of flight mass spectrometry (MALDI-TOF) (Wirth, U. et al. (2002) Proteomics 2(10): 1445-51). The collection of proteins including a specific protein and all modified forms of it is referred to herein as a "protein cluster." The collection of all modified forms of a specific protein, excluding the specific protein, itself, is referred to herein as a "modified protein cluster." Modified forms of any cryptochrome also may be used, themselves, in the methods disclosed herein. In certain cases the modified forms may exhibit better discriminatory power in diagnosis than the specific forms set forth herein. Modified forms can be initially detected by any methodology known in the art.

Alternatively, cryptochrome protein and nucleic acid metabolites can be measured. The term "metabolite" includes any chemical or biochemical product of a metabolic process, such as any compound produced by the processing, cleavage or consumption of a biological molecule (e.g., a protein, nucleic acid, carbohydrate, or lipid). Metabolites can be detected in a variety of ways known to one of skill in the art, including the refractive index spectroscopy (RI), ultra-violet spectroscopy (UV), fluorescence analysis, radiochemical analysis, near-infrared spectroscopy (near-IR), nuclear magnetic resonance spectroscopy (NMR), light scattering analysis (LS), mass spectrometry, pyrolysis mass spectrometry, nephelometry, dispersive Raman spectroscopy, gas chromatography combined with mass spectrometry, liquid chromatography (including high-performance liquid chromatography (HPLC)), which may be combined with mass spectrometry, matrix-assisted laser desorption ionization-time of flight (MALDI-TOF) combined with mass spectrometry, ion spray spectroscopy combined with mass spectrometry, capillary electrophoresis, ion mobility spectrometry, surface-enhanced laser desorption/ionization (SELDI), optical methods, electrochemical methods, atomic force microscopy, radiofrequency methods, surface Plasmon resonance, ellipsometry, NMR and IR detection. (See, International Application Publication Nos. WO 04/056456 and WO 04/088309, each of which are hereby incorporated by reference in their entireties). In this regard, other analytes can be measured using the above-mentioned detection methods, or other methods known to the skilled artisan. For example, circulating calcium ions (Ca2+) can be detected in a sample using fluorescent dyes such as the Fluo series, Fura-2A, Rhod-2, among others. Other metabolites can be similarly detected using reagents that specifically designed or tailored to detect such metabolites.

A Cry-mediated disease or disorder may involve changes in the activity of one or more cryptochromes, or ability of one or more cryptochromes to bind to a target. Without wishing to be bound by theory, cryptochrome proteins are believed to bind to Period proteins Per 1 and/or Per2 as a heterodimer, which then bind to the promoter region of the CLOCK-BMAL1 gene to facilitate transcriptional repression in a feedback loop that can impinge upon numerous metabolic processes. Thus, measuring an effective amount of one or more cryptochromes according to the methods of the invention may involve assessing an increase or decrease in the ability of Cry proteins to bind to Per1 and/or Per2, to the glucocorticoid receptor (GR), or any other binding target of Cry known to those skilled in the art. Measurement of protein-protein interactions may be facilitated by any method known in the art, including co-immunoprecipitation, yeast two-hybrid assay, surface Plasmon resonance, bimolecular fluorescence complementation, tandem affinity purification, phage display, fluorescence polarization/anisotropy, dual polarization interferometry, fluorescence correlation spectroscopy, fluorescence resonance energy transfer, and the like.

The activity of one or more cryptochromes may also be measured by an increase or decrease in the ability to bind to a DNA sequence, i.e., the promoter region of the CLOCK-BMAL1 gene, or other gene that contains binding sites recognized by one or more cryptochromes. "Promoter", "promoter sequence", or "promoter region" refers to a DNA sequence capable of binding RNA polymerase in a cell, initiating transcription of a downstream (3' direction) coding sequence, thereby controlling its expression. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease Si), as well as protein binding domains (consensus sequences) responsible for the binding of RNA polymerase. Promoters may be derived in their entirety from a native gene, or be composed of different elements derived from different promoters found in nature, or even comprise synthetic DNA segments. In most cases the exact boundaries of regulatory sequences have not been completely defined, DNA fragments of different lengths may have identical promoter activity.

The CLOCK-BMAL1 promoter (or any other promoter region containing binding or recognition sites for Cry) may be "operably linked" to a reporter gene. The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation. The term "reporter gene" means a nucleic acid encoding an identifying factor that is able to be identified based upon the reporter gene's effect, wherein the effect is used to track the inheritance of a nucleic acid of interest, to identify a cell or organism that has inherited the nucleic acid of interest, and/or to measure gene expression induction or transcription. Examples of reporter genes known and used in the art include: luciferase (Luc), green fluorescent protein (GFP), alkaline phosphatase (ALP), chloramphenicol acetyltransferase (CAT), β-galactosidase (LacZ), 3-glucuronidase (Gus), and the like. Selectable marker genes may also be considered reporter genes. The promoter-reporter gene construct may be contained in a plasmid or expression vector that is transferred or transfected into a cell. The expression of the reporter gene can be detected by determining the activity of the gene product, for example, an enzyme activity in the case of using a reporter gene exemplified above.

The term "plasmid" refers to an extra chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. The term "expression vector" means a vector, plasmid or vehicle designed to enable the expression of an inserted nucleic acid sequence following transformation into the host. Vectors may be introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter. Any cell may be used to carry out reporter assays, such as a prokaryotic cell or eukaryotic cell. Preferably, the cell may be a bacterial cell, a fungal cell, a yeast cell, a nematode cell, an insect cell, a fish cell, a plant cell, an avian cell, an animal cell, and a mammalian cell. Cells may be primary cells or may be continuously passaged as cell lines. Exemplary cells and cell lines are known to those skilled in the art.

Other methods of measuring the activity or ability of one or more cryptochromes to bind to a DNA sequence include chromatin immunoprecipitation assay, electrophoretic mobility shift assay, DNA pull-down assay, microplate capture and detection, and the like.

Levels of an effective amount of cryptochrome proteins, nucleic acids, polymorphisms, metabolites, or other analytes, or the activities of cryptochrome proteins or targets that are directly or indirectly bound to cryptochrome proteins, can then be determined and compared to a reference value, e.g. a control subject or population whose disease status is known, or an index value or baseline value. The reference sample or index value or baseline value may be taken or derived from one or more subjects who have been exposed to the treatment, or may be taken or derived from one or more subjects who are at low risk of developing a Cry-mediated disease or disorder, or may be taken or derived from subjects who have shown improvements in disease risk factors as a result of exposure to treatment. Alternatively, the reference sample or index value or baseline value may be taken or derived from one or more subjects who have not been exposed to the treatment. For example, samples may be collected from subjects who have received initial treatment for a Cry-mediated disease or disorder and subsequent treatment for the disease or disorder to monitor the progress of the treatment. In some embodiments, a first sample may be taken from a subject at a first period of time, e.g., prior to treatment with a compound of formula I as defined herein, either alone or in combination with one or more additional therapeutic agents, followed by measuring or detecting one or more cryptochromes (or cryptochrome targets) as described herein. Thereafter, a second sample may be taken from a subject at a second period of time, e.g., after treatment with a compound of formula I as defined herein, either alone or in combination with one or more additional therapeutic agents, and measuring the one or more cryptochromes or cryptochrome targets. Any number of samples may be taken at any time interval throughout the course of treatment to assess its effectiveness.

A reference value can also comprise a value derived from risk prediction algorithms or computed indices from population studies such as those disclosed herein. A similar term in this context is a "control", which can be, e.g., the average or median amount of cryptochromes present in comparable samples of normal subjects in normal subjects or in non-disease subjects such as where a Cry-mediated disease or disorder is undetectable. The control amount is measured under the same or substantially similar experimental conditions as in measuring the test amount. The correlation may take into account the presence or absence of the cryptochromes in a test sample and the frequency of detection of the same molecules in a control. The correlation may take into account both of such factors to facilitate determination of disease status.

A reference profile of those subjects who do not have a Cry-mediated disease or disorder, and would not be expected to develop a Cry-mediated disease or disorder may also be prepared according to methods disclosed herein. Measurement of one or more cryptochromes can also be used to generate a "subject profile" taken from subjects who have a Cry-mediated disease or disorder. The subject profiles can be compared to a reference profile to diagnose or identify subjects at risk for developing a Cry-mediated disease or disorder, to monitor the progression of disease, as well as the rate of progression of disease, and to monitor the effectiveness of treatment modalities or subject management.

The reference and subject profiles of the present invention can be contained in a machine-readable medium, such as but not limited to, analog or digital tapes like those readable by a VCR, CD-ROM, DVD-ROM, USB flash media, among others. Such machine-readable media can also contain additional test results, such as, without limitation, measurements of clinical parameters and traditional laboratory risk factors. Alternatively or additionally, the machine-readable media can also comprise subject information such as medical history and any relevant family history. The machine-readable media can also contain information relating to other risk algorithms and computed indices such as those described herein.

In any of the methods disclosed herein, the data from the sample may be fed directly from the detection means into a computer containing the diagnostic algorithm. Alternatively, the data obtained can be fed manually, or via an automated means, into a separate computer that contains the diagnostic algorithm. Accordingly, embodiments of the invention include methods involving correlating the detection of the cryptochromes with a probable diagnosis of a Cry-mediated disease or disorder. The correlation may take into account the amount of the one or more cryptochromes in the sample compared to a control amount (up or down regulation of the cryptochromes) (e.g., in normal subjects in whom a Cry-mediated disease or disorder is undetectable). The correlation may take into account the presence or absence of the cryptochromes in a test sample and the frequency of detection of the same molecules in a control. The correlation may take into account both of such factors to facilitate determination of whether a subject has a Cry-mediated disease or disorder or not.

Data analysis can include the steps of determining signal strength (e.g., height of peaks) of a marker detected and removing "outliers" (data deviating from a predetermined statistical distribution). The observed peaks can be normalized, a process whereby the height of each peak relative to some reference is calculated. For example, a reference can be background noise generated by instrument and chemicals (e.g., energy absorbing molecule) which is set as zero in the scale. The signal strength detected for each molecule of interest can be displayed in the form of relative intensities in the scale desired (e.g., 100). Alternatively, a standard (e.g., a serum protein) may be admitted with the sample so that a peak from the standard can be used as a reference to calculate relative intensities of the signals observed for each molecule of interest detected.

The resulting data can be transformed or converted into various formats for displaying. In one format, referred to as "spectrum view or retentate map," a standard spectral view can be displayed, wherein the view depicts the quantity of molecule reaching the detector at each particular molecular weight. In another format, referred to as "peak map," only the peak height and mass information are retained from the spectrum view, yielding a cleaner image and enabling molecules of interest with nearly identical molecular weights to be more easily seen. In yet another format, referred to as "gel view," each mass from the peak view can be converted into a grayscale image based on the height of each peak, resulting in an appearance similar to bands on electrophoretic gels. In yet another format, referred to as "3-D overlays," several spectra can be overlaid to study subtle changes in relative peak heights. In yet another format, referred to as "difference map view," two or more spectra can be compared, conveniently highlighting unique molecules of interest which are up- or down-regulated between samples.

Profiles (spectra) from any two samples may be compared visually. In yet another format, Spotfire Scatter Plot can be used, wherein molecules of interest that are detected are plotted as a dot in a plot, wherein one axis of the plot represents the apparent molecular weight of the cryptochromes detected and another axis represents the signal intensity of cryptochromes detected. For each sample, molecules of interest that are detected and the amount of molecules present in the sample can be saved in a computer readable medium. This data can then be compared to a control or reference profile or reference value (e.g., a profile or quantity of molecules detected in control, e.g., subjects in whom a Cry-mediated disease or disorder is undetectable).

The data that are generated in the methods disclosed herein can be classified using a pattern recognition process that uses a classification model. In some embodiments, data generated using samples such as "known samples" can then be used to "train" a classification model. A "known sample" is a sample that is pre-classified (e.g., disease or no disease). Data generated using known samples can then be used to "train" a classification model. A "known sample" is a sample that is pre-classified. The data can be used to form the classification model can be referred to as a "training data set". Once trained, the classification model can recognize patterns in data generated using unknown samples. The classification model can then be used to classify the unknown samples into classes. This can be useful, for example, in predicting whether or not a particular biological sample is associated with a certain biological condition (e.g., diseased vs. non diseased). The training data set that is used to form the classification model may comprise raw data or pre-processed data. In some embodiments, raw data can be obtained directly from time-of-flight spectra or mass spectra, and then may be optionally "pre-processed" in any suitable manner. Pre-processing steps such as these can be used to reduce the amount of data that is used to train the classification model.

Classification models can be formed using any suitable statistical classification (or "learning") method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, Vol. 22, No. 1, January 2000, which is herein incorporated by reference in its entirety. In supervised classification, training data containing examples of known categories are presented to a learning mechanism, which learns one more sets of relationships that define each of the known classes. New data may then be applied to the learning mechanism, which then classifies the new data using the learned relationships.

Examples of supervised classification processes include linear regression processes (e.g., multiple linear regression (MLR), partial least squares (PLS) regression and principal components regression (PCR)), binary decision trees (e.g., recursive partitioning processes such as CART—classification and regression trees), artificial neural networks such as back propagation networks, discriminant analyses (e.g., Bayesian classifier or Fischer analysis), logistic classifiers, and support vector classifiers (support vector machines). A preferred supervised classification method is a recursive partitioning process (U.S. Patent Application Publication No. 20020138208). Unsupervised classification attempts to learn classifications based on similarities in the training data set, without pre classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm. Learning algorithms asserted for use in classifying biological information are described in, for example, International Application Publication No. WO 01/31580 and U.S. Patent Application Publication Nos. 20020193950, 20030004402, and 20030055615. Another classification method involves multivariate predictive models using a non-linear version of Unified Maximum Separability Analysis ("USMA") classifiers. Details of USMA classifiers are described in U.S. Patent Application Publication No. 20030055615.

Other classification algorithms and formulae include, but are not limited to, Principal Component Analysis (PCA), cross-correlation, factor rotation, Logistic Regression (LogReg), Linear Discriminant Analysis (LDA), Eigengene Linear Discriminant Analysis (ELDA), Random Forest (RF), Recursive Partitioning Tree (RPART), as well as other related decision tree classification techniques, Shrunken Centroids (SC), StepAIC, Kth-Nearest Neighbor, Boosting, Decision Trees, Neural Networks, Bayesian Networks, Support Vector Machines, Leave-One-Out (LOO), 10-Fold cross-validation (10-Fold CV), and Hidden Markov Models, among others.

Detection and correlation of one or more cryptochromes may also be analyzed using any suitable means, including software packages, for example, Applied Maths, GenExplore™, 2-way cluster analysis, principal component analysis, discriminant analysis, self-organizing maps; BioDiscovery, Inc., Los Angeles, Calif. (ImaGene™, special image processing and data extraction software, powered by MatLab®; GeneSight: hierarchical clustering, artificial neural network (SOM), principal component analysis, time series; AutoGene™; CloneTracker™); GeneData AG (Basel, Switzerland); Molecular Pattern Recognition web site at MIT's Whitehead Genome Center; Rosetta Inpharmatics, Kirkland, Wash. Resolver™ Expression Data Analysis System; Scanalytics, Inc., Fairfax, Va. Its MicroArray Suite enables researchers to acquire, visualize, process, and analyze gene expression microarray data; TIGR (The Institute for Genome Research) offers software tools for array analysis. For example, see also Eisen and Brown, (1999) Methods Enzymol. 303: 179-205.

In certain embodiments of the methods of qualifying disease status, the methods further comprise managing or modifying clinical treatment of a subject based on the status of the disease or disorder. For example, if the result of the methods of the present invention is inconclusive or there is reason that confirmation of status is necessary, the physician may order more tests (e.g., CT scans, PET scans, MRI scans, PET-CT scans, X-rays, biopsies, blood tests. Alternatively, if the status indicates that treatment is appropriate, the physician may schedule the subject for treatment. In other instances, the subject may receive therapeutic treatments (such as administration of therapeutic agents (such as, e.g., the compounds of formula I defined herein, either alone or in combination with one or more additional therapeutic agents), either in lieu of, or in addition to, surgery. No further action may be warranted. Furthermore, if the results show that treatment has been successful, a maintenance therapy or no further management may be necessary.

The subject matter disclosed herein also provides for such methods where the cryptochromes are measured again after clinical treatment of a subject. In these cases, the methods are used to monitor the status of a Cry-mediated disease or disorder, e.g., response to treatment, remission of the disease or progression of the disease. The methods can be repeated after each treatment the subject receives, allowing the physician to follow the effectiveness of the course of treatment. If the results show that the treatment is not effective, the course of treatment can be altered accordingly.

The invention provides kits for qualifying disease status and/or detecting or diagnosing disease, wherein the kits can be used to detect one or more cryptochromes. For example, the kits can be used to detect any one or more of the cryptochromes described herein, which the one or more cryptochromes are differentially present in samples of disease subjects and normal subjects. The kits of the invention have many applications. For example, the kits can be used in any one of the methods of the invention described herein, such as, inter alia, to differentiate if a subject has a Cry-mediated disease or disorder or has a negative diagnosis, thus aiding a diagnosis. In another example, the kits can be used to identify compounds that modulate expression of one or more of the cryptochromes, compounds that modulate the activity of one or more cryptochromes (i.e., that affect the ability of one or more cryptochromes to bind to a target such as Per1, Per2, the glucocorticoid receptor (GR), or a promoter sequence recognized by cryptochromes such as the CLOCK-BMAL1 promoter or any other promoter sequence) by using in vitro or in vivo animal models for a Cry-mediated disease or disorder. In another example, the kits can be used to identify binding targets of one or more cryptochrome proteins as defined herein.

Kits of the present invention may include a detection reagent, e.g., nucleic acids that specifically identify one or more cryptochrome nucleic acids by having homologous nucleic acid sequences, such as oligonucleotide sequences, primers, or aptamers, complementary to a portion of the nucleic acids or antibodies to proteins encoded by the nucleic acids packaged together. The oligonucleotides can be fragments of the genes. The oligonucleotides may be single stranded or double stranded. For example the oligonucleotides can be 200, 150, 100, 50, 25, 10 or less nucleotides in length. Alternatively, the detection reagent may be one or more antibodies that specifically or selectively bind to one or more cryptochrome proteins or targets thereof. The kit may contain in separate containers a nucleic acid or antibody (either already bound to a solid matrix or packaged separately with reagents for binding them to the matrix), control formulations (positive and/or negative), and/or a detectable label such as fluorescein, green fluorescent protein, rhodamine, cyanine dyes, Alexa dyes, luciferase, radiolabels, among others. Instructions (e.g., written, tape, VCR, CD-ROM, etc.) for carrying out the assay and for correlation to disease status may be included in the kit.

For example, detection reagents can be immobilized on a solid matrix such as a porous strip to form at least one detection site. The measurement or detection region of the porous strip may include a plurality of sites containing a nucleic acid. A test strip may also contain sites for negative and/or positive controls. Alternatively, control sites can be located on a separate strip from the test strip. Optionally, the different detection sites may contain different amounts of immobilized nucleic acids, e.g., a higher amount in the first detection site and lesser amounts in subsequent sites. Upon the addition of test sample, the number of sites displaying a detectable signal provides a quantitative indication of the amount of cryptochromes present in the sample. The detection sites may be configured in any suitably detectable shape and are typically in the shape of a bar or dot spanning the width of a test strip. The substrate array can be on, e.g., a solid substrate, e.g., a "chip" as described in U.S. Pat. No. 5,744,305. Alternatively, the substrate array can be a solution array, e.g., xMAP (Luminex, Austin, Tex.), Cyvera (Illumina, San Diego, Calif.), CellCard (Vitra Bioscience, Mountain View, Calif.) and Quantum Dots' Mosaic (Invitrogen, Carlsbad, Calif.). The kit may also contain reagents, and/or enzymes for amplifying or isolating sample DNA. The kits may include reagents for real-time PCR, for example, TaqMan probes and/or primers, and enzymes.

In some embodiments, a kit comprises: (a) a substrate comprising an adsorbent thereon, wherein the adsorbent retains or is otherwise suitable for binding a cryptochrome, and (b) instructions to detect the cryptochrome by contacting a sample with the adsorbent and detecting the cryptochrome retained by the adsorbent. In some embodiments, the kit may comprise an eluant (as an alternative or in combination with instructions) or instructions for making an eluant, wherein the combination of the adsorbent and the eluant allows detection of the cryptochrome using gas phase ion spectrometry.

In other embodiments, the kit may comprise a first substrate comprising an adsorbent thereon (e.g., a particle functionalized with an adsorbent) and a second substrate onto which the first substrate can be positioned to form a probe, which may be removed and inserted into machine, such as, e.g., a gas phase ion spectrometer. In other embodiments, the kit may comprise a single substrate, which is in the form of a probe with adsorbents on the substrate that can be removed and inserted into a machine. In yet another embodiment, the kit may further comprise a pre-fractionation spin column (e.g., Cibacron blue agarose column, anti-HSA agarose column, K-30 size exclusion column, Q-anion exchange spin column, single stranded DNA column, lectin column, etc.). In another embodiment, a kit comprises (a) an antibody that specifically binds to one or more cryptochromes; and (b) a detection reagent. An antibody may be, for example, an antibody directed against the gene products of a cryptochrome gene.

Optionally, the kit may further comprise a standard or control information so that the test sample can be compared with the control information standard to determine if the test amount of one or more cryptochromes detected in a sample is a diagnostic amount consistent with a diagnosis of a Cry-mediated disease or disorder.

Although a few variations have been described in detail above, other modifications or additions are possible. In particular, further features and/or variations may be provided in addition to those set forth herein. For example, the implementations described above may be directed to various combinations and subcombinations of the disclosed features and/or combinations and subcombinations of several further features disclosed above. In addition, the logic flow described herein does not require the particular order shown, or sequential order, to achieve desirable results. Other embodiments may be within the scope of the claims.

EXAMPLES

Example 1: Reaction Schemes for Synthesis of Compounds

The following reaction schemes, Reaction Scheme I, II, III, IV, V, and VI depicts methods of synthesis for compounds of formula I. In the general methods for preparation of the compounds of formula I, the variable $R_1$, $R_2$, $R_3$, $R_4$, $R_5$, $R_6$, $R_7$, a, and b are as previously defined for a compound of formula I unless otherwise stated. The Reaction Schemes herein described are intended to provide a general description of the methodology employed in the preparation of many of the compounds given. However, it will be evident from the detailed descriptions that the modes of preparation employed extend further than the general procedures described herein. In particular, it is noted that the compounds prepared according to the Schemes may be modified further to provide new compounds within the scope of this invention. The reagents and intermediates used in the following compounds are either commercially available or can be prepared according to the standard literature procedures by those skilled in the art of organic synthesis.

Reaction Scheme I, below, depicts the synthesis of compounds of formula I. Treatment of an appropriately substituted bromide derivative of formula IV with an appropriate carbazole of formula V, in an appropriate solvent, such as N,N-dimethylformamide or N,N-dimethylacetamide, within a temperature range of approximately 0° C. to 150° C. for a period of approximately 5 minutes to 24 hours provides the corresponding oxirane compound of formula III. Preferred conditions for reacting the bromide compound of formula IV with the carbazole of formula V to provide compounds of formula III include carrying out the reaction in N,N-dimethylformamide at 0° C. to room temperature in the presence of potassium hydroxide for 20 to 24 hours followed by an extractive workup. Treatment of the compound of formula III with an appropriate amide or urea of formula II, in an appropriate solvent, such as N,N-dimethylformamide, dimethyl sulfoxide or N,N-dimethylacetamide, within a temperature range of approximately room temperature to 150° C. for a period of approximately 5 mins to 3 days provides the corresponding amide or urea compound of formula I. Preferred conditions for reacting the oxirane compound of formula III to provide compounds of formula I include carrying out the reaction in N,N-dimethylformamide with sodium hydride at room temperature for 20 to 24 hours followed by extractive workup. Alternatively, the oxirane compound of formula III can be reacted with the amide or urea of formula II in an appropriate solvent, such as dimethyl sulfoxide, with an appropriate base, such as potassium tert-butoxide, at room temperature for 3 days to provide the compound of formula I.

Reaction Scheme I

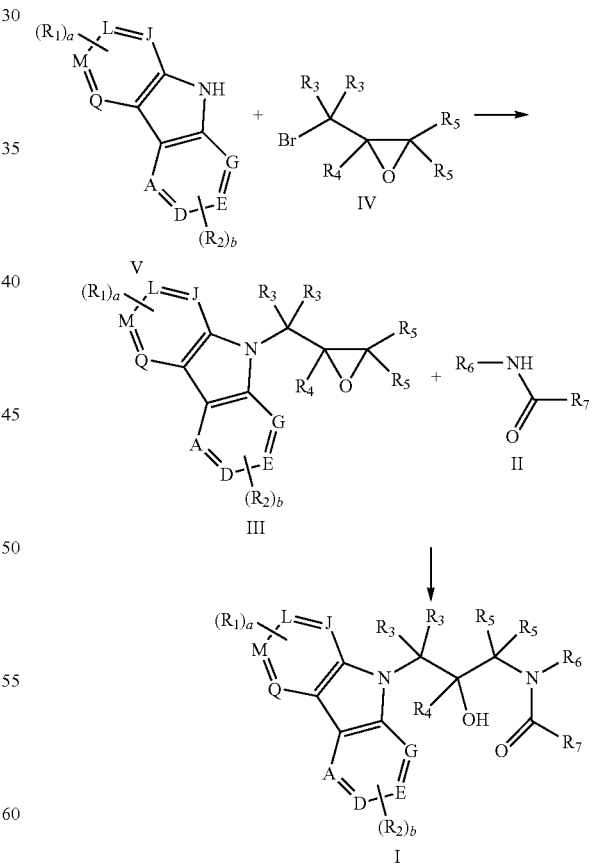

Reaction Scheme II, below, depicts an alternative synthesis of compounds of formula I. Treatment of an appropriately substituted oxirane derivative of formula III with an appropriate diamine of formula VII, in an appropriate solvent, such as ethanol, within a temperature range of 0° C. to 150° C. for a period of approximately 5 minutes to 24 hours provides the corresponding diamine compound of formula VI. Preferred conditions for reacting oxirane compound of formula III with the diamine of formula VII to provide compounds of formula VI include carrying out the reaction in ethanol at 40° C. for 20 to 24 hours. Treatment of the compound of formula VI with an appropriate carbonylating agent, such as 1,1'-carbonyldiimidazole, in an appropriate solvent such as tetrahydrofuran, at room temperature for a period of 5 minutes to 24 hours provides the corresponding compound of formula I.

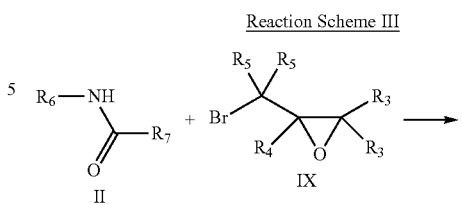

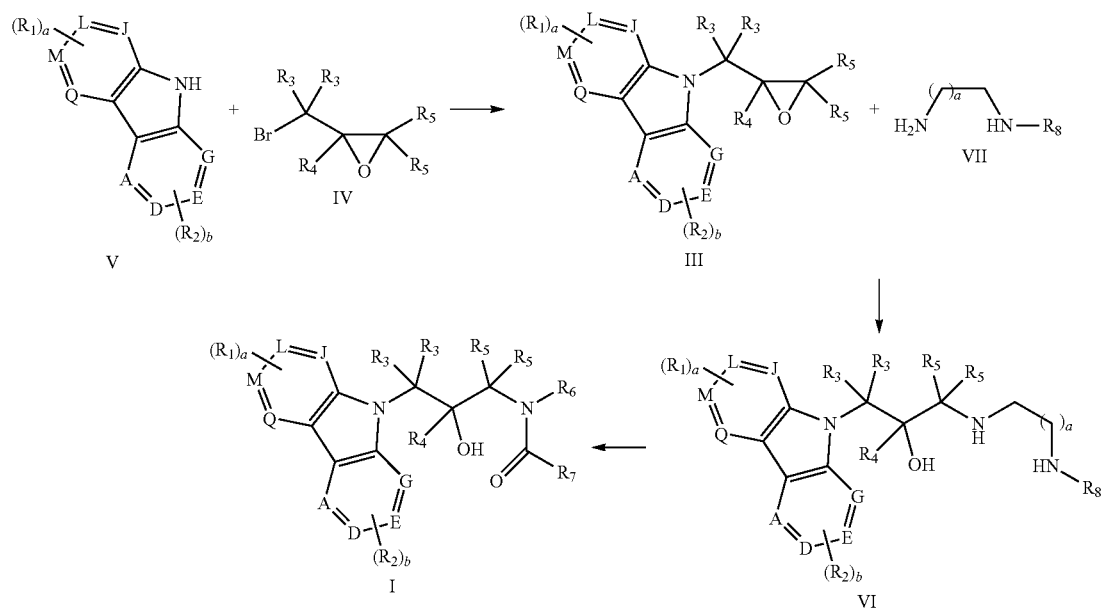

Reaction Scheme III, below, depicts an alternative synthesis of compounds of formula I. Treatment of the amide or urea compound of formula II with an appropriately substituted bromide derivative of formula IX, in an appropriate solvent, such as tetrahydrofuran, within a temperature range of approximately 0° C. to 65° C. for a period of approximately 5 minutes to 24 hours provides the corresponding oxirane compound of formula VIII. Preferred conditions for reacting the bromide compound of formula IX with the amide or urea of formula II to provide compounds of formula VIII include carrying out the reaction in tetrahydrofuran at 0° C. to room temperature in the presence of sodium hydride for 20 to 24 hours followed by an extractive workup. Treatment of the compound of formula VIII with an appropriate carbazole of formula V, in an appropriate solvent, such as N,N-dimethylformamide, within a temperature range of 0° C. to 70° C. for a period of approximately 5 minutes to 24 hours provides the corresponding compound of formula I. Preferred conditions for reacting oxirane compound of formula VIII with the carbazole of formula V to provide compounds of formula I include carrying out the reaction in N,N-dimethylformamide at room temperature to 70° C. in the presence of sodium hydride for 20 to 24 hours to provide the compound of formula I.

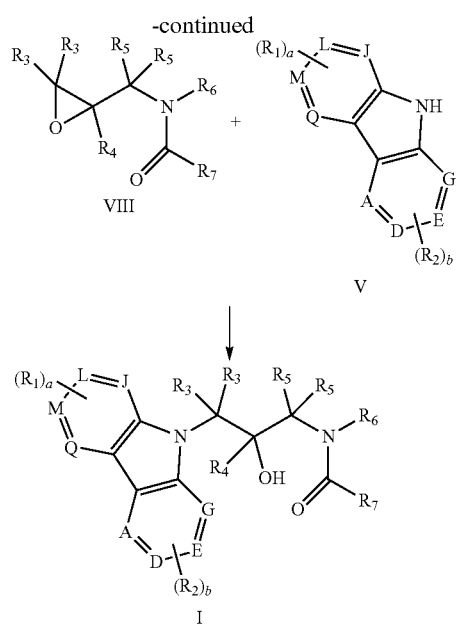

Reaction Scheme IV, below, depicts an alternative synthesis of compounds of formula I. Treatment of the Boc-protected amino acid compound of formula XIII with ammonia, an appropriate coupling reagent, such as N,N,N', N'-tetramethyl-O-(1H-benzotriazol-1-yl)uronium hexafluorophosphate, an appropriate base, such as N,N-diisopropylethylamine and an appropriate solvent, such as dimethylformamide, within a temperature range of approximately 0° C. to 65° C. for a period of approximately 5 minutes to 24 hours provides the corresponding amide compound of formula XII. Treatment of Boc-protected amino amide compound of formula XII with an appropriate reducing agent, such as borane, in an appropriate solvent, such as tetrahydrofuran, within a temperature range of approximately 0° C. to 100° C. for a period of approximately 5 minutes to 24 hours provides the corresponding Boc-protected diamine compound of formula XI. Preferred conditions for reacting oxirane compound of formula III with the Boc-protected diamine of formula XI to provide compounds of formula X include carrying out the reaction in ethanol at 70° C. for 16 to 24 hours. Treatment of the compound of formula X with an appropriate base, such as potassium tert-butoxide, in an appropriate solvent, such as tetrahydrofuran, within a temperature range of approximately 0° C. to 100° C. for a period of approximately 5 minutes to 24 hours provides the corresponding compound of formula I.

Reaction Scheme V, below, depicts an alternative synthesis of compounds of formula I. Treatment of the benzyl-protected diamine compound of formula XVI with an appropriate carbonylating agent, such as 1,1'-carbonyldiimidazole, in an appropriate solvent, such as tetrahydrofuran, at room temperature for a period of 5 minutes to 24 hours provides the corresponding compound of formula XV. Preferred conditions for reacting oxirane compound of formula III with the benzyl-protected urea of formula XV to provide compounds of formula XIV include carrying out the reaction in N,N-dimethylformamide at room temperature to 70° C. in the presence of sodium hydride for 16 to 24 hours. Treatment of the benzyl-protected urea compound of formula XIV with 1 to 50 psi hydrogen in the presence of an appropriate catalyst, such as palladium hydroxide on carbon, with an appropriate acid, such as acetic acid, in an appropriate solvent, such as tetrahydrofuran, within a temperature range of approximately room temperature to 100° C. for a period of approximately 5 minutes to 5 days provides the corresponding compound of formula I.

Reaction Scheme IV

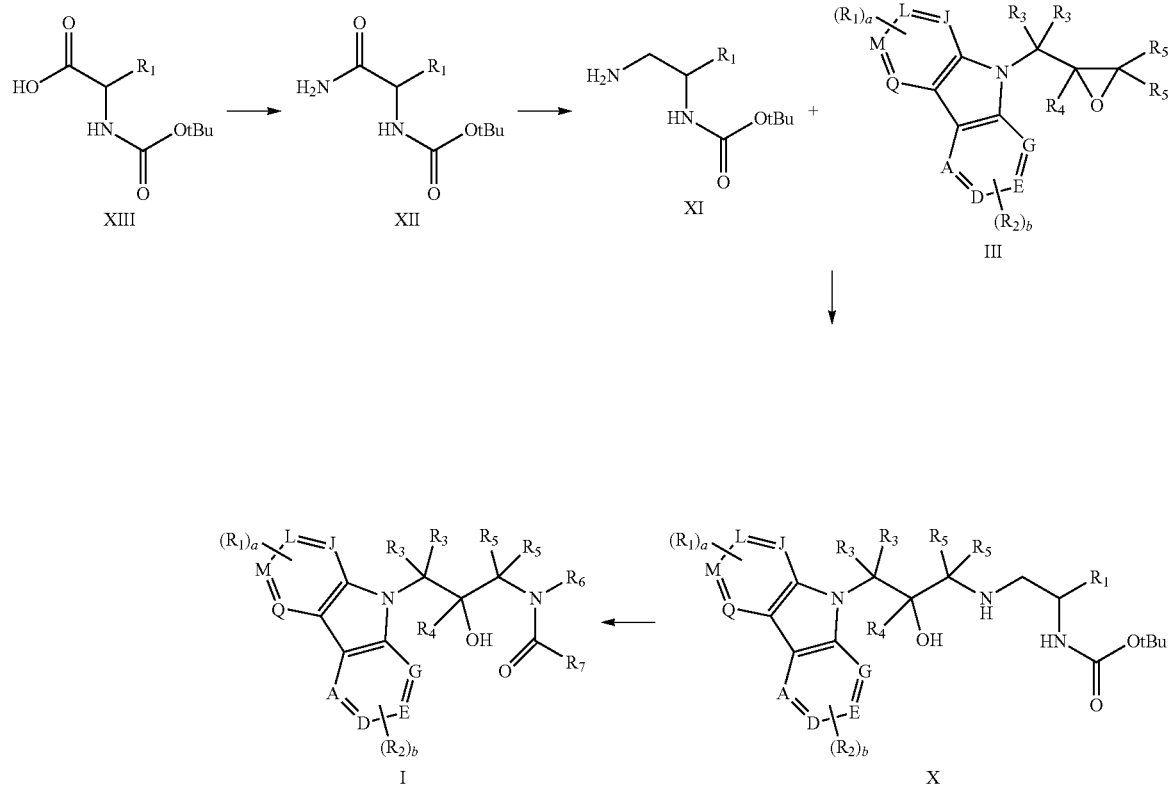

Reaction Scheme V

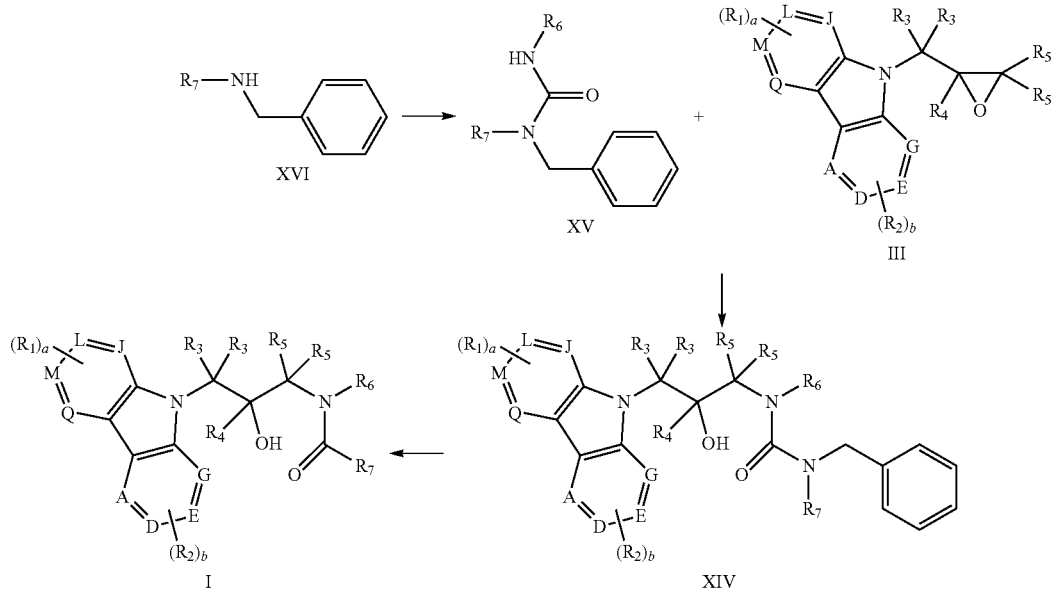

Reaction Scheme VI, below, depicts an alternative synthesis of compounds of formula I. Treatment of an appropriately substituted chiral oxirane derivative of formula XVII or XVIII with an appropriate amide or urea compound of formula II, with an appropriate base, such as sodium hydride, in an appropriate solvent, such as N,N-dimethylformamide or tetrahydrofuran, within a temperature range of 0° C. to 150° C. for a period of approximately 5 minutes to 24 hours provides the corresponding chiral amide or urea compound of formula I.

Reaction Scheme VI

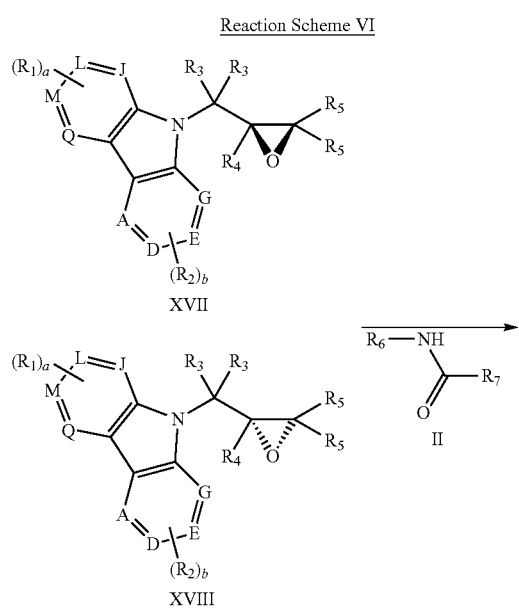

-continued

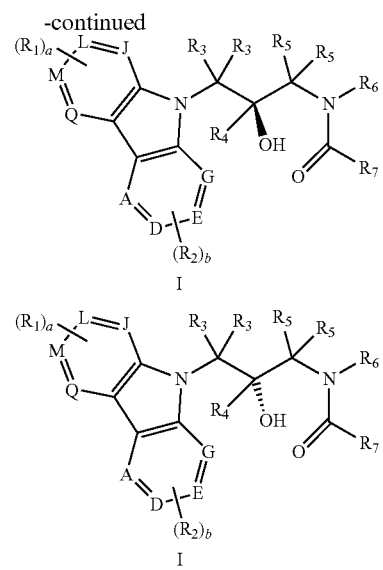

Reaction Scheme VII, below, depicts an alternative synthesis of compounds of formula I. Treatment of an appropriately substituted chiral oxirane derivative of formula XVII or XVIII with an appropriate diamine of formula VII, in an appropriate solvent, such as ethanol, within a temperature range of 0° C. to 150° C. for a period of approximately 5 minutes to 24 hours provides the corresponding chiral diamine compound of formula VI. Preferred conditions for reacting oxirane compound of formula XVII or XVIII with the diamine of formula VII to provide compounds of formula VI include carrying out the reaction in ethanol at 55° C. for 5 to 24 hours. Treatment of the compound of formula VI with an appropriate carbonylating agent, such as 1,1'-carbonyldiimidazole, in an appropriate solvent such as tetrahydrofuran, at room temperature for a period of 5 minutes to 24 hours provides the corresponding compound of formula I.

Reaction Scheme VII

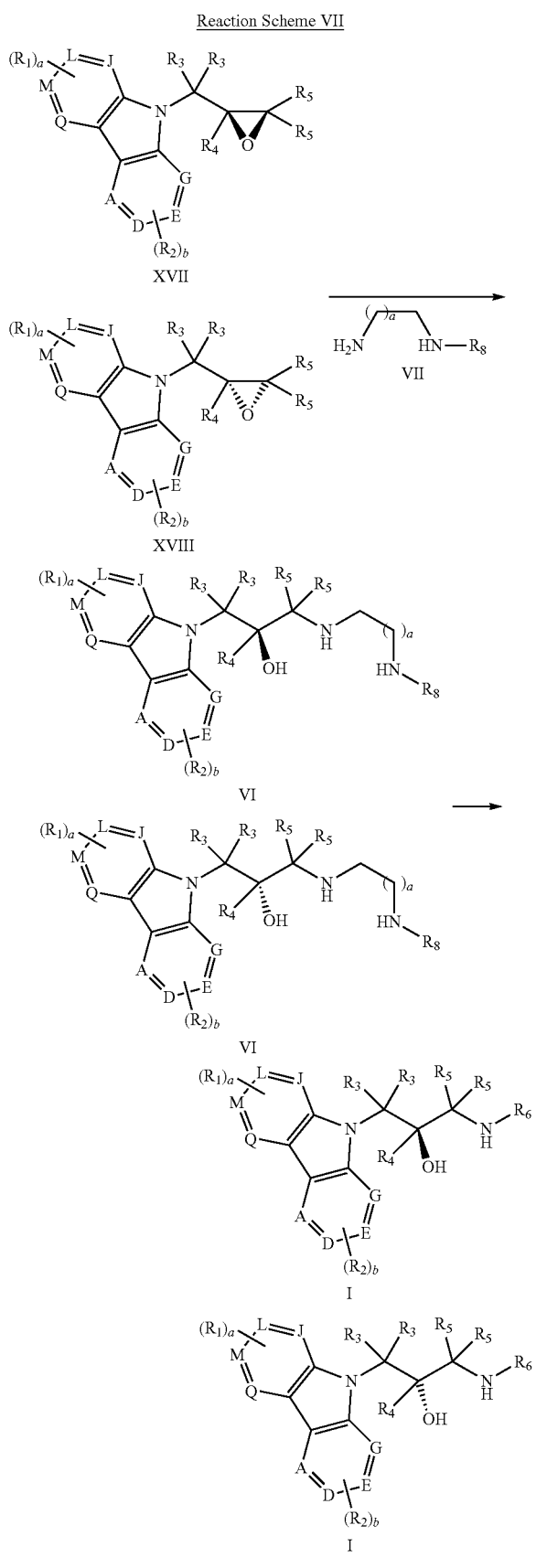

In the reaction schemes described herein it is to be understood that hydroxyl groups in intermediates useful for preparing compounds of formula I may be protected by conventional groups known to those skilled in the art, as required. For example, intermediates containing a hydroxyl group may be protected as the corresponding tert-butyldimethylsilyl ether and subsequently deprotected by treatment with tetra-n-butylammonium fluoride to provide the free hydroxyl derivative. Suitable protecting groups and methods for their removal are illustrated in "Protective Groups in Organic Synthesis", 3$^{rd}$ Ed., T. W. Greene and P. G. M. Wuts (Wiley & Sons, 1999).

$^{1}$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The mass spectra (m/z) were recorded using either electrospray ionization (ESI) or atmospheric pressure chemical ionization (APCI). Where thin layer chromatography (TLC) has been used it refers to silica gel TLC using silica gel 60 F254 plates, Rf is the distance traveled by a compound divided by the distance traveled by the solvent front on a TLC plate. HPLC refers to high performance liquid chromatography.

The following specific examples are included for illustrative purposes and are not to be construed as a limitation to this disclosure.

Preparation of Intermediates

Preparation 1:
2-chloro-4-fluoro-N-(4-fluorophenyl)aniline

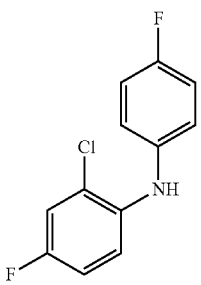 [SMILES: Fc1ccc(Nc2ccc(F)cc2Cl)cc1]

A round bottom flask was charged with 1-bromo-4-fluorobenzene (13.0 g, 74.3 mmol), 2-chloro-4-fluoroaniline (11.354 g, 78.0 mmol), anhydrous toluene (200 mL) and potassium tert-butoxide (10.003 g, 89.1 mmol). The mixture was degassed and back-filled with nitrogen, and then tris (dibenzylideneacetone)dipalladium(0) (2.041 g, 2.2 mmol) and tri-tert-butylphosphine (0.902 g, 4.5 mmol) were added and the reaction was stirred under nitrogen at 100° C. for 16 hours. After cooling, the mixture was treated with 6 M aqueous hydrochloric acid to acidic pH and then adjusted back to basic pH with solid sodium carbonate. The mixture was dried (anhydrous magnesium sulfate), filtered through Celite and the filter cake washed with ethyl acetate. The filtrate was concentrated and the residue purified by silica gel chromatography (0-20% ethyl acetate/hexanes) to afford a yellowish oil (14 g, 79%). $^{1}$H NMR (300 MHz, CDCl$_{3}$): δ 7.14 (dd, 1H, J=8.4, 3.0 Hz), 7.12-6.98 (m, 5H), 6.88 (td, 1H, J=8.7, 3.0 Hz), 5.80 (br s, 1H).

Preparation 2: 3,6-difluoro-9H-carbazole

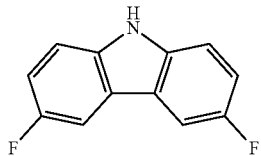 [SMILES: Fc1ccc2[nH]c3ccc(F)cc3c2c1]

A mixture of potassium carbonate (26.528 g, 191.9 mmol), 2-chloro-4-fluoro-N-(4-fluorophenyl)aniline (23.0 g, 96.0 mmol), tricyclohexylphosphonium tetrafluoroborate (3.534 g, 9.6 mmol), palladium diacetate (1.077 g, 4.8 mmol), and anhydrous N,N-dimethylacetamide (200 mL) was stirred under nitrogen at 130° C. for 16 hours. After cooling, the mixture was concentrated and the residue treated with ethyl acetate, filtered through Celite and the filter cake washed with ethyl acetate. The filtrate was concentrated and the residue purified by a short silica gel column (20-50% methylene chloride/hexanes) to afford the crude product which was recrystallized from hexanes-methylene chloride to afford the pure product as a white powder (17.2 g, 88%). $^1$H NMR (300 MHz, CDCl$_3$): δ 8.00 (br s, 1H), 7.67 (dd, 2H, J=8.7, 2.7 Hz), 7.36 (dd, 2H, J=8.7, 4.2 Hz), 7.19 (td, 2H, J=9.0, 2.7 Hz).

Preparation 3: 9-(Oxiran-2-ylmethyl)-9H-carbazole

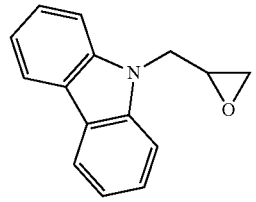 [SMILES: c1ccc2c(c1)c1ccccc1n2CC1CO1]

Powdered potassium hydroxide (3.36 g, 60 mmol) was added to a solution of carbazole (8.36 g, 50 mmol) in anhydrous N,N-dimethylformamide (50 mL) and stirred at ambient temperature for 1 hour. The reaction mixture was cooled in an ice bath and epibromohydrin (10.3 mL, 125 mmol) was added. The ice bath was removed and the reaction was stirred at room temperature for 20 hours. The mixture was partitioned between ethyl acetate and water. The organic layer was washed successively with water and saturated aqueous sodium chloride solutions, dried (anhydrous sodium sulfate), filtered, and concentrated. The crude material was triturated with hexanes, and recrystallized from ethyl acetate/hexanes to yield the desired product as white needles (6.41 g, 58% yield). A second crop of crystals was crystallized from the mother liquor to give additional product (1.2 g, 11%). $^1$H NMR (300 MHz, CDCl$_3$) δ 8.11-8.08 (m, 2H), 7.46-7.44 (m, 4H), 7.28-7.25 (m, 2H), 4.68-4.62 (dd, 1H, J=3.1, 15.8 Hz) 4.45-4.38 (dd, 1H, J=4.8, 15.9 Hz), 3.37 (m, 1H), 2.84-2.81 (dd, 1H, J=4.2, 4.3 Hz), 2.60-2.57 (dd, 1H, J=2.5, 5.0 Hz); HPLC analysis: (C18, 5-95% acetonitrile in water+0.1% trifluoroacetic acid over 20 min: retention time, % area at 254 nm): 7.83 min, 98.7%.

The following compounds were prepared analogously:

| Structure | Name | Characterization |
|---|---|---|
| 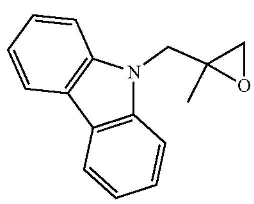 [SMILES: CC1(Cn2c3ccccc3c3ccccc32)CO1] | 9-((2-methyloxiran-2-yl)methyl)-9H-carbazole | $^1$H NMR (300 MHz, CDCl$_3$): δ 8.10-8.07 (dt, 2H, J = 0.9, 7.5 Hz), 7.48-7.46 (m, 4H), 7.27-7.22 (m, 2H), 4.63-4.58, 4.32-4.27 (ABq, 2H, J = 15.6 Hz), 2.69 (s, 2H), 1.34 (s, 3H); HPLC analysis: (C18, 10-90% acetonitrile in water over 20 min: retention time, % area at 254 nm): 13.6 min, 97%. |
| 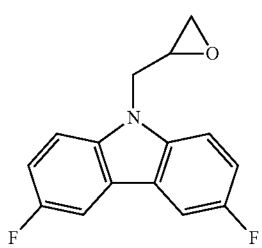 [SMILES: Fc1ccc2c(c1)c1cc(F)ccc1n2CC1CO1] | 3,6-difluoro-9-(oxiran-2-ylmethyl)-9H-carbazole | $^1$H NMR (300 MHz, CDCl$_3$): δ 7.69 (dd, 2H, J = 8.7, 2.7 Hz), 7.39 (dd, 2H, J = 9.0, 3.9 Hz), 7.24 (td, 2H, J = 9.0, 2.7 Hz), 4.68 (dd, 1H, J = 15.9, 3.0 Hz), 4.32 (dd, 1H, J = 15.9, 5.1 Hz), 3.35 (m, 1H), 2.84 (t, 1H, J = 4.5 Hz), 2.55 (dd, 1H, J = 4.5, 2.7 Hz); HPLC analysis: (C18, 10-90% acetonitrile in water + 0.1% trifluoroacetic acid over 20 min: retention time, % area at 254 nm): 13.6 min, >98%. |
| 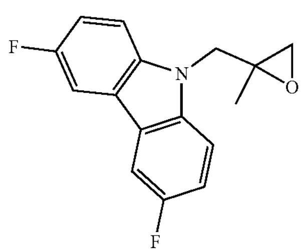 [SMILES: CC1(Cn2c3ccc(F)cc3c3cc(F)ccc32)CO1] | 3,6-difluoro-9-((2-methyloxiran-2-yl)methyl)-9H-carbazole | $^1$H NMR (300 MHz, CDCl$_3$): δ 7.68 (dd, 2H, J = 8.4, 2.4 Hz), 7.41 (dd, 2H, J = 9.0, 4.2 Hz), 7.23 (td, 2H, J = 9.0, 2.4 Hz), 4.62 and 4.22 (AB, 2H, J = 15.6 Hz), 2.71 and 2.66 (AB, 2H, J = 4.5 Hz), 1.33 (s, 3H); HPLC analysis: (C18, 10-90% acetonitrile in water + 0.1% trifluoroacetic acid over 20 min: retention time, % area at 254 nm): 14.2 min, 100%. |

Preparation 4: 1-benzoylpyrrolidin-2-one

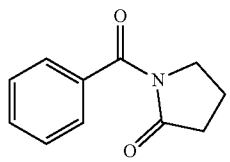 [SMILES: O=C1CCCN1C(=O)c1ccccc1]

To a cold 0° C. solution of 2-pyrrolidinone (4.4 g, 51.7 mmol, 1.0 equiv.) and triethylamine (15.4 mL, 111.2 mmol, 2.1 equiv.) in anhydrous tetrahydrofuran (120 mL) was added 4-dimethylaminopyridine (0.075 g) and benzoyl chloride (6.9 mL, 59.5 mmol, 1.1 equiv.). The resultant mixture was stirred for 16 hrs at room temperature. The mixture was poured into water and extracted with ethyl acetate. The organic fraction was washed with 0.1 M aqueous hydrochloric acid, saturated aqueous sodium bicarbonate, and saturated aqueous sodium chloride solutions, dried over anhydrous sodium sulfate, filtered and concentrated in vacuo to afford a red oil. The crude product was purified by silica gel column chromatography, eluting with a gradient of 20-65% ethyl acetate in hexanes to give an off-white solid (5.63 g, 58%). $^1$H NMR (300 MHz, CDCl$_3$): δ 7.61-7.57 (m, 2H), 7.53-7.47 (tt, 1H, J=1.5, 7.5 Hz), 7.42-7.37 (m, 2H), 3.98-3.94 (t, 2H, J=7.1 Hz), 2.61-2.58 (t, 2H, J=8.0 Hz), 2.20-2.10 (quint, 2H, J=7.5 Hz). ESI (m/z): 190.1 (M+H).

Preparation 5: 1-benzoyl-3-fluoropyrrolidin-2-one

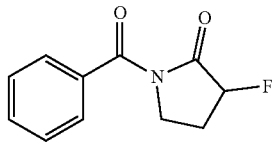 [SMILES: O=C(c1ccccc1)N1CCC(F)C1=O]

To a −78° C. solution of 1-benzoylpyrrolidin-2-one (1 g, 5.3 mmol, 1.0 equiv.) in anhydrous tetrahydrofuran (26 mL) was added lithium diisopropylamide (3.382 mL of a 2 M solution in tetrahydrofuran, 6.8 mmol, 1.3 equiv.) and the mixture stirred at −78° C. for 30 mins. A solution of N-fluorobenzene sulfonimide (2.5 g, 7.9 mmol, 1.5 equiv.) in anhydrous tetrahydrofuran (5 mL) was added slowly at −78° C. and the reaction stirred for 1 hr at −40° C. Saturated aqueous sodium hydrogen carbonate was added, the solution warmed to room temperature and extracted with ethyl acetate. The organic layer was washed with saturated aqueous sodium chloride, dried over anhydrous sodium sulfate, filtered and concentrated in vacuo to afford a yellow solid. The crude product was purified by silica gel column chromatography, eluting from silica gel with a gradient of 15-60% ethyl acetate in hexanes to give a white solid (0.595 g, 54%). $^1$H NMR (300 MHz, CDCl$_3$): δ 7.64-7.61 (m, 2H), 7.57-7.52 (tt, 1H, J=1.5, 7.5 Hz), 7.45-7.39 (m, 2H), 5.28-5.06 (dt, 1H, J=7.8, 51 Hz), 4.15-4.07 (m, 1H), 3.87-3.78 (m, 1H), 2.68-2.56 (m, 1H), 2.45-2.27 (m, 1H). $^{19}$F NMR (282 MHz, CDCl$_3$): δ −188.9 to −189.2 (ddd, J=12.1, 24.2, 51.8 Hz).

Preparation 6: 3-fluoropyrrolidin-2-one

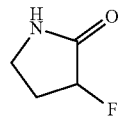

To a solution of 1-benzoyl-3-fluoropyrrolidin-2-one (0.282 g, 1.4 mmol, 1.0 equiv.) in anhydrous tetrahydrofuran (5 mL) was added octylamine (0.259 mL, 1.6 mmol, 1.1 equiv.) and the reaction was stirred for 16 hrs at room temperature. The reaction mixture was concentrated under reduced pressure to give a yellow oil. The crude product was purified by silica gel column chromatography eluting with a gradient of 70-100% ethyl acetate in hexanes to afford a white solid. (0.104 g, 74% yield). $^1$H NMR (300 MHz, CDCl$_3$): δ 7.81 (br s, 1H), 5.11-4.89 (ddd, 1H, J=6.3, 7.8, 52.8 Hz), 3.49-3.42 (m, 1H), 3.36-3.27 (m, 1H), 2.57-2.41 (m, 1H), 2.34-2.13 (m, 1H). $^{13}$C NMR (75 MHz, CDCl$_3$): δ 173.5-173.3 (d, J=20 Hz), 89.9-87.4 (d, J=182 Hz), 39.1 (d, J=4 Hz), 28.6-28.4 (d, J=20 Hz). $^{19}$F NMR (282 MHz, CDCl$_3$): δ −190.1 to −190.4 (ddd, J=15, 27, 52 Hz).

Preparation 7: tert-butyl 2-oxopiperidine-1-carboxylate

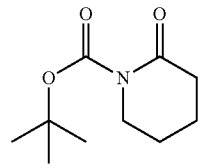

To a stirred solution of piperidin-2-one (5 g, 50.4 mmol, 1.0 equiv.), triethylamine (14.022 mL, 100.9 mmol, 2.0 equiv.) and N,N-4-dimethylaminopyridine (0.123 g, 1.0 mmol) in methylene chloride (100 mL) at 0° C. was added di-tert-butyl dicarbonate (16.512 g, 75.7 mmol, 1.5 equiv.). The mixture was slowly warmed to room temperature and stirred for 48 hrs. The reaction was quenched with water and the organic layer was washed sequentially with 1 N aqueous hydrochloric acid, saturated aqueous sodium bicarbonate and saturated aqueous sodium chloride, and dried over anhydrous sodium sulfate, filtered and concentrated in vacuo. The residue was purified by silica gel column (0-100% ethyl acetate/hexanes) to afford the desired product as a yellow oil (8.5 g, 85%). $^1$H NMR (300 MHz, CDCl$_3$): δ 3.72-3.62 (m, 2H), 2.58-2.48 (m, 2H), 1.90-1.78 (m, 4H), 1.55 (s, 9H).

Preparation 8: tert-butyl 3-fluoro-2-oxopiperidine-1-carboxylate

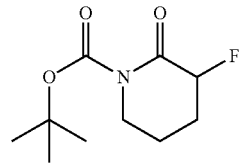

To a stirred solution of tert-butyl 2-oxopiperidine-1-carboxylate (3 g, 15.1 mmol, 1.0 equiv.) in anhydrous tetrahydrofuran (70 mL) under nitrogen at −78° C. was added sodium bis(trimethylsilyl)amide (22.586 mL of a 1 M solution in tetrahydrofuran, 22.6 mmol, 1.5 equiv.) dropwise over a period of 30 mins. The resultant solution was stirred for 45 mins at −78° C., and then a solution of N-fluorobenzene sulfonimide (7.122 g, 22.6 mmol, 1.5 equiv.) in anhydrous tetrahydrofuran (30 mL) was added dropwise over a period of 30 mins. The reaction was stirred at −78° C. for 1 hr and then allowed to slowly warm to room temperature over 2 hrs and stirred at room temperature for 1 hr. The reaction was quenched with saturated aqueous ammonium chloride and extracted with ethyl acetate. The organic phase was washed with saturated aqueous sodium chloride and dried over anhydrous magnesium sulfate, filtered and concentrated in vacuo. The residue was treated with diethyl ether and the solids were discarded. The solution was concentrated and the residue was purified by silica gel column chromatography (0-100% ethyl acetate/hexanes) to afford the crude product fractions and the difluoro byproduct as a white solid (1.5 g). The crude product fraction was further purified by a second run of silica gel chromatography to afford the desired product as a thick oil (0.46 g, 14%). $^1$H NMR (300 MHz, CDCl$_3$): δ 4.92 (ddd, 1H, J=47.4, 8.7, 6.3 Hz), 3.78-3.60 (m, 2H), 2.35 (m, 1H), 2.15-1.80 (m, 3H), 1.55 (s, 9H). $^{19}$F NMR (282 MHz, CDCl$_3$): δ −185.2 (dt, J=45.7, 15.5 Hz).

Preparation 9: 3-fluoropiperidin-2-one

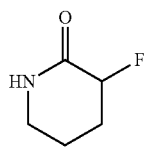

To a 0° C. solution of tert-butyl 3-fluoro-2-oxopiperidine-1-carboxylate (0.450 g, 2.1 mmol, 1.0 equiv.) in methylene chloride (5 mL) was added trifluoroacetic acid (1 mL, 13.5 mmol, 6.5 equiv.) and the resultant solution was stirred for 3 hrs. The reaction was concentrated under reduced pressure and the residue was purified by silica gel column (0-100% ethyl acetate/hexanes and then 0-20% methanol/ethyl acetate) to afford the desired product as a white powder (0.23 g, 95%). $^1$H NMR (300 MHz, CDCl$_3$): δ 6.36 (br s, 1H), 4.85 (ddd, 1H, J=46.8, 8.1, 5.4 Hz), 3.50-3.20 (m, 2H), 2.40-1.70 (m, 4H). $^{19}$F NMR (282 MHz, CDCl$_3$): δ −186.5 (dt, J=46.5, 15.5 Hz).

Preparation 10: 3,3-difluoropiperidin-2-one

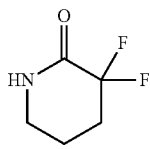

3,3-Difluoropiperidin-2-one was prepared according to the reported procedures (Kim, B. C. et al. *Synthesis* 2012, 44, 3165-3170).

Preparation 11: 1-benzoyl-3,3-difluoropyrrolidin-2-one

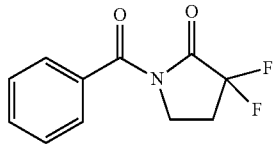 [SMILES: O=C(c1ccccc1)N1CCC(F)(F)C1=O]

To a −78° C. solution of 1-benzoyl-3-fluoropyrrolidin-2-one from Preparation 21B (0.3 g, 1.4 mmol, 1.0 equiv.) and N-fluorobenzene sulfonimide (0.639 g, 2.0 mmol, 1.4 equiv.) in anhydrous tetrahydrofuran (10 mL) was added lithium diisopropylamide (0.905 mL of a 2 M solution in tetrahydrofuran, 1.8 mmol, 1.3 equiv.) and the mixture stirred at −78° C. for 30 mins. Additional portions of lithium diisopropylamide solution (0.5 equiv.) and N-fluorobenzene sulfonimide (0.5 equiv. in 0.5 mL of anhydrous tetrahydrofuran) were added and the mixture stirred for 1 hr at −78° C. Saturated aqueous sodium hydrogen carbonate was added, the mixture warmed to room temperature and extracted with ethyl acetate. The organic layer was washed with saturated aqueous sodium chloride, dried over anhydrous sodium sulfate, filtered and concentrated in vacuo. The crude product was purified by silica gel column chromatography, eluting with a gradient of 15-50% ethyl acetate in hexanes to give a white solid (0.09 g, 23%). $^1$H NMR (300 MHz, CDCl$_3$): δ 7.66-7.61 (m, 2H), 7.59-7.55 (m, 1H), 7.47-7.44 (m, 2H), 4.02-3.97 (m, 2H), 2.70-2.56 (tt, 2H, J=6.6, 14.7 Hz). $^{19}$F NMR (282 MHz, CDCl$_3$): δ −106.0 to −106.1 (t, J=15 Hz).

Preparation 12: 3,3-difluoropyrrolidin-2-one

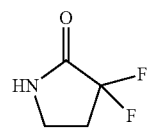

To a solution of 1-benzoyl-3,3-difluoropyrrolidin-2-one (0.085 g, 0.4 mmol, 1.0 equiv.) in anhydrous tetrahydrofuran (1 mL) was added octylamine (0.075 mL, 0.5 mmol, 1.1 equiv.) and the reaction was stirred for 16 hrs at room temperature. The mixture was concentrated under reduced pressure to afford a yellow oil. The crude residue was purified by silica gel column chromatography eluting with a gradient of 50-100% ethyl acetate in hexanes to give a white solid (0.024 g, 52% yield). $^1$H NMR (300 MHz, CDCl$_3$): δ 7.93 (br s, 1H), 3.50-3.46 (br t, 2H, J=6.0 Hz), 2.63-2.48 (tt, 2H, J=6.6, 15.2 Hz). $^{19}$F NMR (282 MHz, CDCl$_3$): δ −107.33 to −107.44 (t, J=15.2 Hz). $^{13}$C NMR (75 MHz, CDCl$_3$): δ 167.5-166.7 (t, J=31 Hz), 121.1-114.4 (t, J=248 Hz), 37.1 (t, J=3.3 Hz), 31.2-30.6 (t, J=23.1 Hz).

Preparation 13: 1-benzyl-3-methylpyrrolidin-2-one; General procedure

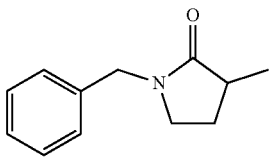

To a cold −78° C. solution of 1-benzyl-2-pyrrolidinone (0.422 g, 2.4 mmol, 1.0 equiv.) in anhydrous tetrahydrofuran (15 mL) was added lithium diisopropylamide (2.4 mL of a 2 M solution, 4.8 mmol, 2.0 equiv.) and the resultant red solution was stirred for 30 mins at −78° C., and iodomethane (0.6 mL, 9.6 mmol, 4.0 equiv.) was added. The solution was stirred at −78° C. for 1 hr and allowed to slowly warm to room temperature for 16 hrs. Saturated aqueous ammonium chloride was added and the mixture extracted with ethyl acetate. The organic fraction was washed with saturated aqueous sodium chloride, dried over anhydrous sodium sulfate, filtered and concentrated in vacuo. The crude product was purified by silica gel column chromatography, eluting with a gradient of 35-80% ethyl acetate in hexanes to afford the product as a tan liquid (0.374 g, 82%). $^1$H NMR (300 MHz, CDCl$_3$): δ 7.37-7.34 (m, 5H), 4.52-4.41 and 4.46-4.41 (ABq, 2H, J=14.6 Hz), 3.27-3.15 (m, 2H), 2.60-2.46 (m, 1H), 2.28-2.15 (m, 1H), 1.68-1.58 (m, 1H), 1.28-1.25 (d, 3H, J=7.2 Hz).

The following compounds were prepared analogously:

| Structure | Name | Characterization |
|---|---|---|
| 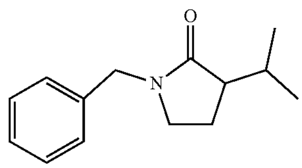 [SMILES: CC(C)C1CCN(Cc2ccccc2)C1=O] | 1-benzyl-3-isopropylpyrrolidin-2-one | $^1$H NMR (300 MHz, CDCl$_3$): δ 7.34-7.20 (m, 5H), 4.56-4.51 and 4.39-4.34 (ABq, 2H, J = 14.6 Hz), 3.18-3.13 (m, 2H), 2.51-2.43 (td, 1H, J = 4.5, 9.0 Hz), 2.33-2.22 (m, 1H), 2.05-1.92 (m, 1H), 1.83-1.74 (m, 1H), 1.02-1.00 (d, 3H, J = 6.6 Hz), 0.89-0.87 (d, 3H, J = 6.6 Hz). |
| 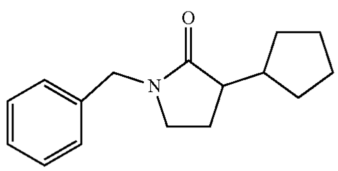 [SMILES: O=C1C(C2CCCC2)CCN1Cc1ccccc1] | 1-benzyl-3-cyclopentylpyrrolidin-2-one | $^1$H NMR (300 MHz, CDCl$_3$): δ 7.34-7.19 (m, 5H), 4.54-4.49 and 4.39-4.34 (ABq, 2H, 14.6 Hz), 3.20-3.13 (m, 2H), 2.57-2.49 (m, 1H), 2.26-1.90 (m, 4H), 1.77-1.51 (m, 5H), 1.41-1.19 (m, 2H); ESI (m/z): 244.2 (M + H). |
| 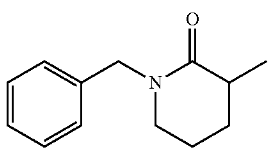 | 1-benzyl-3-methylpiperidin-2-one | $^1$H NMR (300 MHz, CDCl$_3$) δ 7.34-7.20 (m, 5H), 4.68-4.63, 4.52-4.47 (ABq, 2H, J = 14.7 Hz), 3.23-3.18 (dd, 2H, J = 5.3, 7.2 Hz), 2.52-2.45 (m, 1H), 2.02-1.68 (m, 3H), 1.59-1.47 (m, 1H), 1.31-1.29 (d, 3H, J = 7.2 Hz); ESI (m/z): 204.1 (M + H). |
| 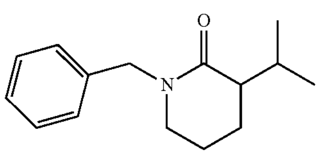 [SMILES: CC(C)C1CCCN(Cc2ccccc2)C1=O] | 1-benzyl-3-isopropylpiperidin-2-one | $^1$H NMR (300 MHz, CDCl$_3$): δ 7.33-7.21 (m, 5H), 4.71-4.65 and 4.56-4.21 (ABq, 2H, J = 14.7 Hz), 3.20-3.16 (m, 2H), 2.69-2.63 (m, 1H), 2.36-2.29 (m, 1H), 1.91-1.48 (m, 4H), 0.99-0.97 (d, 3H, J = 6.9 Hz), 0.88-0.86 (d, 3H, J = 6.9 Hz); ESI (m/z): 232.2 (M + H). |
| 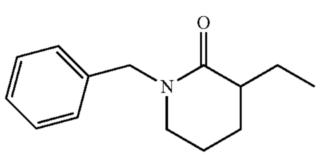 [SMILES: CCC1CCCN(Cc2ccccc2)C1=O] | 1-benzyl-3-ethylpiperidin-2-one | $^1$H NMR (300 MHz, CDCl$_3$): δ 7.33-7.21 (m, 5H), 4.58 (s, 2H), 3.21-3.17 (dd, 2H, J = 5.0, 6.9 Hz), 2.05-1.53 (m, 6H), 1.00-0.95 (t, 3H, J = 7.5 Hz); ESI (m/z): 218.2 (M + H). |
| 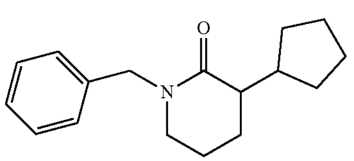 [SMILES: O=C1C(C2CCCC2)CCCN1Cc1ccccc1] | 1-benzyl-3-cyclopentylpiperidin-2-one | $^1$H NMR (300 MHz, CDCl$_3$): δ 7.33-7.20 (m, 5H), 4.71-4.67 and 4.51-4.46 (ABq, 2H, J = 14.7 Hz), 3.20-3.16 (m, 2H), 2.52-2.39 (m, 2H), 1.94-1.54 (m, 10H), 1.53-1.19 (m, 2H); ESI (m/z): 258.2 (M + H). |
| 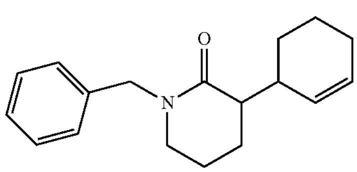 [SMILES: O=C1C(C2C=CCCC2)CCCN1Cc1ccccc1] | 1-benzyl-3-(cyclohex-2-en-1-yl)piperidin-2-one | ESI (m/z): 270.2 (M + H). |

Preparation 14: 1-benzyl-3-cyclohexylpiperidin-2-one

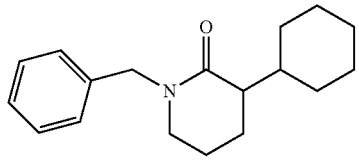 [SMILES: O=C1C(C2CCCCC2)CCCN1Cc1ccccc1]

Under a nitrogen atmosphere, 10% palladium on carbon (0.09 g) was added to a solution of 1-benzyl-3-(cyclohex-2-en-1-yl)piperidin-2-one (0.6 g, 2.3 mmol) in ethanol (10 mL). The mixture was placed under an atmosphere of hydrogen and stirred for 2 days. The suspension was filtered through Celite and concentrated under reduced pressure to afford the desired product as a clear liquid (0.578 g, 98%). $^1$H NMR (300 MHz, CDCl$_3$): δ 7.33-7.22 (m, 5H), 4.66-4.61 and 4.59-4.54 (ABq, 2H, J=14.7 Hz), 3.19-3.14 (m, 2H), 2.34-2.21 (m, 2H), 1.86-1.52 (m, 9H), 1.39-1.04 (m, 5H); ESI (m/z): 272.2 (M+H).

Preparation 15: 1-benzyl-3-phenylpiperidin-2-one

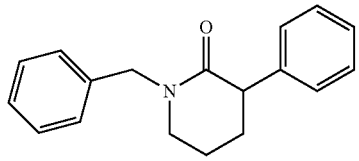 [SMILES: O=C1C(c2ccccc2)CCCN1Cc1ccccc1]

Synthesized according to the procedure from de Filippis, A. et al. *Tetrahedron*, 2004, 60, 9757. To a cold (−20° C.) stirred solution of N-benzyl-2-piperidinone (1.326 g, 7.0 mmol, 2.2 equiv.) in anhydrous tetrahydrofuran (14 mL, 0.5 M) was added lithium bis(trimethylsilyl)amide (6.4 mL of a 1 M solution in anhydrous tetrahydrofuran, 6.4 mmol, 2.0 equiv.) and the mixture was stirred for 20 mins at −20° C. A solution of zinc chloride (0.955 g, 7.0 mmol, 2.2 equiv.) in anhydrous tetrahydrofuran (8 mL) was added and the solution stirred for 20 mins at −20° C. The resulting solution was cannulated into a solution of 2-dicyclohexylphosphino-2'-(N,N-dimethylamino)biphenyl (0.094 g), tris(dibenzylideneacetone)dipalladium(0) (0.092 g), and bromobenzene (0.335 mL, 3.2 mmol, 1.0 equiv.) in anhydrous tetrahydrofuran (6 mL), and the resultant mixture was heated at 70° C. for 6 hrs. The reaction was quenched with aqueous ammonium chloride and extracted with ethyl acetate. The organic fraction was washed with saturated aqueous sodium chloride, dried over anhydrous sodium sulfate, filtered and concentrated in vacuo. The crude product was purified by silica gel column chromatography, eluting with a gradient of 15-60% ethyl acetate in hexanes to give a yellow liquid (0.629 g, 74%). $^1$H NMR (300 MHz, CDCl$_3$): δ 7.38-7.21 (m, 10H), 4.74-4.69 and 4.66-4.61 (AB, 2H, J=14.4 Hz), 3.77-3.72 (dd, 1H, J=6.0, 8.1 Hz), 3.41-3.28 (m, 2H), 2.23-2.13 (m, 1H), 2.05-1.69 (m, 3H).

Preparation 16: 3-methylpyrrolidin-2-one

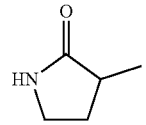

Trifluoromethanesulfonic acid (0.604 mL, 6.8 mmol, 4.0 equiv.) was added to a solution of 1-benzyl-3-methylpyrrolidin-2-one (0.323 g, 1.7 mmol, 1.0 equiv.) in toluene (2 mL, 1 M). The mixture was heated at 195° C. in a microwave reactor for 25 mins. The mixture was poured into a small amount of saturated aqueous sodium bicarbonate, extracted with ethyl acetate, washed with saturated aqueous sodium chloride, and the combined aqueous layers extracted again with ethyl acetate. The combined organic fractions were dried over anhydrous sodium sulfate, filtered, and concentrated in vacuo. The crude residue was purified by silica gel column chromatography eluting with 0-10% methanol in methylene chloride to give the desired product (0.087 g). $^1$H NMR (300 MHz, CDCl$_3$): δ 6.49 (br s), 3.37-3.26 (m, 2H), 2.53-2.28 (m, 2H), 1.80-1.65 (m, 1H), 1.21-1.19 (d, 3H, J=6.6 Hz).

The following compounds were prepared analogously:

| Structure | Name | Characterization |
|---|---|---|
| 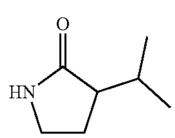 | 3-isopropylpyrrolidin-2-one | $^1$H NMR (300 MHz, CDCl$_3$): δ 6.01 (br s, 1H), 3.30-3.28 (m, 2H), 2.39-2.32 (m, 1H), 2.27-2.05 (m, 2H), 1.99-1.86 (m, 1H), 1.02-0.99 (d, 3H, J = 6.6 Hz), 0.91-0.88 (d, 3H, J = 6.6 Hz). ESI (m/z): 128.2 (M + H). |
| 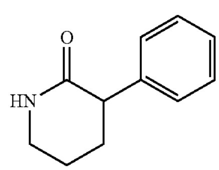 [SMILES: O=C1NCCCC1c1ccccc1] | 3-phenylpiperidin-2-one | $^1$H NMR (300 MHz, CDCl$_3$): δ 7.38-7.13 (m, 5H), 6.02 (br s, 1H), 3.67-3.63 (dd, 1H, J = 6.3, 8.3 Hz), 3.49-3.41 (m, 2H), 2.25-1.75 (m, 4H). ESI (m/z): 176.2 (M + H). |
| 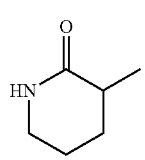 | 3-methylpiperidin-2-one | $^1$H NMR (300 MHz, CDCl$_3$): δ 5.83 (br s, 1H), 3.33-3.28 (m, 2H), 2.40-2.32 (m, 1H), 2.02-1.69 (m, 3H), 1.59-1.46 (m, 1H), 1.26-1.24 (d, 3H, J = 7.2 Hz). |

| Structure | Name | Characterization |
|---|---|---|
| 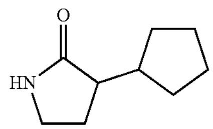 [SMILES: O=C1NCCC1C1CCCC1] | 3-cyclopentylpyrrolidin-2-one | $^1$H NMR (300 MHz, CDCl$_3$): δ 5.56 (br s, 1H), 3.34-3.28 (m, 2H), 2.44-2.36 (m, 1H), 2.27-2.13 (m, 2H), 1.96-1.87 (m, 2H), 1.77-1.54 (m, 5H), 1.40-1.26 (m, 2H). ESI (m/z): 154.2 (M + H). |
| 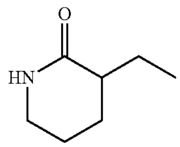 | 3-ethylpiperidin-2-one | $^1$H NMR (300 MHz, CDCl$_3$): δ 5.91 (br s, 1H), 3.31-3.26 (m, 2H), 2.27-2.17 (m, 1H), 1.99-1.47 (m, 6H), 1.00-0.93 (t, 3H, J = 7.8 Hz). |
| 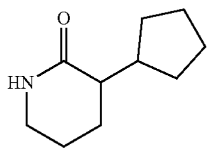 [SMILES: O=C1NCCCC1C1CCCC1] | 3-cyclopentylpiperidin-2-one | $^1$H NMR (300 MHz, CDCl$_3$): δ 5.75 (br s, 1H), 3.31-3.24 (m, 2H), 2.46-2.29 (m, 2H), 1.94-1.19 (m, 12H); ESI (m/z): 168.2 (M + H). |
| 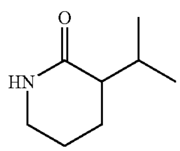 | 3-isopropylpiperidin-2-one | $^1$H NMR (300 MHz, CDCl$_3$): δ 5.92 (br s, 1H), 3.34-3.15 (m, 2H), 2.60-2.49 (m, 1H), 2.28-2.21 (m, 1H), 1.94-1.47 (m, 4H), 0.98-0.95 (d, 3H, J = 6.9 Hz), 0.88-0.85 (d, 3 Hz, J = 7.2 Hz); ESI (m/z): 142.2 (M + H). |
| 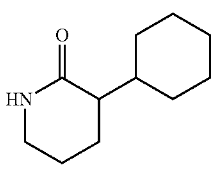 [SMILES: O=C1NCCCC1C1CCCCC1] | 3-cyclohexylpiperidin-2-one | $^1$H NMR (300 MHz, CDCl$_3$): δ 5.89 (br s, 1H), 3.30-3.19 (m, 2H), 2.26-2.10 (m, 2H), 1.91-1.03 (m, 14H); ESI (m/z): 182.2 (M + H). |

Preparation 17:
1-benzyl-3-(1-hydroxycyclobutyl)pyrrolidin-2-one

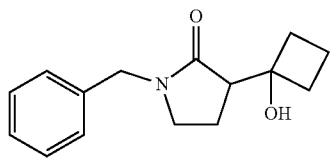 [SMILES: O=C1C(C2(O)CCC2)CCN1Cc1ccccc1]

To a cold (−78° C.) solution of 1-benzyl-2-pyrrolidinone (1.0 g, 5.7 mmol, 1.0 equiv.) in anhydrous tetrahydrofuran (19 mL) was added lithium diisopropylamide (3.15 mL of a 2 M solution in tetrahydrofuran, 1.1 eq.) and the mixture stirred for 1 hr at −78° C. Cyclobutanone (0.426 mL, 5.7 mmol, 1.0 equiv.) and boron trifluoride diethyl etherate (0.704 mL, 5.7 mmol, 1.0 equiv.) were added and the reaction mixture stirred at −78° C. for 4 hrs. The reaction was quenched with saturated aqueous ammonium chloride and extracted with ethyl acetate. The organic fraction was washed with saturated aqueous sodium chloride, dried over anhydrous sodium sulfate, filtered and concentrated under reduced pressure. The crude product was purified by silica gel column chromatography eluting from silica gel with a gradient of 50-100% ethyl acetate in hexanes to give a white solid (0.714 g, 51%). $^1$H NMR (300 MHz, CDCl$_3$): δ 7.36-7.20 (m, 5H), 4.56-4.51 and 4.42-4.37 (AB, 2H, J=14.7 Hz), 4.24 (s, 1H), 3.28-3.21 (m, 2H), 2.78-2.72 (t, 1H, J=2.7 Hz), 2.34-1.89 (m, 7H), 1.66-1.52 (m, 1H); ESI (m/z): 246.0 (M+H).

The following compound was prepared analogously:

| Structure | Name | Characterization |
|---|---|---|
| 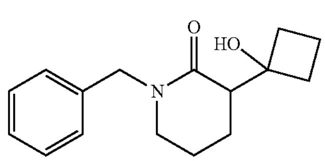 [SMILES: O=C1C(C2(O)CCC2)CCCN1Cc1ccccc1] | 1-benzyl-3-(1-hydroxycyclobutyl)piperidin-2-one | $^1$H NMR (300 MHz, CDCl$_3$): δ 7.38-7.21 (m, 5H), 5.35 (s, 1H), 4.67-4.62 and 4.55-4.50 (ABq, 2H, J = 14.3 Hz), 3.26-3.22 (m, 2H), 2.55-2.49 (m, 2H), 2.37-2.34 (m, 1H), 2.33-2.28 (m, 1H), 2.20-1.57 (m, 9H); ESI (m/z): 260.1 (M + H). |

Preparation 18:
1-benzyl-3-cyclobutylidenepyrrolidin-2-one

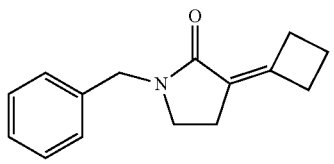 [SMILES: O=C1C(=C2CCC2)CCN1Cc1ccccc1]

To a cold (0° C.) solution of 1-benzyl-3-(1-hydroxycyclobutyl)pyrrolidin-2-one (0.7 g, 2.9 mmol, 1.0 equiv.) in anhydrous methylene chloride (12 mL) was added N,N-diisopropylethylamine (2.485 mL, 14.3 mmol, 5.0 equiv.), N,N-4-dimethylaminopyridine (0.07 g, 0.6 mmol, 0.2 equiv.), and methanesulfonyl chloride (0.331 mL, 4.3 mmol, 1.5 equiv.). The mixture was stirred at 0° C. for 2 hrs, 16 hrs at room temperature, and at reflux for 3 hrs. The mixture was cooled to room temperature and partitioned between ethyl acetate and saturated aqueous ammonium chloride. The organic layer was washed with saturated aqueous sodium chloride, dried over anhydrous sodium sulfate, filtered and concentrated in vacuo to afford an orange oil. The crude product was purified by silica gel column chromatography, eluting with a gradient of 20-60% ethyl acetate in hexanes to give a yellow oil (0.25 g, 38%). $^1$H NMR (300 MHz, CDCl$_3$): δ 7.33-7.23 (m, 5H), 4.47 (s, 2H), 3.27-3.19 (m, 4H), 2.75-2.69 (m, 2H), 2.52-2.46 (m, 2H), 2.18-2.08 (quint, 2H, J=7.8 Hz); ESI (m/z): 228.2 (M+H).

The following compound was prepared analogously:

| Structure | Name | Characterization |
|---|---|---|
| 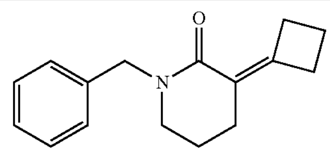 [SMILES: O=C1C(=C2CCC2)CCCN1Cc1ccccc1] | 1-benzyl-3-cyclobutylidene-piperidin-2-one | $^1$H NMR (300 MHz, CDCl$_3$): δ 7.30-7.23 (m, 5H), 4.62 (s, 2H), 3.28-3.22 (m, 4H), 2.78-2.72 (m, 2H), 2.34-2.29 (m, 2H), 2.12-2.02 (quint, 2H, J = 6.9 Hz), 1.82-1.76 (m, 2H); ESI (m/z): 242.2 (M + H). |

Preparation 19:
1-benzyl-3-cyclobutylpyrrolidin-2-one

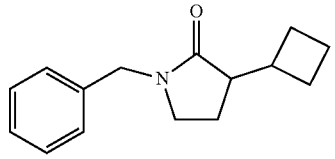 [SMILES: O=C1C(C2CCC2)CCN1Cc1ccccc1]

To a solution of 1-benzyl-3-cyclobutylidenepyrrolidin-2-one (0.25 g, 1.0 mmol) in ethanol (11 mL) was added 10% palladium on carbon (0.05 g), and the reaction mixture stirred under an atmosphere of hydrogen for 72 hrs. The mixture was filtered through Celite and concentrated under reduced pressure to afford a clear oil (0.242 g, 100%). $^1$H NMR (300 MHz, CDCl$_3$): δ 7.34-7.20 (m, 5H), 4.49-4.47 and 4.40-4.35 (ABq, 2H, J=14.4 Hz), 3.18-3.13 (m, 2H), 2.69-2.47 (m, 2H), 2.20-1.64 (m, 8H); ESI (m/z): 230.2 (M+H).

The following compound was prepared analogously:

| Structure | Name | $^1$H NMR |
|---|---|---|
| 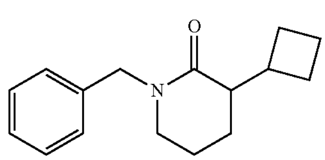 [SMILES: O=C1C(C2CCC2)CCCN1Cc1ccccc1] | 1-benzyl-3-cyclobutylpiperidin-2-one | (300 MHz, CDCl$_3$): δ 7.34-7.20 (m, 5H), 4.55 (s, 2H), 3.19-3.14 (dd, 2H, J = 5.4, 6.9 Hz), 2.71-2.59 (m, 1H), 2.39-1.47 (m, 11H). |

Preparation 20: 3-cyclobutylpyrrolidin-2-one

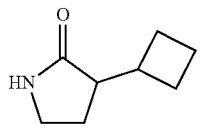

Prepared from 1-benzyl-3-cyclobutylpyrrolidin-2-one analogously to Preparation 18. $^1$H NMR (300 MHz, CDCl$_3$): δ 5.45 (br s, 1H), 3.34-3.27 (m, 2H), 2.65-2.54 (m, 1H), 2.43-2.35 (m, 1H), 2.28-1.79 (m, 8H).

The following compound was prepared analogously:

| Structure | Name | $^1$H NMR |
|---|---|---|
| 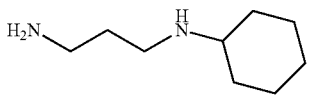 | 3-cyclobutylpiperidin-2-one | (300 MHz, CDCl$_3$): δ 5.47 (br s, 1H), 3.30-3.23 (m, 2H), 2.70-2.56 (m, 1H), 2.30-1.66 (m, 10H), 1.57-1.44 (m, 1H). |

Preparation 21: N1-cyclohexylethane-1,2-diamine

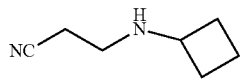

To a mixture of cyclohexanone (6.26 g, 63.8 mmol), ethylenediamine (42.64 mL, 637.8 mmol, 10.0 equiv.), acetic acid (36.515 mL, 637.8 mmol, 10.0 equiv.), and 4 Å molecular sieves (25 g) in anhydrous methanol (250 mL) was added sodium cyanoborohydride (8.017 g, 127.6 mmol, 2.0 equiv.). The mixture was stirred for 48 hrs, filtered to remove solids, and concentrated to a semi-solid. The crude material was dissolved in 3 N aqueous sodium hydroxide (150 mL) and extracted with methylene chloride three times. The combined organic fractions were washed with a slightly basic saturated aqueous sodium chloride solution, dried over anhydrous sodium sulfate, filtered, and concentrated in vacuo to afford a pale yellow liquid, which was purified by vacuum distillation to give a clear liquid (4.1 g, 45%). $^1$H NMR (300 MHz, CDCl$_3$): δ 2.80-2.76 (td, 2H, J=0.9, 6.0 Hz), 2.68-2.64 (td, 2H, J=0.9, 6.0 Hz), 2.43-2.34 (m, 1H), 1.89-1.83 (m, 2H), 1.74-1.70 (m, 2H), 1.62-1.57 (m, 1H), 1.32-0.98 (m, 8H).

Preparation 22: 3-(cyclobutylamino)propanenitrile

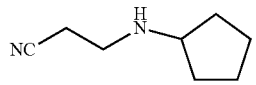

At room temperature, cyclobutylamine (5.90 mL, 59.8 mmol, 1.0 equiv.) was added dropwise, over 15 mins to a solution of acrylonitrile (4.76 g, 89.7 mmol, 1.5 equiv.) in methanol (7 mL). The mixture was stirred at room temperature for 30 mins and at reflux for 1 hr, cooled to room temperature, concentrated under reduced pressure and the desired product distilled under vacuum to provide a clear liquid (7.7 g, 98%). $^1$H NMR (300 MHz, CDCl$_3$): δ 3.29-3.21 (m, 1H), 2.88-2.83 (t, 2H, J=6.6 Hz), 2.50-2.46 (t, 2H, J=6.6 Hz), 2.26-2.20 (m, 2H), 1.76-1.63 (m, 4H), 1.30 (br s, 1H).

Preparation 23: N1-cyclobutylpropane-1,3-diamine

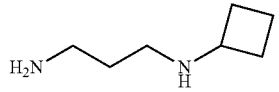

To a cooled (0° C.) suspension of lithium aluminum hydride (3.056 g, 80.5 mmol, 2.0 equiv.) in anhydrous ether (120 mL) was added a solution of 3-(cyclobutylamino)propanenitrile (5.0 g, 40.3 mmol, 1.0 equiv.) in anhydrous diethyl ether (40 mL) dropwise over 45 mins. The reaction mixture was stirred at room temperature for 15 mins and at reflux for 4 hrs, cooled to room temperature and stirred for 1 hr. The mixture was cooled to 0° C. and vigorously stirred while water (3.1 mL) was added dropwise, followed by 15% aqueous sodium hydroxide (3.1 mL), and finally water (9.3 mL). The resultant slurry was warmed to room temperature, stirred for 15 mins, and magnesium sulfate was added, stirring for additional 15 mins. Solid materials were removed by filtration through a glass fritted filter, washing multiple times with warm methylene chloride, and the organic solution was concentrated under reduced pressure to give the desired product as a pale yellow liquid (3.44 g, 66%). $^1$H NMR (300 MHz, CDCl$_3$): δ 3.14 (m, 1H), 2.69-2.62 (m, 2H), 2.53-2.45 (m, 2H), 2.13-2.10 (m, 2H), 1.56-1.48 (m, 6H), 1.33 (br s, 3H).

Preparation 24: 3-(cyclopentylamino)propanenitrile

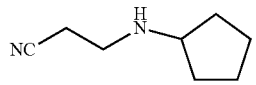

At room temperature, cyclopentylamine (5.794 mL, 58.7 mmol, 1.0 equiv.) was added dropwise to a solution of acrylonitrile (5.79 mL, 88.1 mmol, 1.5 equiv.) in methanol (7 mL). The solution was stirred at room temperature for 30 mins and at reflux for 1 hr, cooled to room temperature, concentrated under reduced pressure and the desired product distilled under vacuum to provide a clear liquid (7.4 g, 91%). $^1$H NMR (300 MHz, CDCl$_3$): δ 3.14-3.04 (quin, 1H, J=6.3 Hz), 2.91-2.87 (t, 2H, J=6.9 Hz), 2.53-2.48 (td, 2H, J=0.9, 6.9 Hz), 1.88-1.78 (m, 2H), 1.73-1.49 (m, 4H), 1.36-1.24 (m, 2H), 1.19 (br s, 1H).

Preparation 25: N1-cyclopentylpropane-1,3-diamine

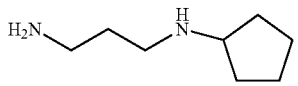

To a cooled (0° C.) suspension of lithium aluminum hydride (3.295 g, 86.8 mmol, 2.0 equiv.) in anhydrous diethyl ether (150 mL) was added a solution of 3-(cyclopentylamino)propanenitrile (6.0 g, 43.4 mmol, 1.0 equiv.) in anhydrous diethyl ether (40 mL), dropwise over 45 mins. The reaction mixture was stirred at room temperature for 15 mins and at reflux for 4 hrs, cooled to room temperature and stirred for 1 hr. The mixture was cooled to 0° C. and vigorously stirred while water (3.4 mL) was added dropwise, followed by 15% aqueous sodium hydroxide (3.4 mL), and finally water (10.2 mL). The resultant slurry was warmed to room temperature, stirred for 15 mins, and magnesium sulfate was added, stirring for an additional 15 mins. Solid materials were removed by filtration through a glass fritted filter, washing multiple times with warm methylene chloride, and the organic solution was concentrated under reduced pressure to give the desired product as a clear oil (4.5 g, 73%). $^1$H NMR (300 MHz, CDCl$_3$): δ 3.05-2.96 (quint, 1H, J=6.6 Hz), 2.74-2.71 (t, 2H, J=6.6 Hz), 2.68-2.58 (t, 2H, J=6.9 Hz), 1.85-1.68 (m, 2H), 1.62-1.42 (m, 6H), 1.34 (br s, 3H), 1.30-1.21 (m, 2H).

Preparation 26: 1-((3-(cyclohexylamino)propyl)amino)-3-(3,6-difluoro-9H-carbazol-9-yl)-2-methyl-propan-2-ol; General procedure

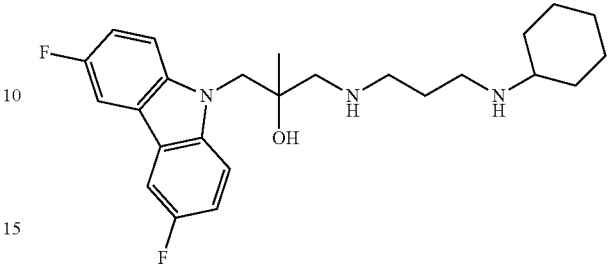

To a solution of a N-cyclohexyl-1,3-propanediamine (or other N-functionalized 1,3-propanediamine, 8.0 equiv.) in ethanol (1 M) was added 3,6-difluoro-9-((2-methyloxiran-2-yl)methyl)-9H-carbazole (1.0 eq, or alternatively 3,6-difluoro-9-(oxiran-2-ylmethyl)-9H-carbazole) and the reaction mixture was stirred at 70° C. for 16 hrs or until reaction was determined complete by LCMS, cooled to room temperature, concentrated in vacuo to give a crude residue, which was purified by column chromatography, eluting from HP silica gel with an appropriate gradient of methanol in methylene chloride and 0.1% triethylamine to give the desired product.

| Structure | Name | Characterization |
|---|---|---|
| 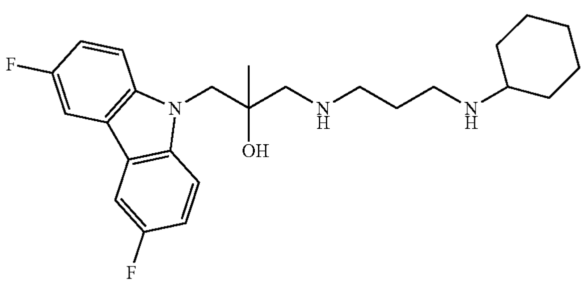 | 1-((3-(cyclohexylamino)propyl)amino)-3-(3,6-difluoro-9H-carbazol-9-yl)-2-methylpropan-2-ol | $^1$H NMR (300 MHz, CDCl$_3$): δ 7.63-7.60 (dd, 2H, J = 2.6, 8.6 Hz), 7.49-7.45 (dd, 2H, J = 4.2, 9.0 Hz), 7.20-7.13 (td, 2H, J = 2.4, 9.0 Hz), 2.68-2.53 (m, 6H), 2.36-2.29 (m, 1H), 1.84-1.50 (m, 6H), 1.30-0.94 (m, 6H), 1.23 (s, 3H); ESI (m/z): 430.3 (M + H). |
| 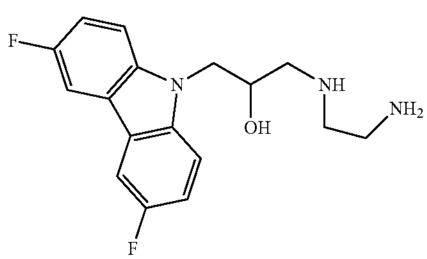 [SMILES: NCCNCC(O)Cn1c2ccc(F)cc2c2cc(F)ccc21] | 1-((2-aminoethyl)amino)-3-(3,6-difluoro-9H-carbazol-9-yl)propan-2-ol | $^1$H NMR (300 MHz, CDCl$_3$): δ 7.68-7.64 (dd, 2H, J = 2.3, 9.0 Hz), 7.41-7.37 (dd, 2H, J = 4.0, 9.0 Hz), 7.23-7.16 (td, 2H, J = 2.4, 9.0 Hz), 4.33-4.31 (d, 2H, J = 5.7 Hz), 4.16-4.09, (m, 1H), 2.80-2.70 (m, 3H), 2.63-2.55 (m, 3H), 1.74 (br s, 4H); ESI (m/z): 320.1 (M + H); HPLC analysis: (C18, 10-90% acetonitrile in water + 0.1% trifluoroacetic acid over 20 min: retention time, % area at 254 nm): 7.39 min, 97%. |
| 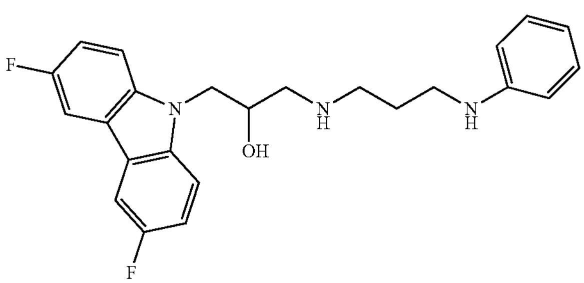 [SMILES: OC(CNCCCNc1ccccc1)Cn1c2ccc(F)cc2c2cc(F)ccc21] | 1-(3,6-difluoro-9H-carbazol-9-yl)-3-((3-(phenylamino)propyl)amino)propan-2-ol | $^1$H NMR (300 MHz, CDCl$_3$): δ 7.65-7.62 (dd, 2H, J = 2.7, 8.7 Hz), 7.45-7.41 (dd, 2H, J = 4.2, 9.0 Hz), 7.25-7.13 (m, 3H), 6.72-6.66 (tt, 1H, J = 1.1, 8.7 Hz), 6.59-6.55 (m, 2H), 4.34-4.32 (d, 2H, J = 5.4 Hz), 4.17-4.11 (m, 1H), 3.17-3.13 (t, 2H, J = 6.8 Hz), 2.81-2.56 (m, 6H), 1.79-1.70 (m, 2H); ESI (m/z): 410.2 (M + H). |

-continued

| Structure | Name | Characterization |
|---|---|---|
| 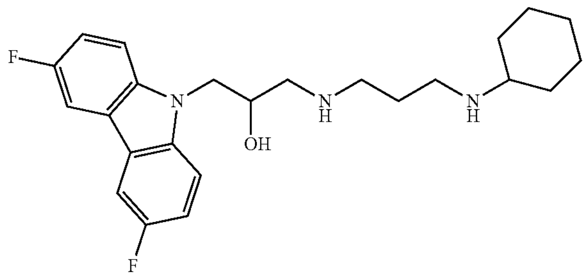 [SMILES: OC(CNCCCNC1CCCCC1)Cn1c2ccc(F)cc2c2cc(F)ccc21] | 1-((3-(cyclohexylamino)propyl)amino)-3-(3,6-difluoro-9H-carbazol-9-yl)propan-2-ol: | $^1$H NMR (300 MHz, CDCl$_3$): δ 7.66-7.62 (dd, 2H, J = 2.7, 8.7 Hz), 7.40-7.35 (dd, 2H, J = 4.2, 9.0 Hz), 7.22-7.15 (td, 2H, J = 2.5, 9.0 Hz), 4.29-4.27 (d, 2H, J = 5.4 Hz), 4.11-4.06 (m, 1H), 2.72-2.62 (dd, 1H, J = 3.6, 12.0 Hz), 2.68-2.47 (m, 5H), 2.35-2.26 (tt, 1H, J = 3.6, 10.7 Hz), 1.80-1.49 (m, 7H), 1.26-0.93 (m, 7H). |
| 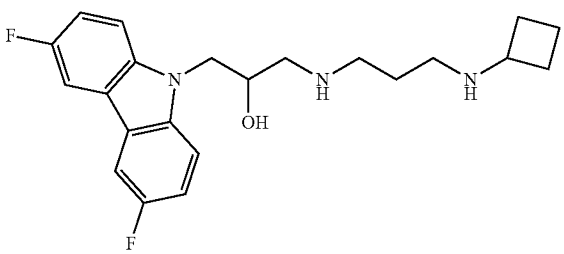 [SMILES: OC(CNCCCNC1CCC1)Cn1c2ccc(F)cc2c2cc(F)ccc21] | 1-((3-(cyclobutylamino)propyl)amino)-3-(3,6-difluoro-9H-carbazol-9-yl)propan-2-ol | $^1$H NMR (300 MHz, CDCl$_3$): δ 7.65-7.61 (dd, 2H, J = 2.6, 8.6 Hz), 7.39-7.34 (dd, 2H, J = 4.2, 8.7 Hz), 7.22-7.14 (m, 2H), 4.27-4.21 (m, 2H), 4.10-4.03 (m, 1H), 3.14-1.44 (m, 10H). |
| 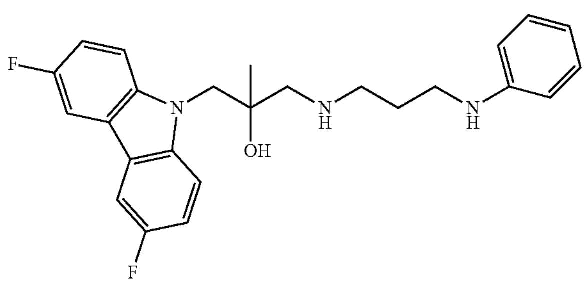 [SMILES: CC(O)(CNCCCNc1ccccc1)Cn1c2ccc(F)cc2c2cc(F)ccc21] | 1-(3,6-difluoro-9H-carbazol-9-yl)-2-methyl-3-((3-(phenylamino)propyl)amino)propan-2-ol | $^1$H NMR (300 MHz, CDCl$_3$): δ 7.66-7.63 (dd, 2H, J = 2.6, 8.9 Hz), 7.50-7.45 (dd, 2H, J = 4.2, 9.0 Hz), 7.22-7.14 (m, 4H), 6.73-6.67 (tt, 1H, J = 1.0, 7.4 Hz), 6.57-6.54 (m, 2H), 4.27 (d, 2H, J = 1.5 Hz), 3.12-3.07 (t, 2H, J = 6.8 Hz), 2.73-2.63 (m, 5H), 1.79-1.67 (quint, 2H, J = 6.8 Hz), 1.28 (s, 3H); ESI (m/z): 424.2 (M + H). |
| 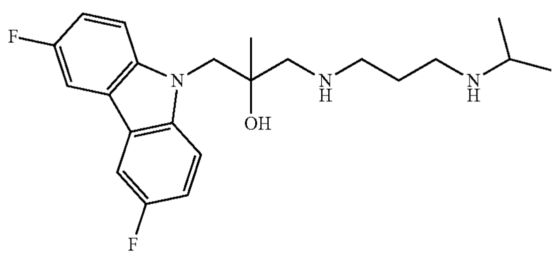 [SMILES: CC(C)NCCCNCC(C)(O)Cn1c2ccc(F)cc2c2cc(F)ccc21] | 1-(3,6-difluoro-9H-carbazol-9-yl)-3-((3-(isopropylamino)propyl)amino)-2-methylpropan-2-ol | $^1$H NMR (300 MHz, CDCl$_3$): δ 7.64-7.60 (dd, 2H, J = 2.6, 8.6 Hz), 7.48-7.44 (dd, 2H, J = 4.2, 9.0 Hz), 7.19-7.13 (td, 2H, J = 2.6, 9.0 Hz), 4.20 (s, 2H), 2.78-2.51 (m, 8H), 1.62-1.53 (quint, 2H, J = 6.7 Hz), 1.22 (s, 3H), 1.05-1.03 (d, 3H, J = 6.3 Hz), 1.04-1.02 (d, 3H, J = 6.3 Hz); ESI (m/z): 390.2 (M + H). |
| 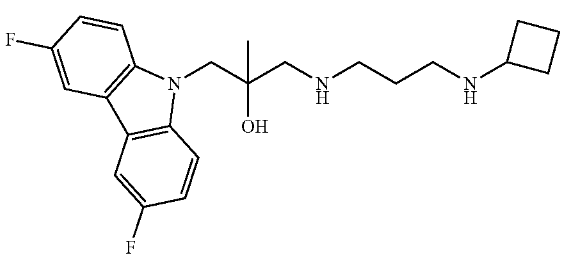 [SMILES: CC(O)(CNCCCNC1CCC1)Cn1c2ccc(F)cc2c2cc(F)ccc21] | 1-((3-(cyclobutylamino)propyl)amino)-3-(3,6-difluoro-9H-carbazol-9-yl)-2-methylpropan-2-ol | $^1$H NMR (300 MHz, CDCl$_3$): δ 7.66-7.62 (dd, 2H, J = 2.6, 9.0 Hz), 7.55-7.51 (dd, 2H, J = 4.2, 9.0 Hz), 7.23-7.16 (td, 2H, J = 2.6, 9.0 Hz), 4.38-4.27 (m, 2H), 3.38-3.29 (quint, 1H, J = 8.0 Hz), 3.00-2.96 (d, 1H, J = 12.3 Hz), 2.86-2.71 (m, 3H), 2.24-1.66 (m, 6H), 1.28 (s, 3H); ESI (m/z): 402.2 (M + H). |
| 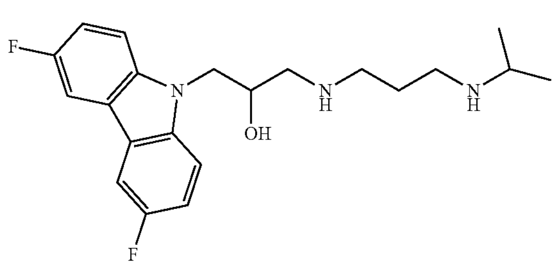 [SMILES: CC(C)NCCCNCC(O)Cn1c2ccc(F)cc2c2cc(F)ccc21] | 1-(3,6-difluoro-9H-carbazol-9-yl)-3-((3-(isopropylamino)propyl)amino)propan-2-ol | $^1$H NMR (300 MHz, CDCl$_3$) δ 7.66-7.62 (dd, 2H, J = 2.7, 8.7 Hz), 7.39-7.35 (dd, 2H, J = 4.2, 9.0 Hz), 7.21-7.15 (td, 2H, J = 2.5, 9.0 Hz), 4.29-4.27 (d, 2H, J = 5.4 Hz), 4.12-4.04 (m, 1H), 2.75-2.44 (m, 8H), 1.57-1.48 (quint, 2H, J = 6.9 Hz), 1.01-0.98 (d, 6H, J = 6.3 Hz); ESI (m/z): 376.2 (M + H). |

| Structure | Name | Characterization |
|---|---|---|
| 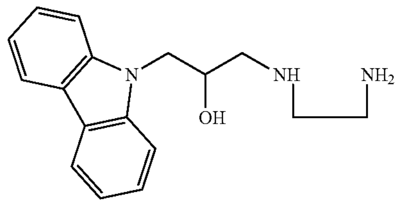 [SMILES: NCCNCC(O)Cn1c2ccccc2c2ccccc21] | 1-((2-aminoethyl)amino)-3-(9H-carbazol-9-yl)propan-2-ol | $^1$H NMR (300 MHz, CDCl$_3$): δ 8.09 (m, 2H), 7.50-7.42 (m, 4H), 7.25-7.20 (m, 2H), 4.44-4.35 (m, 2H), 4.22-4.14 (m, 1H), 2.78-2.53 (m, 7H), 1.64 (br s, 3H); ESI (m/z): 284.1 (M + H); HPLC analysis: (C18, 10-90% acetonitrile in water + 0.1% trifluoroacetic acid over 20 min: retention time, % area at 254 nm): 6.5 min, 94%. |

Preparation 27: tert-butyl (1-amino-1-oxopropan-2-yl)carbamate

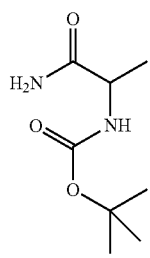

A mixture of Boc-DL-alanine (5.0 g, 26.4 mmol, 1.0 equiv.), N,N,N',N'-tetramethyl-O-(1H-benzotriazol-1-yl) uronium hexafluorophosphate (15.033 g, 39.6 mmol, 1.5 equiv.), N,N-diisopropylethylamine (8.735 mL, 52.9 mmol, 2.0 equiv.) and anhydrous dimethylformamide (50 mL) was stirred at room temperature for 20 mins, and then cooled with ice-water and ammonia (2.250 g, 132.1 mmol, 5.0 equiv.) was slowly bubbled into the mixture. The reaction was stirred at room temperature for 3 hrs in a sealed vessel. The reaction was diluted with water and extracted with ethyl acetate. The organic layers were washed with saturated aqueous sodium chloride, dried over anhydrous sodium sulfate, filtered and concentrated in vacuo. The obtained solids were washed with cold ethyl acetate and ether and dried to afford the product as a white powder (2.9 g, 58%). $^1$H NMR (300 MHz, CDCl$_3$): δ 6.20 (br s, 1H), 5.50 (br s, 1H), 5.00 (br s, 1H), 4.20 (m, 1H), 1.47 (s, 9H), 1.40 (d, 3H, J=7.2 Hz).

Preparation 28: tert-butyl (1-aminopropan-2-yl)carbamate

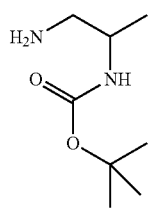

tert-butyl (1-amino-1-oxopropan-2-yl)carbamate (2.2 g) was dissolved in anhydrous tetrahydrofuran (100 mL) and borane (40 mL of 1 M solution in tetrahydrofuran) was added. The mixture was stirred at room temperature for 2 hrs and then heated at 90° C. for 2 hrs. After cooling to room temperature, the reaction was quenched with methanol until no bubbles were generated. The mixture was heated at 90° C. for 1 hr and then concentrated down to dryness to afford the crude product as a syrup (2.2 g), which was used directly for the next step reaction. $^1$H NMR (300 MHz, CDCl$_3$): δ 4.60 (br s, 1H), 3.65 (m, 1H), 2.76 (dd, 1H, J=12.9, 5.1 Hz), 2.64 (dd, 1H, J=12.9, 6.3 Hz), 1.47 (s, 9H), 1.14 (d, 3H, J=6.9 Hz).

Preparation 29: tert-butyl (1-((3-(3,6-difluoro-9H-carbazol-9-yl)-2-hydroxypropyl)amino)propan-2-yl)carbamate

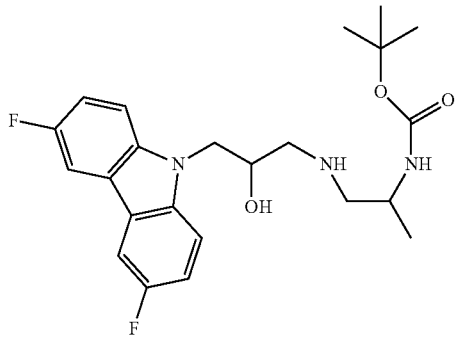 [SMILES: CC(CNCC(O)Cn1c2ccc(F)cc2c2cc(F)ccc21)NC(=O)OC(C)(C)C]

Under a nitrogen atmosphere, a solution of 3,6-difluoro-9-(oxiran-2-ylmethyl)-9H-carbazole (0.7 g) and tert-butyl (1-aminopropan-2-yl)carbamate (1.5 g) in ethanol (50 mL) was stirred at 70° C. for 16 hrs. The mixture was concentrated under reduced pressure and purified by silica gel column chromatography, eluting with a gradient of 0-20% methanol in methylene chloride to give an off-white foam (1.28 g). The product was used directly in the next step without additional purification: $^1$H NMR (300 MHz, CDCl$_3$): δ 7.67 (dd, 2H, J=8.7, 2.7 Hz), 7.42-7.37 (m, 2H), 7.22 (td, 2H, J=9.0, 2.7 Hz), 4.55-4.30 (m, 3H), 4.13 (m, 1H), 3.78 (br s, 1H), 2.88 and 2.82 (dd, 1H, J=12.0, 3.6 Hz), 2.70-2.50 (m, 3H), 1.45 (s, 9H), 1.13 and 1.11 (d, 3H, J=6.6 Hz); ESI (m/z): 434.0 (M+H).

Preparation 30: 3-(cyclopropylamino)propanenitrile

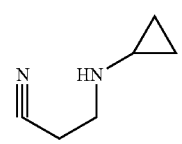

Cyclopropylamine (4.214 mL, 60.8 mmol, 1.0 equiv.) was added slowly to a solution of acrylonitrile (4.840 g, 91.2 mmol, 1.5 equiv.) in methanol (7 mL) at room temperature and stirred for 30 mins. The reaction was heated to reflux and stirred for 1 hour, cooled, concentrated and distilled under vacuum to give 5.5 g of clear liquid (5.5 g, 82%). $^1$H NMR (300 MHz; CDCl$_3$): δ 2.99 (t, 2H, J=6.3 Hz), 2.51 (t, 2H, J=6.3 Hz), 2.12 (m, 1H), 1.78 (br s, 1H), 0.49-0.32 (m, 4H); ESI (m/z): 111.5 (M+H).

Preparation 31: N1-cyclopropylpropane-1,3-diamine

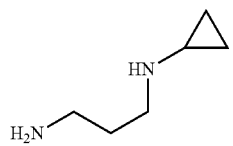

To a cooled (0° C.) suspension of lithium aluminum hydride (3.445 g, 90.8 mmol, 2.0 equiv.) in anhydrous tetrahydrofuran (120 mL) was slowly added over ten minutes a solution of 3-(cyclopropylamino)propanenitrile (5.000 g, 45.4 mmol, 1.0 equiv.) in anhydrous tetrahydrofuran (20 mL). The reaction was stirred at room temperature for 15 mins, than heated to reflux and stirred for 3 hours. The mixture was cooled to room temperature and sodium sulfate decahydrate was added until foaming stopped. The suspension was stirred for 10 mins and the solids filtered off (washing with tetrahydrofuran). The solution was concentrated under reduced pressure to give a crude product, which was used directly in the next step. $^1$H NMR (300 MHz, CDCl$_3$): δ 2.74-2.69 (m, 4H), 2.10-2.04 (m, 1H), 1.65-1.56 (m, 2H), 0.43-0.27 (m, 4H); ESI (m/z): 115.4 (M+H).

Preparation 32:
1-ethyltetrahydropyrimidin-2(1H)-one; General method for synthesis of ureas from diamines

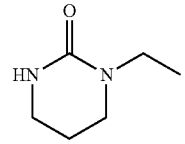

With vigorous stirring, the appropriate N-functionalized 1,3-propanediamine or 1,2-ethylenediamine (10.0 mmol, 1.0 equiv.) was added to a solution of 1,1'-carbonyldiimidazole (1.622 g, 10.0 mmol, 1.0 equiv.) in anhydrous tetrahydrofuran (0.05 M), which was kept at 0° C. with an external ice bath. The solution was allowed to slowly warm to room temperature and stirred for 16 hrs. The mixture was worked up by either: i) the mixture was concentrated under reduced pressure and purified by column chromatography eluting from silica gel with a gradient of methanol in methylene chloride to give the desired product; or ii) the mixture was diluted with ethyl acetate and successively washed twice with 1 N aqueous hydrochloric acid and once with saturated aqueous sodium chloride, back-extracting organic layer once with ethyl acetate, dried combined organic fractions over anhydrous sodium sulfate, filtered, and concentrated in vacuo to afford the desired product, which was used without further purification.

| Structure | Name | Characterization |
|---|---|---|
| 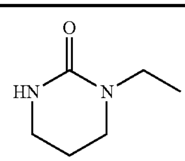 | 1-ethyltetrahydropyrimidin-2(1H)-one | $^1$H NMR (300 MHz, CDCl$_3$): δ 4.74 (br s, 1H), 3.40-3.33 (q, 2H, J = 6.9 Hz), 3.29-3.23 (m, 4H), 1.97-1.89 (quin, 2H, J = 5.9 Hz), 1.14-1.09 (t, 3H, J = 7.2 Hz). |
| 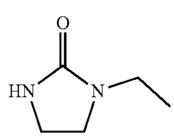 | 1-ethylimidazolidin-2-one | $^1$H NMR (300 MHz, CDCl$_3$): δ 3.44 (br s, 4H), 3.28-3.21 (q, 2H, J = 7.4 Hz), 2.08 (s 1H), 1.15-1.10 (t, 3H, J = 7.1 Hz). |
| 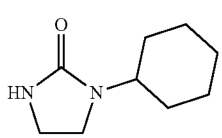 [SMILES: O=C1NCCN1C1CCCCC1] | 1-cyclohexylimidazolidin-2-one | $^1$H NMR (300 MHz, CDCl$_3$): δ 4.47 (s, 1H), 3.73-3.66 (m, 1H), 3.44-3.35 (m, 4H), 1.81-1.63 (m, 5H), 1.45-1.26 (m, 4H), 1.14-1.04 (m, 1H). |
| 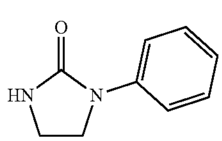 [SMILES: O=C1NCCN1c1ccccc1] | 1-phenylimidazolidin-2-one | $^1$H NMR (300 MHz, CDCl$_3$): δ 7.55-7.52 (m, 2H), 7.37-7.30 (m, 2H), 7.08-7.02 (m, 1H), 4.88 (s, 1H), 3.98-3.93 (m, 2H), 3.61-3.56 (t, 2H, J = 7.7 Hz). |
| 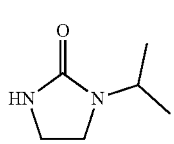 | 1-isopropylimidazolidin-2-one | $^1$H NMR (300 MHz, CDCl$_3$): δ 4.70 (s, 1H), 4.20-4.07 (sept, 1H, J = 6.9 Hz), 3.40-3.35 (m, 4H), 1.14-1.12 (d, 6H, J = 6.9 Hz). |

| Structure | Name | Characterization |
|---|---|---|
| 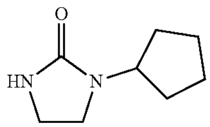 [SMILES: O=C1NCCN1C1CCCC1] | 1-cyclopentylimidazolidin-2-one | $^1$H NMR (300 MHz, CDCl$_3$): δ 4.45 (s, 1H), 4.32-4.24 (m, 1H), 3.42-3.41 (m, 4H), 1.87-1.77 (m, 2H), 1.71-1.45 (m, 6H). |
| 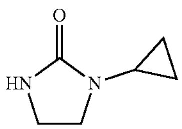 | 1-cyclopropylimidazolidin-2-one | $^1$H NMR (300 MHz, CDCl$_3$): δ 4.72 (s, 1H), 3.39-3.32 (m, 4H), 2.51-2.36 (m, 1H), 0.76-0.63 (m, 4H). |
| 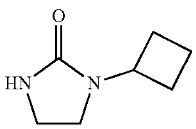 | 1-cyclobutylimidazolidin-2-one | $^1$H NMR (300 MHz, CDCl$_3$): δ 4.80 (s, 1H), 4.49-4.37 (m, 1H), 3.53-3.37 (m, 4H), 2.19-2.03 (m, 4H), 1.69-1.60 (m, 2H). |
| 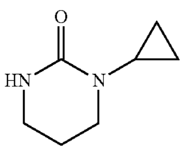 | 1-cyclopropyltetrahydropyrimidin-2(1H)-one | $^1$H NMR (300 MHz, CDCl$_3$): δ 3.57-3.52, 3.06-3.01 (ABq, 2H, J = 14.4 Hz), 3.42 (m, 4H), 2.68-2.67, 2.61-2.60 (ABq, 2H, J = 4.5 Hz), 2.43-2.36 (m, 1H), 1.33 (s, 3H), 0.74-0.62 (m, 4H); ESI (m/z): 197.1 (M + H). |
| 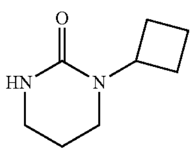 [SMILES: O=C1NCCCN1C1CCC1] | 1-cyclobutyltetrahydropyrimidin-2(1H)-one | $^1$H NMR (300 MHz, CDCl$_3$): δ 4.98-4.87 (quin, 1H, J = 8.9 Hz), 4.76 (br s, 1H), 3.30-3.23 (m, 4H), 2.13-2.04 (m, 4H), 1.96-1.88 (m, 2H), 1.66-1.58 (m, 2H). |

Preparation 31: 1-ethyl-3-(oxiran-2-ylmethyl)tetrahydropyrimidin-2(1H)-one; General method for preparation of (oxiran-2-ylmethyl)-functionalized ureas To a solution of 1-ethyltetrahydropyrimidin-2(1H)-one, or alternative cyclic urea generated in Preparation 6 (1.0 equiv.), in anhydrous tetrahdrofuran (0.2 M) was added 60% sodium hydride in mineral oil (1.1 equiv.) and the resultant suspension was stirred for 1 hour at room temperature. Epibromohydrin (3.0 equiv.) was added and the mixture stirred for 24 hrs at either room temperature or 35° C. Silica gel was added and the suspension concentrated under reduced pressure and directly purified by silica gel column chromatography—eluting the desired product with an appropriate gradient of methanol in methylene chloride.

| Structure | Name | Characterization |
|---|---|---|
| 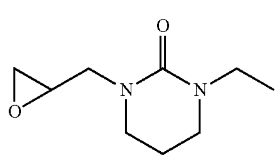 | 1-ethyl-3-(oxiran-2-ylmethyl)tetrahydropyrimidin-2(1H)-one | $^1$H NMR (300 MHz, CDCl$_3$): δ 3.95-3.90 (m, 1H), 3.44-3.20 (m, 6H), 3.11-3.00 (m, 2H), 2.73-2.70 (m, 1H), 2.49-2.47 (m, 1H), 1.96-1.88 (m, 2H), 1.09-1.04 (m, 3H). |
| 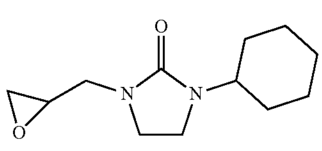 [SMILES: O=C1N(CC2CO2)CCN1C1CCCCC1] | 1-cyclohexyl-3-(oxiran-2-ylmethyl)imidazolidin-2-one | $^1$H NMR (300 MHz, CDCl$_3$): δ 3.78-3.72 (dd, 1H, J = 2.6, 14.6 Hz), 3.71-3.66 (m, 1H), 3.50-3.41 (m, 1H), 3.35-3.25 (m, 3H), 3.11-3.05 (m, 1H), 2.98-2.90 (dd, 1H, J = 6.6, 14.7 Hz), 2.78-2.75 (dd, 1H, J = 4.1, 4.5 Hz), 2.57-2.54 (dd, 1H, J = 2.3, 5.0 Hz), 1.80-1.62 (m, 5H), 1.40-1.30 (m, 4H), 1.09-1.05 (m, 1H). |

| Structure | Name | Characterization |
|---|---|---|
| 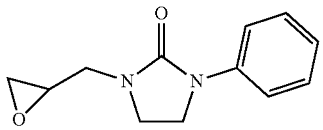 [SMILES: O=C1N(CC2CO2)CCN1c1ccccc1] | 1-(oxiran-2-ylmethyl)-3-phenylimidazolidin-2-one | $^1$H NMR (300 MHz, CDCl$_3$): δ 7.56-7.52 (m, 2H), 7.36-7.30 (m, 2H), 7.07-7.01 (m, 1H), 3.92-3.79 (m, 3H), 3.73-3.65 (m, 1H), 3.59-3.46 (m, 1H), 3.18-3.05 (m, 2H), 2.83-2.80 (t, 1H, J = 4.2 Hz), 2.63-2.60 (dd, 1H, J = 2.6, 4.7 Hz). |
| 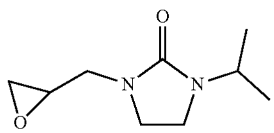 | 1-isopropyl-3-(oxiran-2-ylmethyl)imidazolidin-2-one | $^1$H NMR (300 MHz, CDCl$_3$): δ 4.21-4.08 (sept, 1H, J = 6.8 Hz), 3.78-3.73 (dd, 1H, J = 2.7, 14.7 Hz), 3.52-3.24 (m, 4H), 3.11-3.06 (m, 1H), 2.98-2.91 (dd, 1H, J = 6.6, 14.7 Hz), 2.79-2.76 (dd, 1H, J = 3.6, 4.8 Hz), 2.57-2.55 (dd, 1H, J = 2.7, 4.5 Hz), 1.47-1.12 (dd, 6H, J = 1.2, 6.9 Hz). |
| 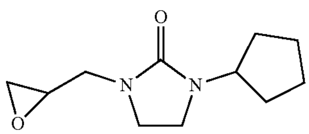 [SMILES: O=C1N(CC2CO2)CCN1C1CCCC1] | 1-cyclopentyl-3-(oxiran-2-ylmethyl)imidazolidin-2-one | $^1$H NMR (300 MHz, CDCl$_3$): δ 4.32-4.22 (quint, 1H, J = 8.0 Hz), 3.78-3.72 (dd, 1H, J = 2.7, 14.7 Hz), 3.51-3.26 (m, 4H), 3.09-3.06 (m, 1H), 2.97-2.90 (dd, 1H, J = 6.5, 14.6 Hz), 2.78-2.75 (t, 1H, J = 4.4 Hz), 2.57-2.54 (dd, 1H, J = 2.6, 4.7 Hz), 1.84-1.47 (m, 8H). |
| 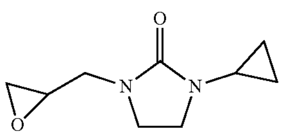 [SMILES: O=C1N(CC2CO2)CCN1C1CC1] | 1-cyclopropyl-3-(oxiran-2-ylmethyl)imidazolidin-2-one | $^1$H NMR (300 MHz, CDCl$_3$): δ 3.76-3.70 (dd, 1H, J = 3.0, 14.7 Hz), 3.47-3.28 (m, 4H), 3.09-3.03 (m, 1H), 2.97-2.90 (dd, 1H, J = 6.3, 14.7 Hz), 2.77-2.74 (t, 1H, J = 4.5 Hz), 2.56-2.53 (dd, 1H, J = 2.7, 4.8 Hz), 2.43-2.36 (m, 1H), 0.73-0.61 (m, 4H). |
| 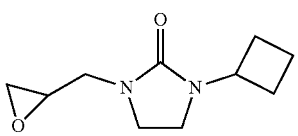 [SMILES: O=C1N(CC2CO2)CCN1C1CCC1] | 1-cyclobutyl-3-(oxiran-2-ylmethyl)imidazolidin-2-one | $^1$H NMR (300 MHz, CDCl$_3$): δ 4.50-4.38 (quint, 1H, J = 8.7 Hz), 3.77-3.71 (dd, 1H, J = 2.6, 14.6 Hz), 3.51-3.33 (m, 5H), 3.10-3.04 (m, 1H), 2.98-2.91 (dd, 1H, J = 6.6, 14.7 Hz), 2.78-2.75 (t, 1H, J = 4.4 Hz), 2.57-2.54 (dd, 1H, J = 2.6, 5.0 Hz), 2.18-2.04 (m, 4H), 1.70-1.59 (m, 2H). |
| 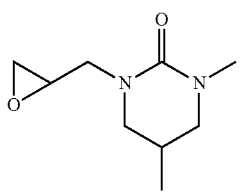 | 1,5-dimethyl-3-(oxiran-2-ylmethyl)tetrahydropyrimidin-2(1H)-one | ESI (m/z): 185.1 (M + H). |

Preparation 32: 1-ethyl-3-((2-methyloxiran-2-yl)methyl)tetrahydropyrimidin-2(1H)-one; General method for preparation of N-((2-methyloxiran-2-yl)methyl) functionalized ureas To a solution of cyclic urea generated in Preparation 7 (1.0 equiv.) in anhydrous tetrahdrofuran (0.2 M) was added 60% sodium hydride in mineral oil (1.1 equiv.) and the resultant suspension was stirred for 1 hr at room temperature. 2-(Chloromethyl)-2-methyloxirane (4.0 equiv.) was added at room temperature and the mixture stirred at 70-90° C. in a sealed tube overnight. Silica gel was added and the suspension concentrated under reduced pressure and directly purified by silica gel column chromatography—eluting the desired product with a gradient of methanol in methylene chloride.

| Structure | Name | Characterization |
|---|---|---|
| 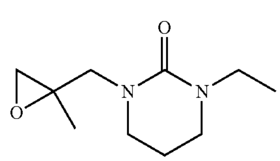 | 1-ethyl-3((2-methyloxiran-2-yl)methyl)tetrahydropyrimidin-2(1H)-one | $^1$H NMR (300 MHz, CDCl$_3$): δ 3.78-3.73 (d, 1H, J = 14.7 Hz), 3.40-3.24 (m, 7H), 2.63-2.61 and 2.59-2.57 (ABq, 2H, J = 4.8 Hz), 1.97-1.89 (quint, 2H, J = 5.9 Hz), 1.31 (s, 3H), 1.11-1.08 (m, 3H). |

Preparation 33: 3-(methylamino)butanenitrile

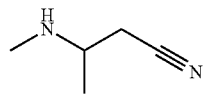

A mixture of methylamine (158.584 mL of a 40% w/w aqueous solution, 1842.3 mmol, 10.0 equiv.) and crotononitrile (15 mL, 184.2 mmol, 1.0 equiv.) was stirred at room temperature for 16 hrs. The reaction was extracted with methylene chloride (3×100 mL) and the combined organic layers were dried over anhydrous sodium sulfate, filtered and concentrated in vacuo to afford the desired product as a colorless oil (18 g, 100%). $^1$H NMR (300 MHz, CDCl$_3$): δ 2.96 (m, 1H), 2.47 (d, 2H, J=6.0 Hz), 2.46 (s, 3H), 1.36 (d, 3H, J=6.6 Hz).

Preparation 34: N3-methylbutane-1,3-diamine

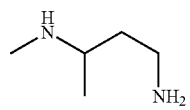

A Parr shaker flask was charged with methanol (100 mL), cooled to 0° C. and bubbled with ammonia. 3-(Methylamino)butanenitrile (4.8 g, 48.9 mmol, 1.0 equiv.) and a spoonful of Raney Ni were added. The reaction was shaken under hydrogen at 50 psi for 10 hrs. The reaction was filtered through Celite and the filtrate concentrated in vacuo to afford a clear oil (5.0 g, 100%). $^1$H NMR (300 MHz, CDCl$_3$): δ 2.90-2.60 (m, 3H), 2.43 (s, 3H), 1.70-1.40 (m, 2H), 1.08 (d, 3H, J=6.0 Hz).

Preparation 35: 1,6-dimethyltetrahydropyrimidin-2(1H)-one

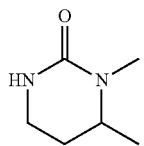

To a stirred solution of N3-methylbutane-1,3-diamine (5.0 g, 48.9 mmol, 1.0 equiv.) in anhydrous tetrahydrofuran (100 mL) at 0° C. was added 1,1'-carbonyldiimidazole (7.935 g, 48.9 mmol, 1.0 equiv.). The mixture was slowly warmed to room temperature and stirred for 16 hrs. The reaction was concentrated under reduced pressure and the residue treated with saturated aqueous ammonium chloride and extracted twice with methylene chloride. The combined organic layers were washed with saturated aqueous sodium chloride, dried over anhydrous sodium sulfate, filtered and concentrated in vacuo. The residue was purified by silica gel column (0-20% ethanol/methylene chloride) to afford the desired product as a white solid (1.8 g, 29%).

$^1$H NMR (300 MHz, CDCl$_3$): δ 4.66 (br s, 1H), 3.53-3.35 (m, 2H), 3.25 (m, 1H), 2.95 (s, 3H), 2.05 (m, 1H), 1.70 (m, 1H), 1.24 (d, 3H, J=6.3 Hz).

Preparation 36: 2-(aminomethyl)-N-benzylaniline

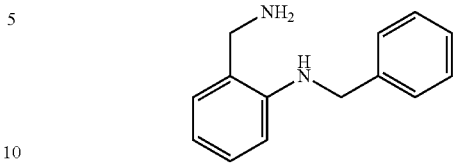

Under a nitrogen atmosphere, a solution of 2-(benzylamino)benzonitrile (4.0 g, 19.2 mmol, 1.0 equiv.) in anhydrous tetrahydrofuran (25 mL) was added slowly to a cold (0° C.) suspension of lithium aluminum hydride (2.187 g, 57.6 mmol, 3.0 equiv.) in anhydrous tetrahydrofuran (60 mL). The mixture was cooled and sodium sulfate decahydrate was added until foaming stopped (cooling with external water/ice bath). The mixture was filtered to remove solids and the solution concentrated in vacuo to a clear liquid (3.2 g, 79%). $^1$H NMR (300 MHz, CDCl$_3$): δ 7.42-7.23 (m, 5H), 7.17-7.11 (td, 1H, J=1.8, 7.5 Hz), 7.07-7.04 (m, 1H), 6.68-6.61 (m, 2H), 6.29 (br s, 1H), 4.40 (s, 2H), 3.99 (s, 2H), 1.31 (br s, 2H).

Preparation 37: 1-benzyl-3,4-dihydroquinazolin-2(1H)-one

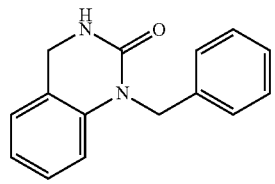 [SMILES: O=C1NCc2ccccc2N1Cc1ccccc1]

To a solution of 2-(aminomethyl)-N-benzylaniline (1.5 g, 7.1 mmol, 1.0 equiv.) in anhydrous tetrahydrofuran (142 mL) was added 1,1'-carbonyldiimidazole (1.318 g, 8.1 mmol, 1.1 equiv.) and the solution stirred at room temperature for 24 hrs. 1 N aqueous hydrochloric acid (20 mL) was added and the mixture extracted three times with ethyl acetate. The organic fractions were dried with anhydrous sodium sulfate, filtered and concentrated in vacuo to afford a white solid (1.68 g, 99%). $^1$H NMR (300 MHz, CDCl$_3$): δ 7.33-7.20 (m, 5H), 7.11-7.03 (m, 2H), 6.95-6.91 (m, 1H), 6.74-6.71 (d, 1H, J=8.1 Hz), 5.13 (s, 2H), 4.54 (s, 2H), 1.60 (br s, 2H).

ESI (m/z): 239.2 (M+H).

Preparation 38: 1-benzyl-3-(3-(3,6-difluoro-9H-carbazol-9-yl)-2-hydroxypropyl)-3,4-dihydroquinazolin-2(1H)-one

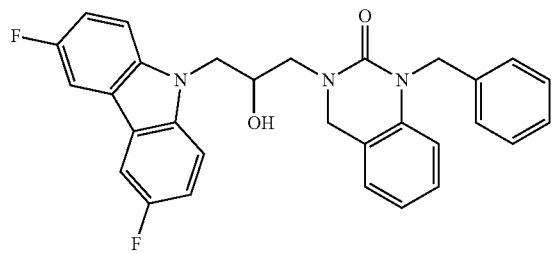 [SMILES: O=C1N(CC(O)Cn2c3ccc(F)cc3c3cc(F)ccc32)Cc2ccccc2N1Cc1ccccc1]

To a stirred solution of 1-benzyl-3,4-dihydroquinazolin-2(1H)-one (0.105 g, 0.4 mmol, 1.8 equiv.) in anhydrous dimethylformamide (1 mL) was added 60% sodium hydride in mineral oil (0.01 g, 0.3 mmol, 1.0 equiv.) and the mixture was stirred for 30 mins. 3,6-Difluoro-9-(oxiran-2-ylmethyl)-9H-carbazole (0.065 g, 0.3 mmol, 1.0 equiv.) was added and the mixture stirred for 16 hrs at 55° C. The mixture was poured into saturated aqueous ammonium chloride and extracted three times with ethyl acetate. The organic fractions were dried over anhydrous sodium sulfate, filtered and concentrated to afford a tan oil. The crude residue was purified by silica gel column chromatography, eluting with a gradient of 20-60% ethyl acetate/hexanes to give product that was used directly in the next step without additional purification (35%). ESI (m/z): 498.2 (M+H); HPLC analysis: (C18, 5-95% acetonitrile in water+0.1% trifluoroacetic acid over 20 min: retention time, % area at 254 nm): 15.2 mins, 51%.

Preparation 39: 1-benzyl-3-(3-(3,6-difluoro-9H-carbazol-9-yl)-2-hydroxy-2-methylpropyl)-3,4-dihydroquinazolin-2(1H)-one

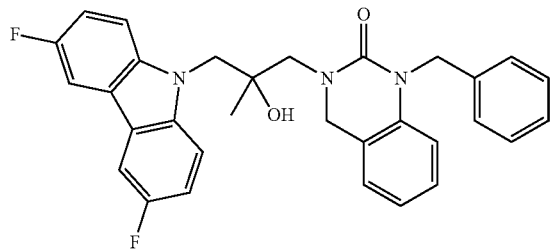 [SMILES: CC(O)(CN1Cc2ccccc2N(Cc2ccccc2)C1=O)Cn1c2ccc(F)cc2c2cc(F)ccc21]

To a stirred solution of 1-benzyl-3,4-dihydroquinazolin-2(1H)-one (0.099 g, 0.4 mmol, 1.8 equiv.) in anhydrous dimethylformamide (1 mL) was added 60% sodium hydride in mineral oil (0.01 g, 0.3 mmol, 1.0 equiv.) and the mixture stirred for 30 mins. 3,6-Difluoro-9-((2-methyloxiran-2-yl)methyl)-9H-carbazole (0.065 g, 0.2 mmol, 1.0 equiv.) was added and the mixture stirred at 55° C. for 16 hrs. The mixture was poured into saturated aqueous ammonium chloride and extracted three times with ethyl acetate. The organic fractions were dried over sodium sulfate, filtered and concentrated to afford a tan oil. The crude residue was purified by silica gel column chromatography, eluting with a gradient of 20-60% ethyl acetate/hexanes to give an off-white solid (0.086 g, 65%). $^1$H NMR (300 MHz, CDCl$_3$): δ 7.66-7.62 (dd, 2H, J=2.4, 8.7 Hz), 7.45-7.40 (dd, 2H, J=4.1, 8.9 Hz), 7.30-7.09 (m, 8H), 7.04-6.93 (m, 2H), 6.75-6.72 (d, 1H, J=8.1 Hz), 5.20-5.15 and 5.08-5.03 (ABq, 2H, J=16.6 Hz), 4.74-4.69 and 4.59-4.54 (ABq, 2H, J=14.3 Hz), 4.39-4.34 and 4.32-4.26 (ABq, 2H, J=15.3 Hz), 4.09 (s, 1H), 3.97-3.93 and 3.51-3.47 (ABq, 2H, J=14.4 Hz), 1.36 (s, 3H); ESI (m/z): 512.3 (M+H).

Preparation 40: (R)-(2-methyloxiran-2-yl)methanol

A mixture of crushed 4 Å activated molecular sieves (15.0 g) and methylene chloride (300 mL) was cooled to −10° C., titanium(IV) isopropoxide (2.072 mL, 7.0 mmol, 0.05 equiv.) and (−)-diethyl-D-tartrate (2.126 g, 10.3 mmol, 0.07 equiv.) were added by syringe followed by 80% cumene hydroperoxide (50.000 g, 262.8 mmol, 1.8 equiv.). The mixture was stirred at −10° C. for 30 mins. The mixture was cooled to −35° C. and a solution of 2-methyl-2-propen-1-ol (10.620 g, 147.3 mmol, 1.0 equiv.) in dichloromethans (10 mL) was added by syringe, in 1-2 mL portions over 30 mins. The reaction mixture was stirred at −35° C. for 1 h and then placed in a −20° C. freezer for 3 days. The mixture was warmed to 0° C., water was added and stirred for 30 mins at room temperature. The mixture was cooled to 0° C. and a solution of 30% sodium hydroxide in saturated aqueous sodium chloride (10 mL) was added and stirred at this temperature for 1 h. The mixture was filtered through a pad of Celite and washed with methylene chloride (50 mL). The aqueous portion was separated and extracted with methylene chloride (3×30 mL). The organic layer was combined and dried (anhydrous magnesium sulfate), filtered and concentrated in vacuo to a colorless liquid. The crude residue was purified by silica gel column chromatography, eluting with a gradient of 20-100% diethyl ether/hexanes to give a colorless oil (6.2349 g 48%). $^1$H NMR (300 MHz, CDCl$_3$): δ 3.76 (dd, 1H, J=4.5, 12.3 Hz), 3.6 (dd, 1H, J=8.1, 12.3 Hz), 2.92 (d, 1H, J=4.5 Hz), 2.66 (d, 1H, J=4.8 Hz), 1.79 (br m, 1H), 1.36 (s, 3H).

The (S) enantiomer was synthesized in a similar manner from the (+)-diethyl tartrate.

Preparation 41: (S)-(2-methyloxiran-2-yl)methyl 3-nitrobenzenesulfonate

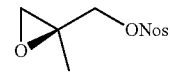

To a stirred solution of (R)-(2-methyloxiran-2-yl)methanol (5.000 g, 56.8 mmol, 1.0 equiv.), N,N-4-dimethylaminopyridine (0.100 g, 0.8 mmol, 1.4 mol %) and N,N-diisopropylethylamine (15.776 mL, 88.9 mmol, 2.0 equiv.) in anhydrous methylene chloride (100 mL) at −20° C. was slowly added 3-nitrobenzenesulfonyl chloride (15.092 g, 68.1 mmol, 1.2 equiv.) in small portions over 15 mins. The mixture was allowed to reach 0° C. and stirred for 3 h. The reaction was quenched with water and extracted with methylene chloride. The combined organic layers were washed sequentially with water, 1 N aqueous hydrochloric acid, saturated aqueous sodium bicarbonate, and saturated aqueous sodium chloride. The organic layer was dried (anhydrous sodium sulfate), filtered and concentrated in vacuo. The crude residue was purified by silica gel column (0-80% ethyl acetate/hexanea) to afford the desired product as a yellow oil (6.73 g, 43.4%). $^1$H NMR (300 MHz, CDCl$_3$): δ 8.77 (t, 1H, J=1.8 Hz), 8.54 (m, 1H), 8.27 (m, 1H), 7.84 (t, 1H, J=7.95 Hz), 4.29 (d, 1H, J=11.1 Hz), 4.05 (d, 1H, J=11.1 Hz), 2.73 (dd, 2H, J=17.7, 4.8 Hz), 1.37 (s, 3H).

The (R) enantiomer was synthesized in a similar manner.

Preparation 42:
(S)-9-(oxiran-2-ylmethyl)-9H-carbazole

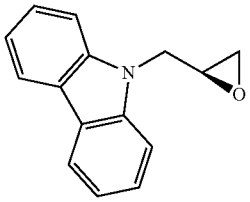 [SMILES: c1ccc2c(c1)c1ccccc1n2C[C@H]1CO1]

To a stirred solution of carbazole (5.15 g, 30.8 mmol, 1.0 equiv.) in anhydrous dimethylformamide (100 mL) at 0° C. was added 60% sodium hydride in mineral oil (1.355 g, 33.9 mmol, 1.1 equiv.) and the mixture was stirred at 0° C. for 1 hr. (R)-(−)-glycidyl nosylate (9.981 g, 38.5 mmol, 1.3 equiv.) was added and the reaction mixture stirred for 1 hr and then slowly warmed to room temperature and stirred for 16 hrs. The mixture was partitioned between water and ethyl acetate. The organic layer was washed with saturated aqueous sodium chloride, dried (anhydrous sodium sulfate), filtered and concentrated under reduced pressure to give a red oil. The crude residue was purified by silica gel column (15-80% methylene chloride/hexanes) to afford the desired product as a white solid (4.95 g, 72%). $^1$H NMR (300 MHz, CDCl$_3$): δ 8.11-8.08 (dt, 2H, J=0.9, 7.5 Hz), 7.48-7.46 (m, 4H), 7.28-7.23 (m, 2H), 4.67-4.61 (dd, 1H, J=2.4, 15.9 Hz), 4.45-4.38 (dd, 1H, J=5.0, 15.9 Hz), 3.39-3.34 (m, 1H), 2.83-2.80 (t, 1H, J=4.2 Hz), 2.60-2.57 (dd, 1H, J=2.4, 4.8 Hz). HPLC analysis: (C18, 5-95% acetonitrile in water+0.1% trifluoroacetic acid over 20 min: retention time, % area at 254 nm): 13.2 mins, 99.5%. Chiral HPLC analysis: (Chiralcel AD-H, 5-15% isopropanol in hexanes over 20 mins: retention time, % area at 254 nm): 8.12 mins, 3.8%; 8.54 mins, 96.1% (92.2% ee).

The following compounds were prepared analogously:

| Structure | Name | Characterization |
|---|---|---|
| 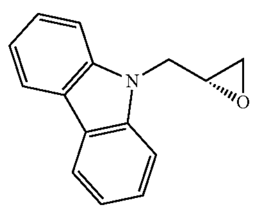 [SMILES: c1ccc2c(c1)c1ccccc1n2C[C@@H]1CO1] | (R)-9-(oxiran-2-ylmethyl)-9H-carbazole | $^1$H NMR (300 MHz, CDCl$_3$): δ 8.11-8.08 (dt, 2H, J = 0.9, 7.5 Hz), 7.48-7.46 (m, 4H), 7.28-7.23 (m, 2H), 4.67-4.61 (dd, 1H, J = 2.4, 15.9 Hz), 4.45-4.38 (dd, 1H, J = 5.0, 15.9 Hz), 3.39-3.34 (m, 1H), 2.83-2.80 (t, 1H, J = 4.2 Hz), 2.60-2.57 (dd, 1H, J = 2.4, 4.8 Hz); HPLC analysis: (C18, 5-95% acetonitrile in water + 0.1% trifluoroacetic acid over 20 min: retention time, % area at 254 nm): 13.2 mins, 99.4%; Chiral HPLC analysis: (Chiralcel AD-H, 5-15% isopropanol in hexanes over 20 mins: retention time, % area at 254 nm): 8.13 mins, 94.9%; 8.55 mins, 5.0% (89.9% ee). |
| 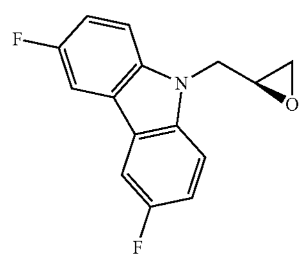 [SMILES: Fc1ccc2c(c1)c1cc(F)ccc1n2C[C@H]1CO1] | (S)-3,6-difluoro-9-(oxiran-2-ylmethyl)-9H-carbazole | $^1$H NMR (300 MHz, CDCl$_3$): δ 7.68-7.65 (dd, 2H, J = 2.6, 8.6 Hz), 7.39-7.35 (dd, 2H, J = 4.2, 9.0 Hz), 7.24-7.18 (td, 2H, J = 2.6, 9.0 Hz), 4.69-4.62 (dd, 1H, J = 2.9, 5.0 Hz), 4.33-4.26 (dd, 1H, J = 5.0, 16.1 Hz), 3.35-3.31 (m, 1H), 2.84-2.81 (t, 1H, J = 4.2 Hz), 2.54-2.52 (dd, 1H, J = 2.6, 4.7 Hz); HPLC analysis: (C18, 5-95% acetonitrile in water + 0.1% trifluoroacetic acid over 20 min: retention time, % area at 254 nm): 13.8 mins, 100%; Chiral HPLC analysis: (Chiralcel OD-H, 25% isopropanol in hexanes over 20 mins: retention time, % area at 254 nm): 7.7 mins, 1.8%; 10.1 mins, 98.2% (96.4% ee). |
| 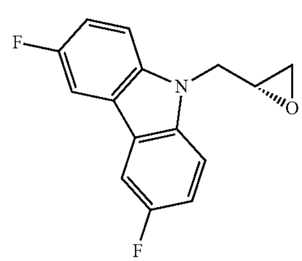 [SMILES: Fc1ccc2c(c1)c1cc(F)ccc1n2C[C@@H]1CO1] | (R)-3,6-difluoro-9-(oxiran-2-ylmethyl)-9H-carbazole | $^1$H NMR (300 MHz, CDCl$_3$): δ 7.68-7.65 (dd, 2H, J = 2.6, 8.6 Hz), 7.39-7.35 (dd, 2H, J = 4.2, 9.0 Hz), 7.24-7.18 (td, 2H, J = 2.6, 9.0 Hz), 4.69-4.62 (dd, 1H, J = 2.9, 5.0 Hz), 4.33-4.26 (dd, 1H, J = 5.0, 16.1 Hz), 3.35-3.31 (m, 1H), 2.84-2.81 (t, 1H, J = 4.2 Hz), 2.54-2.52 (dd, 1H, J = 2.3, 4.7 Hz); HPLC analysis: (C18, 5-95% acetonitrile in water + 0.1% trifluoroacetic acid over 20 min: retention time, % area at 254 nm): 13.7 mins, 100%; Chiral HPLC analysis: (Chiralcel OD-H, 25% isopropanol in hexanes over 20 mins: retention time, % area at 254 nm): 7.7 mins, 98.8%; 10.2 mins, 1.2% (97.5% ee). |
| 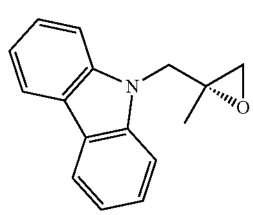 [SMILES: C[C@@]1(Cn2c3ccccc3c3ccccc32)CO1] | (R)-9-((2-methyloxiran-2-yl)methyl)-9H-carbazole | $^1$H NMR (300 MHz, CDCl$_3$): δ 8.09-8.12 (m, 2H), 7.49 (d, 4H, J = 3.9 Hz), 7.23-7.28 (m, 2H), 4.63 (d, 1H, J = 15.9 Hz), 4.32 (d, 1H, J = 15.9 Hz), 2.69 (s, 2H), 1.33 (s, 3H); HPLC analysis: (C18, 10-90% acetonitrile in water + 0.1% trifluoroacetic acid over 20 min: retention time, % area at 254 nm): 13.65 min, 89.2%; Chiral HPLC analysis (Phenomenex Lux 3μ cellulose-2, 4% isopropanol in hexanes over 20 mins: retention time, % area at 254 nm): 6.94 min, 90.0%, 7.83 min, 10.0% (80.0% ee). |

| Structure | Name | Characterization |
|---|---|---|
| 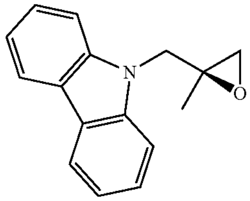 [SMILES: C[C@]1(Cn2c3ccccc3c3ccccc32)CO1] | (S)-9-((2-methyloxiran-2-yl)methyl)-9H-carbazole | $^1$H NMR (300 MHz, CDCl$_3$): δ 8.09-8.12 (m, 2H), 7.49 (d, 4H, J = 3.9 Hz), 7.23-7.28 (m, 2H), 4.63 (d, 1H, J = 15.9 Hz), 4.32 (d, 1H, J = 15.9 Hz), 2.69 (s, 2H), 1.33 (s, 3H); HPLC analysis: (C18, 10-90% acetonitrile in water + 0.1% trifluoroacetic acid over 20 min: retention time, % area at 254 nm): 13.68 min, 100%; Chiral HPLC analysis (Phenomenex Lux 3μ cellulose-2, 4% isopropanol in hexanes over 20 mins: retention time, % area at 254 nm): 6.95 min, 7.1%, 7.83 min, 92.9% (85.8% ee). |
| 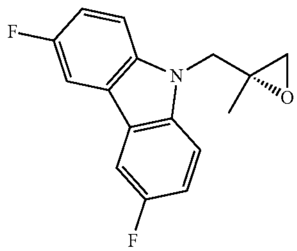 [SMILES: C[C@@]1(Cn2c3ccc(F)cc3c3cc(F)ccc32)CO1] | (R)-3,6-difluoro-9-((2-methyloxiran-2-yl)methyl)-9H-carbazole | $^1$H NMR (300 MHz, CDCl$_3$): δ 7.69 (dd, 2H, J = 9.0, 2.4 Hz), 7.42 (dd, 2H, J = 8.7, 3.9 Hz), 7.25 (td, 2H, J = 9.0, 2.4 Hz), 4.63 (d, 1H, J = 15.9 Hz), 4.23 (d, 1H, J = 15.9 Hz), 2.69 (dd, 2H, J = 15.3, 4.8 Hz), 1.31 (s, 3H); HPLC analysis: (C18, 10-90% acetonitrile in water + 0.1% trifluoroacetic acid over 20 min: retention time, % area at 254 nm): 14.1 min, 98.4%; Chiral HPLC analysis: (Chiralcel AD-H, 4% ethanol in hexanes over 20 mins: retention time, % area at 254 nm): 11.7 mins, 95.4%; 15.7 mins, 4.6% (90.8% ee). |
| 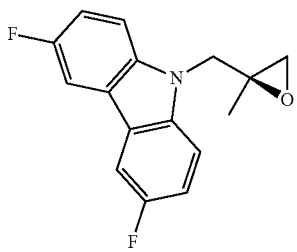 [SMILES: C[C@]1(Cn2c3ccc(F)cc3c3cc(F)ccc32)CO1] | (S)-3,6-difluoro-9-((2-methyloxiran-2-yl)methyl)-9H-carbazole | $^1$H NMR (300 MHz, CDCl$_3$): δ 7.69 (dd, 2H, J = 9.0, 2.4 Hz), 7.42 (dd, 2H, J = 8.7, 3.9 Hz), 7.25 (td, 2H, J = 9.0, 2.4 Hz), 4.63 (d, 1H, J = 15.9 Hz), 4.23 (d, 1H, J = 15.9 Hz), 2.69 (dd, 2H, J = 15.3, 4.8 Hz), 1.31 (s, 3H); HPLC analysis: (C18, 10-90% acetonitrile in water + 0.1% trifluoroacetic acid over 20 min: retention time, % area at 254 nm): 14.1 min, 100%; Chiral HPLC analysis: (Chiralcel AD-H, 4% ethanol in hexanes over 20 mins: retention time, % area at 254 nm): 11.7 mins, 4.4%; 15.9 mins, 95.6% (91.2% ee). |

Preparation 43:
(1S,4R)-2-azabicyclo[2.2.1]heptan-3-one

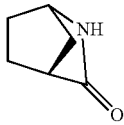

A mixture of (1R)-(−)-2-azabicyclo[2.2.1]hept-5-en-3-one (1.0 g, 9.2 mmol) and 10% palladium on carbon (0.4 g) in methanol (50 mL) was stirred under an atmosphere of hydrogen for 3 hrs. The mixture was filtered through Celite and the filter cake washed with methanol. The combined organics were concentrated in vacuo to afford the require product (1 g, 98%). $^1$H NMR (300 MHz, CDCl$_3$): δ 5.91 (br s, 1H), 3.89 (s, 1H), 2.74 (s, 1H), 1.96-1.59 (m, 5H), 1.42-1.37 (m, 1H).

Preparation 44:
(1R,4S)-2-azabicyclo[2.2.1]heptan-3-one

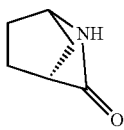

A mixture of (1S)-(+)-2-azabicyclo[2.2.1]hept-5-en-one (1.0 g, 9.2 mmol, 1.0 equiv.) and 10% palladium on carbon (0.4 g) in methanol (40 mL) was stirred under an atmosphere of hydrogen at ambient temperature for 2 hrs. The mixture was filtered through Celite and the filter cake washed with methanol. The combined organics were concentrated in vacuo to afford the required product (1 g, 98%). $^1$H NMR (300 MHz, CDCl$_3$): δ 5.83 (br s, 1H), 3.89 (s, 1H), 2.74 (s, 1H), 1.96-1.59 (m, 5H), 1.42-1.38 (m, 1H).

Preparation 45:
(R)-5-(hydroxymethyl)-2-pyrrolidinone p-toluenesulfonate

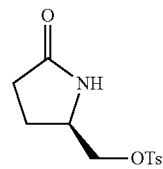 [SMILES: Cc1ccc(S(=O)(=O)OC[C@H]2CCC(=O)N2)cc1]

(R)-(−)-5-(hydroxymethyl)-2-pyrrolidinone (1.0 g, 8.7 mmol, 1.0 equiv.) was dissolved in methylene chloride (40 mL). Triethylamine (1.569 mL, 11.3 mmol, 1.3 equiv.), p-toluenesulfonyl chloride (1.904 g, 10.0 mmol, 1.1 equiv.) and 4-(dimethylamino)pyridine (0.12 g) were added under ice-cooling, and the mixture stirred at room temperature for 18 hrs. The reaction mixture was concentrated under reduced pressure, 0.5 N aqueous hydrochloric acid was added, and the mixture extracted with ethyl acetate. The organic layer was washed with 0.5 N aqueous hydrochloric acid, water, saturated aqueous sodium hydrogen carbonate, and saturated aqueous sodium chloride. The organic fraction was dried (anhydrous sodium sulfate), filtered and concentrated under reduced pressure to afford a white solid (1.91 g, 81%). $^1$H NMR (300 MHz, CDCl$_3$): δ 7.79-7.76 (m, 2H), 7.38-7.35 (m, 2H), 5.73 (br s, 1H), 4.08-4.04 (dd, 1H, J=3.5, 9.5 Hz), 3.98-3.93 (m, 1H), 3.85-3.82 (dd, 1H, J=7.5, 9.5 Hz), 2.47 (s, 3H), 2.36-2.22 (m, 3H), 1.81-1.73 (m, 1H).

Preparation 46: (S)-5-(iodomethyl)pyrrolidin-2-one

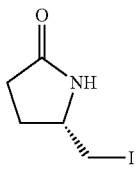

(S)-(5-oxopyrrolidin-2-yl)methyl 4-methylbenzenesulfonate (4.5 g, 16.7 mmol, 1.0 equiv.) was dissolved in anhydrous acetonitrile (140 mL), sodium iodide (5.009 g, 33.4 mmol, 2.0 equiv.) was added, and the mixture heated to reflux for 8 hrs. The reaction mixture was cooled to room temperature, concentrated under reduced pressure, water added, and the mixture extracted with ethyl acetate. The organic layer was washed with saturated aqueous sodium thiosulfate, water, and saturated aqueous sodium chloride. The organic fraction was dried (anhydrous sodium sulfate), filtered and concentrated in vacuo to give the title compound as a white solid (2.0 g, 53%). $^1$H NMR (300 MHz, CDCl$_3$): δ 6.42 (br s, 1H), 3.90-3.82 (s, 1H), 3.27-3.16 (m, 2H), 2.53-2.29 (m, 3H), 1.88-1.17 (m, 1H).

Preparation 47: (R)-5-(iodomethyl)pyrrolidin-2-one

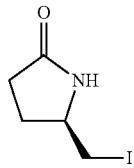

(R)-5-(hydroxymethyl)-2-pyrrolidinone p-toluenesulfonate (1.9 g, 7.1 mmol, 1.0 equiv.) was dissolved in anhydrous acetonitrile (60 mL), sodium iodide (2.09 g) was added, and the mixture heated at reflux for 8 hrs. The reaction mixture was cooled to room temperature, concentrated under reduced pressure, water added, and the mixture extracted with ethyl acetate. The organic layer was washed with saturated aqueous sodium thiosulfate, water and saturated aqueous sodium chloride. The organic fraction was dried (anhydrous sodium sulfate), filtered and concentrated in vacuo to give the title compound as an off-white solid (0.97 g, 61%). $^1$H NMR (300 MHz, CDCl$_3$): δ 5.92 (br s, 1H), 3.89-3.85 (m, 1H), 3.28-3.15 (m, 2H), 2.53-2.30 (m, 3H), 1.88-1.78 (m, 1H).

Preparation 48: (R)-5-methylpyrrolidin-2-one

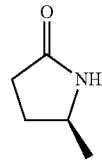

(S)-5-(Iodomethyl)pyrrolidin-2-one (2.0 g, 8.9 mmol, 1.0 equiv.) was dissolved in ethanol (60 mL), sodium carbonate (1.036 g, 9.8 mmol, 1.1 equiv.) and 10% palladium on carbon (0.4 g) were added, and the mixture stirred for 16 hrs under a hydrogen atmosphere. The mixture was filtered through Celite and the filtrate concentrated under reduced pressure to afford an orange semi-solid. To the obtained residue was added 5% aqueous sodium thiosulfate, and the mixture extracted with ethyl acetate. The organic layer was dried (anhydrous sodium sulfate), filtered and concentrated in vacuo to give the title compound as a pale yellow oil (0.564 g, 64%). $^1$H NMR (300 MHz, CDCl$_3$): δ 6.61 (br s, 1H), 3.82-3.72 (sext, 1H, J=6.6 Hz), 2.45-2.22 (m, 3H), 1.71-1.59 (m, 1H), 1.23-1.21 (d, 3H, J=6.6 Hz).

Preparation 49: (S)-5-methylpyrrolidin-2-one

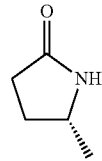

(S)-5-Iodomethylpyrrolidin-2-one (1.12 g) was dissolved in ethanol (30 mL), sodium carbonate (0.53 g) and 10% palladium on carbon (0.22 g) were added, and the mixture was stirred for 8 hrs under a hydrogen atmosphere. The mixture was filtered through Celite, and the filtrate concentrated under reduced pressure. To the obtained residue was added 5% aqueous sodium thiosulfate, and the mixture extracted with ethyl acetate. The organic layer was dried (anhydrous sodium sulfate), filtered and concentrated in vacuo to give the title compound (0.263 g, 61%). $^1$H NMR (300 MHz, CDCl$_3$): δ 6.34 (br s, 1H), 3.83-3.72 (sext, 1H, J=6.3 Hz), 2.46-2.21 (m, 3H), 1.72-1.60 (m, 1H), 1.23-1.21 (d, 3H, J=6.0 Hz).

Preparation 50: (S)-1-((2-aminoethyl)amino)-3-(3,6-difluoro-9H-carbazol-9-yl)propan-2-ol

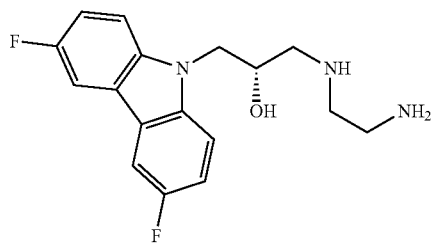 [SMILES: NCCNC[C@H](O)Cn1c2ccc(F)cc2c2cc(F)ccc21]

A mixture of (R)-3,6-difluoro-9-(oxiran-2-ylmethyl)-9H-carbazole (0.1 g, 0.4 mmol, 1.0 equiv.) and ethylenediamine (0.232 g, 3.9 mmol, 10.0 equiv.) in ethanol (2 mL) was stirred at 55° C. for 5 hrs. The reaction mixture was cooled to room temperature, and concentrated in vacuo to afford a light yellow syrup which slowly solidified to form an off-white solid (0.122 g, 96%). $^1$H NMR (300 MHz, CDCl$_3$): δ 7.68 (dd, 2H, J=8.7, 2.7 Hz), 7.42 (dd, 2H, J=8.7, 4.2 Hz), 7.22 (td, 2H, J=9.0, 2.7 Hz), 4.33-4.31 (d, 2H, J=5.4 Hz), 4.15 (m, 1H), 2.85-2.55 (m, 6H) 1.84 (br s, 4H). ESI (m/z): 320.2 (M+H).

Preparation 51: (R)-4-benzyl-3-(4-bromobutanoyl)oxazolidin-2-one

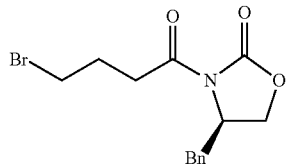 [SMILES: O=C(CCCBr)N1C(=O)OC[C@H]1Cc1ccccc1]

A round bottomed flask was charged with 4-bromobutyric acid (19.226 g, 115.1 mmol, 1.0 equiv.) and dry diethyl ether (500 mL). The resulting solution was cooled to −78° C., and triethylamine (16.473 mL, 118.5 mmol, 1.1 equiv.) was added followed by trimethylacetyl chloride (14.596 mL, 118.5 mmol, 1.1 equiv.). A white precipitate formed, upon which time the cold bath was removed and the reaction mixture allowed to warm to 0° C. and stirred for 2 h, the slurry was the re-cooled to −78° C. In a separate reaction vessel, 2.5 M n-butyllithium solution in hexanes (45.146 mL, 112.9 mmol, 1.0 equiv.) was added dropwise to a solution of (R)-4-benzyl-2-oxazolidinone (20.000 g, 112.9 mmol, 1.0 equiv.) stirring in anhydrous tetrahydrofuran (170 mL) at −78° C. After 10 min, the resulting slurry was added, by wide-bore cannula, to the mixed anhydride (washed with approx. 100 mL anhydrous tetrahydrofuran). After 15 min at −78° C., the mixture was allowed to warm to 0° C. over 30 min and then maintained at this temperature for 1 h. The slurry was then quenched carefully with water (180 mL), stirred for an additional 5 min, and then warmed to room temperature. The resulting solution was extracted with ethyl acetate (2×500 mL). The combined organic extracts were washed with water, saturated aqueous sodium bicarbonate (500 mL), saturated aqueous sodium chloride (400 mL), dried (anhydrous sodium sulfate), filtered, and concentrated in vacuo. The crude residue was purified by flash chromatography (silica gel, 10-50% ethyl acetate/hexanes) to afford a clear oil (26.0 g, 71%). $^1$H NMR (300 MHz, CDCl$_3$): δ 7.19-7.37 (m, 5H), 4.63-4.71 (m, 1H), 4.16-4.25 (m, 2H), 3.52 (t, 2H, J=6.5 Hz), 3.29 (dd, 1H, J=3.3, 13.5 Hz), 3.08-3.18 (m, 2H), 2.78 (dd, 1H, J=9.6, 13.5 Hz), 2.21-2.30 (m, 2H).

The (S) enantiomer was synthesized in a similar manner.

Preparation 52: (R)-3-(4-azidobutanoyl)-4-benzyloxazolidin-2-one

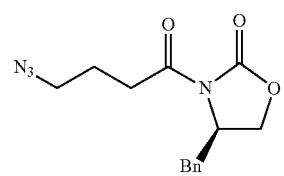 [SMILES: [N-]=[N+]=NCCCC(=O)N1C(=O)OC[C@H]1Cc1ccccc1]

Sodium azide (7.623 g, 117.3 mmol, 1.5 equiv.) was added to stirred solution of (R)-4-benzyl-3-(4-bromobutanoyl)oxazolidin-2-one (25.500 g, 78.2 mmol, 1.0 equiv.) in anhydrous N,N-dimethylformamide (225 mL). The resulting solution was heated at 55° C. for 15 min and 2 h at 70° C. After cooling to room temperature, the solution was poured into saturated aqueous sodium chloride/ethyl acetate (1.4 L) and washed with water and saturated aqueous sodium chloride, dried (anhydrous sodium sulfate), filtered, and concentrated in vacuo to give an oil (22.0 g, 98%), which was used without further purification. $^1$H NMR (300 MHz, CDCl$_3$): δ 7.36-7.19 (m, 5H), 4.62-4.72 (m, 1H), 4.10-4.25 (m, 2H), 3.41 (t, 2H, J=6.6 Hz), 3.30 (dd, 1H, J=3.3, 13.2 Hz), 2.99-3.10 (m, 2H), 2.79 (dd, 2H, J=9.9, 13.5 Hz), 1.93-2.02 (m, 2H); HPLC analysis: (C18, 10-90% acetonitrile in water+0.1% trifluoroacetic acid over 20 min: retention time, % area at 254 nm): 12.3 min, 95%.

The (S) enantiomer was synthesized in a similar manner.

Preparation 53: (R)-3-((R)-4-azido-2-methylbutanoyl)-4-benzyloxazolidin-2-one

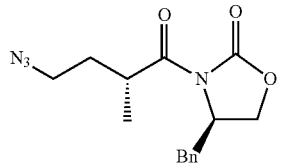

To a solution of (R)-3-(4-azidobutanoyl)-4-benzyloxazolidin-2-one (20.600 g, 71.5 mmol, 1.0 equiv.) stirring in anhydrous tetrahydrofuran at −78° C. (125 mL) was slowly added 1.0 M sodium bis(trimethylsilyl)amide solution in tetrahydrofuran (119.088 mL, 71.5 mmol, 1.0 equiv.). After 15 min, the resulting solution was treated with iodomethane (4.671 mL, 75.0 mmol, 1.0 equiv.). The cooling bath was removed, and after 5 min the reaction vessel was placed in an ice-water bath and stirred for an additional 15 min. The reaction was quenched with saturated aqueous sodium bicarbonate (300 mL) and extracted with ethyl acetate (2×300 mL). The combined organic extracts were washed with saturated aqueous sodium chloride (2×200 mL), dried (anhydrous magnesium sulfate), filtered, and concentrated in vacuo. Purification by flash chromatography (400 g silica gel, 10-50% ethyl acetate/hexanes) afforded the desired product as a clear oil (9.7 g, 45%). $^1$H NMR (300 MHz, CDCl$_3$): δ 7.20-7.38 (m, 5H), 4.65-4.72 (m, 1H), 4.15-4.26 (m, 2H), 3.85-3.79 (m, 1H), 3.35 (app. t, 2H, J=6.0 Hz), 3.25 (dd, 1H, J=13.5, 3.6 Hz), 2.78 (dd, 1H, J=13.0 Hz, 9.0 Hz), 2.04-2.18 (m, 1H), 1.67-1.78 (m, 1H), 1.27 (d, 3H, J=6.9 Hz); HPLC analysis: (C18, 10-90% acetonitrile in water+0.1% trifluoroacetic acid over 20 min: retention time, % area at 254 nm): 13.0 min, 99.4%.

The (S) enantiomer was synthesized in a similar manner.

Preparation 54: (R)-3-methylpyrrolidin-2-one

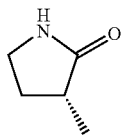

To a solution of (R)-3-((R)-4-azido-2-methylbutanoyl)-4-benzyloxazolidin-2-one (9.650 g, 31.9 mmol, 1.0 equiv.) stirring in anhydrous tetrahydrofuran (125 mL) at room temperature was added triphenylphosphine (16.744 g, 63.8 mmol, 2.0 equiv.). After 5 min (solution turns yellow and bubbles), water (0.575 mL, 31.9 mmol, 1.0 equiv.) was added and the reaction mixture was stirred at 25° C. for 18 h. The mixture was concentrated and the resulting residue purified by flash chromatography (silica gel, 75-100% ethyl acetate/hexanes, then 100% to 90% ethyl acetate/methanol gradient) to afford the desired product (2.98 g, 95%). $^1$H NMR (300 MHz, CDCl$_3$): δ 6.10 (br. s, 1H), 3.25-3.35 (m, 2H), 2.27-2.50 (m, 2H), 1.68-1.80 (m, 1H), 1.20 (d, 3H, J=7.5 Hz).

The (S) enantiomer was synthesized in a similar manner.

Preparation 55:
(S)-3-((trimethylsilyl)oxy)pyrrolidin-2-one

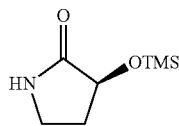

Following the procedure of Harris, B. D. et al. *Synth. Commun.* 1986, 16, 1815. Trimethylsilyl chloride (0.805 mL, 6.3 mmol, 0.1 equiv.) was added to a stirred mixture of (S)-(−)-4-amino-2-hydroxybutyric acid (15.000 g, 125.9 mmol, 1.0 equiv.) in xylene (1 L) and hexamethyldisilazane (184.757 mL, 881.5 mmol, 7.0 equiv.) at room temperature. The reaction mixture was heated to reflux for 4 h, cooled to room temperature, and diluted with absolute ethanol/methanol (1 L). The solvents were removed under reduced pressure to give the crude product which was purified by column chromatography using ethyl acetate/methylene chloride (30-80% gradient) as eluant to afford a white solid. (17.9 g, 82%). $^1$H NMR (300 MHz, CDCl$_3$): δ 6.49 (br s, 1H), 4.28-4.23 (t, 1H, J=7.7 Hz), 3.40-3.21 (m, 2H), 2.42-2.32 (m, 2H), 2.08-1.95 (m, 2H), 0.18 (s, 9H).

Preparation 56: (S)-tert-butyl 2-oxo-3-((trimethylsilyl)oxy)pyrrolidine-1-carboxylate

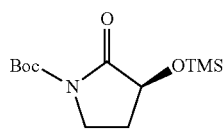

Following the procedure of DiRocco, D. A. et al. *J. Am. Chem. Soc.* 2009, 131, 10872 & DiRocco, D. A. et al. WO 2012/009372. To a solution of (S)-3-(trimethylsilyloxy)pyrrolidin-2-one (6.00 g, 34.62 mmol, 1.0 equiv) in anhydrous methylene chloride (150 mL) was added di-tert-butyl dicarbonate (15.11 g, 69.24 mmol, 2.0 equiv), triethylamine (4.82 mL, 34.62 mmol, 1.0 equiv), and 4-dimethylaminopyridine (4.23 g, 34.62 mmol, 1.0 equiv). The mixture was stirred overnight at room temperature, then 1 N aqueous hydrochloric acid (100 mL) was added, and the layers separated. The organic layer was washed with 1 N aqueous hydrochloric acid (2×50 mL), and saturated aqueous sodium chloride (1×50 mL), dried (anhydrous sodium sulfate) and filtered.

The solution was concentrated in vacuo to afford a crude oil, which was purified by silica gel chromatography (eluting with 0-15% ethyl acetate/hexanes) to afford a clear viscous oil, which solidified in freezer. (3.93 g, 42%). $^1$H NMR (300 MHz, CDCl$_3$): δ 4.32-4.26 (dd, 1H, J=8.4, 9.3 Hz), 3.82-3.74 (ddd, 1H, J=2.1, 9.0, 11.1 Hz), 3.50-3.41 (m, 1H), 2.28-2.25 (m, 1H), 1.94-1.87 (m, 1H), 1.51 (s, 9H), 0.18 (s, 9H).

Preparation 57: (R)-3-fluoropyrrolidin-2-one

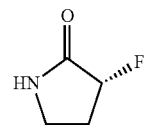

A solution of (S)-tert-butyl 2-oxo-3-((trimethylsilyl)oxy)pyrrolidine-1-carboxylate (3 g, 11 mmol) in anhydrous methylene chloride (55 mL) was cooled to −78° C. at which point diethylaminosulfur trifluoride (2.9 mL, 22 mmol, 2.0 equiv) was added dropwise. The solution was then allowed to slowly warm to room temperature and saturated aqueous sodium bicarbonate (50 mL) was then added to quench the reaction. The layers were separated and the organic layer was then washed with saturated aqueous ammonium chloride (2×25 mL), dried (anhydrous sodium sulfate), filtered, and concentrated in vacuo to yield a crude solid. This crude material was then dissolved in methylene chloride (40 mL) and trifluoroacetic acid (2.5 mL, 33 mmol, 3.0 equiv) was added. The solution was stirred for 3 h at which point the evolution of gas had subsided. Concentration in vacuo afforded a tan liquid which was purified by silica gel chromatography (eluting with 0-10% methanol/methylene chloride) yielding the desired product as a white solid (0.77 g, 68%). $^1$H NMR (300 MHz, CDCl$_3$): δ 7.35 (br s, 1H), 5.15-4.93 (dt, 1H, J=7.6, 53.4 Hz), 3.50-3.34 (m, 2H), 2.53 (m, 1H), 2.39-2.21 (m, 1H).

Preparation 58: (R)-3-hydroxypyrrolidin-2-one

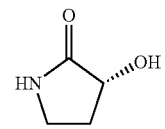

To a stirring mixture of 4-nitrobenzoic acid (9.273 g, 55.5 mmol, 1.1 equiv.) and (S)-(−)-3-3ydroxy-2-pyrrolidone (5.100 g, 50.4 mmol, 1.0 equiv.) in anhydrous tetrahydrofuran (175 mL) under a nitrogen atmosphere, triphenylphosphine (26.461 g, 100.9 mmol, 2.0 equiv.) was added. To this reaction mixture, disopropyl azodicarboxylate (14.898 mL, 75.7 mmol, 1.5 equiv.) was added dropwise (with external cooling with cold water bath). The reaction was stirred at room temperature overnight. The reaction mixture was concentrated in vacuo to afford a crude residue. Methanol (130 mL) was added to the residue followed by potassium carbonate (0.38 g) at room temperature. The reaction mixture was stirred at room temperature for 8 h. The reaction mixture was diluted with methylene chloride and filtered through Celite. The Celite bed was washed with 1% methanol in methylene chloride. The filtrates were combined and concentrated to dryness. The residue was partitioned between ethyl acetate: dilute aqueous hydrochloric acid (20 mL, 9:1) and stirred for 15 min. The layers were separated and the aqueous layer washed with ethyl acetate three times. The aqueous layer was concentrated to dryness and a solid residue was obtained. The crude residue was washed with 1-2% methanol in methylene chloride (3×50 mL), dried (anhydrous sodium sulfate), filtered, and concentrated to afford a tan oil (3.3 g, 60%). ¹H NMR (300 MHz, CDCl₃): δ 4.32-4.27 (t, 1H, J=8.5 Hz), 3.36-3.19 (m, 2H), 2.48-2.40 (m, 1H), 2.07-1.93 (m, 1H), 1.16-1.14 (d, 1H, J=6.3 Hz).

Preparation 59: (R)-3-((trimethylsilyl)oxy)pyrrolidin-2-one

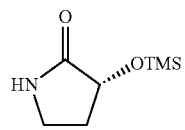

Trimethylsilyl chloride (0.405 mL, 3.2 mmol, 0.1 equiv.) was added to a stirred suspension of (R)-3-hydroxy-2-pyrrolidone (3.200 g, 31.7 mmol, 1.0 equiv.), xylene (45 mL), and hexamethyldisilazane (39.8 mL, 189 mmol, 6.0 equiv.) at room temperature. The reaction mixture was heated at reflux temperature for 5 h, and diluted with absolute ethanol (50 mL). The solvents were removed under reduced pressure. The crude product was purified by column chromatograph using ethyl acetate in methylene chloride (30-80% gradient) as eluant to afford a clear oil that solidifies to an off-white solid upon standing. (2.57 g, 47%). ¹H NMR (300 MHz, CDCl₃): δ 6.89 (br s, 1H), 4.28-4.23 (t, 1H, J=8.1 Hz), 3.40-3.21 (m, 2H), 2.42-2.32 (m, 1H), 2.08-1.95 (m, 1H), 0.18 (s, 9H).

Preparation 60: (R)-tert-butyl 2-oxo-3-((trimethylsilyl)oxy)pyrrolidine-1-carboxylate

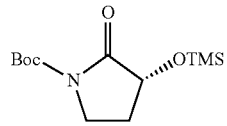

To a solution of (R)-3-((trimethylsilyl)oxy)pyrrolidin-2-one (2.770 g, 16.0 mmol, 1.0 equiv.) in anhydrous methylene chloride (75 mL) was added di-tert-butyl dicarbonate (6.971 g, 31.9 mmol, 2.0 equiv.), triethylamine (2.222 mL, 16.0 mmol, 1.0 equiv.), and N,N-4-dimethylaminopyridine (1.953 g, 16.0 mmol, 1.0 equiv.). The mixture was stirred overnight at room temperature then diluted with methylene chloride and washed with 0.1 N aqueous hydrochloric acid (100 mL). The organic layer was washed with 0.1 N aqueous hydrochloric acid (2×100 mL), and saturated aqueous sodium chloride (1×100 mL), dried (anhydrous sodium sulfate), and filtered. The solution was concentrated in vacuo and purified by silica gel chromatography (eluting with 0-15% ethyl acetate/hexanes) to afford a clear viscous oil (2.1 g, 48%). ¹H NMR (300 MHz, CDCl₃): δ 4.32-4.26 (dd, 1H, J=8.1, 9.3 Hz), 3.82-3.74 (ddd, 1H, J=2.1, 9.0, 11.1 Hz), 3.50-3.41 (m, 1H), 2.32-2.23 (m, 1H), 1.97-1.87 (m, 1H), 1.54 (s, 9H), 0.18 (s, 9H).

Preparation 61: (S)-3-fluoropyrrolidin-2-one

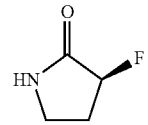

A solution of (R)-tert-butyl 2-oxo-3-((trimethylsilyl)oxy) pyrrolidine-1-carboxylate (2.100 g, 7.7 mmol, 1.0 equiv.) in anhydrous methylene chloride (37 mL) was cooled to −78° C. at which point diethylaminosulfur trifluoride (2.030 mL, 15.4 mmol, 2.0 equiv.) was added dropwise. The solution was then allowed to slowly warm to room temperature and saturated aqueous sodium bicarbonate (33 mL) was then added to quench the reaction. The layers were separated and the organic layer washed with saturated aqueous ammonium chloride (2×16 mL), dried (anhydrous sodium sulfate), filtered, and concentrated in vacuo to yield a crude solid. This crude material was then dissolved in dichloromethane (30 mL) and trifluoroacetic acid (1.7 mL, 33 mmol, 3.0 equiv) was added. The solution was stirred for 3 h at which point the evolution of gas had subsided. Concentration in vacuo and purification by silica gel chromatography (eluting with 0-10% methanol/methylene chloride) yielded the desired product as an off-white solid (0.71 g, 90%). ¹H NMR (300 MHz, CDCl₃): δ 7.35 (br s, 1H), 5.15-4.93 (dt, 1H, J=7.6, 53.4 Hz), 3.50-3.34 (m, 2H), 2.53 (m, 1H), 2.39-2.21 (m, 1H).

Preparation 62: methyl 4-methyl-5-oxopentanoate

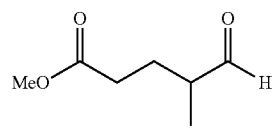

Following the procedure of Oikawa, M. et al. *Tetrahedron*, 1995, 51, 62377. A flask containing piperidine (54.425 mL, 551.0 mmol, 2.0 equiv.) and potassium carbonate (13.774 g, 99.7 mmol, 0.4 equiv.) was immersed in a water bath, and propionaldehyde (16.000 g, 275.5 mmol, 1.0 equiv.) was added over 20 min with vigorous stirring. After being stirred for 18 h, the insoluble material was removed by filtering through a pad of Celite (pad washed with diethyl ether). The filtrate was dried (anhydrous sodium sulfate), filtered and concentrated in vacuo. The crude enamine thus obtained was dissolved in acetonitrile (150 mL), and to this was added methyl acylate (47.433 g, 551.0 mmol, 2.0 equiv.) dropwise. The reaction mixture was stirred at reflux for 24 h, followed by the addition of acetic acid (31.541 mL, 551.0 mmol, 2.0 equiv.) and water (150 mL). After being stirred at reflux for 24 h, it was saturated with sodium chloride and extracted with diethyl ether (3×100 mL). The combined organic extracts were dried (anhydrous magnesium sulfate), filtered, and concentrated in vacuo. Purification by silica gel flash chromatography (0-20% ethyl acetate/hexanes) afforded the adduct as a colorless oil (22 g, 55%). ¹H NMR (300 MHz, CDCl₃): δ 9.64 (d, 1H, J=1.8 Hz), 3.69 (s, 3H), 2.50-2.35 (m, 3H), 2.07 (sext, 1H, J=7.2 Hz), 1.71 (sext, 1H, J=7.2 Hz), 1.14 (d, 3H, J=7.2 Hz).

Preparation 63: (3R,8S,8aR)-8-methyl-3-phenyltetrahydro-2H-oxazolo[3,2-a]pyridin-5(3H)-one and (3R,8R,8aS)-8-methyl-3-phenyltetrahydro-2H-oxazolo[3,2-a]pyridin-5 (3H)-one

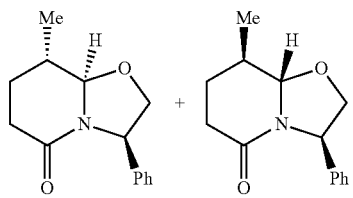 [SMILES: C[C@H]1CCC(=O)N2[C@@H]1OC[C@H]2c1ccccc1 ; C[C@@H]1CCC(=O)N2[C@H](c3ccccc3)CO[C@@H]12]

Following the procedure of Amat, M. et al. *J. Org. Chem.* 2014, 79, 2792. To a stirred solution of methyl 4-methyl-5-oxopentanoate (5.780 g, 40.1 mmol, 1.0 equiv.) in toluene (100 mL) was added (R)-(−)-phenylglycinol (5.500 g, 40.1 mmol, 1.0 equiv.). The reaction mixture was heated at reflux for 25 h with azeotropic removal of the produced water with Dean-Stark apparatus. After cooling, the mixture was concentrated in vacuo and the residue was purified by silica gel column (column was pre-treated with TEA, then eluted with 0-70% ethyl acetate/hexanes) to afford the desired products: (3R,8S,8aS)-8-methyl-3-phenyltetrahydro-2H-oxazolo[3,2-a]pyridin-5(3H)-one as a light yellow solid (1.3 g, 14%) and (3R,8S,8aR)-8-methyl-3-phenyltetrahydro-2H-oxazolo[3,2-a]pyridin-5(3H)-one as a colorless syrup (6.5 g, 70%). (3R,8S,8aS)-8-methyl-3-phenyltetrahydro-2H-oxazolo[3,2-a]pyridin-5(3H)-one: $^1$H NMR (300 MHz, CDCl$_3$): δ 7.40-7.20 (m, 5H), 5.25 (t, 1H, J=7.5 Hz), 4.61 (d, 1H, J=8.4 Hz), 4.48 (t, 1H, J=8.7 Hz), 3.75 (dd, 1H, J=9.0, 7.8 Hz), 2.55 (dd, 1H, J=18.0, 6.0 Hz), 2.46-2.33 (m, 1H), 1.88-1.51 (m, 3H), 1.19 (d, 3H, J=5.7 Hz); ESI (m/z): 232.7 (M+H). (3R,8S,8aR)-8-methyl-3-phenyltetrahydro-2H-oxazolo[3,2-a]pyridin-5(3H)-one: $^1$H NMR (300 MHz, CDCl$_3$): δ 7.40-7.20 (m, 5H), 4.93 (d, 1H, J=6.3 Hz), 4.44 (d, 1H, J=9.3 Hz), 4.14 (dd, 1H, J=8.7, 6.3 Hz), 4.01 (dd, 1H, J=8.7, 1.2 Hz), 2.47-2.25 (m, 2H), 2.05-1.87 (m, 2H), 1.60-1.43 (m, 1H), 1.20 (d, 3H, J=6.6 Hz); ESI (m/z): 232.7 (M+H).

Preparation 64: (S)-1-((R)-2-hydroxy-1-phenylethyl)-5-methylpiperidin-2-one

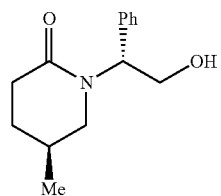 [SMILES: C[C@H]1CCC(=O)N([C@@H](CO)c2ccccc2)C1]

Following the procedure of Amat, M. et al. *J. Org. Chem.* 2014, 79, 2792. To a stirred solution of (3R,8S,8aR)-8-methyl-3-phenyltetrahydro-2H-oxazolo[3,2-a]pyridin-5 (3H)-one (3.600 g, 15.6 mmol, 1.0 equiv.) in anhydrous methylene chloride (100 mL) was added triethylsilane (7.458 mL, 46.7 mmol, 3.0 equiv.) and titanium (IV) chloride (7.697 mL, 70.0 mmol, 4.5 equiv.), and the mixture was stirred at 50° C. for 24 h. Then, additional titanium (IV) chloride (7.7 mL) and triethylsilane (7.5 mL) were added, and the stirring was continued at 50° C. for 24 h. The mixture was poured into saturated aqueous sodium bicarbonate (100 mL). The aqueous phase was filtered over Celite and extracted with methylene chloride. The combined organic extracts were dried (anhydrous sodium sulfate), filtered, and concentrated in vacuo to afford a residue which was chromatographed over silica gel (0-100% ethyl acetate/hexanes, then pure ethyl acetate) to afford the desired product as a colorless oil (1.6 g, 44%) and starting material (0.6 g) was recovered. $^1$H NMR (300 MHz, CDCl$_3$): δ 7.40-7.20 (m, 5H), 5.80 (dd, 1H, J=9.6, 4.8 Hz), 4.20-4.00 (m, 2H), 2.97 (ddd, 1H, J=11.7, 4.8, 2.4 Hz), 2.84 (dd, 1H, J=11.7, 9.9 Hz), 2.70 (br s, 1H), 2.59 (ddd, 1H, J=17.7, 6.3, 3.0 Hz), 2.47 (ddd, 1H, J=17.7, 11.1, 6.6 Hz), 1.90-1.75 (m, 2H), 1.50 (m, 1H), 0.93 (d, 3H, J=6.3 Hz).

Preparation 65: (S)-5-methylpiperidin-2-one

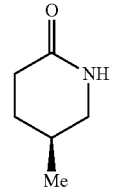

In a two-necked flask, fitted with a dry ice condenser, was charged (S)-1-((R)-2-hydroxy-1-phenylethyl)-5-methylpiperidin-2-one (1.600 g, 6.9 mmol, 1.0 equiv.) and anhydrous tetrahydrofuran (20 mL). The mixture was cooled to −78° C. under a nitrogen atmosphere, and then ammonia (50 mL) was condensed. The reaction temperature was raised to −33° C. Small pieces of metal sodium were added until the blue color persisted, and the mixture was stirred at −33° C. for 5 min. The reaction was quenched by addition of solid ammonium chloride until the blue color disappeared. The mixture was stirred at room temperature for 5 h and methylene chloride was added. The mixture was filtered through Celite and the filtrate concentrated in vacuo. The residue was purified by silica gel column (0-100% ethyl acetate/hexanes and then 20% methanol/ethyl acetate) to afford the desired product as a colorless oil (0.480 g, 62%). $^1$H NMR (300 MHz, CDCl$_3$): δ 5.84 (br s, 1H), 3.10 (m, 1H), 2.94 (t, 1H, J=10.8 Hz), 2.50-2.28 (m, 2H), 2.05-1.80 (m, 2H), 1.50 (m, 1H), 1.03 (d, 3H, J=6.9 Hz).

Preparation 66: (R)-1-((R)-2-hydroxy-1-phenylethyl)-5-methylpiperidin-2-one

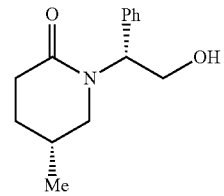 [SMILES: C[C@@H]1CCC(=O)N([C@@H](CO)c2ccccc2)C1]

Following the procedure of Amat, M. et al. *J. Org. Chem.* 2014, 79, 2792. To a stirred solution of (3R,8R,8aS)-8-methyl-3-phenyltetrahydro-2H-oxazolo[3,2-a]pyridin-5 (3H)-one (1.000 g, 4.3 mmol, 1.0 equiv.) in anhydrous methylene chloride (50 mL) was added triethylsilane (2.072 mL, 13.0 mmol, 3.0 equiv.) and titanium (IV) chloride (2.138 mL, 19.5 mmol, 4.5 equiv.), and the mixture was stirred at 50° C. for 6 h. The mixture was poured into saturated aqueous sodium bicarbonate (50 mL). The aqueous phase was filtered over Celite and extracted with methylene chloride. The combined organic extracts were dried (anhydrous sodium sulfate), filtered, and concentrated in vacuo to afford a residue, which was chromatographed (0-100% ethyl acetate/hexanes and then ethyl acetate) to afford the desired product as a colorless syrup (0.200 g, 20%). $^1$H NMR (300 MHz, CDCl$_3$): δ 7.40-7.20 (m, 5H), 5.67 (dd, 1H, J=7.8, 6.3 Hz), 4.20-4.05 (m, 2H), 3.15-3.00 (m, 2H), 2.65-2.40 (m, 3H), 2.00-1.75 (m, 2H), 1.40 (m, 1H), 0.89 (d, 3H, J=6.9 Hz).

Preparation 67: (R)-5-methylpiperidin-2-one

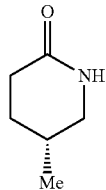

In a two-necked flask, fitted with a dry ice condenser, was charged (R)-1-((S)-2-hydroxy-1-phenylethyl)-5-methylpiperidin-2-one (0.200 g, 0.9 mmol, 1.0 equiv.) and anhydrous tetrahydrofuran (5 mL). The mixture was cooled to −78° C. under a nitrogen atmosphere, and then ammonia (15 mL) was condensed. The reaction temperature was raised to −33° C. Small pieces of metal sodium was added until the blue color persisted, and the mixture was stirred at −33° C. for 5 min. The reaction was quenched by addition of solid ammonium chloride until the blue color disappeared. The mixture was stirred at room temperature for 5 h and methylene chloride was added. The mixture was filtered through Celite and the filtrate concentrated in vacuo. The residue was purified by silica gel column (0-100% ethyl acetate/hexanes and then 20% methanol/ethyl acetate) to afford the desired product as a yellow oil (0.080 g, 82%). $^1$H NMR (300 MHz, CDCl$_3$): δ 5.85 (br s, 1H), 3.10 (m, 1H), 2.93 (t, 1H, J=10.8 Hz), 2.50-2.28 (m, 2H), 2.05-1.80 (m, 2H), 1.50 (m, 1H), 1.03 (d, 3H, J=6.6 Hz).

Preparation 68: (S)-tert-butyl (1-amino-1-oxopropan-2-yl)carbamate

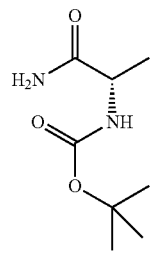

A mixture of Boc-Ala-OMe (5.000 g, 24.6 mmol, 1.0 equiv.) and 28% aqueous ammonium hydroxide (100.00 mL, 1479.7 mmol, 60.1 equiv.) in methanol (100 mL) was stirred for 16 h at room temperature. The reaction mixture was concentrated in vacuo to afford the desired product as a white solid (4.65 g, 100%). $^1$H NMR (300 MHz, CDCl$_3$): δ 6.15 (br, 1H), 5.55 (br, 1H), 4.95 (br, 1H), 4.20 (br, 1H), 1.46 (s, 9H), 1.39 (d, 3H, J=7.2 Hz).

Preparation 69: (S)-tert-butyl (1-aminopropan-2-yl)carbamate

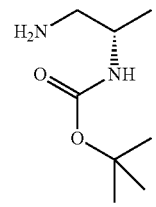

To a stirred solution of Boc-Ala-NH$_2$ (4.600 g, 24.4 mmol, 1.0 equiv.) in anhydrous tetrahydrofuran (100 mL) under nitrogen was added 1.0 M borane-tetrahydrofuran complex in tetrahydrofuran (85.536 mL, 85.5 mmol, 3.5 equiv.). The mixture was stirred for 16 h at room temperature and then heated at 70° C. for 2 h. After cooling, the reaction was quenched with methanol until no bubbles generated. The mixture was heated at 70° C. for 2 h and then concentrated in vacuo. The residue was purified by silica gel column (0-100% ethyl acetate/hexanes and then 0-30% methanol/methylene chloride) to afford the desired product as a semi-solid (1.4 g, 33%). $^1$H NMR (300 MHz, CDCl$_3$): δ 4.60 (br s, 1H), 3.65 (m, 1H), 2.76 (dd, 1H, J=12.9, 4.8 Hz), 2.64 (dd, 1H, J=12.9, 6.6 Hz), 1.45 (s, 9H), 1.13 (d, 3H, J=6.9 Hz).

Preparation 70: tert-butyl ((S)-1-(((S)-3-(3,6-difluoro-9H-carbazol-9-yl)-2-hydroxypropyl)amino)propan-2-yl)carbamate

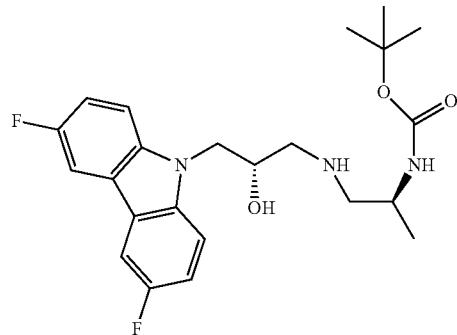 [SMILES: C[C@@H](CNC[C@H](O)Cn1c2ccc(F)cc2c2cc(F)ccc21)NC(=O)OC(C)(C)C]

A mixture of (R)-3,6-difluoro-9-(oxiran-2-ylmethyl)-9H-carbazole (0.600 g, 2.3 mmol, 1.0 equiv.) and (S)-tert-butyl-(1-aminopropan-2-yl)carbamate (1.210 g, 6.9 mmol, 3.0 equiv.) in ethanol (10 mL) was stirred at 70° C. After 15 h, the reaction mixture was concentrated in vacuo and purified by silica gel column (0-100% ethyl acetate/hexanes then 0-30% methanol/methylene chloride) to afford the desired product as a white foam (0.750 g, 75%) and recovered amine starting material (0.2 g). $^1$H NMR (300 MHz, CDCl$_3$): δ 7.67 (dd, 2H, J=8.7, 2.4 Hz), 7.42 (dd, 2H, J=8.7, 3.9 Hz), 7.22 (td, 2H, J=9.0, 2.7 Hz), 4.50-4.25 (m, 3H), 4.13 (m, 1H), 3.78 (br s, 1H), 2.86 (dd, 1H, J=12.0, 3.6 Hz), 2.70-2.50 (m, 3H), 1.43 (s, 9H), 1.10 (d, 3H, J=6.3 Hz); ESI (m/z): 434.0 (M+H).

Preparation 71: tert-butyl ((S)-1-(((S)-3-(9H-carbazol-9-yl)-2-hydroxypropyl)amino)propan-2-yl)carbamate

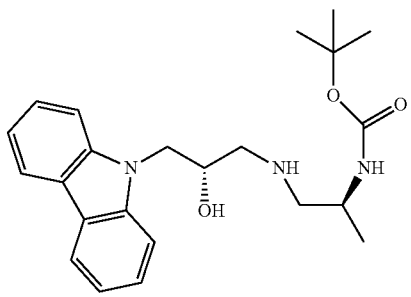 [SMILES: C[C@@H](CNC[C@H](O)Cn1c2ccccc2c2ccccc21)NC(=O)OC(C)(C)C]

A mixture of (R)-9-(oxiran-2-ylmethyl)-9H-carbazole (0.150 g, 0.7 mmol, 1.0 equiv.) and (S)-tert-butyl (1-aminopropan-2-yl)carbamate (0.200 g, 1.1 mmol, 1.7 equiv.) in ethanol (5 mL) was stirred at 70° C. After 15 h, the reaction mixture was concentrated in vacuo and purified by silica gel column (0-100% ethyl acetate/hexanes) to afford the desired product as a white foam (0.120 g, 45%). $^1$H NMR (300 MHz, CDCl$_3$): δ 8.09 (d, 2H, J=7.8 Hz), 7.52-7.41 (m, 4H), 7.25-7.20 (m, 2H), 4.50-4.35 (m, 3H), 4.17 (m, 1H), 3.73 (m, 1H), 2.83 (dd, 1H, J=11.7, 3.6 Hz), 2.66-2.47 (m, 3H), 1.43 (s, 9H), 1.08 (d, 3H, J=6.6 Hz); ESI (m/z): 398.1 (M+H).

Preparation 72: (R)-tert-butyl (1-amino-1-oxopropan-2-yl)carbamate

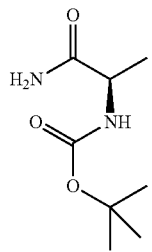

A mixture of Boc-D-Ala-OMe (5.000 g, 24.6 mmol, 1.0 equiv.) and 28% aqueous ammonium hydroxide (100 mL, 1479.7 mmol, 60.1 equiv.) in methanol (100 mL) was stirred for 16 h at room temperature. The reaction mixture was concentrated in vacuo to afford the desired product as a white solid (4.65 g, 100%). $^1$H NMR (300 MHz, CDCl$_3$): δ 6.15 (br, 1H), 5.60 (br, 1H), 5.00 (br, 1H), 4.20 (br, 1H), 1.46 (s, 9H), 1.39 (d, 3H, J=6.9 Hz).

Preparation 73: (R)-tert-butyl (1-aminopropan-2-yl)carbamate

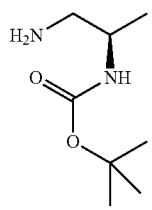

To a stirred solution of Boc-D-Ala-NH$_2$ (4.600 g, 24.4 mmol, 1.0 equiv.) in anhydrous tetrahydrofuran (100 mL) under nitrogen was added 1.0 M borane-tetrahydrofuran complex in tetrahydrofuran (97.756 mL, 97.8 mmol, 4.0 equiv.). The mixture was stirred for 16 h at room temperature and then heated at 70° C. for 2 h. After cooling, the reaction was quenched with methanol until no bubbles generated. The mixture was heated at 70° C. for 2 h and then concentrated in vacuo. The residue was purified by silica gel column (0-30% methanol/methylene chloride) to afford the desired product as a colorless oil (1.5 g, 35%). $^1$H NMR (300 MHz, CDCl$_3$): δ 4.60 (br s, 1H), 3.65 (m, 1H), 2.75 (dd, 1H, J=12.9, 5.1 Hz), 2.63 (dd, 1H, J=12.9, 6.6 Hz), 1.45 (s, 9H), 1.41 (s, 2H), 1.12 (d, 3H, J=6.3 Hz).

Preparation 74: tert-butyl ((R)-1-(((S)-3-(3,6-difluoro-9H-carbazol-9-yl)-2-hydroxypropyl)amino)propan-2-yl)carbamate

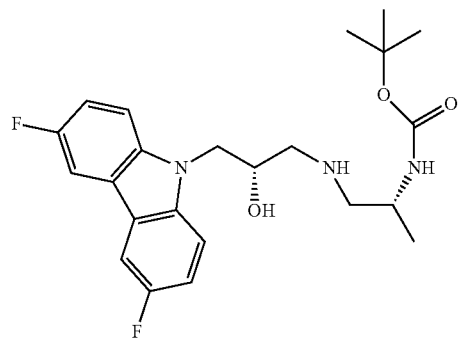 [SMILES: C[C@H](CNC[C@H](O)Cn1c2ccc(F)cc2c2cc(F)ccc21)NC(=O)OC(C)(C)C]

A mixture of (R)-3,6-difluoro-9-(oxiran-2-ylmethyl)-9H-carbazole (0.200 g, 0.8 mmol, 1.0 equiv.) and (R)-tert-butyl (1-aminopropan-2-yl)carbamate (0.403 g, 2.3 mmol, 3.0 equiv.) in ethanol (10 mL) was stirred at 70° C. After 15 h, the reaction mixture was concentrated in vacuo and purified by silica gel column (0-30% methanol/methylene chloride) to isolate the desired product as a white powder (0.250 g, 75%). $^1$H NMR (300 MHz, CDCl$_3$): δ 7.68 (dd, 2H, J=8.7, 2.7 Hz), 7.41 (dd, 2H, J=9.3, 4.2 Hz), 7.22 (td, 2H, J=9.3, 2.4 Hz), 4.43 (br s, 1H), 4.35 (d, 2H, J=5.7 Hz), 4.12 (m, 1H), 3.78 (br s, 1H), 2.80 (dd, 1H, J=12.3, 3.6 Hz), 2.63 (dd, 1H, J=12.3, 5.7 Hz), 2.57 (d, 2H, J=7.2 Hz), 1.44 (s, 9H), 1.11 (d, 3H, J=6.6 Hz); ESI (m/z): 434.0 (M+H).

Preparation 75: tert-butyl ((R)-1-(((S)-3-(9H-carbazol-9-yl)-2-hydroxypropyl)amino)propan-2-yl)carbamate

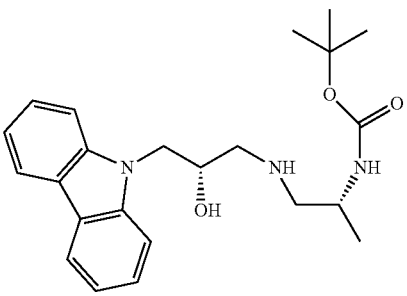 [SMILES: C[C@H](CNC[C@H](O)Cn1c2ccccc2c2ccccc21)NC(=O)OC(C)(C)C]

A mixture of (R)-9-(oxiran-2-ylmethyl)-9H-carbazole (0.150 g, 0.7 mmol, 1.0 equiv.) and (R)-tert-butyl (1-aminopropan-2-yl)carbamate (0.351 g, 2.0 mmol, 3.0 equiv.) in ethanol (10 mL) was stirred at 70° C. After 15 h, the reaction mixture was concentrated in vacuo and purified by silica gel column (0-30% methanol/methylene chloride) to isolate the desired product as a white foam (0.210 g, 78%). $^1$H NMR (300 MHz, CDCl$_3$): δ 8.10 (d, 2H, J=7.5 Hz), 7.55-7.40 (m, 4H), 7.27-7.20 (m, 2H), 4.60-4.30 (m, 3H), 4.16 (m, 1H), 3.78 (m, 1H), 2.80 (dd, 1H, J=12.3, 3.6 Hz), 2.67 (dd, 1H, J=12.0, 8.4 Hz), 2.60-2.50 (m, 2H), 1.44 (s, 9H), 1.10 (d, 3H, J=6.6 Hz); ESI (m/z): 398.1 (M+H).

Example 2: Preparation of Compounds of Formula I

Compound 1: 1-(3-(9H-carbazol-9-yl)-2-hydroxypropyl)piperidin-2-one

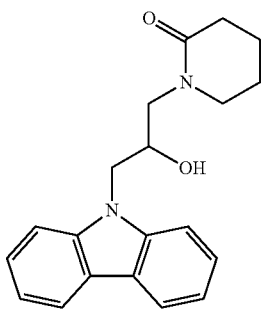 [SMILES: O=C1CCCCN1CC(O)Cn1c2ccccc2c2ccccc21]

To a stirred solution of piperidin-2-one (0.133 g, 1.3 mmol) in dimethyl sulfoxide (5 mL) was added potassium tert-butoxide (0.151 g, 1.3 mmol) and the mixture was stirred at room temperature for 1 hour. 9-(oxiran-2-ylmethyl)-9H-carbazole (0.150 g, 0.7 mmol) was added and the mixture was stirred at room temperature for 16 hours. The mixture was diluted with water and extracted with ethyl acetate. The organic layer was washed with saturated aqueous sodium chloride, dried (anhydrous sodium sulfate), filtered and concentrated in vacuo. The residue was purified by silica gel column (50-100% ethyl acetate/hexanes) and then by prep-HPLC (C18, 30-80% acetonitrile/water with 0.1% formic acid over 0-8 min) to afford the product as a white foam (0.098 g, 45%). $^1$H NMR (300 MHz, CDCl$_3$): δ 8.08 (d, 2H, J=7.8 Hz), 7.50-7.40 (m, 4H), 7.28-7.18 (m, 2H), 4.60-4.25 (m, 4H), 3.87 (dd, 1H, J=14.1, 7.8 Hz), 3.15-2.95 (m, 3H), 2.36 (t, 2H, J=5.7 Hz), 1.85-1.55 (m, 4H); ESI (m/z): 323.2 (M+H).

Compounds 2 to 72

Compounds 2 to 72 were prepared by procedures analogous to those used for Compound 1 or by using sodium hydride (0.4 equiv.) instead of potassium tert-butoxide. Alternatively, phosphazene base P4-t-Bu can be used instead of potassium tert-butoxide also. In cases where the starting materials for the targets below were not commercially available, the syntheses are described in the preceding preparation examples.

| Cpd | Structure | Name | $^1$H NMR | ESI (m/z) |
|---|---|---|---|---|
| 2 | 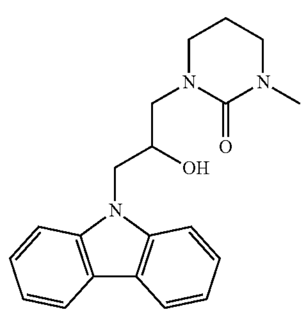 [SMILES: CN1CCCN(CC(O)Cn2c3ccccc3c3ccccc32)C1=O] | 1-(3-(9H-carbazol-9-yl)-2-hydroxypropyl)-3-methyltetrahydropyrimidin-2(1H)-one | (300 MHz, CDCl$_3$) δ 8.10 (d, 2H, J = 7.8 Hz), 7.55-7.40 (m, 4H), 7.32-7.20 (m, 2H), 5.31 (s, 1H), 4.55-4.25 (m, 3H), 3.88 (dd, 1H, J = 14.4, 8.4 Hz), 3.30-2.85 (m, 8H), 2.00-1.80 (m, 2H). | 338.2 (M + H) |
| 3 | 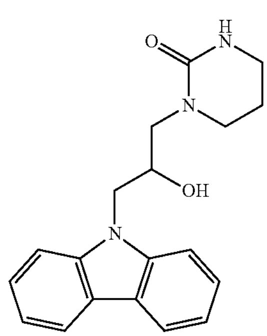 [SMILES: O=C1NCCCN1CC(O)Cn1c2ccccc2c2ccccc21] | 1-(3-(9H-carbazol-9-yl)-2-hydroxypropyl) tetrahydropyrimidin-2(1H)-one | (300 MHz, CDCl$_3$) δ 8.10 (d, 2H, J = 7.5 Hz), 7.54-7.42 (m, 4H), 7.32-7.20 (m, 2H), 5.10 (s, 1H), 4.77 (s, 1H), 4.50-4.28 (m, 3H), 3.87 (dd, 1H, J = 14.7, 8.1 Hz), 3.35-3.20 (m, 2H), 3.15-2.90 (m, 3H), 1.92-1.80 (m, 2H). | 324.2 (M + H) |

-continued

| Cpd | Structure | Name | ¹H NMR | ESI (m/z) |
|---|---|---|---|---|
| 4 | 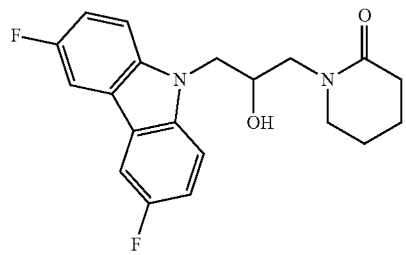 [SMILES: O=C1CCCCN1CC(O)Cn1c2ccc(F)cc2c2cc(F)ccc21] | 1-(3-(3,6-difluoro-9H-carbazol-9-yl)-2-hydroxypropyl) piperidin-2-one | (300 MHz, CDCl₃) δ 7.68 (dd, 2H, J = 8.4, 2.7 Hz), 7.39 (dd, 2H, J = 9.0, 4.2 Hz), 7.23 (td, 2H, J = 9.0, 2.7 Hz), 4.50-4.25 (m, 4H), 3.91 (dd, 1H, J = 14.4, 8.1 Hz), 3.25-3.08 (m, 2H), 3.02 (d, 1H, J = 14.1 Hz), 2.50-2.38 (m, 2H), 1.90-1.65 (m, 4H). | 359.1 (M + H) |
| 5 | 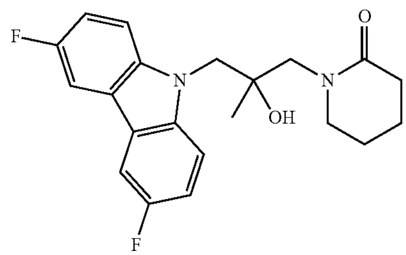 [SMILES: CC(O)(CN1CCCCC1=O)Cn1c2ccc(F)cc2c2cc(F)ccc21] | 1-(3-(3,6-difluoro-9H-carbazol-9-yl)-2-hydroxy-2-methylpropyl) piperidin-2-one | (300 MHz, CDCl₃) δ 7.67 (dd, 2H, J = 8.7, 2.7 Hz), 7.46 (dd, 2H, J = 9.0, 4.2 Hz), 7.21 (td, 2H, J = 9.0, 2.7 Hz), 4.88 (s, 1H), 4.30 (s, 2H), 3.99 (d, 1H, J = 14.1 Hz), 3.55-3.30 (m, 2H), 3.17 (d, 1H, J = 14.4 Hz), 2.47 (m, 2H), 1.95-1.70 (m, 4H), 1.30 (s, 3H). | 373.0 (M + H) |
| 6 | 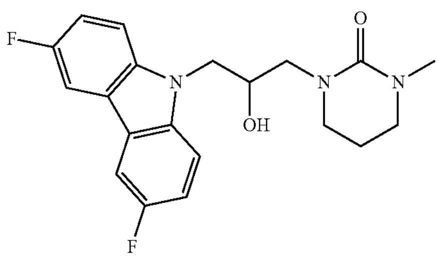 [SMILES: CN1CCCN(CC(O)Cn2c3ccc(F)cc3c3cc(F)ccc32)C1=O] | 1-(3-(3,6-difluoro-9H-carbazol-9-yl)-2-hydroxypropyl)-3-methyltetrahydropyrimidin-2(1H)-one | (300 MHz, CDCl₃) δ 7.68 (dd, 2H, J = 8.7, 2.7 Hz), 7.40 (dd, 2H, J = 8.7, 4.2 Hz), 7.22 (td, 2H, J = 8.7, 2.7 Hz), 5.27 (br s, 1H), 4.50-4.20 (m, 3H), 3.82 (m, 1H), 3.32-3.00 (m, 4H), 2.95 (s, 3H), 2.92 (dd, 1H, J = 14.4, 1.5 Hz), 1.91 (5 peaks, 2H, J = 6.0 Hz). | 374.1 (M + H) |
| 7 | 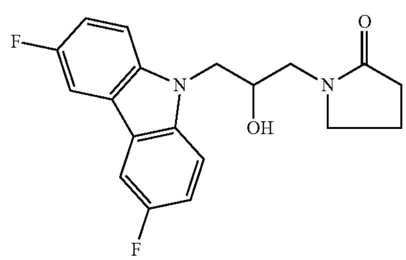 [SMILES: O=C1CCCN1CC(O)Cn1c2ccc(F)cc2c2cc(F)ccc21] | 1-(3-(3,6-difluoro-9H-carbazol-9-yl)-2-hydroxypropyl) pyrrolidin-2-one | (300 MHz, CDCl₃) δ 7.68 (dd, 2H, J = 8.4, 2.7 Hz), 7.37 (dd, 2H, J = 8.7, 4.2 Hz), 7.23 (td, 2H, J = 9.0, 2.7 Hz), 4.45-4.25 (m, 3H), 3.89 (br s, 1H), 3.60-3.25 (m, 4H), 2.45 (t, 2H, J = 8.4 Hz), 2.15-1.95 (m, 2H). | 345.0 (M + H) |
| 8 | 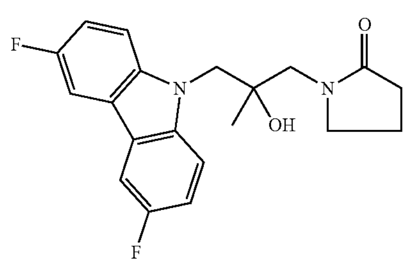 [SMILES: CC(O)(CN1CCCC1=O)Cn1c2ccc(F)cc2c2cc(F)ccc21] | 1-(3-(3,6-difluoro-9H-carbazol-9-yl)-2-hydroxy-2-methylpropyl) pyrrolidin-2-one | (300 MHz, CDCl₃) δ 7.67 (dd, 2H, J = 8.7, 2.7 Hz), 7.44 (dd, 2H, J = 9.0, 4.2 Hz), 7.21 (td, 2H, J = 9.0, 2.7 Hz), 4.34 and 4.28 (AB, 2H, J = 15.3 Hz), 3.70-3.50 (m, 4H), 3.38 (d, 1H, J = 14.1 Hz), 2.47 (t, 2H, J = 8.7 Hz), 2.20-2.00 (m, 2H), 1.29 (s, 3H). | 359.0 (M + H) |
| 9 | 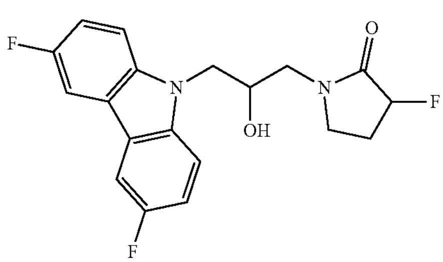 [SMILES: O=C1C(F)CCN1CC(O)Cn1c2ccc(F)cc2c2cc(F)ccc21] | 1-(3-(3,6-difluoro-9H-carbazol-9-yl)-2-hydroxypropyl)-3-fluoropyrrolidin-2-one | (300 MHz, CDCl₃): δ 7.68 (dd, 2H, J = 8.7, 2.7 Hz), 7.36 (dd, 2H, J = 8.7, 4.2 Hz), 7.23 (td, 2H, J = 9.0, 2.7 Hz), 5.14 (dm, 1H, J = 52.2 Hz), 4.50-4.30 (m, 3H), 3.62-3.30 (m, 4H), 3.12 and 3.05 (d, 1H, J = 4.2 Hz), 2.60-2.10 (m, 2H). | 363.1 (M + H) |

| Cpd | Structure | Name | ¹H NMR | ESI (m/z) |
|---|---|---|---|---|
| 10 | 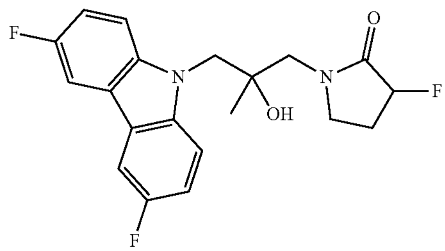 [SMILES: CC(O)(CN1CCC(F)C1=O)Cn1c2ccc(F)cc2c2cc(F)ccc21] | 1-(3-(3,6-difluoro-9H-carbazol-9-yl)-2-hydroxy-2-methylpropyl)-3-fluoropyrrolidin-2-one | (300 MHz, CDCl₃): δ 7.68 (dd, 2H, J = 8.4, 2.7 Hz), 7.42 (dd, 2H, J = 9.0, 4.2 Hz), 7.22 (td, 2H, J = 9.0, 2.7 Hz), 5.15 (ddd, 1H, J = 52.5, 7.5, 5.7 Hz), 4.40-4.25 (m, 2H), 3.76 (m, 1H), 3.65-3.48 (m, 3H), 2.70-2.20 (m, 3H), 1.32 and 1.30 (s, 3H). | 377.0 (M + H) |
| 11 | 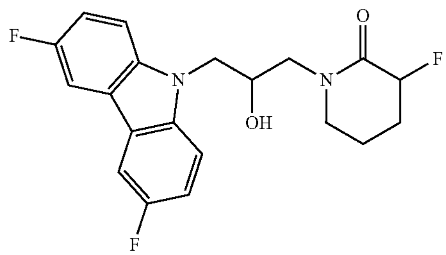 [SMILES: O=C1C(F)CCCN1CC(O)Cn1c2ccc(F)cc2c2cc(F)ccc21] | 1-(3-(3,6-difluoro-9H-carbazol-9-yl)-2-hydroxypropyl)-3-fluoropiperidin-2-one | (300 MHz, CDCl₃): δ 7.67 (dd, 2H, J = 8.7, 2.7 Hz), 7.38 (dd, 2H, J = 9.0, 4.2 Hz), 7.27-7.18 (m, 2H), 4.84 (dm, 1H, J = 47.1 Hz), 4.50-4.25 (m, 3H), 3.80-3.10 (m, 5H), 2.30-1.90 (m, 3H), 1.80 (m, 1H). | 377.1 (M + H) |
| 12 | 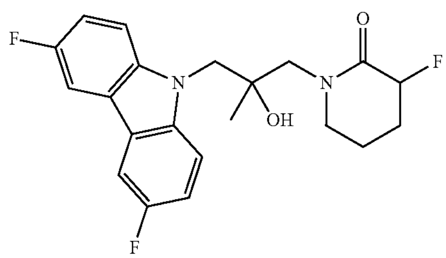 [SMILES: CC(O)(CN1CCCC(F)C1=O)Cn1c2ccc(F)cc2c2cc(F)ccc21] | 1-(3-(3,6-difluoro-9H-carbazol-9-yl)-2-hydroxy-2-methylpropyl)-3-fluoropiperidin-2-one | (300 MHz, CDCl₃): δ 7.67 (dd, 2H, J = 8.7, 2.7 Hz), 7.47-7.40 (m, 2H), 7.21 (td, 2H, J = 9.0, 2.7 Hz), 4.91 (dm, 1H, J = 46.5 Hz), 4.32 (d, 2H, J = 5.4 Hz), 3.87 (dd, 1H, J = 19.8, 13.8 Hz), 3.70-3.30 (m, 4H), 2.35-1.80 (m, 4H), 1.31 (s, 3H). | 391.1 (M + H) |
| 13 | 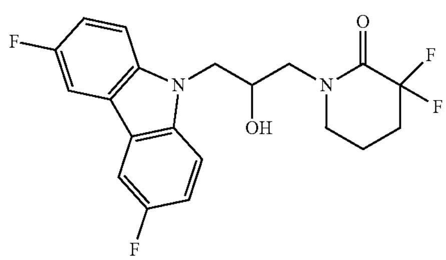 [SMILES: O=C1N(CC(O)Cn2c3ccc(F)cc3c3cc(F)ccc32)CCCC1(F)F] | 1-(3-(3,6-difluoro-9H-carbazol-9-yl)-2-hydroxypropyl)-3,3-difluoropiperidin-2-one | (300 MHz, CDCl₃): δ 7.68 (dd, 2H, J = 8.7, 2.7 Hz), 7.38 (dd, 2H, J = 8.7, 4.2 Hz), 7.23 (td, 2H, J = 9.0, 2.7 Hz), 4.50 (m, 1H), 4.39 (dd, 1H, J = 15.0, 4.8 Hz), 4.33 (dd, 1H, J = 15.0, 7.8 Hz), 3.62-3.55 (m, 2H), 3.54-3.35 (m, 2H), 2.75 (d, 1H, J = 4.5 Hz), 2.40-2.20 (m, 2H), 2.08-1.96 (m, 2H). | 395.1 (M + H) |
| 14 | 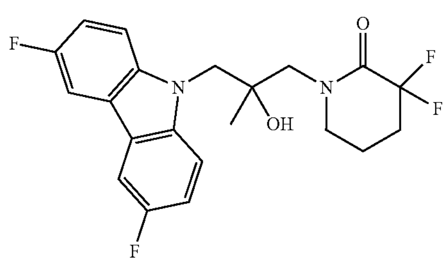 [SMILES: CC(O)(CN1CCCC(F)(F)C1=O)Cn1c2ccc(F)cc2c2cc(F)ccc21] | 1-(3-(3,6-difluoro-9H-carbazol-9-yl)-2-hydroxy-2-methylpropyl)-3,3-difluoropiperidin-2-one | (300 MHz, CDCl₃): δ 7.68 (dd, 2H, J = 8.7, 2.7 Hz), 7.42 (dd, 2H, J = 8.7, 4.2 Hz), 7.22 (td, 2H, J = 9.0, 2.7 Hz), 4.32 (s, 2H), 3.78 and 3.60 (ABq, 2H, J = 13.8 Hz), 3.73-3.58 (m, 2H), 2.60 (s, 1H), 2.45-2.28 (m, 2H), 2.18-2.00 (m, 2H), 1.32 (s, 3H). | 409.0 (M + H) |
| 15 | 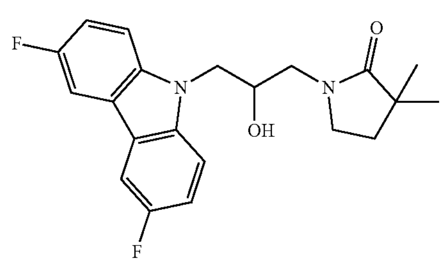 [SMILES: CC1(C)CCN(CC(O)Cn2c3ccc(F)cc3c3cc(F)ccc32)C1=O] | 1-(3-(3,6-difluoro-9H-carbazol-9-yl)-2-hydroxypropyl)-3,3-dimethylpyrrolidin-2-one | (300 MHz, CDCl₃): δ 7.68-7.65 (dd, 2H, J = 2.7, 8.7 Hz), 7.38-7.33 (dd, 2H, J = 4.1, 9.0 Hz), 7.21-7.14 (td, 2H, J = 2.5, 9.0 Hz), 4.37-4.28 (m, 3H), 3.98-3.97 (d, 1H, J = 3.9 Hz), 3.56-3.49 (dd, 1H, J = 7.1, 14.4 Hz), 3.34-3.17 (m, 3H), 1.90-1.85 (m, 2H), 1.18 (s, 3H), 1.17 (s, 3H). | 373.1 (M + H) |

-continued

| Cpd | Structure | Name | ¹H NMR | ESI (m/z) |
|---|---|---|---|---|
| 16 | 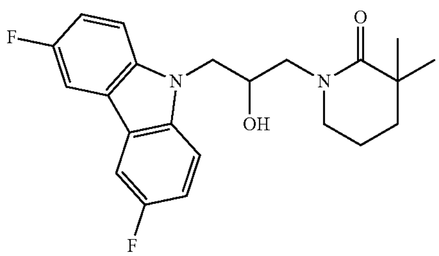 [SMILES: CC1(C)CCCN(CC(O)Cn2c3ccc(F)cc3c3cc(F)ccc32)C1=O] | 1-(3-(3,6-difluoro-9H-carbazol-9-yl)-2-hydroxypropyl)-3,3-dimethylpiperidin-2-one | (300 MHz, CDCl₃): δ 7.67-7.64 (dd, 2H, J = 2.4, 8.7 Hz), 7.38-7.34 (dd, 2H, J = 4.2, 8.7 Hz), 7.24-7.17 (td, 2H, J = 2.5, 9.0 Hz), 4.54-4.53 (d, 1H, J = 3.0 Hz), 4.36-4.25 (m, 3H), 3.94-3.86 (m, 1H), 3.18-3.11 (m, 2H), 2.95-2.90 (m, 1H), 1.81-1.61 (m, 4H), 1.22 (s, 3H), 1.20 (s, 3H). | 387.1 (M + H) |
| 17 | 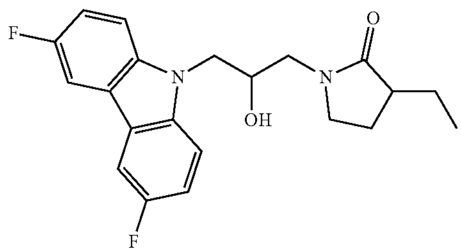 [SMILES: CCC1CCN(CC(O)Cn2c3ccc(F)cc3c3cc(F)ccc32)C1=O] | 1-(3-(3,6-difluoro-9H-carbazol-9-yl)-2-hydroxypropyl)-3-ethylpyrrolidin-2-one | (300 MHz, CDCl₃): δ 7.68-7.64 (dd, 2H, J = 2.7, 8.7 Hz), 7.37-7.33 (dd, 2H, J = 4.1, 9.0 Hz), 7.21-7.14 (td, 2H, J = 2.6, 9.0 Hz), 4.36-4.26 (m, 3H), 4.06-4.05 (d, 1H, J = 3.0 Hz), 3.57-3.16 (m, 4H), 2.44-2.34 (m, 1H), 2.24-2.12 (m, 1H), 1.91-1.82 (m, 1H), 1.77-1.66 (m, 1H), 1.49-1.37 (m, 1H), 0.99-0.94 (td, 3H, J = 1.9, 7.5 Hz). | 373.1 (M + H) |
| 18 | 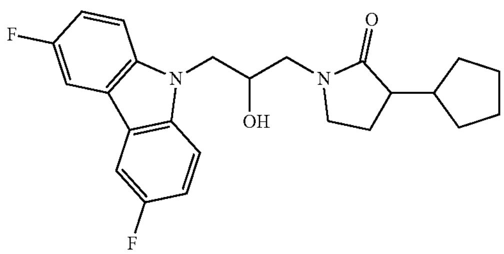 [SMILES: O=C1C(C2CCCC2)CCN1CC(O)Cn1c2ccc(F)cc2c2cc(F)ccc21] | 3-cyclopentyl-1-(3-(3,6-difluoro-9H-carbazol-9-yl)-2-hydroxypropyl)pyrrolidin-2-one | (300 MHz, CDCl₃): δ 7.63-7.64 (dd, 2H, J = 2.6, 8.6 Hz), 7.37-7.33 (dd, 2H, J = 4.1, 8.9 Hz), 7.24-7.17 (td, 2H, J = 2.7, 9.0 Hz), 4.36-4.26 (m, 3H), 4.09-4.00 (dd, 1H, J = 2.7, 24.9 Hz), 3.59-3.43 (m, 1H), 3.35-3.14 (m, 3H), 2.55-2.46 (m, 1H), 2.15-2.06 (m, 2H), 1.94-1.63 (m, 7H), 1.52-1.19 (m, 2H). | 413.1 (M + H) |
| 19 | 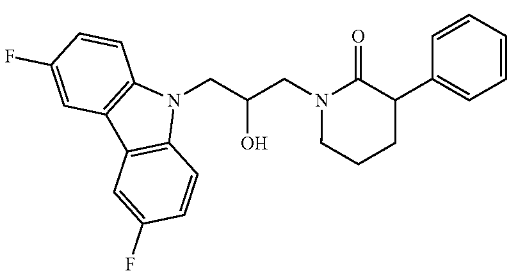 [SMILES: O=C1C(c2ccccc2)CCCN1CC(O)Cn1c2ccc(F)cc2c2cc(F)ccc21] | 1-(3-(3,6-difluoro-9H-carbazol-9-yl)-2-hydroxypropyl)-3-phenylpiperidin-2-one | (300 MHz, CDCl₃): δ 7.69-7.65 (dd, 2H, J = 2.7, 8.7 Hz), 7.41-7.13 (m, 9H), 4.49-4.15 (m, 4H), 4.05-3.93 (m, 1H), 3.71-3.63 (m, 1H), 3.37-3.21 (m, 2H), 3.13-3.03 (m, 1H), 2.18-2.07 (m, 1H), 1.99-1.70 (m, 3H). | 435.1 (M + H) |
| 20 | 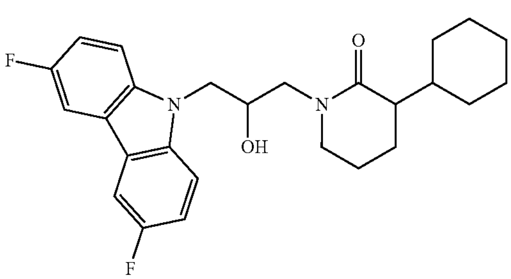 [SMILES: O=C1C(C2CCCCC2)CCCN1CC(O)Cn1c2ccc(F)cc2c2cc(F)ccc21] | 3-cyclohexyl-1-(3-(3,6-difluoro-9H-carbazol-9-yl)-2-hydroxypropyl)piperidin-2-one | (300 MHz, CDCl₃, mixture of diastereomers): δ 7.67-7.66 (two overlapping sets of dd, 2H, J = 2.3, 8.7 Hz), 7.39-7.34 (two overlapping sets of dd, 2H, J = 4.2, 8.7 Hz), 7.24-7.16 (two overlapping sets of td, 2H, J = 2.6, 9.0 Hz), 4.90 (s, 0.5H), 4.40-4.23 (m, 3.5H), 4.16-4.15 (d, 0.5H, J = 3.0 Hz), 3.95-3.87 (m, 1H), 3.28-3.21 (m, 0.5H), 3.14-3.02 (m, 2.5H), 2.89-2.84 (dd, 0.5H, J = 1.5, 14.1 Hz), 2.29-2.08 (m, 2H), 1.84-0.99, (m, 14H). | 441.2 (M + H) |

-continued

| Cpd | Structure | Name | ¹H NMR | ESI (m/z) |
|---|---|---|---|---|
| 21 | 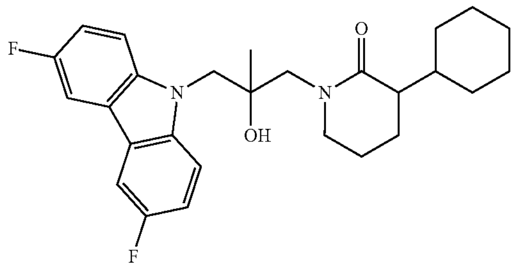 [SMILES: CC(O)(CN1CCCC(C2CCCCC2)C1=O)Cn1c2ccc(F)cc2c2cc(F)ccc21] | 3-cyclohexyl-1-(3-(3,6-difluoro-9H-carbazol-9-yl)-2-hydroxy-2-methylpropyl) piperidin-2-one | (300 MHz, CDCl₃, mixture of diastereomers): δ 7.66-7.62 (two overlapping sets of dd, 2H, J = 2.4, 8.7 Hz), 7.45-7.41 (dd, 2H, J = 3.9, 9.0 Hz), 7.22-7.15 (two sets of overlapping td, 2H, J = 2.4, 9.0 Hz), 5.24 (s, 0.5H), 5.11 (s, 0.5 H), 4.31-4.07 (m, 2H), 4.12-4.07 (m, 2H), 3.12-3.07 (ABq, 1H, J = 14.1 Hz), 3.92-3.87, 3.25-3.16 (ABq, 1H, J = 14.1 Hz), 3.55-3.25 (m, 2H), 2.37-2.05 (m, 2H), 1.93-0.84 (m, 14H), 1.24 (s, 3H). | 455.1 (M + H) |
| 22 | 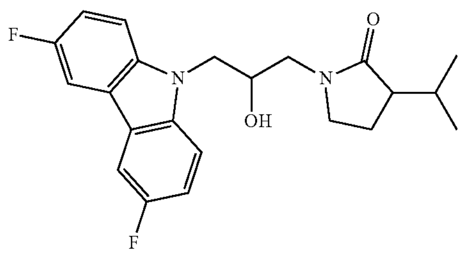 [SMILES: CC(C)C1CCN(CC(O)Cn2c3ccc(F)cc3c3cc(F)ccc32)C1=O] | 1-(3-(3,6-difluoro-9H-carbazol-9-yl)-2-hydroxypropyl)-3-isopropylpyrrolidin-2-one | (300 MHz, CDCl₃, mixture of diastereomers): δ 7.68-7.64 (dd, 2H, J = 2.4, 8.7 Hz), 7.37-7.33 (dd, 2H, J = 4.0, 9.0 Hz), 4.36-4.26 (m, 3H), 4.10-4.00 (m, 1H), 3.61-3.14 (m, 4H), 2.49-2.40 (m, 1H), 2.24-2.17 (m, 1H), 2.04-1.98 (m, 1H), 1.89-1.79 (m, 1H), 1.01-0.98 (two overlapping sets of d, 3H, J = 6.9 Hz), 0.89-0.86 (two overlapping sets of d, 3H, J = 6.9 Hz). | 387.1 (M + H) |
| 23 | 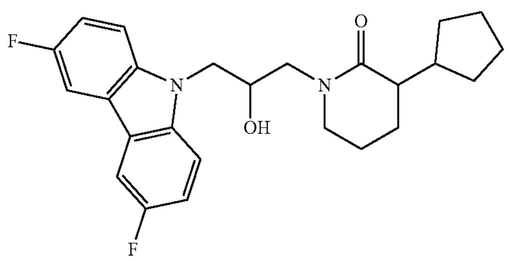 [SMILES: O=C1C(C2CCCC2)CCCN1CC(O)Cn1c2ccc(F)cc2c2cc(F)ccc21] | 3-cyclopentyl-1-(3-(3,6-difluoro-9H-carbazol-9-yl)-2-hydroxypropyl) piperidin-2-one | (300 MHz, CDCl₃, mixture of diastereomers): δ 7.68-7.64 (dd, 1H, J = 2.1, 8.4 Hz), 7.67-7.63 (dd, 1H, J = 2.3, 9.0 Hz), 7.39-7.34 (dd, 2H, J = 4.4, 9.0 Hz), 7.24-7.17 (td, 1H, J = 2.6, 9.0 Hz), 7.23-7.17 (td, 1H, J = 2.4, 9.0 Hz), 4.76-4.75 (d, 0.5H, J = 2.4 Hz), 4.38-4.23 (m, 3.5H), 3.98-3.84 (m, 1H), 3.25-2.90 (m, 3H), 2.41-2.29 (m, 1H), 1.87-1.15 (m, 12H). | 427.1 (M + H) |
| 24 | 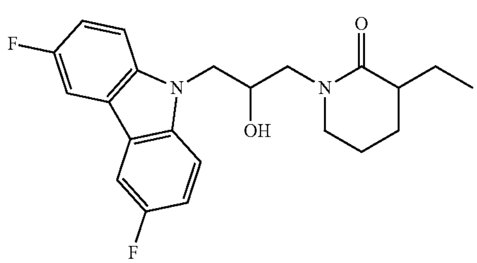 [SMILES: CCC1CCCN(CC(O)Cn2c3ccc(F)cc3c3cc(F)ccc32)C1=O] | 1-(3-(3,6-difluoro-9H-carbazol-9-yl)-2-hydroxypropyl)-3-ethylpiperidin-2-one | (300 MHz, CDCl₃, mixture of diastereomers): δ 7.67-7.64 (dd, 1H, J = 2.4, 8.7 Hz), 7.67-7.64 (dd, 1H, J = 2.4, 8.7 Hz), 7.38-7.34 (dd, 2H, J = 4.2, 9.0 Hz), 7.24-7.17 (td, 1H, J = 2.7, 9.0 Hz), 7.24-7.16 (td, 1H, J = 2.7, 9.0 Hz), 4.70 (br s, 0.5H), 4.38-4.26 (m, 3.5H), 3.95-3.83 (m, 1H), 3.20-2.87 (m, 3H), 2.28-2.20 (m, 1H), 2.00-1.43 (m, 6H), 0.96-0.89 (m, 3H). | 387.1 (M + H) |
| 25 | 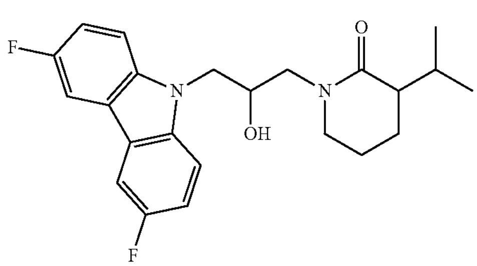 [SMILES: CC(C)C1CCCN(CC(O)Cn2c3ccc(F)cc3c3cc(F)ccc32)C1=O] | 1-(3-(3,6-difluoro-9H-carbazol-9-yl)-2-hydroxypropyl)-3-isopropylpiperidin-2-one | (300 MHz, CDCl₃, mixture of diastereomers): δ 7.67-7.64 (dd, 1H, J = 2.1, 8.7 Hz), 7.67-7.63 (dd, 1H, J = 2.4, 8.7 Hz), 7.38-7.34 (dd, 2H, J = 4.2, 8.7 Hz), 7.24-7.17 (td, 1H, J = 2.4, 9.0 Hz), 7.24-7.16 (td, 1H, J = 2.4, 9.0 Hz), 4.83 (br s, 0.5H), 4.38-4.22 (m, 3H), 4.15 (br s, 0.5H), 3.95-3.88 (m, 1H), 3.31-3.22 (m, 0.5H), 3.16-2.86 (m, 2.5H), 2.59-2.47 (m, 1H), 2.32-2.20 (m, 1H), 1.87-1.39 (m, 4H), 0.96-0.93 (dd, 3H, J = 2.0, 7.2 Hz), 0.85-0.77 (dd, 3H, J = 6.6, 15.6 Hz). | 401.1 (M + H) |

-continued

| Cpd | Structure | Name | ¹H NMR | ESI (m/z) |
|---|---|---|---|---|
| 26 | 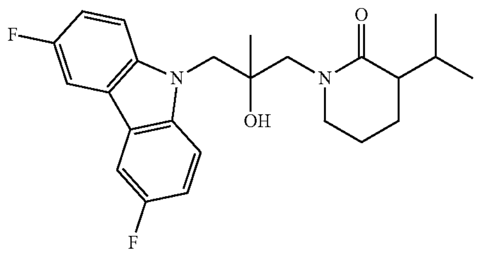 [SMILES: CC(C)C1CCCN(CC(C)(O)Cn2c3ccc(F)cc3c3cc(F)ccc32)C1=O] | 1-(3-(3,6-difluoro-9H-carbazol-9-yl)-2-hydroxy-2-methylpropyl)-3-isopropylpiperidin-2-one | (300 MHz, CDCl₃, mixture of diastereomers): δ 7.66-7.62 (dd, 2H, J = 2.6, 8.7 Hz), 7.45-7.41 (two overlapping sets of dd, 2H, J = 4.1, 8.7 Hz), 7.21-7.14 (td, 2H, J = 2.7, 9.0 Hz), 5.14 (s, 0.5H), 5.03 (s, 0.5 H), 4.31-4.09 (m, 2.5 H), 3.92-3.87, 3.21-3.17 (ABq, 1H, J = 14.1 Hz), 3.57-3.25 (m, 2H), 3.11-3.06 (d, 0.5H, J = 14.1 Hz), 2.59-2.50 (m, 1H), 2.38-2.26 (m, 1H), 1.95-1.49 (m, 5H), 1.27 (s, 3H), 0.97-0.94 (dd, 3H, J = 2.0, 7.5 Hz), 0.87-0.80 (dd, 3H, J = 6.9, 14.4 Hz). | 415.1 (M + H) |
| 27 | 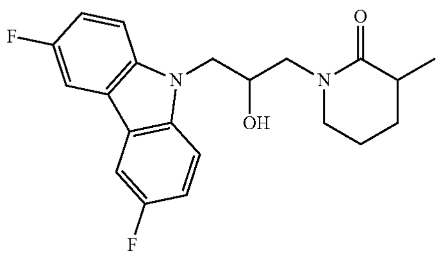 [SMILES: CC1CCCN(CC(O)Cn2c3ccc(F)cc3c3cc(F)ccc32)C1=O] | 1-(3-(3,6-difluoro-9H-carbazol-9-yl)-2-hydroxypropyl)-3-methylpiperidin-2-one | (300 MHz, CDCl₃, mixture of diastereomers): δ 7.68-7.64 (dd, 2H, J = 2.6, 8.7 Hz), 7.39-7.35 (dd, 2H, J = 4.2, 8.7 Hz), 7.25-7.17 (td, 2H, J = 2.4, 9.0 Hz), 4.60-4.59 (d, 0.5H, J = 3.0 Hz), 4.39-4.27 (m, 3.5H), 3.97-3.80 (m, 1H), 3.25-3.04 (m, 2.5H), 2.91-2.86 (m, 0.5H), 2.46-2.39 (m, 1H), 1.99-1.62 (m, 3H), 1.55-1.39 (m, 1H), 1.26-1.21 (t, 3H, J = 7.5 Hz). | 373.1 (M + H) |
| 28 | 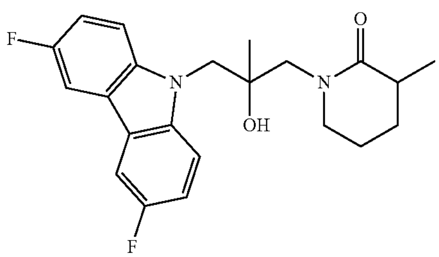 [SMILES: CC1CCCN(CC(C)(O)Cn2c3ccc(F)cc3c3cc(F)ccc32)C1=O] | 1-(3-(3,6-difluoro-9H-carbazol-9-yl)-2-hydroxy-2-methylpropyl)-3-methylpiperidin-2-one | (300 MHz, CDCl₃, mixture of diastereomers): δ 7.65-7.62 (dd, 2H, J = 2.6, 8.6 Hz), 7.45-7.40 (dd, 2H, J = 4.2, 9.2 Hz), 7.21-7.14 (td, 2H, J = 2.7, 9.0 Hz), 5.02 (s, 0.5H), 4.88 (s, 0.5H), 4.25 (s, 2H), 3.98-3.89 (t, 1H, J = 14.1 Hz), 3.53-3.30 (m, 2H), 3.21-3.17 (d, 0.5H, J = 14.1Hz), 3.10-3.05 (d, 0.5H, J = 14.1 Hz), 2.51-2.43 (m, 1H), 2.03-1.75 (m, 3H), 1.67-1.46 (m, 1H), 1.28 (s, 1.5H), 1.27-1.25 (d, 1.5H, J = 7.5 Hz), 1.26 (s, 1.5H), 1.23-1.21 (d, 1.5H, J = 7.5 Hz). | 387.0 (M + H) |
| 29 | 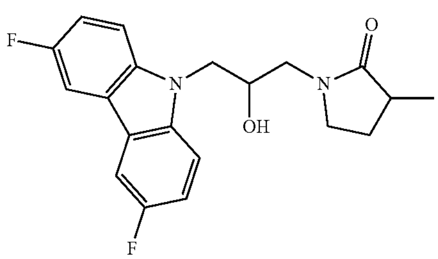 [SMILES: CC1CCN(CC(O)Cn2c3ccc(F)cc3c3cc(F)ccc32)C1=O] | 1-(3-(3,6-difluoro-9H-carbazol-9-yl)-2-hydroxypropyl)-3-methylpyrrolidin-2-one | (300 MHz, CDCl₃, mixture of diastereomers): δ 7.69-7.65 (dd, 2H, J = 2.6, 8.7 Hz), 7.38-7.33 (dd, 2H, J = 4.1, 9.0 Hz), 4.38-4.28 (m, 3H), 4.00-3.94 (dd, 1H, J = 4.2, 14.7 Hz), 3.56-3.15 (m, 4H), 2.55-2.50 (m, 1H), 2.28-2.21 (m, 1H), 1.69-1.60 (m, 1H), 1.23-1.21 (d, 3H, J = 6.9 Hz). | 359.1 (M + H) |
| 30 | 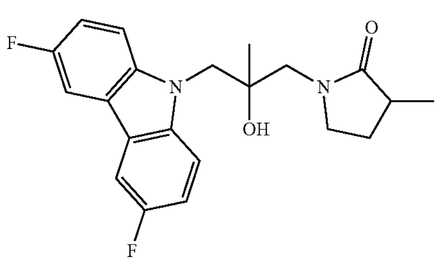 [SMILES: CC1CCN(CC(C)(O)Cn2c3ccc(F)cc3c3cc(F)ccc32)C1=O] | 1-(3-(3,6-difluoro-9H-carbazol-9-yl)-2-hydroxy-2-methylpropyl)-3-methylpyrrolidin-2-one | (300 MHz, CDCl₃): δ 7.65-7.61 (dd, 2H, J = 2.7, 8.7 Hz), 7.43-7.38 (dd, 2H, J = 4.4, 8.9 Hz), 7.20-7.13 (td, 2H, J = 2.6, 8.9 Hz), 4.30-4.20 (m, 2H), 3.75-3.73 (d, 1H, J = 3.3 Hz), 3.59-3.27 (m, 4H), 2.54-2.48 (m, 1H), 2.30-2.26 (m, 1H), 1.75-1.65 (m, 1H), 1.29-1.18 (m, 6H). | 373.0 (M + H) |

| Cpd | Structure | Name | ¹H NMR | ESI (m/z) |
|---|---|---|---|---|
| 31 | 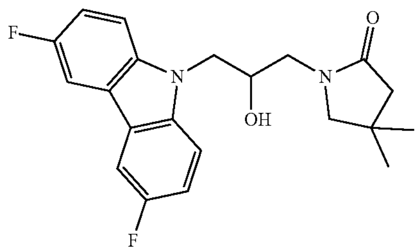 [SMILES: CC1(C)CC(=O)N(CC(O)Cn2c3ccc(F)cc3c3cc(F)ccc32)C1] | 1-(3-(3,6-difluoro-9H-carbazol-9-yl)-2-hydroxypropyl)-4,4-dimethylpyrrolidin-2-one | (300 MHz, CDCl₃): δ 7.68-7.65 (dd, 2H, J = 2.6, 8.6 Hz), 7.38-7.33 (dd, 2H, J = 4.1, 9.1 Hz), 7.25-7.17 (td, 2H, J = 2.5, 9.1 Hz), 4.37-4.33 (m, 3H), 3.62-3.52 (m, 2H), 3.26-3.21 (m, 1H), 3.17-3.14, 3.12-3.08 (ABq, 2H, J = 9.4 Hz), 2.25 (s, 2H), 1.16 (s, 2H), 1.16 (s, 3H), 1.14 (s, 1H). | 373.1 (M + H) |
| 32 | 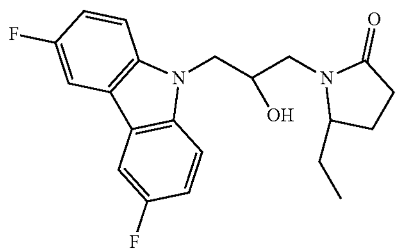 [SMILES: CCC1CCC(=O)N1CC(O)Cn1c2ccc(F)cc2c2cc(F)ccc21] | 1-(3-(3,6-difluoro-9H-carbazol-9-yl)-2-hydroxypropyl)-5-ethylpyrrolidin-2-one | (300 MHz, CDCl₃, unequal mixture of diastereomers approx. 1:4): δ 7.69-7.65 (dd, 2H, J = 2.6, 8.6 Hz), 7.38-7.33 (dd, 2H, J = 4.1, 8.9 Hz), 7.25-7.18 (td, 2H, J = 2.5, 9.0 Hz), 4.80-4.79 (d, 0.2H, J = 2.7 Hz), 4.39-4.26 (m, 3H), 4.09-4.08 (m, 0.8H), 3.72-3.64 (m, 1H), 3.48-3.40 (m, 1H), 3.12-3.03 (m, 1H), 2.44-2.33 (m, 2H), 2.22-2.09 (m, 1H), 1.76-1.66 (m, 1H), 1.57-1.49 (m, 1H), 1.28-1.18 (m, 1H), 0.81-0.76 (t, 2.5H, J = 7.5 Hz), 0.65-0.60 (t, 0.5H, J = 7.4 Hz). | 373.0 (M + H) |
| 33 | 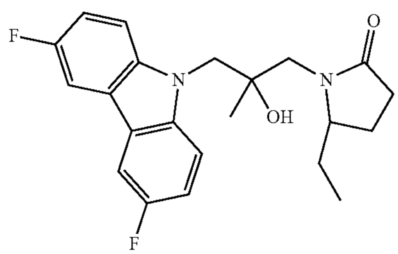 [SMILES: CCC1CCC(=O)N1CC(C)(O)Cn1c2ccc(F)cc2c2cc(F)ccc21] | 1-(3-(3,6-difluoro-9H-carbazol-9-yl)-2-hydroxy-2-methylpropyl)-5-ethylpyrrolidin-2-one | (300 MHz, d⁶-DMSO): δ 7.66-7.62 (dd, 2H, J = 2.3, 8.9 Hz), 7.46-7.41 (dd, 2H, J = 4.1, 8.9 Hz), 7.22-7.15 (td, 2H, J = 2.6, 8.9 Hz), 4.33-4.19 (m, 3H), 3.67-3.57 (m, 2H), 3.28-3.23 (d, 1H, J = 14.4 Hz), 2.94 (s, 0.5H), 2.86-2.86 (d, 0.5H, J = 3.3 Hz), 2.50-2.32 (m, 2H), 2.24-2.12 (m, 1H), 1.80-1.70 (m, 2H), 1.14-1.34 (m, 1H), 1.22 (s, 3H), 0.91-0.86 (t, 3H, J = 7.4 Hz). | 387.0 (M + H) |
| 34 | 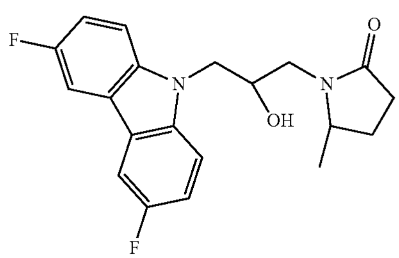 [SMILES: CC1CCC(=O)N1CC(O)Cn1c2ccc(F)cc2c2cc(F)ccc21] | 1-(3-(3,6-difluoro-9H-carbazol-9-yl)-2-hydroxypropyl)-5-methylpyrrolidin-2-one | (300 MHz, CDCl₃): δ 7.68-7.64 (dd, 2H, J = 2.6, 8.6 Hz), 7.38-7.33 (dd, 2H, J = 4.1, 8.9 Hz), 7.24-7.18 (m, 2H), 4.73-4.72 (d, 0.5H, J = 3.0 Hz), 4.38-4.25 (m, 3H), 4.08-4.06 (d, 0.5H, J = 3.6 Hz), 3.69-3.57 (m, 1H), 3.49-3.35 (m, 1H), 3.11-3.04 (m, 1H), 2.49-2.01 (m, 3H), 1.67-1.53 (m, 1H), 1.05-1.03 (d, 1.5H, J = 6.3 Hz), 0.84-0.82 (d, 1.5H, J = 6.3 Hz). | 359.1 (M + H) |
| 35 | 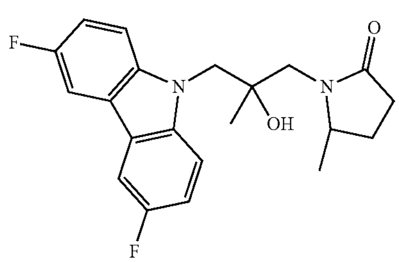 [SMILES: CC1CCC(=O)N1CC(C)(O)Cn1c2ccc(F)cc2c2cc(F)ccc21] | 1-(3-(3,6-difluoro-9H-carbazol-9-yl)-2-hydroxy-2-methylpropyl)-5-methylpyrrolidin-2-one | (300 MHz, CDCl₃): δ 7.67-7.63 (dd, 2H, J = 2.6, 8.9 Hz), 7.46-7.42 (dd, 2H, J = 4.1, 8.9 Hz), 7.23-7.16 (td, 2H, J = 2.7, 9.0 Hz), 4.34-4.21 (m, 3H), 3.82-3.72 (sext, 1H, J = 6.6 Hz), 3.60-3.56, 3.32-3.27 (ABq, 2H, J = 14.4 Hz), 2.49-2.20 (m, 3H), 1.71-1.61 (m, 1H), 1.24 (s, 3H), 1.23-1.21 (d, 3H, J = 6.6 Hz). | 373.0 (M + H) |

| Cpd | Structure | Name | ¹H NMR | ESI (m/z) |
|---|---|---|---|---|
| 36 | 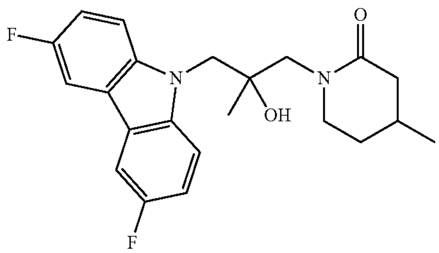 [SMILES: CC1CCN(CC(C)(O)Cn2c3ccc(F)cc3c3cc(F)ccc32)C(=O)C1] | 1-(3-(3,6-difluoro-9H-carbazol-9-yl)-2-hydroxy-2-methylpropyl)-4-methylpiperidin-2-one | (300 MHz, CDCl₃): δ 7.67-7.63 (dd, 2H, J = 2.6, 9.0 Hz), 7.46-7.41 (dd, 2H, J = 4.1, 8.9 Hz), 7.22-7.15 (td, 2H, J = 2.5, 8.9 Hz), 4.96 (s, 0.5H), 4.72 (s, 0.5H), 4.28 (s, 2H), 4.05-4.01, 3.34-3.29 (ABq, 1H, J = 14.1 Hz), 3.89-3.84, 3.06-3.01 (ABq, 1H, J = 14.1 Hz), 3.57-3.37 (m, 2H), 2.60-2.48 (m, 1H), 2.10-1.84 (m, 2H), 1.57-1.48 (m, 2H), 1.28 (s, 3H), 1.05-1.03 (d, 3H, J = 6.3 Hz); HPLC analysis: (C18, 10-90% acetonitrile in water over 20 min: retention time, % area at 254 nm): 13.2 min, 98%. | 387.1 (M + H) |
| 37 | 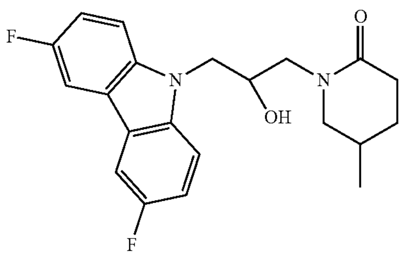 [SMILES: CC1CCC(=O)N(CC(O)Cn2c3ccc(F)cc3c3cc(F)ccc32)C1] | 1-(3-(3,6-difluoro-9H-carbazol-9-yl)-2-hydroxypropyl)-5-methylpiperidin-2-one | (300 MHz, CDCl₃): δ 7.67-7.62 (m, 2H), 7.38-7.33 (dd, 2H, J = 4.1, 9.0 Hz), 7.23-7.16 (m, 2H), 4.55-4.54 (d, 0.5H, J = 3.3 Hz), 4.37-4.24 (m, 3H), 4.20-4.18 (d, 0.5H, J = 3.6 Hz), 3.88-3.81 (dd, 0.5H, J = 8.6, 14.1 Hz), 3.77-3.70 (dd, 0.5H, J = 8.4, 14.1 Hz), 3.18-2.76 (m, 2H), 2.49-2.28 (m, 2H), 1.92-1.77 (m, 2H), 1.49-1.30 (m, 1H), 0.94-0.93 (d, 1.5H, J = 3.0 Hz), 0.92-0.91 (d, 1.5H, J = 3.0 Hz). | 373.1 (M + H) |
| 38 | 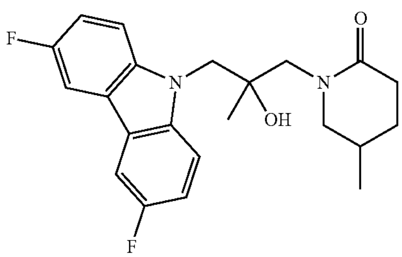 [SMILES: CC1CCC(=O)N(CC(C)(O)Cn2c3ccc(F)cc3c3cc(F)ccc32)C1] | 1-(3-(3,6-difluoro-9H-carbazol-9-yl)-2-hydroxy-2-methylpropyl)-5-methylpiperidin-2-one | (300 MHz, CDCl₃): δ 7.67-7.63 (dd, 2H, J = 2.4, 8.9 Hz), 7.46-7.41 (dd, 2H, J = 4.1, 8.9 Hz), 7.22-7.15 (td, 2H, J = 2.4, 9.0 Hz), 4.97 (s, 0.5H), 4.76 (s, 0.5H), 4.33-4.22 (m, 2H), 4.02 (d, 0.5H, J = 14.1 Hz), 3.90-3.85 (d, 0.5H, J = 14.1 Hz), 3.50-2.95 (m, 3H), 2.57-2.38 (m, 2H), 2.01-1.85 (m, 2H), 1.62-1.40 (m, 1H), 1.29 (s, 3H), 1.04-0.99 (t, 3H, J = 6.8 Hz). | 387.1 (M + H) |
| 39 | 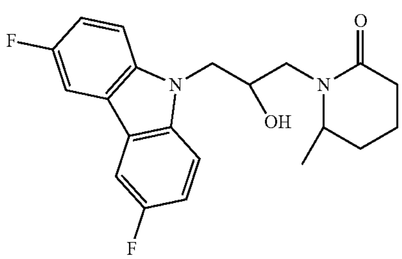 [SMILES: CC1CCCC(=O)N1CC(O)Cn1c2ccc(F)cc2c2cc(F)ccc21] | 1-(3-(3,6-difluoro-9H-carbazol-9-yl)-2-hydroxypropyl)-6-methylpiperidin-2-one | (300 MHz, CDCl₃): δ 7.68-7.64 (dd, 2H, J = 2.6, 8.6 Hz), 7.40-7.35 (dd, 2H, J = 4.2, 9.0 Hz), 7.25-7.18 (td, 1H, J = 2.7, 9.0 Hz), 7.25-7.18 (td, 1H, J = 2.5, 9.0 Hz), 5.51-5.50 (d, 0.5H, J = 2.1 Hz), 4.84-4.83 (d, 0.5H, J = 2.4 Hz), 4.39-4.22 (m, 3H), 4.06-3.98 (dd, 0.5H, J = 8.6, 14.4 Hz), 3.83-3.76 (dd, 0.5H, J = 8.0, 14.1 Hz), 3.21-3.13 (m, 1H), 2.96-2.91 (dd, 0.5H, J = 0.9, 14.1 Hz), 2.86-2.81 (dd, 0.5H, J = 1.5 14.1 Hz), 2.41-2.35 (m, 2H), 1.87-1.38 (m, 4H), 0.96-0.94 (d, 1.5H, J = 6.6 Hz), 0.67-0.65 (d, 1.5H, J = 6.6 Hz). | 373.1 (M + H) |
| 40 | 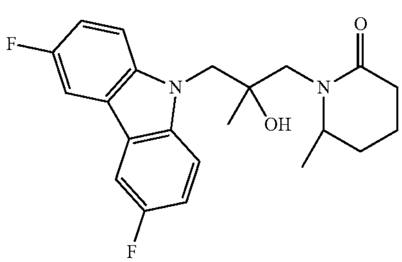 | 1-(3-(3,6-difluoro-9H-carbazol-9-yl)-2-hydroxy-2-methylpropyl)-6-methylpiperidin-2-one | (300 MHz, CDCl₃): δ 7.66-7.62 (dd, 2H, J = 2.6, 9.0 Hz), 7.45-7.41 (dd, 2H, J = 4.2, 9.0 Hz), 7.21-7.15 (td, 2H, J = 2.4, 9.0 Hz), 5.13 (s, 1H), 4.34-4.29, 4.21-4.16 (ABq, 2H, J = 14.9 Hz), 4.05-4.00 (m, 1H, J = 14.7 Hz), 3.68-3.64 (m, 1H), 3.26-3.21 (d, 1H, J = 14.4 Hz), 2.52-2.47 (m, 2H), 1.96-1.70 (m, 4H), 1.26-1.23 (d, 3H, J = 6.6 Hz), 1.22 (s, 3H). | 373.1 (M + H) |

| Cpd | Structure | Name | ¹H NMR | ESI (m/z) |
|---|---|---|---|---|
| 41 | 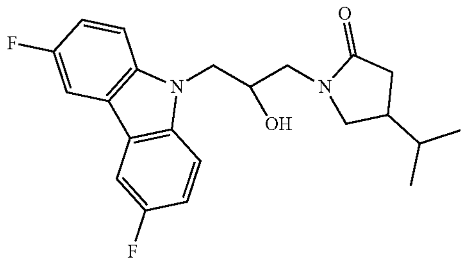 [SMILES: CC(C)C1CC(=O)N(CC(O)Cn2c3ccc(F)cc3c3cc(F)ccc32)C1] | 1-(3-(3,6-difluoro-9H-carbazol-9-yl)-2-hydroxypropyl)-4-isopropylpyrrolidin-2-one | (300 MHz, CDCl₃): δ 7.69-7.65 (dd, 2H, J = 2.6, 8.6 Hz), 7.38-7.33 (dd, 2H, J = 4.1, 8.9 Hz), 7.25-7.18 (m, 2H), 4.37-4.28 (m, 3H), 3.87-3.85 (m, 1H), 3.58-3.03 (m, 5H), 2.55-2.46 (m, 1H), 2.21-2.02 (m, 2H), 0.92-0.89 (dd, 3H, J = 3.2, 6.8 Hz), 0.86-0.84 (dd, 3H, J = 1.5, 6.3 Hz). | 387.1 (M + H) |
| 42 | 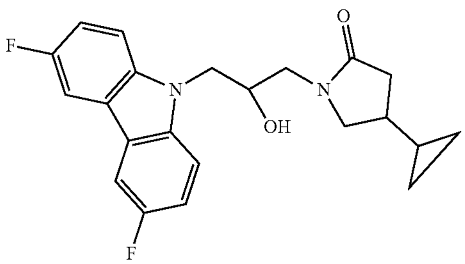 [SMILES: O=C1CC(C2CC2)CN1CC(O)Cn1c2ccc(F)cc2c2cc(F)ccc21] | 4-cyclopropyl-1-(3-(3,6-difluoro-9H-carbazol-9-yl)-2-hydroxypropyl)pyrrolidin-2-one | (300 MHz, CDCl₃): δ 7.69-7.65 (dd, 2H, J = 2.4, 8.4 Hz), 7.38-7.34 (dd, 2H, J = 4.1, 8.9 Hz), 7.25-7.18 (td, 2H, J = 2.4, 9.0 Hz), 4.40-4.29 (m, 3H), 3.80-3.79 (d, 1H, J = 3.9 Hz), 3.60-3.17 (m, 4H), 2.61-2.52 (dd, 1H, J = 8.9, 17.0 Hz), 2.33-2.23 (m, 1H), 1.76-1.63 (m, 1H), 0.80-0.75 (m, 1H), 0.56-0.45 (m, 2H), 0.19-0.08 (m, 2H). | 385.1 (M + H) |
| 43 | 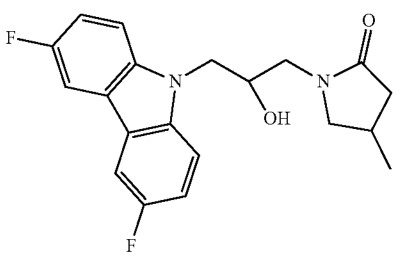 [SMILES: CC1CC(=O)N(CC(O)Cn2c3ccc(F)cc3c3cc(F)ccc32)C1] | 1-(3-(3,6-difluoro-9H-carbazol-9-yl)-2-hydroxypropyl)-4-methylpyrrolidin-2-one | (300 MHz, CDCl₃): δ 7.69-7.65 (dd, 2H, J = 2.6, 8.6 Hz), 7.38-7.33 (dd, 2H, J = 4.1, 8.9 Hz), 7.25-7.18 (td, 2H, J = 2.6, 8.9 Hz), 4.37-4.28 (m, 3H), 1.11-1.15 (m, 1H), 3.57-3.38 (m, 2H), 3.28-3.20 (m, 1H), 3.03-2.93 (m, 1H), 2.64-2.55 (dd, 1H, J = 8.6, 16.5 Hz), 2.53-2.40 (oct, 1H, J = 6.9 Hz), 2.12-2,08 (t, 0.5H, J = 6.6 Hz), 2.06-2.02 (t, 0.5H, J = 2.5 Hz), 1.13-1.10 (d, 1.5H, J = 6.6 Hz), 1.16-1.09 (d, 1.5H, J = 6.6 Hz). | 359.1 (M + H) |
| 44 | 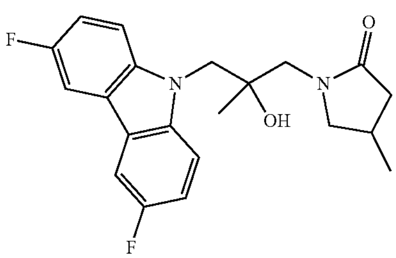 [SMILES: CC1CC(=O)N(CC(C)(O)Cn2c3ccc(F)cc3c3cc(F)ccc32)C1] | 1-(3-(3,6-difluoro-9H-carbazol-9-yl)-2-hydroxy-2-methylpropyl)-4-methylpyrrolidin-2-one | (300 MHz, CDCl₃): δ 7.67-7.64 (dd, 2H, J = 2.4, 8.7 Hz), 7.44-7.40 (dd, 2H, J = 3.8, 8.6 Hz), 7.22-7.16 (td, 2H, J = 2.5, 9.0 Hz), 4.34-4.23 (m, 2H), 3.74-3.50 (m, 3H), 3.38-3.32 (dd, 1H, J = 3.6, 14.1 Hz), 3.24-3.19 (dd, 0.5H, J = 5.4, 10.2 Hz), 3.16-3.11 (dd, 0.5H, J = 6.5, 6.6 Hz), 2.66-2.46 (m, 2H), 2.14-2.05 (m, 1H), 1.27 (s, 3H), 1.19-1.17 (d, 1.5H, J = 6.3 Hz), 1.16-1.14 (d, 1.5H, J = 6.3 Hz). | 373.0 (M + H) |
| 45 | 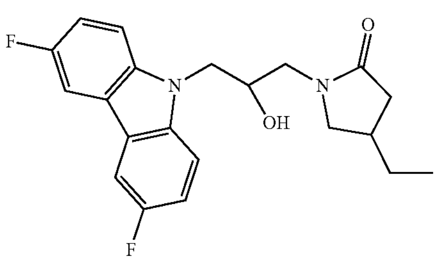 [SMILES: CCC1CC(=O)N(CC(O)Cn2c3ccc(F)cc3c3cc(F)ccc32)C1] | 1-(3-(3,6-difluoro-9H-carbazol-9-yl)-2-hydroxypropyl)-4-ethylpyrrolidin-2-one | (300 MHz, CDCl₃): δ 7.69-7.65 (dd, 2H, J = 2.6, 8.6 Hz), 7.38-7.33 (dd, 2H, J = 4.1, 9.0 Hz), 7.24-7.18 (td, 2H, J = 2.6, 9.0 Hz), 4.37-4.27 (m, 3H), 3.81 (d, 1H, J = 2.1 Hz), 3.58-3.19 (m, 3H), 3.08-2.98 (m, 1H), 2.60-2.52 (dd, 1H, J = 8.7, 16.2 Hz), 2.31-2.23 (m, 1H), 2.16-2.01 (m, 1H), 1.50-1.39 (m, 1H), 0.93-0.88 (t, 1.5H, J = 7.5 Hz), 0.92-0.97 (t, 1.5H, J = 7.5 Hz). | 373.1 (M + H) |
| 46 | 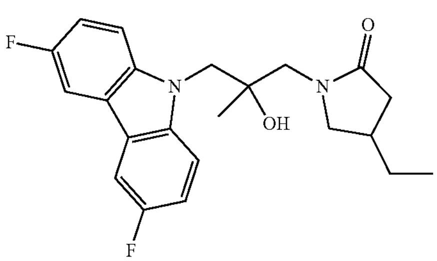 [SMILES: CCC1CC(=O)N(CC(C)(O)Cn2c3ccc(F)cc3c3cc(F)ccc32)C1] | 1-(3-(3,6-difluoro-9H-carbazol-9-yl)-2-hydroxy-2-methylpropyl)-4-ethylpyrrolidin-2-one | (300 MHz, CDCl₃): δ 7.67-7.63 (dd, 2H, J = 2.3, 8.9 Hz), 7.44-7.40 (dd, 2H, J = 4.1, 8.9 Hz), 7.22-7.16 (td, 2H, J = 2.4, 9.0 Hz), 4.33-4.22 (m, 2H), 3.71-3.53 (m, 3H), 3.39-3.15 (m, 2H), 2.63-2.54 (ddd, 1H, J = 2.7, 8.4, 16.8 Hz), 2.38-2.27 (sept, 1H, J = 7.8 Hz), 2.19-2.11 (m, 1H), 1.54-1.44 (m, 2H), 1.26 (s, 3H), 0.98-0.91 (m, 3H). | 387.1 (M + H) |

| Cpd | Structure | Name | ¹H NMR | ESI (m/z) |
|---|---|---|---|---|
| 47 | 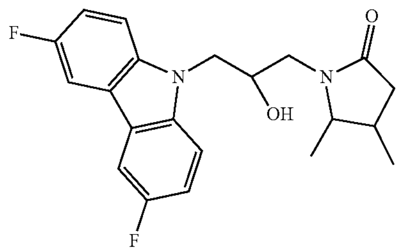 [SMILES: CC1CC(=O)N(CC(O)Cn2c3ccc(F)cc3c3cc(F)ccc32)C1C] | 1-(3-(3,6-difluoro-9H-carbazol-9-yl)-2-hydroxypropyl)-4,5-dimethylpyrrolidin-2-one | (300 MHz, CDCl₃): δ 7.68-7.64 (dd, 2H, J = 2.6, 8.6 Hz), 7.37-7.33 (dd, 2H, J = 4.1, 8.9 Hz), 7.24-7.17 (td, 2H, J = 2.5, 9.0 Hz), 4.64-4.59 (m, 0.5H), 4.38-4.24 (m, 3.5H), 3.88-2.97 (m, 3H), 2.63-2.40 (m, 2H), 2.13-1.88 (m, 1H), 1.11-0.77 (m, 6H). | 373.1 (M + H) |
| 48 | 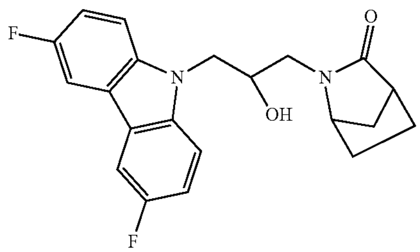 [SMILES: O=C1C2CCC(C2)N1CC(O)Cn1c2ccc(F)cc2c2cc(F)ccc21] | 2-(3-(3,6-difluoro-9H-carbazol-9-yl)-2-hydroxypropyl)-2-azabicyclo[2.2.1]heptan-3-one | (300 MHz, CDCl₃): δ 7.69-7.66 (dd, 1H, J = 2.1, 8.7 Hz), 7.69-7.65 (dd, 1H, J = 2.1, 8.7 Hz), 7.38-7.34 (dd, 1H, J = 3.9, 8.7 Hz), 7.38-7.33 (dd, 1H, J = 2.1, 8.7 Hz), 7.25-7.18 (td, 1H, J = 3.0, 9.0 Hz), 7.24-7.17 (td, 1H, J = 3.0, 9.0 Hz), 4.40-4.25 (m, 4H), 3.73 (br s, 0.5H), 3.64 (br s, 0.5H), 3.48-3.39 (m, 1H), 3.03-2.85 (m, 2H), 1.96-1.55 (m, 5H), 1.43-1.36 (m, 1H). | 371.1 (M + H) |
| 49 | 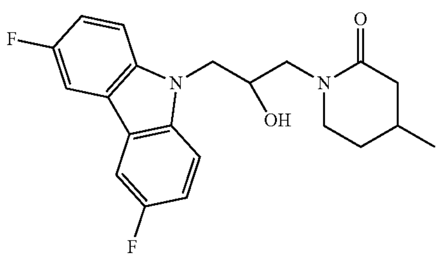 [SMILES: CC1CCN(CC(O)Cn2c3ccc(F)cc3c3cc(F)ccc32)C(=O)C1] | 1-(3-(3,6-difluoro-9H-carbazol-9-yl)-2-hydroxypropyl)-4-methylpiperidin-2-one | (300 MHz, CDCl₃): δ 7.68-7.64 (dd, 2H, J = 2.7, 8.7 Hz), 7.39-7.35 (dd, 2H, J = 4.2, 8.7 Hz), 7.24-7.17 (td, 1H, J = 2.6, 9.0 Hz), 7.23-7.17 (td, 1H, J = 2.6, 9.0 Hz), 4.52 (br s, 0.5H), 4.39-4.27 (m, 3H), 4.20-4.19 (d, 0.5H, J = 3.0 Hz), 3.97-3.89 (m, 0.5H), 3.85-3.78 (dd, 0.5H, J = 8.0, 14.1 Hz), 3.28-3.07 (m, 2.5H), 2.94-2.89 (m, 0.5H), 2.53-2.45 (m, 1H), 2.05-1.75 (m, 3H), 1.48-1.33 (m, 1H), 1.01-0.98 (d, 3H, J = 6.3 Hz). | 373.1 (M + H) |
| 50 | 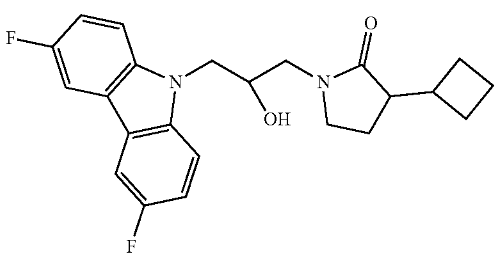 [SMILES: O=C1C(C2CCC2)CCN1CC(O)Cn1c2ccc(F)cc2c2cc(F)ccc21] | 3-cyclobutyl-1-(3-(3,6-difluoro-9H-carbazol-9-yl)-2-hydroxypropyl)pyrrolidin-2-one | (300 MHz, CDCl₃): δ 7.68-7.64 (dd, 2H, J = 2.6, 8.6 Hz), 7.37-7.33 (dd, 2H, J = 14.1, 8.9 Hz), 7.24-7.17 (td, 2H, J = 2.5, 9.0 Hz), 4.36-4.27 (m, 3H), 4.05-4.03 (d, 0.5H, J = 4.5 Hz), 3.95-3.94 (d, 0.5H, J = 3.9 Hz), 3.55-3.44 (m, 1H), 3.31-3.16 (m, 3H), 2.55-2.48 (m, 2H), 2.15-2.73 (m, 8H). | 399.1 (M + H) |
| 51 | 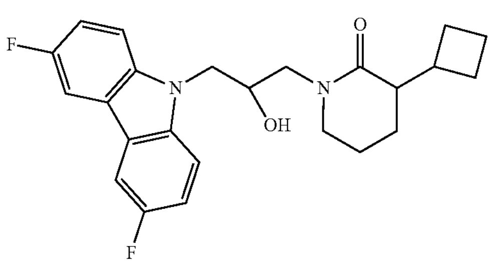 [SMILES: O=C1C(C2CCC2)CCCN1CC(O)Cn1c2ccc(F)cc2c2cc(F)ccc21] | 3-cyclobutyl-1-(3-(3,6-difluoro-9H-carbazol-9-yl)-2-hydroxypropyl)piperidin-2-one | (300 MHz, CDCl₃): δ 7.68-7.64 (dd, 2H, J = 2.6, 8.6 Hz), 7.39-7.34 (dd, 1H, J = 4.1, 8.7 Hz), 7.38-7.34 (dd, 1H, J = 4.2, 9.0 Hz), 7.24-7.17 (td, 2H, J = 2.6, 8.9 Hz), 4.60-4.59 (d, 0.5H, J = 3.3 Hz), 4.38-4.25 (m, 3H), 4.24-4.22 (d, 0.5H, J = 3.6 Hz), 3.95-3.84 (m, 1H), 3.17-2.87 (m, 3H), 2.57-2.51 (m, 1H), 2.34-2.26 (m, 1H), 2.14-1.39 (m, 9H). | 413.1 (M + H) |
| 52 | 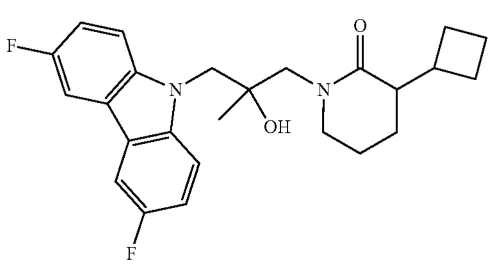 | 3-cyclobutyl-1-(3-(3,6-difluoro-9H-carbazol-9-yl)-2-hydroxy-2-methylpropyl)piperidin-2-one | (300 MHz, CDCl₃): δ 7.66-7.62 (dd, 2H, J = 2.6, 8.9 Hz), 7.45-7.41 (dd, 2H, J = 4.1, 8.9 Hz), 7.21-7.15 (td, 1H, J = 2.6, 8.9 Hz), 7.21-7.14 (td, 1H, J = 2.6, 8.9 Hz), 4.92 (s, 0.5H), 4.87 (s, 0.5H), 4.31-4.20 (m, 2H), 3.22-3.18 (ABq, 1H, J = 14.1 Hz), 3.88-3.83, 3.06-3.02 (ABq, 1H, J = 14.1 Hz), 3.49-3.27 (m, 2H), 2.63-2.52 (m, 1H), 2.39-2.27 (m, 1H), 2.16-1.47 (m, 10H), 1.27 (s, 3H). | 413.1 (M + H) |

-continued

| Cpd | Structure | Name | ¹H NMR | ESI (m/z) |
|---|---|---|---|---|
| 53 | 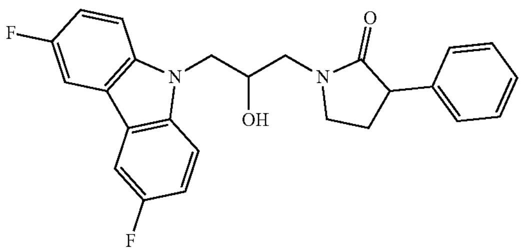 [SMILES: O=C1C(c2ccccc2)CCN1CC(O)Cn1c2ccc(F)cc2c2cc(F)ccc21] | 1-(3-(3,6-difluoro-9H-carbazol-9-yl)-2-hydroxypropyl)-3-phenylpyrrolidin-2-one | (300 MHz, CDCl₃): δ 7.69-7.65 (dd, 2H, J = 2.6, 8.6 Hz), 7.37-7.17 (m, 9H), 4.40-4.32 (m, 3H), 3.80-3.26 (m, 6H), 2.57-2.46 (m, 1H), 2.23-2.11 (m, 1H). | 421.1 (M + H) |
| 54 | 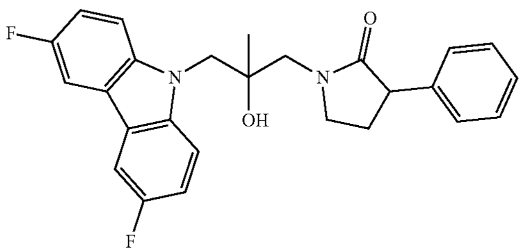 [SMILES: CC(O)(CN1CCC(c2ccccc2)C1=O)Cn1c2ccc(F)cc2c2cc(F)ccc21] | 1-(3-(3,6-difluoro-9H-carbazol-9-yl)-2-hydroxy-2-methylpropyl)-3-phenylpyrrolidin-2-one | (300 MHz, CDCl₃): δ 7.67-7.64 (dd, 2H, J = 2.4, 8.7 Hz), 7.44-7.40 (dd, 2H, J = 3.9, 9.0 Hz), 7.36-7.15 (m, 7H), 4.37-4.25 (m, 2H), 3.79-3.31 (m, 6H), 2.62-2.54 (m, 1H), 2.29-2.16 (m, 1H), 1.31 (s, 1.5H), 1.30 (s, 1.5H). | 435.1 (M + H) |
| 55 | 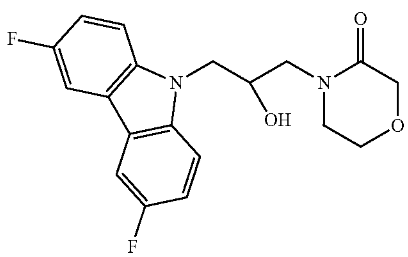 [SMILES: O=C1COCCN1CC(O)Cn1c2ccc(F)cc2c2cc(F)ccc21] | 4-(3-(3,6-difluoro-9H-carbazol-9-yl)-2-hydroxypropyl)morpholin-3-one | (300 MHz, CDCl₃): δ 7.68-7.64 (dd, 2H, J = 2.6, 8.6 Hz), 7.39-7.34 (dd, 2H, J = 4.1, 9.0 Hz), 7.24-7.18 (td, 2H, J = 2.4, 9.0 Hz), 4.43-4.41 (m, 1H), 4.34 (s, 1H), 4.32 (d, 1H, J = 0.9 Hz), 4.18 (s, 2H), 3.84-3.79 (m, 2H), 3.76-3.68 (dd, 1H, J = 8.6, 17.4 Hz), 3.53-3.51 (d, 1H, J = 3.9 Hz), 3.41-3.28 (m, 3H). | 361.1 (M + H) |
| 56 | 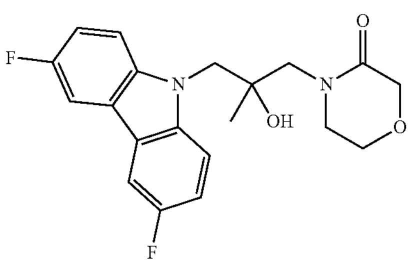 [SMILES: CC(O)(CN1CCOCC1=O)Cn1c2ccc(F)cc2c2cc(F)ccc21] | 4-(3-(3,6-difluoro-9H-carbazol-9-yl)-2-hydroxy-2-methylpropyl)morpholin-3-one | (300 MHz, CDCl₃): δ 7.67-7.64 (dd, 2H, J = 2.4, 8.7 Hz), 7.44-7.40 (dd, 2H, J = 4.1, 8.9 Hz), 7.23-7.16 (td, 1H, J = 2.4, 8.9 Hz), 4.30 (s, 2H), 4.24 (s, 2H), 3.91-3.86 (m, 3H), 3.61-3.56 (m, 2H), 3.53 (s, 1H), 3.40-3.35 (d, 1H, J = 14.1 Hz), 1.31 (s, 3H). | 375.0 (M + H) |
| 57 | 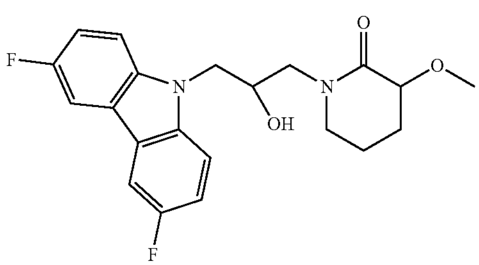 [SMILES: COC1CCCN(CC(O)Cn2c3ccc(F)cc3c3cc(F)ccc32)C1=O] | 1-(3-(3,6-difluoro-9H-carbazol-9-yl)-2-hydroxypropyl)-3-methoxypiperidin-2-one | (300 MHz, CDCl₃): δ 7.67-7.63 (dd, 2H, J = 2.3, 8.9 Hz), 7.39-7.34 (dd, 2H, J = 4.2, 8.7 Hz), 7.24-7.17 (td, 2H, J = 2.6, 9.0 Hz), 7.23-7.16 (td, 1H, J = 2.6, 9.0 Hz), 4.38-4.30 (m, 3H), 3.90-3.59 (m, 3H), 3.53 (s, 3H), 3.32-3.06 (m, 3H), 1.99-1.88 (m, 2H), 1.70-1.65 (m, 2H). | 389.1 (M + H) |
| 58 | 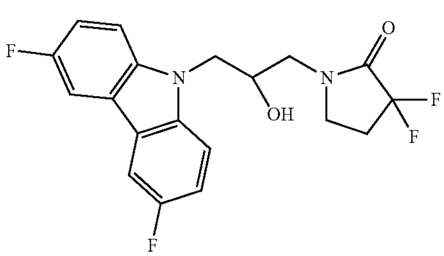 [SMILES: O=C1N(CC(O)Cn2c3ccc(F)cc3c3cc(F)ccc32)CCC1(F)F] | 1-(3-(3,6-difluoro-9H-carbazol-9-yl)-2-hydroxypropyl)-3,3-difluoropyrrolidin-2-one | (300 MHz, CDCl₃): δ 7.69-7.65 (dd, 2H, J = 2.4, 8.7 Hz), 7.37-7.32 (dd, 2H, J = 3.9, 8.7 Hz), 7.25-7.18 (td, 2H, J = 3.0, 8.7 Hz), 4.49-4.43 (m, 1H), 4.36-4.32 (m, 2H), 3.62-3.45 (m, 4H), 2.67-2.66 (d, 1H, J = 4.5 Hz), 2.67-2.45 (m, 2H); ¹⁹F NMR (282 MHz, CDCl₃): δ −105.1 to −105.2 (m), −123.57 to −123.4 (t, J = 10.7 Hz). | NA |

-continued

| Cpd | Structure | Name | ¹H NMR | ESI (m/z) |
|---|---|---|---|---|
| 59 | 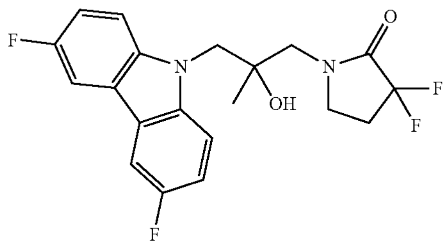 [SMILES: CC(O)(CN1CCC(F)(F)C1=O)Cn1c2ccc(F)cc2c2cc(F)ccc21] | 1-(3-(3,6-difluoro-9H-carbazol-9-yl)-2-hydroxy-2-methylpropyl)-3,3-difluoropyrrolidin-2-one | (300 MHz, CDCl₃): δ 7.68-7.64 (dd, 2H, J = 2.7, 8.6 Hz), 7.41-7.36 (dd, 2H, J = 4.1, 8.9 Hz), 7.24-7.17 (td, 2H, J = 2.7, 8.7 Hz), 4.30 (s, 2H), 3.74-3.69 (m, 2H), 3.67-3.62, 3.56-3.51 (ABq, 2H, J = 14.1 Hz), 2.64-2.49 (m, 2H), 2.14 (s, 1H), 1.30 (s, 3H); ¹⁹F NMR (282 MHz, CDCl₃): δ −105.6 to −105.74 (t, J = 15.2 Hz), −123.6 to −123.6 (t, J = 10.6 Hz). | NA |
| 60 | 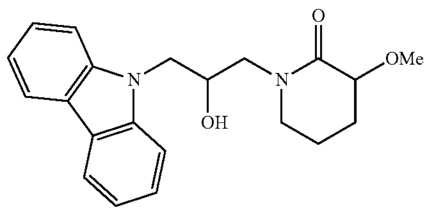 [SMILES: COC1CCCN(CC(O)Cn2c3ccccc3c3ccccc32)C1=O] | 1-(3-(9H-carbazol-9-yl)-2-hydroxypropyl)-3-methoxypiperidin-2-one | (300 MHz, CDCl₃): δ 8.07 (d, 2H, J = 6.9 Hz), 7.47-7.41 (m, 4H), 7.27-7.19 (m, 2H), 4.41-4.26 (m, 3H), 3.96 (dd, 1H, J = 6.6, 11.1 Hz), 3.76-3.52 (m, 2H), 3.50 (s, 3H), 3.29-2.98 (m, 3H), 1.97-1.78 (m, 3H), 1.65-1.55 (m, 1H); HPLC analysis: (C18, 10-90% acetonitrile in water + 0.1% trifluoroacetic acid over 20 min: retention time, % area at 254 nm): 11.2 min, 99.6%. | 354.1 (M + H) |
| 61 | 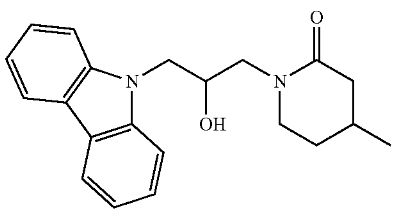 [SMILES: CC1CCN(CC(O)Cn2c3ccccc3c3ccccc32)C(=O)C1] | 2-(3-(9H-carbazol-9-yl)-2-hydroxypropyl)-4-methylpiperidin-2-one | (300 MHz, CDCl₃): δ 8.09 (dd, 2H, J = 1.2, 7.2 Hz), 7.50-7.44 (m, 4H), 7.29-7.20 (m, 2H), 4.54-4.14 (m, 4H), 3.98-3.81 (m, 1H), 3.20-2.64 (m, 3H), 2.50-2.28 (m, 2H), 1.85-1.74 (m, 2H), 1.48-1.28 (m, 1H), 0.88, 0.87 (two overlapping dd, 3H, J = 6.6 Hz); HPLC analysis: (C18, 10-90% acetonitrile in water + 0.1% trifluoroacetic acid over 20 min: retention time, % area at 254 nm): 12.1 min. 98.7%. | 337.7 (M + H) |
| 62 | 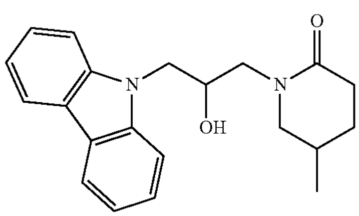 [SMILES: CC1CCC(=O)N(CC(O)Cn2c3ccccc3c3ccccc32)C1] | 1-(3-(9H-carbazol-9-yl)-2-hydroxypropyl)-5-methylpiperidin-2-one | (300 MHz. CDCl₃): δ 8.09 (d, 2H, J = 7.2 Hz), 7.49-7.41 (m, 4H), 7.28-7.20 (m, 2H), 4.52 (br s, 0.5H), 4.44-4.29 (m, 3H), 4.21 (d, 0.5H, J = 3.6 Hz), 3.99-3.81 (m, 1H), 3.20-2.89 (m, 3H), 2.51-2.43 (m, 1H), 2.03-1.31 (m, 4H), 0.97 (d, 3H, J = 6.6 Hz); HPLC analysis: (C18, 10-90% acetonitrile in water + 0.1% trifluoroacetic acid over 20 min: retention time, % area at 254 nm): 12.1 min, 98.5%. | 337.9 (M + H) |
| 63 | 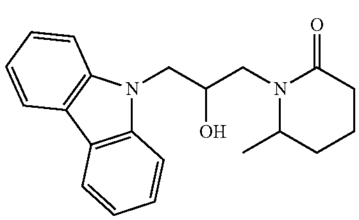 [SMILES: CC1CCCC(=O)N1CC(O)Cn1c2ccccc2c2ccccc21] | 1-(3-(9H-carbazol-9-yl)-2-hydroxypropyl)-6-methylpiperidin-2-one | (300 MHz, CDCl₃): δ 8.09 (d, 2H, J = 7.5 Hz), 2.48-2.45 (m, 4H), 7.27-7.21 (m, 2H), 5.50 (s, 0.6 H), 4.84 (d, 0.4H, J = 3.6 Hz), 4.46-4.27 (m, 3H), 4.07 (dd, 0.4 H, J = 8.1, 14.1 Hz), 3.82 (dd, 0.6H, J = 7.6, 14.0 Hz), 3.15-3.07 (m, 1H), 2.97 (d, 0.6H, J = 14.1 Hz), 2.85 (d, 0.4H, J = 14.1 Hz), 2.40-2.33 (m, 2H), 1.76-1.32 (m, 4H), 0.86 (d, 1.2H, J = 6.3 Hz), 0.59 (d, 1.8 H, J = 6.6 Hz); HPLC analysis: (C18,10-90% acetonitrile in water + 0.1% trifluoroacetic acid over 20 min: retention time, % area at 254 nm): 12.1 min, 95.2%. | 337.5 (M + H) |

-continued

| Cpd | Structure | Name | ¹H NMR | ESI (m/z) |
|---|---|---|---|---|
| 64 | 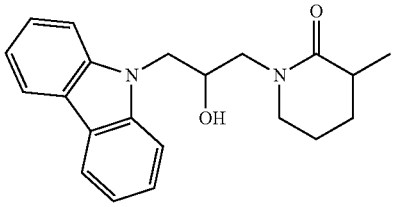 [SMILES: CC1CCCN(CC(O)Cn2c3ccccc3c3ccccc32)C1=O] | 1-(3-(9H-carbazol-9-yl)-2-hydroxypropyl)-3-methylpiperidin-2-one | (300 MHz, CDCl$_3$): δ 8.08 (d, 2H, J = 7.5 Hz), 7.45-7.42 (m, 4H), 7.28-7.21 (m, 2H), 4.59 (br s, 0.4H), 4.43-4.26 (m, 3.6H), 3.94 (dd, 0.5H, J = 8.0, 13.7 Hz), 3.81 (dd, 0.5H, J = 7.5, 14.1 Hz), 3.17-2.89 (m, 3H), 2.42-2.33 (m, 1H), 1.94-1.33 (m, 4H), 1.23-1.19 (m, 3H); HPLC analysis: (C18, 10-90% acetonitrile in water + 0.1% trifluoroacetic acid over 20 min: retention time, % area at 254 nm): 12.2 min, 96.5%. | 337.9 (M + H) |
| 65 | 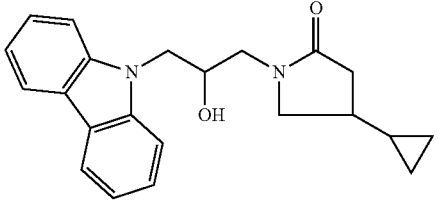 [SMILES: O=C1CC(C2CC2)CN1CC(O)Cn1c2ccccc2c2ccccc21] | 1-(3-(9H-carbazol-9-yl)-2-hydroxypropyl)-4-cyclopropyl-pyrrolidin-2-one | (300 MHz, CDCl$_3$): δ 8.08 (d, 2H, J = 7.5 Hz), 7.48-7.42 (m, 4H), 7.28-7.21, m, 2H), 4.39-4.29 (m, 3H), 3.87 (d, 1H, J = 14.7 Hz), 3.57-3.10 (m, 4H), 2.52 (dd, 0.5H, J = 5.1, 9.0 Hz), 2.46 (dd, 0.5H, J = 8.3, 9.0 Hz), 2.24 (t, 0.5H, J = 6.9 Hz), 2.18 (t, 0.5H, J = 6.8 Hz), 1.75-1.60 (m, 1H), 0.75-0.68 (m, 1H), 0.49-0.38 (m, 2H), 0.14-0.02 (m, 2H); HPLC analysis: (C18, 10-90% acetonitrile in water + 0.1% trifluoroacetic acid over 20 min: retention time, % area at 254 mn): 12.4 min, 99.4%. | 349.3 (M + H) |
| 66 | 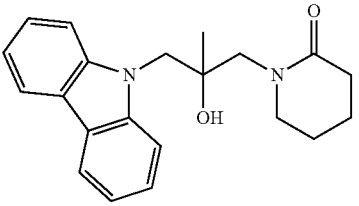 [SMILES: CC(O)(CN1CCCCC1=O)Cn1c2ccccc2c2ccccc21] | 1-(3-(9H-carbazol-9-yl)-2-hydroxy-2-methylpropyl)piperidin-2-one | (300 MHz, CDCl$_3$): δ 8.08 (d, 2H, J = 8.1 Hz), 7.54-7.42 (m, 4H), 7.26-7.20 (m, 2H), 4.70 (s, 1H), 4.33 (s, 2H), 4.02 (d, 1H, J = 14.1 Hz), 3.43-3.38 (m, 1H), 3.32-3.26 (m, 1H), 3.19 (d, 1H, J = 13.8 Hz), 2.44 (br t, 1H, J = 6.2 Hz), 1.86-1.76 (m, 4H), 1.29 (s, 3H); HPLC analysis: (C18, 10-90% acetonitrile in water + 0.1% trifluoroacetic acid over 20 min: retention time, % area at 254 nm): 12.1 min, 100%. | 337.2 (M + H) |
| 67 | 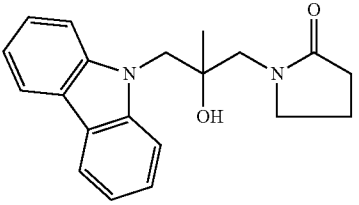 [SMILES: CC(O)(CN1CCCC1=O)Cn1c2ccccc2c2ccccc21] | 1-(3-(9H-carbazol-9-yl)-2-hydroxy-2-methylpropyl)pyrrolidin-2-one | (300 MHz, CDCl$_3$): δ 8.08 (d, 2H, J = 7.5 Hz), 7.53-7.42 (m, 4H), 7.26-7.21 (m, 2H), 4.33 (d, 2H, J = 2.4 Hz), 3.59-3.35 (m, 5H), 2.42 (t, 2H, J = 8.3 Hz), 2.11-1.99 (m, 2H), 1.27 (s, 3H); HPLC analysis: (C18, 10-90% acetonitrile in water + 0.1% trifluoroacetic acid over 20 min: retention time, % area at 254 nm): 11.3 min, 100%. | 323.0 (M + H) |
| 68 | 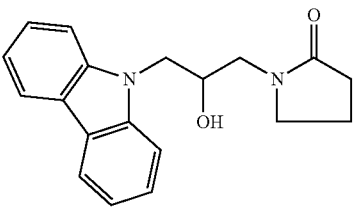 [SMILES: O=C1CCCN1CC(O)Cn1c2ccccc2c2ccccc21] | 1-(3-(9H-carbazol-9-yl)-2-hydroxypropyl)pyrrolidin-2-one | (300 MHz, CDCl$_3$): δ 8.09 (d, 2H, J = 7.8 Hz), 7.49-7.42 (m, 4H), 7.29-7.21 (m, 2H), 4.42-4.29 (m, 3H), 3.87 (d, 1H, J = 3.3 Hz), 3.51 (dd, 1H, J = 6.9, 14.0 Hz), 3.39-3.20 (m, 3H), 2.40 (t, 2H, J = 8.3 Hz), 1.99 (quin, 2H, J = 7.5 Hz); HPLC analysis: (C18, 10-90% acetonitrile in water + 0.1% trifluoroacetic acid over 20 min: retention time, % area at 254 nm): 10.7 min, 100%. | 309.0 (M + H) |
| 69 | 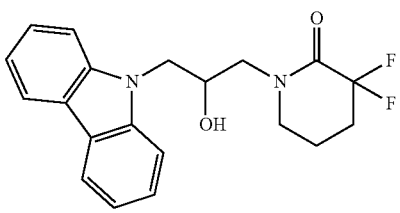 [SMILES: O=C1N(CC(O)Cn2c3ccccc3c3ccccc32)CCCC1(F)F] | 1-(3-(9H-carbazol-9-yl)-2-hydroxypropyl)-3,3-difluoropiperidin-2-one | (300 MHz, CDCl$_3$): δ 8.10-8.07 (m, 2H), 7.47-7.44 (m, 4H), 7.28-7.22 (m, 2H), 4.50 (br m, 1H), 4.20-4.38 (d, 2H, J = 6.1 Hz), 3.66-3.51 (m, 2H), 3.41-3.30 (m, 2H), 2.77 (d, 1H, J = 3.6 Hz), 2.31-2.18 (m, 2H), 1.96 (quin, 2H, J = 6.3 Hz); HPLC analysis: (C18, 10-90% acetonitrile in water + 0.1% trifluoroacetic acid over 20 min: retention time, % area at 254 mn): 12.1 min, 98.9%. | 359.0 (M + H) |

| Cpd | Structure | Name | ¹H NMR | ESI (m/z) |
|---|---|---|---|---|
| 70 | 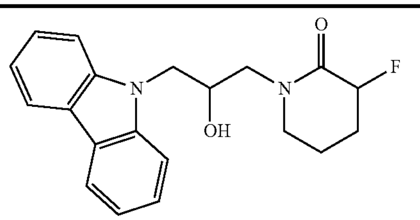 | 1-(3-(9H-carbazol-9-yl)-2-hydroxypropyl)-3-fluoropiperidin-2-one | (300 MHz, CDCl₃): δ 8.09 (d, 2H, J = 7.8 Hz), 7.50-7.44 (m, 4H), 7.29-7.20 (m, 2H), 4.94-4.71 (m, 1H), 4.45-4.34 (m, 3H), 3.73 (ddd, 1H, J = 8.4, 14.4, 34.5 Hz), 3.57-3.07 (m, 4H), 2.15-1.88 (m, 3H), 1.77-1.66 (m, 1H); HPLC analysis: (C18, 10-90% acetonitrile in water + 0.1% trifluoroacetic acid over 20 min: retention time, % area at 254 nm): 11.3 min, 100%. | 341.2 (M + H) |

Compound 71: 1-(3-(3,6-difluoro-9H-carbazol-9-yl)-2-hydroxypropyl)tetrahydropyrimidin-2(1H)-one

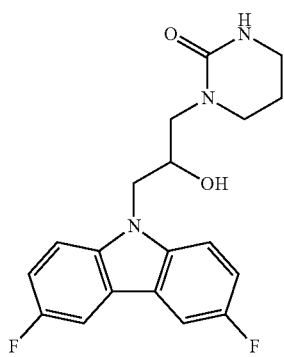 [SMILES: O=C1NCCCN1CC(O)Cn1c2ccc(F)cc2c2cc(F)ccc21]

A mixture of 3,6-difluoro-9-(oxiran-2-ylmethyl)-9H-carbazole (0.06 g, 0.2 mmol) and 1,3-diaminopropane (0.195 mL, 2.3 mmol) in ethanol (2 mL) was stirred at 40° C. for 5 hrs. The reaction mixture was concentrated in vacuo to afford a light yellow oil. ESI (m/z): 334.2 (M+H).

The residue was dissolved in methylene chloride (10 mL) at 0° C. were added 4-dimethylaminopyridine (0.005 g) and 1,1'-carbonyldiimidazole (0.056 g, 0.3 mmol). The mixture was warmed to room temperature and stirred for 16 hrs. The reaction was concentrated in vacuo and the residue purified by silica gel chromatography (0-10% methanol/methylene chloride) to afford the desired product as a white powder (0.060 g, 72%). ¹H NMR (300 MHz, d⁶-DMSO): δ 7.99 (dd, 2H, J=9.6, 2.7 Hz), 7.56 (dd, 2H, J=9.0, 4.2 Hz), 7.30 (td, 2H, J=9.0, 2.7 Hz), 6.29 (s, 1H), 5.24 (d, 1H, J=5.4 Hz), 4.35 (dd, 1H, J=15.0, 3.6 Hz), 4.24 (dd, 1H, J=15.0, 8.1 Hz), 4.07 (m, 1H), 3.55-3.05 (m, 6H), 1.90-1.70 (m, 2H); ESI (m/z): 360.1 (M+H).

Compounds 72 to 84

Compounds 72 to 84 were prepared by procedures analogous to those used for Compound 71 using an appropriate diamine such as N-methyl-1,3-diaminopropane, ethylenediamine, N-ethylethlenediamine, N1-cyclohexylpropane-1,3-diamine, N1-cyclobutylpropane-1,3-diamine, N1-cyclopentylpropane-1,3-diamine or propane-1,2-diamine instead of 1,3-diaminopropane. Preparation of non-commercially available diamines used are described in the preparation of intermediates.

| Cpd # | Structure | Name | ¹H NMR | ESI (m/z) |
|---|---|---|---|---|
| 72 | 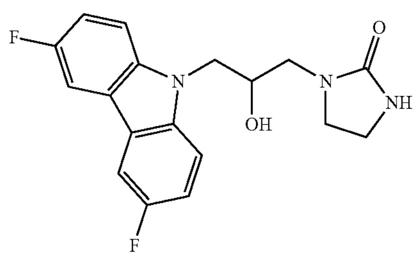 [SMILES: O=C1NCCN1CC(O)Cn1c2ccc(F)cc2c2cc(F)ccc21] | 1-(3-(3,6-difluoro-9H-carbazol-9-yl)-2-hydroxypropyl)imidazolidin-2-one | (300 MHz, CDCl₃): δ 7.69-7.65 (dd, 2H, J = 2.4, 8.7 Hz), 7.40-7.36 (dd, 2H, J = 4.0, 9.0 Hz), 7.24-7.18 (td, 2H, J = 2.7, 9.0 Hz), 4.42-4.35 (m, 4H), 4.24-4.22 (m, 1H), 3.50-3.21 (m, 6H). | 346.1 (M + H) |
| 73 | 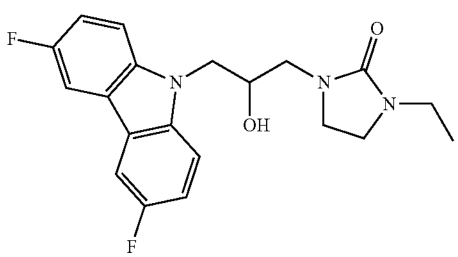 [SMILES: CCN1CCN(CC(O)Cn2c3ccc(F)cc3c3cc(F)ccc32)C1=O] | 1-(3-(3,6-difluoro-9H-carbazol-9-yl)-2-hydroxypropyl)-3-ethylimidazolidin-2-one | (300 MHz, CDCl₃): δ 7.68-7.64 (dd, 2H, J = 2.4, 8.7 Hz), 7.39-7.35 (dd, 2H, J = 4.2, 9.0 Hz), 7.23-7.17 (td, 2H, J = 2.7, 8.7 Hz), 4.80 (br s, 1H), 4.40-4.30 (m, 3H), 3.34-3.07 (m, 8H), 1.15-1.10 (t, 3H, J = 7.2 Hz). | 373.4 (M + H) |

| Cpd # | Structure | Name | ¹H NMR | ESI (m/z) |
|---|---|---|---|---|
| 74 | 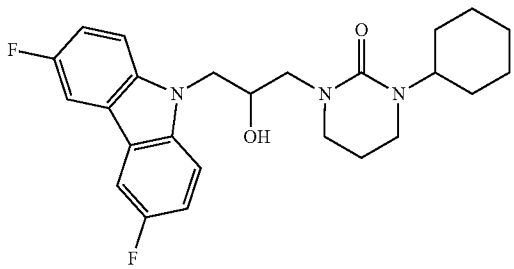 [SMILES: O=C1N(CC(O)Cn2c3ccc(F)cc3c3cc(F)ccc32)CCCN1C1CCCCC1] | 1-cyclohexyl-3-(3-(3,6-difluoro-9H-carbazol-9-yl)-2-hydroxypropyl)tetrahydropyrimidin-2(1H)-one | (300 MHz, CDCl$_3$): δ 7.67-7.64 (dd, 2H, J = 2.0, 8.4 Hz), 7.40-7.36 (dd, 2H, J = 4.1, 9.0 Hz), 7.23-7.16 (td, 2H, J = 2.4, 9.0 Hz), 5.66-5.65 (d, 1H, J = 2.1 Hz), 4.40-4.17 (m, 4H), 3.88-3.81 (m, 1H), 3.21-2.94 (m, 4H), 2.85-2.80 (dd, 1H, J = 1.7, 14.4 Hz), 1.85-1.61 (m, 7H), 1.45-1.26 (m, 4H), 1.10-1.01 (m, 1H). | 442.1 (M + H) |
| 75 | 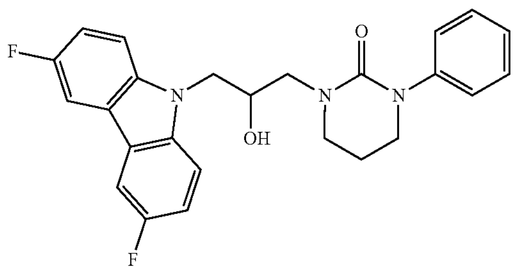 [SMILES: O=C1N(CC(O)Cn2c3ccc(F)cc3c3cc(F)ccc32)CCCN1c1ccccc1] | 1-(3-(3,6-difluoro-9H-carbazol-9-yl)-2-hydroxypropyl)-3-phenyltetrahydropyrimidin-2(1H)-one | (300 MHz, CDCl$_3$): δ 7.68-7.64 (dd, 2H, J = 2.7, 8.7 Hz), 7.41-7.36 (dd, 2H, J = 4.1, 8.7 Hz), 7.34-7.32 (m, 2H), 7.24-7.16 (m, 5H), 5.07-5.06 (d, 1H, J = 3.0 Hz), 4.40-4.26 (m, 3H), 3.93-3.85 (dd, 1H, J = 8.7, 14.7 Hz), 3.67-3.63 (m, 2H), 3.26-3.18 (m, 2H), 3.00-3.95 (dd, 1H, J = 2.0, 14.6 Hz), 2.10-1.99 (m, 2H). | 436.2 (M + H) |
| 76 | 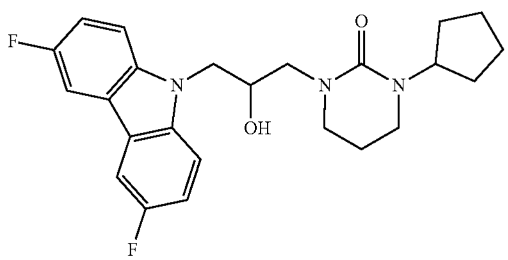 [SMILES: O=C1N(CC(O)Cn2c3ccc(F)cc3c3cc(F)ccc32)CCCN1C1CCCC1] | 1-cyclopentyl-3-(3-(3,6-difluoro-9H-carbazol-9-yl)-2-hydroxypropyl)tetrahydropyrimidin-2(1H)-one | (300 MHz, CDCl$_3$): δ 7.67-7.63 (dd, 2H, J = 2.4, 8.7 Hz), 7.40-7.35 (dd, 2H, J = 4.2, 8.7 Hz), 7.23-7.16 (td, 2H, J = 2.4, 9.0 Hz), 5.65-5.65 (d, 1H, J = 2.4 Hz), 4.84-4.73 (quint, 1H, J = 8.4 Hz), 4.40-4.21 (m, 3H), 3.88-3.81 (m, 1H), 3.18-2.95 (m, 4H), 2.85-2.80 (dd, 1H, J = 1.5, 14.7 Hz), 1.88-1.34 (m, 10H). | 428.2 (M + H) |
| 77 | 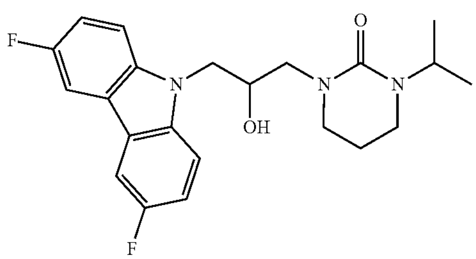 [SMILES: CC(C)N1CCCN(CC(O)Cn2c3ccc(F)cc3c3cc(F)ccc32)C1=O] | 1-(3-(3,6-difluoro-9H-carbazol-9-yl)-2-hydroxypropyl)-3-isopropyltetrahydropyrimidin-2(1H)-one | (300 MHz, CDCl$_3$): δ 7.67-7.64 (dd, 2H, J = 2.1, 8.9 Hz), 7.40-7.35 (dd, 2H, J = 4.2, 9.0 Hz), 7.23-7.17 (td, 2H, J = 2.6, 9.0 Hz), 5.65-5.64 (d, 1H, J = 2.4 Hz), 4.74-4.60 (sept, 1H, J = 6.9 Hz), 4.41-4.21 (m, 3H), 3.91-3.82 (m, 1H), 3.18-2.84 (m, 4H), 2.85-2.79 (dd, 1H, J = 1.7, 14.6 Hz), 1.90-1.75 (m, 2H), 1.09-1.07 (d, 6H, J = 6.9 Hz); HPLC analysis: (C18, 10-90% acetonitrile in water over 20 min: retention time, % area at 254 nm): 13.5 min, 100%. | 402.1 (M + H) |
| 78 | 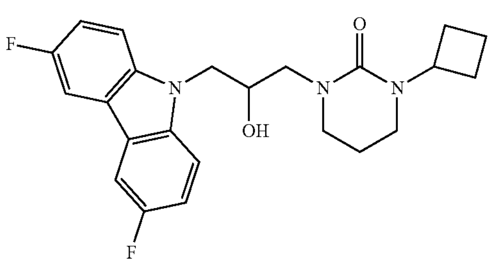 [SMILES: O=C1N(CC(O)Cn2c3ccc(F)cc3c3cc(F)ccc32)CCCN1C1CCC1] | 1-cyclobutyl-3-(3-(3,6-difluoro-9H-carbazol-9-yl)-2-hydroxypropyl)tetrahydropyrimidin-2(1H)-one | (300 MHz, CDCl$_3$): δ 7.67-7.64 (dd, 2H, J = 2.4, 8.7 Hz), 7.39-7.35 (dd, 2H, J = 4.2, 8.7 Hz), 7.24-7.16 (td, 2H, J = 2.2, 8.7 Hz), 5.46-5.45 (d, 1H, J = 1.8 Hz), 4.90-4.79 (quint, 1H, J = 8.7 Hz), 4.41-4.21 (m, 3H), 3.86-3.79 (m, 1H), 3.31-2.99 (m, 5H), 2.87-2.81 (dd, 1H, J = 1.5, 14.4 Hz), 2.09-2.02 (m, 4H), 1.90-1.83 (m, 2H), 1.67-1.60 (m, 2H). | 414.2 (M + H) |

-continued

| Cpd # | Structure | Name | ¹H NMR | ESI (m/z) |
|---|---|---|---|---|
| 79 | 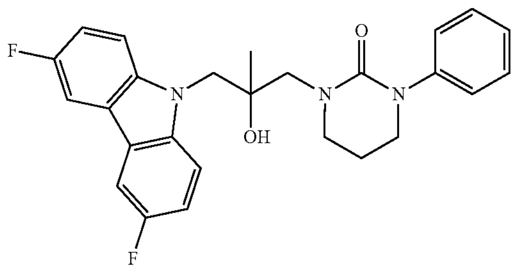 [SMILES: CC(O)(CN1CCCN(c2ccccc2)C1=O)Cn1c2ccc(F)cc2c2cc(F)ccc21] | 1-(3-(3,6-difluoro-9H-carbazol-9-yl)-2-hydroxy-2-methylpropyl)-3-phenyltetrahydropyrimidin-2(1H)-one | (300 MHz, CDCl₃): δ 7.64-7.60 (dd, 2H, J = 2.7, 8.7 Hz), 7.46-7.42 (dd, 2H, J = 4.1, 9.0 Hz), 7.35-7.30 (m, 2H), 7.23-7.13 (m, 5H), 5.48 (s, 1H), 4.27-4.26 (d, 2H, J = 3.0 Hz,) 4.00-3.95-3.86, 3.13-3.08 (ABq, 2H, J = 14.6 Hz), 3.72-3.46 (m, 4H), 2.18-2.05 (m, 2H), 1.33 (s, 3H). | 450.1 (M + H) |
| 80 | 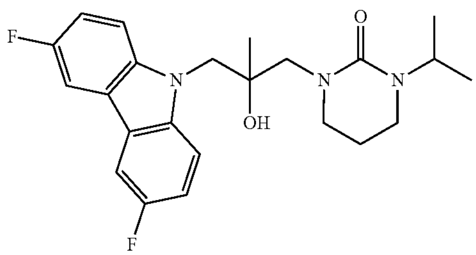 [SMILES: CC(C)N1CCCN(CC(C)(O)Cn2c3ccc(F)cc3c3cc(F)ccc32)C1=O] | 1-(3-(3,6-difluoro-9H-carbazol-9-yl)-2-hydroxy-2-methylpropyl)-3-isopropyltetrahydropyrimidin-2(1H)-one | (300 MHz, CDCl₃): δ 7.65-7.61 (dd, 2H, J = 2.7, 8.7 Hz), 7.47-7.43 (dd, 2H, J = 4.2, 9.0 Hz), 7.20-7.13 (td, 2H, J = 2.6, 9.0 Hz), 6.07 (s, 1H), 4.70-4.60 (sept, 1H, J = 6.9 Hz), 4.25-4.21 (d, 2H, J = 5.1 Hz), 3.92-3.87, 3.03-2.98 (ABq, 2H, J = 14.4 Hz), 3.39-3.10 (m, 4H), 1.98-1.90 (m, 2H), 1.27 (s, 3H). | 416.1 (M + H) |
| 81 | 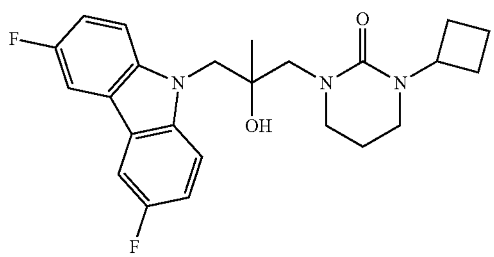 [SMILES: CC(O)(CN1CCCN(C2CCC2)C1=O)Cn1c2ccc(F)cc2c2cc(F)ccc21] | 1-cyclobutyl-3-(3-(3,6-difluoro-9H-carbazol-9-yl)-2-hydroxy-2-methylpropyl)tetrahydropyrimidin-2(1H)-one | (300 MHz, CDCl₃): δ 7.65-7.61 (dd, 2H, J = 2.6, 8.6 Hz), 7.47-7.42 (dd, 2H, J = 4.1, 8.9 Hz), 7.20-7.13 (td, 2H, J = 2.5, 9.0 Hz), 5.91 (s, 1H), 4.87-4.76 (quint, 1H, J = 8.6 Hz), 4.25-4.24 (d, 2H, J = 4.5 Hz), 3.92-3.87, 3.12-2.96 (ABq, 2H, J = 14.7 Hz), 3.42-3.21 (m, 4H), 2.13-1.91 (m, 6H), 1.66-1.55 (m, 2H) 1.26 (s, 3H). | 428.1 (M + H) |
| 82 | 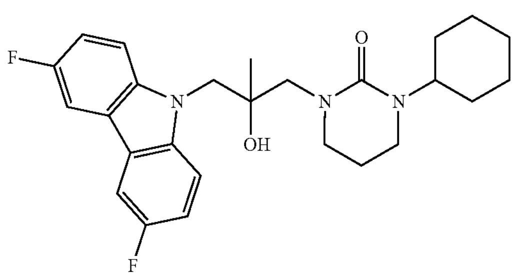 [SMILES: CC(O)(CN1CCCN(C2CCCCC2)C1=O)Cn1c2ccc(F)cc2c2cc(F)ccc21] | 1-cyclohexyl-3-(3-(3,6-difluoro-9H-carbazol-9-yl)-2-hydroxy-2-methylpropyl)tetrahydropyrimidin-2(1H)-one | (300 MHz, CDCl₃): δ 7.64-7.60 (dd, 2H, J = 2.7, 8.7 Hz), 7.47-7.43 (dd, 2H, J = 4.2, 9.0 Hz), 7.20-7.13 (td, 2H, J = 2.6, 9.0 Hz), 6.07 (s, 1H), 4.25-4.24 (d, 2H, J = 3.6 Hz), 4.20-4.16 (m, 1H), 3.91-3.87, 3.02-2.97 (ABq, 2H, J = 14.6 Hz), 3.41-3.10 (m, 4H), 1.97-1.62 (m, 6H), 1.38-1.27 (m, 3H) 1.26 (s, 3H), 1.07-1.00 (m, 1H). | 456.2 (M + H) |
| 83 | 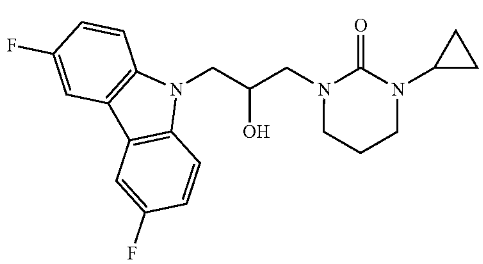 [SMILES: O=C1N(CC(O)Cn2c3ccc(F)cc3c3cc(F)ccc32)CCCN1C1CC1] | 1-cyclopropyl-3-(3-(3,6-difluoro-9H-carbazol-9-yl)-2-hydroxypropyl)tetrahydropyrimidin-2(1H)-one | (300 MHz, CDCl₃): δ 7.66-7.63 (dd, 2H, J = 2.3, 9.0 Hz), 7.39-7.34 (dd, 2H, J = 4.2, 9.0 Hz), 7.22-7.19 (td, 2H, J = 2.6, 9.0 Hz), 5.24 (s, 1H), 4.39-4.21 (m, 3H), 3.84-3.76 (m, 1H), 3.25-3.19 (m, 2H), 3.11-2.95 (m, 2H), 2.92-2.86 (m, 1H), 2.61-2.54 (m, 1H), 1.87-1.79 (quint, 2H, J = 6.0 Hz), 0.78-0.65 (m, 2H), 0.64-0.57 (m, 2H). | 400.2 (M + H) |

-continued

| Cpd # | Structure | Name | ¹H NMR | ESI (m/z) |
|---|---|---|---|---|
| 84 | ![structure] | 1-(3-(9H-carbazol-9-yl)-2-hydroxypropyl)imidazolidin-2-one | (300 MHz, d⁶-DMSO): δ 8.11 (d, 2H, J = 7.5 Hz), 7.57 (d, 2H, J = 8.1 Hz), 7.44-7.38 (m, 2H), 7.16 (t, 2H, J = 7.1 Hz), 6.30 (s, 1H), 5.16 (d, 1H, J = 6.0 Hz), 4.34 (dd, 1H, J = 4.8, 14.7 Hz), 4.25 (dd, 1H, J = 7.5, 15.0 Hz), 4.09-4.02 (m, 1H), 3.45-3.17 (m, 5H), 3.10 (dd, 1H, J = 7.2, 13.8 Hz); HPLC analysis: (C18, 10-90% acetonitrile in water + 0.1% trifluoroacetic acid over 20 min: retention time, % area at 254 nm): 10.1 min, 100%. | 310.0 (M + H) |

Compound 85: 1-(3-(3,6-difluoro-9H-carbazol-9-yl)-2-hydroxypropyl)-4-methylimidazolidin-2-one

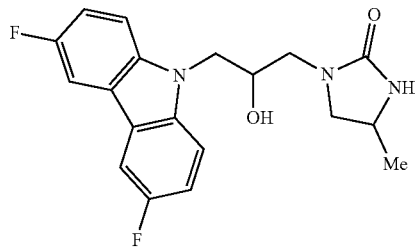

A mixture of tert-butyl (1-((3-(3,6-difluoro-9H-carbazol-9-yl)-2-hydroxypropyl)amino)propan-2-yl)carbamate (1.400 g, 80% pure, 2.6 mmol, 1.0 equiv.) and potassium tert-butoxide (0.290 g, 2.6 mmol, 1.0 equiv.) in anhydrous tetrahydrofuran (270 mL) was stirred at reflux for 2 hrs. The reaction mixture was cooled to room temperature, acetic acid (0.1 mL) and silica gel were added, and the mixture concentrated under reduced pressure to a slurry. The crude residue was purified by silica gel column chromatography by eluting with a gradient of 0-10% methanol/methylene chloride to give a solid. The solid was crystallized from ethyl acetate to give a white solid (0.673 g, 72%). ¹H NMR (300 MHz, CDCl₃; mixture of diastereomers): δ 7.69-7.65 (dd, 2H, J=2.7, 8.7 Hz), 7.40-7.35 (dd, 2H, J=4.1, 9.0 Hz), 7.24-7.18 (td, 2H, J=2.7, 9.0 Hz), 4.47-4.19 (m, 5H), 3.82 (br m, 1H), 3.58-2.93 (m, 4H), 1.26-1.24 (d, 3H, J=6.3 Hz); ESI (m/z): 360.9 (M+H).

Compound 86: 1-(3-(3,6-difluoro-9H-carbazol-9-yl)-2-hydroxypropyl)-3-ethyltetrahydropyrimidin-2(1H)-one

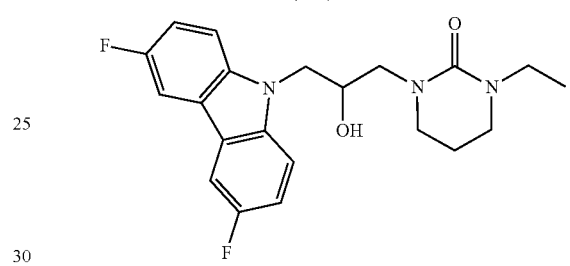

To a solution of 3,6-difluoro-9H-carbazole (0.065 g, 0.3 mmol) in anhydrous N,N-dimethylformamide (0.3 mL) was added 60% sodium hydride in mineral oil (0.009 g, 0.2 mmol) and the mixture stirred at room temperature for 30 min. A solution of 1-ethyl-3-(oxiran-2-ylmethyl)tetrahydropyrimidin-2(1H)-one (0.055 g, 0.3 mmol) in anhydrous N,N-dimethylformamide (0.3 mL) was added and the mixture was heated at 70° C. for 8 hrs. The reaction mixture was diluted with methanol, filtered, and purified by preparative HPLC (C18, 30-95% acetonitrile in water) to afford a white solid (0.072 g, 62%). ¹H NMR (300 MHz, CDCl₃): δ 7.67-7.63 (dd, 2H, J=2.6, 9.0 Hz), 7.39-7.35 (dd, 2H, J=4.2, 8.7 Hz), 7.23-7.16 (td, 2H, J=2.4, 9.0 Hz), 5.52 (d, 1H, J=2.7 Hz), 4.37-4.21 (m, 3H), 3.86-3.79 (m, 1H), 3.43-2.98 (m, 6H), 2.88-2.83 (dd, 1H, J=1.8, 14.7 Hz), 1.91-1.83 (quin, 2H, J=5.9 Hz), 1.12-1.07 (t, 3H, J=7.4 Hz); ESI (m/z): 388.1 (M+H); HPLC analysis: (C18, 10-90% acetonitrile in water over 20 min: retention time, % area at 254 nm): 12.8 min, 100%.

Compounds 87-100

Compounds 87-100 were prepared by procedures analogous to those used for Compound 88.

| Cpd # | Structure | Name | ¹H NMR | ESI (m/z) |
|---|---|---|---|---|
| 87 | ![structure] | 1-(3-(3,6-difluoro-9H-carbazol-9-yl)-2-hydroxy-2-methylpropyl)-3-ethyltetrahydropyrimidin-2(1H)-one | (300 MHz, CDCl₃): δ 7.64-7.61 (dd, 2H, J = 2.5, 8.6 Hz), 7.47-7.42 (dd, 2H, J = 4.2, 9.0 Hz), 7.20-7.13 (td, 2H, J = 2.7, 9.0 Hz), 5.97 (s, 1H), 4.30-4.18 (m, 2H,) 3.91-3.86, 3.03-2.98 (ABq, 2H, J = 14.9 Hz), 3.46-3.23 (m, 6H), 1.99-1.93 (m, 2H), 1.26 (s, 3H), 1.12-1.07 (t, 3H, J = 7.0 Hz). | 402.1 (M + H) |

-continued

| Cpd # | Structure | Name | ¹H NMR | ESI (m/z) |
|---|---|---|---|---|
| 88 | 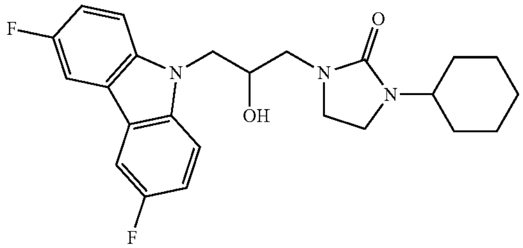 [SMILES: O=C1N(CC(O)Cn2c3ccc(F)cc3c3cc(F)ccc32)CCN1C1CCCCC1] | 1-cyclohexyl-3-(3-(3,6-difluoro-9H-carbazol-9-yl)-2-hydroxypropyl)imidazolidin-2-one | (300 MHz, CDCl₃): δ 7.68-7.64 (dd, 2H, J = 2.6, 8.6 Hz), 7.39-7.35 (dd, 2H, J = 4.2, 8.7 Hz), 7.39-7.17 (td, 2H, J = 2.4, 9.0 Hz), 5.14-5.13 (d, 1H, J = 2.7 Hz), 4.40-4.30 (m, 3H,) 3.73-3.64 (m, 1H), 3.30-2.96 (m, 6H), 1.80-1.70 (m, 5H), 1.45-1.24 (m, 4H), 1.13-1.05 (m, 1H). | 428.2 (M + H) |
| 89 | 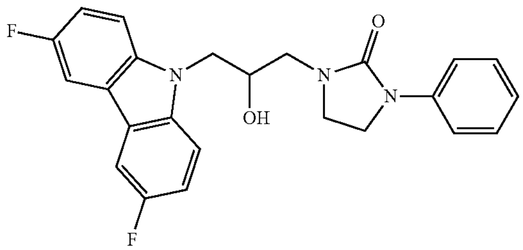 [SMILES: O=C1N(CC(O)Cn2c3ccc(F)cc3c3cc(F)ccc32)CCN1c1ccccc1] | 1-(3-(3,6-difluoro-9H-carbazol-9-yl)-2-hydroxypropyl)-3-phenylimidazolidin-2-one | (300 MHz, CDCl₃): δ 7.69-7.66 (dd, 2H, J = 2.6, 8.6 Hz), 7.53-7.50 (m, 2H), 7.41-7.32 (m, 4H), 7.39-7.17 (td, 2H, J = 2.5, 9.0 Hz), 7.10-7.05 (br t, 1H, J = 7.4 Hz), 4.43-4.37 (m, 3H), 4.01-3.99 (d, 1H, J = 4.2 Hz) 3.86-3.80 (m, 2H), 3.53-3.29 (m, 4H). | 422.1 (M + H) |
| 90 | 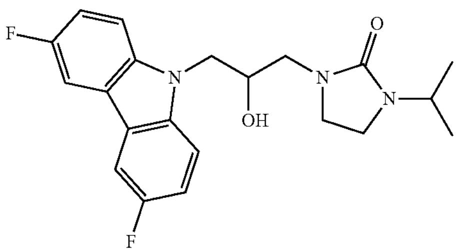 [SMILES: CC(C)N1CCN(CC(O)Cn2c3ccc(F)cc3c3cc(F)ccc32)C1=O] | 1-(3-(3,6-difluoro-9H-carbazol-9-yl)-2-hydroxypropyl)-3-isopropylimidazolidin-2-one | (300 MHz, CDCl₃): δ 7.66-7.62 (dd, 2H, J = 2.4, 8.6 Hz), 7.38-7.33 (dd, 2H, J = 4.1, 8.9 Hz), 7.22-7.15 (td, 2H, J = 2.5, 9.0 Hz), 5.00-5.00 (d, 1H, J = 2.1 Hz), 4.37-4.06 (m, 3H), 4.15-4.06 (m, 1H), 3.29-3.00 (m, 6H), 1.15-1.11 (t, 6H, J = 6.3 Hz). | 388.2 (M + H) |
| 91 | 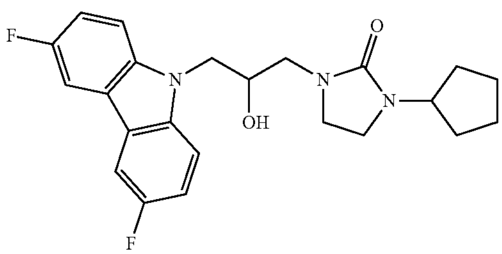 [SMILES: O=C1N(CC(O)Cn2c3ccc(F)cc3c3cc(F)ccc32)CCN1C1CCCC1] | 1-cyclopentyl-3-(3-(3,6-difluoro-9H-carbazol-9-yl)-2-hydroxypropyl)imidazolidin-2-one | (300 MHz, CDCl₃): δ 7.66-7.65 (dd, 2H, J = 2.6, 8.6 Hz), 7.40-7.35 (dd, 2H, J = 4.2, 8.7 Hz), 7.24-7.17 (td, 2H, J = 2.6, 9.0 Hz), 4.98-4.97 (d, 1H, J = 1.5 Hz), 4.41-4.22 (m, 3H), 3.32-3.00 (m, 7H), 1.86-1.48 (m, 10H). | 414.2 (M + H) |
| 92 | 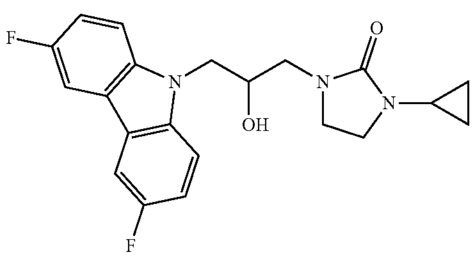 [SMILES: O=C1N(CC(O)Cn2c3ccc(F)cc3c3cc(F)ccc32)CCN1C1CC1] | 1-cyclopropyl-3-(3-(3,6-difluoro-9H-carbazol-9-yl)-2-hydroxypropyl)imidazolidin-2-one | (300 MHz, CDCl₃): δ 7.66-7.62 (dd, 2H, J = 2.6, 8.9 Hz), 7.38-7.34 (dd, 2H, J = 4.1, 8.9 Hz), 7.22-7.15 (td, 2H, J = 2.5, 9.0 Hz), 4.81-4.80 (d, 1H, J = 4.5 Hz), 4.37-4.28 (m, 3H), 3.31-3.00 (m, 6H), 2.44-2.37 (m, 1H), 0.76-0.61 (m, 4H). | 386.2 (M + H) |
| 93 | 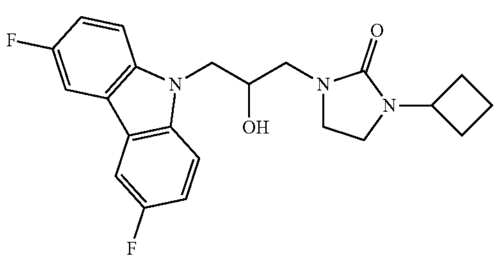 [SMILES: O=C1N(CC(O)Cn2c3ccc(F)cc3c3cc(F)ccc32)CCN1C1CCC1] | 1-cyclobutyl-3-(3-(3,6-difluoro-9H-carbazol-9-yl)-2-hydroxypropyl)imidazolidin-2-one | (300 MHz, CDCl₃): δ 7.66-7.62 (dd, 2H, J = 2.6, 9.0 Hz), 7.37-7.33 (dd, 2H, J = 4.1, 9.0 Hz), 7.22-7.15 (td, 2H, J = 2.5, 9.0 Hz), 4.80-4.79 (d, 1H, J = 4.5 Hz), 4.43-4.27 (m, 4H), 3.40-3.04 (m, 6H), 2.16-2.04 (m, 4H), 1.71-1.60 (m, 2H). | 400.1 (M + H) |

| Cpd # | Structure | Name | ¹H NMR | ESI (m/z) |
|---|---|---|---|---|
| 94 | 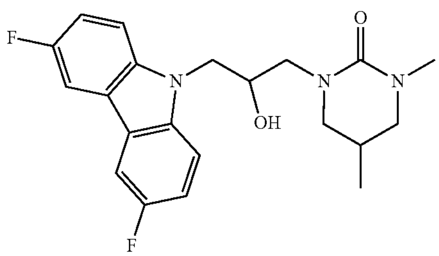 [SMILES: CC1CN(C)C(=O)N(CC(O)Cn2c3ccc(F)cc3c3cc(F)ccc32)C1] | 1-(3-(3,6-difluoro-9H-carbazol-9-yl)-2-hydroxypropyl)-3,5-dimethyltetrahydropyrimidin-2(1H)-one | (300 MHz, CDCl₃): δ 7.68-7.64 (dd, 2H, J = 2.7, 8.7 Hz), 7.40-7.36 (dd, 2H, J = 4.2, 9.0 Hz), 7.23-7.17 (td, 2H, J = 2.6, 9.0 Hz), 5.31 (br s, 0.5H), 5.15 (br s, 0.3H), 4.39-4.21 (m, 3H), 3.85-3.73 (m, 1H), 3.17-2.76 (m, 8H), 2.17-2.12 (m, 1H), 0.93-0.90 (two overlapping d, 3H, J = 6.9 Hz). | 388.2 (M + H) |
| 95 | 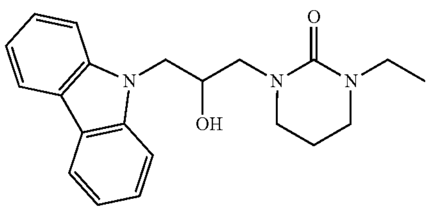 [SMILES: CCN1CCCN(CC(O)Cn2c3ccccc3c3ccccc32)C1=O] | 1-(3-(9H-carbazol-9-yl)-2-hydroxypropyl)-3-ethyltetrahydropyrimidin-2(1H)-one | (300 MHz, CDCl₃): δ 8.08 (d, 2H, J = 8.1 Hz), 7.49-7.42 (m, 4H), 7.26-7.21 (m, 2H), 5.44 (d, 1H, J = 3.0 Hz), 4.43-4.25 (m, 3H), 3.87 (dd, 1H, J = 14.1, 8.6 Hz), 3.45-2.84 (m, 7H), 1.82 (quin, 2H, J = 6.0 Hz), 1.09 (t, 3H, J = 7.1 Hz); HPLC analysis: (C18, 10-95% acetonitrile in water + 0.1% trifluoroacetic acid over 15 min: retention time, % area at 254 nm): 12.2 min, 98.3%. | 352.2 (M + H) |
| 96 | 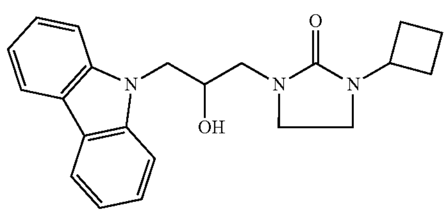 [SMILES: O=C1N(CC(O)Cn2c3ccccc3c3ccccc32)CCN1C1CCC1] | 1-(3-(9H-carbazol-9-yl)-2-hydroxypropyl)-3-cyclobutylimidazolidin-2-one | (300 MHz, CDCl₃): δ 8.11-8.07 (m, 2H), 7.48-7.42 (m, 4H), 7.28-7.21 (m, 2H), 4.74-4.73 (m, 1H), 4.45-4.34 (m, 4H), 3.35 (t, 2H, J = 7.8 Hz), 3.24-2.99 (m, 4H), 2.17-2.07 (m, 4H), 1.71-1.61 (m, 2H); HPLC analysis: (C18, 10-95% acetonitrile in water + 0.1% trifluoroacetic acid over 15 min: retention time, % area at 254 nm): 12.7 min, 95.1%. | 365.0 (M + H) |
| 97 | 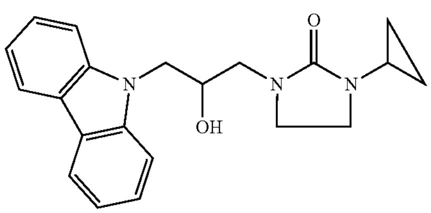 [SMILES: O=C1N(CC(O)Cn2c3ccccc3c3ccccc32)CCN1C1CC1] | 1-(3-(9H-carbazol-9-yl)-2-hydroxypropyl)-3-cyclopropylimidazolidin-2-one | (300 MHz, CDCl₃): δ 8.09 (d, 2H, J = 7.2 Hz), 7.48-7.42 (m, 4H), 7.27-7.21 (m, 2H), 4.75 (br s, 1H), 4.45-4.35 (m, 3H), 3.28-2.94 (m, 6H), 2.45-2.40 (m, 1H), 0.75-0.62 (m, 4H); HPLC analysis: (C18, 10-95% acetonitrile in water + 0.1% trifluoroacetic acid over 15 min: retention time, % area at 254 nm): 11.1 min, 96.2%. | 351.0 (M + H) |
| 98 | 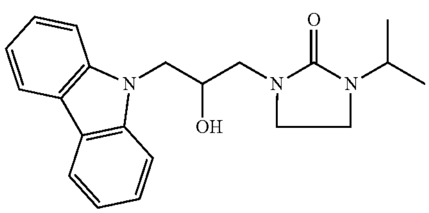 [SMILES: CC(C)N1CCN(CC(O)Cn2c3ccccc3c3ccccc32)C1=O] | 1-(3-(9H-carbazol-9-yl)-2-hydroxypropyl)-3-isopropylimidazolidin-2-one | (300 MHz, CDCl₃): δ 8.09 (d, 2H, J = 7.8 Hz), 7.49-7.42 (m, 4H), 7.27-7.21 (m, 2H), 4.96-4.94 (m, 1H), 4.48-4.35 (m, 3H), 4.13 (sept, 1H, J = 6.6 Hz), 3.26-2.94 (m, 6H), 1.15 (d, 3H, J = 7.5 Hz), 1.12 (d, 3H, J = 7.2 Hz); HPLC analysis: (C18, 10-95% acetonitrile in water + 0.1% trifluoroacetic acid over 15 min: retention time, % area at 254 nm): 11.6 min, 98.3%. | 353.0 (M + H) |
| 99 | 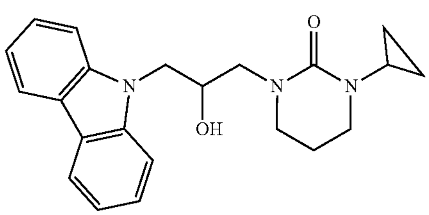 [SMILES: O=C1N(CC(O)Cn2c3ccccc3c3ccccc32)CCCN1C1CC1] | 1-(3-(9H-carbazol-9-yl)-2-hydroxypropyl)-3-cyclopropyltetrahydropyrimidin-2(1H)-one | (300 MHz, CDCl₃): δ 8.09 (d, 2H, J = 7.5 Hz), 7.48-7.42 (m, 4H), 7.26-7.21 (m, 2H), 5.25 (d, 1H, J = 3.0 Hz), 4.45-4.26 (m, 3H), 3.91-3.83 (dd, 1H, J = 9.0, 14.7 Hz), 3.21-3.17 (m, 2H), 3.04-2.85 (m, 3H), 2.62-2.56 (m, 1H), 1.78 (quint, 2H, J = 6.0 Hz), 0.88-0.57 (m, 4H); HPLC analysis: (C18, 10-95% acetonitrile in water + 0.1% trifluoroacetic acid over 15 min: retention time, % area at 254 nm): 12.1 min, 97.5%. | 364.1 (M + H) |

| Cpd # | Structure | Name | ¹H NMR | ESI (m/z) |
|---|---|---|---|---|
| 100 | 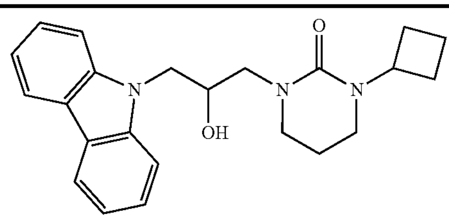 | 1-(3-(9H-carbazol-9-yl)-2-hydroxypropyl)-3-cyclobutyltetrahydropyrimidin-2(1H)-one | (300 MHz, CDCl₃): δ 8.10-8.07 (m, 2H), 7.48-7.42 (m, 4H), 7.26-7.21 (m, 2H), 5.41 (d, 1H, J = 2.4 Hz), 4.85 (quint, 1H, J = 9.0 Hz), 4.45-4.25 (m, 3H), 3.87 (dd, 1H, J = 8.9, 14.6 Hz), 3.35-3.11 (m, 2H), 3.03-2.87 (m, 3H), 2.10-2.00 (m, 4H) 1.85-1.77 (m, 2H), 1.66-1.58 (m, 2H); HPLC analysis: (C18, 10-95% acetonitrile in water + 0.1% trifluoroacetic acid over 15 min: retention time, % area at 254 nm): 13.3 min, 95.6%. | 378.2 (M + H) |

Compound 101: 1-(3-(3,6-difluoro-9H-carbazol-9-yl)-2-hydroxypropyl)-3,4-dimethyltetrahydropyrimidin-2(1H)-one To a stirred solution of 3,6-difluoro-9H-carbazole (0.38 g, 1.9 mmol, 1.2 equiv.) in anhydrous N,N-dimethylacetamide (2 mL) was added 60% sodium hydride in mineral oil (0.075 g, 1.9 mmol, 1.2 equiv.). After stirring at room temperature for 2 hrs, the resulting carbazole sodium solution was ready for use.

To a stirred solution of 1,6-dimethyltetrahydropyrimidin-2(1H)-one (0.2 g, 1.6 mmol, 1.0 equiv.) in dry N,N-dimethylacetamide (3 mL) at 0° C. was added 60% sodium hydride in mineral oil (0.075 g, 1.9 mmol, 1.2 equiv.) and the mixture was stirred for 1 hr at room temperature. Epibromohydrin (0.155 mL, 1.9 mmol, 1.2 equiv.) was added at 0° C. and the mixture was slowly warmed to room temperature and stirred for 16 hrs. The carbazole sodium solution was added and the mixture was heated at 70° C. for 5 hrs. The reaction was diluted with water and extracted with ethyl acetate. The organic layers were washed with saturated aqueous sodium chloride, dried over sodium sulfate, filtered and concentrated in vacuo. The residue was purified by silica gel column (0-100% ethyl acetate/hexane) to afford the pure product as a white foam (0.116 g, 19%). ¹H NMR (300 MHz, CDCl₃): (a mixture of two diastereomers) δ 7.68 (dd, 2H, J=8.7, 2.7 Hz), 7.40 (dd, 2H, J=9.0, 4.2 Hz), 7.27-7.18 (m, 2H), 5.51 and 5.06 (d, 1H, J=2.7 Hz), 4.50-4.20 (m, 3H), 3.90-3.74 (m, 1H), 3.50-2.75 (m, 7H), 2.05 (m, 1H), 1.60 (m, 1H), 1.21 and 1.17 (d, 3H, J=6.6 Hz); ESI (m/z): 388.2 (M+H).

Compound 102: 3-(3-(3,6-difluoro-9H-carbazol-9-yl)-2-hydroxy-2-methylpropyl)-3,4-dihydroquinazolin-2(1H)-one A mixture of 1-benzyl-3-(3-(3,6-difluoro-9H-carbazol-9-yl)-2-hydroxy-2-methylpropyl)-3,4-dihydroquinazolin-2(1H)-one (0.102 g, 0.2 mmol, 1.0 equiv.) and 20% palladium hydroxide on carbon (0.035 g) in acetic acid (4 mL) and tetrahydrofuran (2 mL) was stirred under 50 psi of hydrogen for 48 hrs. 20% palladium hydroxide on carbon (0.02 g) and 10% palladium on carbon (0.01 g) were added and the reaction mixture stirred under 50 psi of hydrogen for 72 hrs. The mixture was filtered, concentrated, and purified by preparative HPLC (C18, 40-80% acetonitrile in water) to give a white solid (0.013 g, 15%). ¹H NMR (300 MHz, CD₃OD): δ 7.73-7.70 (dd, 2H, J=2.6, 8.6 Hz), 7.55-7.51 (dd, 2H, J=4.1, 9.2 Hz), 7.27-7.05 (m, 3H), 7.07-7.05 (d, 1H, J=7.2 Hz), 6.96-6.91 (td, 1H, J=1.1, 7.5 Hz), 6.81-6.78 (d, 1H, J=8.1 Hz), 4.71 (s, 2H), 4.33 (s, 2H) 3.75-3.70, 3.59-3.54 (ABq, 2H, J=14.4 Hz), 1.22 (s, 3H); ESI (m/z): 422.1 (M+H); HPLC analysis: (C18, 5-95% acetonitrile in water+ 0.1% trifluoroacetic acid over 20 min: retention time, % area at 254 nm): 13.5 min, 91.5%.

The following compound was prepared by procedures analogous to those used for Compound 102.

| Cpd # | Structure | Name | ¹H NMR & HPLC | ESI (m/z) |
|---|---|---|---|---|
| 103 | ![structure 103] | 3-(3-(3,6-difluoro-9H-carbazol-9-yl)-2-hydroxypropyl)-3,4-dihydroquinazolin-2(1H)-one | (300 MHz, CD$_3$OD): δ 7.75-7.71 (dd, 2H, J = 2.4, 8.7 Hz), 7.51-7.47 (dd, 2H, J = 4.2, 8.9 Hz), 7.20-7.11 (m, 3H), 7.04-7.02 (m, 1H), 6.94-6.89 (td, 1H, J = 1.1, 7.2 Hz), 6.78-6.76 (d, 1H, J = 7.8 Hz), 4.67-4.62, 4.58-4.53 (ABq, 2H, J = 14.1 Hz), 4.42-4.32 (m, 3H), 3.81-3.75 (dd, 1H, J = 3.9, 14.1 Hz), 3.41-3.34 (dd, 1H, J = 4.2, 14.1 Hz); HPLC analysis: (C18, 5-95% acetonitrile in water + 0.1% trifluoroacetic acid over 20 min: retention time, % area at 254 nm): 12.8 min, 96%. | 408.2 (M + H) |

Compound 104: (1S,4R)-2-((R)-3-(3,6-difluoro-9H-carbazol-9-yl)-2-hydroxypropyl)-2-azabicyclo[2.2.1]heptan-3-one

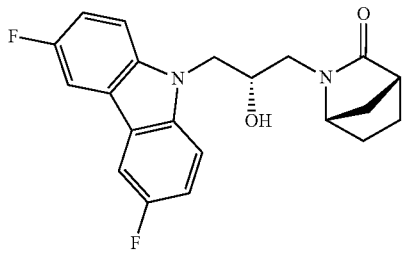 [SMILES: O=C1[C@@H]2CC[C@@H](C2)N1C[C@H](O)Cn1c2ccc(F)cc2c2cc(F)ccc21]

To a stirred solution of (1S,4R)-2-azabicyclo[2.2.1]heptan-3-one (0.051 g, 0.5 mmol, 2.0 equiv.) in anhydrous tetrahydrofuran (1.5 mL) was added 60% sodium hydride in mineral oil (0.009 g, 0.2 mmol, 1.0 equiv.) and the mixture was stirred at room temperature for 60 mins. (R)-3,6-Difluoro-9-(oxiran-2-ylmethyl)-9H-carbazole (0.060 g, 0.2 mmol, 1.0 equiv.) was added and the mixture was stirred at 80° C. in a sealed tube for 16 hrs. The mixture was cooled to room temperature and 1 N acetic acid (0.02 mL) in methanol was added and then concentrated under reduced pressure. The crude residue was purified by preparative HPLC (C18, 30-95% acetonitrile in water) to give a white solid (0.053 g, 61%). ¹H NMR (300 MHz, CDCl$_3$): δ 7.68-7.65 (dd, 2H, J=2.6, 8.6 Hz), 7.38-7.33 (dd, 2H, J=4.1, 8.9 Hz), 7.24-7.17 (td, 2H, J=2.5, 9.0 Hz), 4.38-4.28 (m, 4H), 3.64 (br s, 1H), 3.43-3.38 (dd, 1H, J=2.7, 14.1 Hz), 3.02-2.96 (dd, 1H, J=2.7, 14.4 Hz), 2.90-2.89 (m, 1H), 1.96-1.40 (m, 6H); ESI (m/z): 371.1 (M+H); HPLC analysis: (C18, 5-95% acetonitrile in water+0.1% trifluoroacetic acid over 20 min: retention time, % area at 254 nm): 12.2 min, 100%; Chiral HPLC analysis (Chiralcel AD-H, 15% ethanol in hexanes over 42 mins: retention time, % area at 254 nm): 7.7 min, 98.5%; 12.6 min, 0.7% (98.5% de).

Compounds 105-138

Compounds 105-138 were prepared by procedures analogous to those used for Compound 104.

| Cpd # | Structure | Name | ¹H NMR & HPLC | ESI (m/z) |
|---|---|---|---|---|
| 105 | ![structure 105] | (1R,4S)-2-((R)-3-(3,6-difluoro-9H-carbazol-9-yl)-2-hydroxypropyl)-2-azabicyclo[2.2.1]heptan-3-one | (300 MHz, CDCl$_3$): δ 7.69-7.65 (dd, 2H, J = 2.6, 8.7 Hz), 7.38-7.33 (dd, 2H, J = 3.9, 9.0 Hz), 7.25-7.19 (td, 2H, J = 2.6, 9.0 Hz), 4.40-4.23 (m, 4H), 3.73 (br s, 1H), 3.48-3.41 (dd, 1H, J = 7.4, 14.1 Hz), 2.95-2.90 (dd, 1H, J = 1.7, 13.7 Hz), 2.86-2.85 (dd, 1H, J = 1.2, 3.9 Hz), 1.92-1.36 (m, 6H); HPLC analysis: (C18, 5-95% acetonitrile in water + 0.1% trifluoroacetic acid over 20 min: retention time, % area at 254 nm): 12.2 min, 100%; Chiral HPLC analysis (Chiralcel AD-H, 15% ethanol in hexanes over 42 mins: retention time, % area at 254 nm): 21.1 min, 97.6%; 39.0 min, 2.3% (95.2% de). | 371.1 (M + H) |

| Cpd # | Structure | Name | ¹H NMR & HPLC | ESI (m/z) |
|---|---|---|---|---|
| 106 | 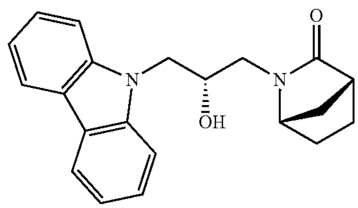 [SMILES: O=C1[C@@H]2CC[C@@H](C2)N1C[C@H](O)Cn1c2ccccc2c2ccccc21] | (1S,4R)-2-((R)-3-(9H-carbazol-9-yl)-2-hydroxypropyl)-2-azabicyclo[2.2.1]heptan-3-one | (300 MHz, CDCl$_3$): δ 8.10-8.07 (m, 2H), 7.46-7.44 (m, 4H), 7.26-7.21 (m, 2H), 4.35-4.34 (m, 4H), 3.61 (br s, 1H), 3.41-3.36 (m, 1H), 3.02-2.95 (m, 1H), 2.88-2.86 (m, 1H), 1.97-1.55 (m, 4H), 1.39-1.36 (br d, 1H, J = 10.2 Hz); HPLC analysis: (C18, 5-95% acetonitrile in water + 0.1% trifluoroacetic acid over 20 min: retention time, % area at 254 nm): 11.5 min, 100%; Chiral HPLC analysis (Chiralcel AD-H, 15% ethanol in hexanes over 30 mins: retention time, % area at 254 nm): 9.2 min, 98.1%; 12.0 min, 1.7% (96.4% de). | 335.2 (M + H) |
| 107 | 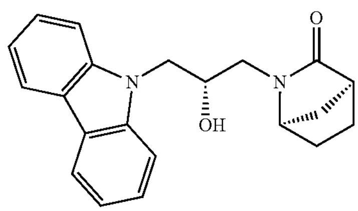 [SMILES: O=C1[C@H]2CC[C@H](C2)N1C[C@H](O)Cn1c2ccccc2c2ccccc21] | (1R,4S)-2-((R)-3-(9H-carbazol-9-yl)-2-hydroxypropyl)-2-azabicyclo[2.2.1]heptan-3-one | (300 MHz, CDCl$_3$): δ 8.12-8.09 (dd, 2H, J = 0.9, 7.8 Hz), 7.51-7.43 (m, 4H), 7.28-7.23 (m, 2H), 4.47-4.26 (m, 4H), 3.69 (s, 1H), 3.50-3.43 (s, dd, 1H, J = 7.5, 13.8 Hz), 2.95-2.91 (d, 1H, J = 14.1 Hz), 2.84-2.83 (d, 1H, J = 3.6 Hz), 1.89-1.31 (m, 6H); HPLC analysis: (C18, 5-95% acetonitrile in water + 0.1% trifluoroacetic acid over 20 min: retention time, % area at 254 nm): 11.6 min, 98.5%; Chiral HPLC analysis (Chiralcel AD-H, 15% ethanol in hexanes over 30 mins: retention time, % area at 254 nm): 9.7 min, 99.0%; 15.3 min, 0.3% (99.4% de). | 335.2 (M + H) |
| 108 | 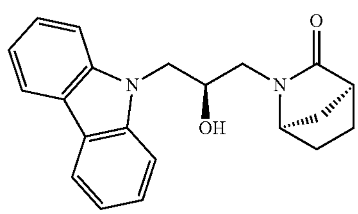 [SMILES: O=C1[C@H]2CC[C@H](C2)N1C[C@@H](O)Cn1c2ccccc2c2ccccc21] | (1R,4S)-2-((S)-3-(9H-carbazol-9-yl)-2-hydroxypropyl)-2-azabicyclo[2.2.1]heptan-3-one | (300 MHz, CDCl$_3$): δ 8.11-8.07 (m, 2H), 7.47-7.45 (m, 4H), 7.26-7.21 (m, 2H), 4.35-4.34 (m, 4H), 3.62 (br s, 1H), 3.42-3.37 (m, 1H), 3.02-2.95 (m, 1H), 2.88-2.86 (m, 1H), 1.98-1.55 (m, 4H), 1.40-1.36 (br d, 1H, J = 9.6 Hz); HPLC analysis: (C18, 5-95% acetonitrile in water + 0.1% trifluoroacetic acid over 20 min: retention time, % area at 254 nm): 11.5 min, 100%; Chiral HPLC analysis (Chiralcel AD-H, 15% ethanol in hexanes over 30 mins: retention time, % area at 254 nm): 9.9 min, 1.5%, 15.2 min, 98.2% (96.9% de). | 335.2 (M + H) |
| 109 | 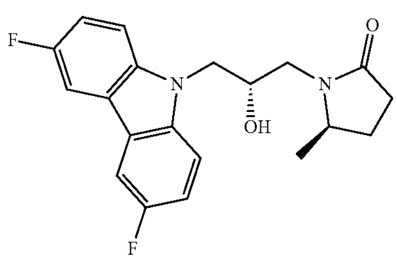 [SMILES: C[C@@H]1CCC(=O)N1C[C@H](O)Cn1c2ccc(F)cc2c2cc(F)ccc21] | (R)-1-((R)-3-(3,6-difluoro-9H-carbazol-9-yl)-2-hydroxypropyl)-5-methylpyrrolidin-2-one | (300 MHz, CDCl$_3$): δ 7.69-7.65 (dd, 2H, J = 2.6, 8.6 Hz), 7.38-7.34 (dd, 2H, J = 3.9, 9.3 Hz), 7.25-7.18 (td, 2H, J = 2.6, 9.3 Hz), 4.38-4.28 (m, 3H), 4.07-4.06 (d, 1H, J = 3.0 Hz), 3.69-3.56 (m, 2H), 3.08-3.04 (d, 1H, J = 13.5 Hz), 2.46-2.18 (m, 3H), 1.66-1.55 (m, 1H), 1.04-1.02 (d, 3H, J = 6.0 Hz); HPLC analysis: (C18, 5-95% acetonitrile in water + 0.1% trifluoroacetic acid over 20 min: retention time, % area at 254 nm): 12.1 min, 100%; Chiral HPLC analysis (Chiralcel AD-H, 15% isopropanol in hexanes over 25 mins: retention time, % area at 254 nm): 8.4 min, 99.2%, 11.5 min, 0.8% (98.4 de). | 359.1 (M + H) |

| Cpd # | Structure | Name | ¹H NMR & HPLC | ESI (m/z) |
|---|---|---|---|---|
| 110 | 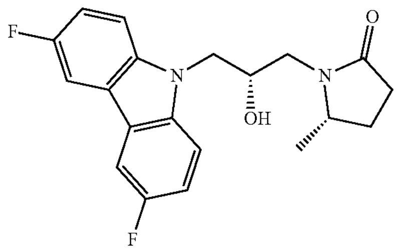 [SMILES: C[C@H]1CCC(=O)N1C[C@H](O)Cn1c2ccc(F)cc2c2cc(F)ccc21] | (S)-1-((R)-3-(3,6-difluoro-9H-carbazol-9-yl)-2-hydroxypropyl)-5-methylpyrrolidin-2-one | (300 MHz, CDCl₃): δ 7.68-7.65 (dd, 2H, J = 2.3, 8.6 Hz), 7.38-7.34 (dd, 2H, J = 3.9, 8.7 Hz), 7.25-7.18 (td, 2H, J = 2.5, 9.0 Hz), 4.73-4.72 (d, 1H, J = 3.0 Hz), 4.38-4.28 (m, 3H), 3.47-3.35 (m, 2H), 3.10-3.05 (m, 1H), 2.42-2.27 (m, 2H), 2.20-2.10 (m, 1H), 1.57-1.52 (m, 1H), 0.83-0.81 (d, 3H, J = 6.3 Hz); HPLC analysis: (C18, 5-95% acetonitrile in water + 0.1% trifluoroacetic acid over 20 min: retention time, % area at 254 nm): 11.5 min, 100%; Chiral HPLC analysis (Chiralcel AD-H, 15% isopropanol in hexanes over 25 mins: retention time, % area at 254 nm): 8.4 min, 99.2%, 11.5 min, 0.8% (98.4% de). | 359.6 (M + H) |
| 111 | 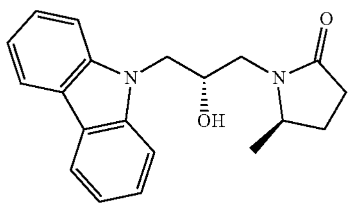 [SMILES: C[C@@H]1CCC(=O)N1C[C@H](O)Cn1c2ccccc2c2ccccc21] | (R)-1-((R)-3-(9H-carbazol-9-yl)-2-hydroxypropyl)-5-methylpyrrolidin-2-one | (300 MHz, CDCl₃): δ 8.10-8.07 (d, 2H, J = 8.4 Hz), 7.46-7.44 (m, 4H), 7.27-7.22 (m, 2H), 4.43-4.32 (m, 3H), 4.04-4.03 (d, 1H, J = 3.3 Hz), 3.74-3.69 (dd, 1H, J = 7.2, 14.7 Hz), 3.60-3.51 (sext, 1H, J = 6.3 Hz), 3.08-3.03 (m, 1H), 2.44-2.36 (m, 2H), 2.24-2.00 (m, 1H), 1.63-1.53 (m, 1H), 0.97-0.96 (d, 3H, J = 5.7 Hz); HPLC analysis: (C18, 5-95% acetonitrile in water + 0.1% trifluoroacetic acid over 20 min: retention time, % area at 254 nm): 11.4 min, 99.5%; Chiral HPLC analysis (Phenomenex Lux 3μ cellulose-2, 8% isopropanol in hexanes over 60 mins: retention time, % area at 254 nm): 42.0 min, 4.9%, 47.8 min, 95.0% (90.0% de). | 323.1 (M + H) |
| 112 | 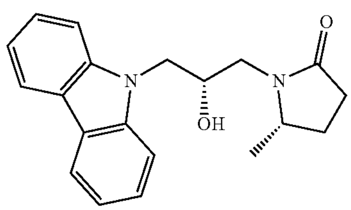 [SMILES: C[C@H]1CCC(=O)N1C[C@H](O)Cn1c2ccccc2c2ccccc21] | (S)-1-((R)-3-(9H-carbazol-9-yl)-2-hydroxypropyl)-5-methylpyrrolidin-2-one | (300 MHz, CDCl₃): δ 8.10-8.07 (d, 2H, J = 8.4 Hz), 7.46-7.44 (m, 4H), 7.27-7.22 (m, 2H), 4.73-4.72 (d, 1H, J = 2.4 Hz), 4.43-4.28 (m, 3H), 3.44-3.34 (m, 2H), 3.12-3.07 (m, 1H), 2.45-2.27 (m, 2H), 2.17-2.07 (m, 1H), 1.57-1.48 (m, 1H), 0.76-0.74 (d, 3H, J = 6.0 Hz); HPLC analysis: (C18, 5-95% acetonitrile in water + 0.1% trifluoroacetic acid over 20 min: retention time, % area at 254 nm): 11.4 min, 100%; Chiral HPLC analysis (Phenomenex Lux 3μ cellulose-2, 8% isopropanol in hexanes over 60 mins: retention time, % area at 254 nm): 40.0 min, 1.1%, 44.1 min, 97.6% (97.8% de). | 323.1 (M + H) |
| 113 | 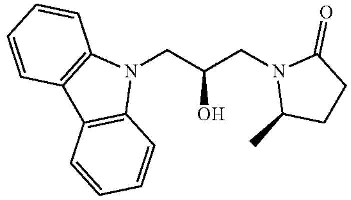 [SMILES: C[C@@H]1CCC(=O)N1C[C@@H](O)Cn1c2ccccc2c2ccccc21] | (R)-1-((S)-3-(9H-carbazol-9-yl)-2-hydroxypropyl)-5-methylpyrrolidin-2-one | (300 MHz, CDCl₃): δ 8.10-8.07 (d, 2H, J = 8.4 Hz), 7.46-7.44 (m, 4H), 7.27-7.22 (m, 2H), 4.73-4.72 (d, 1H, J = 3.0 Hz), 4.43-4.28 (m, 3H), 3.44-3.34 (m, 2H), 3.12-3.07 (m, 1H), 2.45-2.27 (m, 2H), 2.17-2.07 (m, 1H), 1.57-1.48 (m, 1H), 0.76-0.74 (d, 3H, J = 6.0 Hz); HPLC analysis: (C18, 5-95% acetonitrile in water + 0.1% trifluoroacetic acid over 20 min: retention time, % area at 254 nm): 11.5 min, 100%; Chiral HPLC analysis (Phenomenex Lux 3μ cellulose-2, 8% isopropanol in hexanes over 60 mins: retention time, % area at 254 nm): 42.6 min, 98.0%, 48.3 min, 1.9% (96.1% de). | 323.1 (M + H) |

| Cpd # | Structure | Name | ¹H NMR & HPLC | ESI (m/z) |
|---|---|---|---|---|
| 114 | 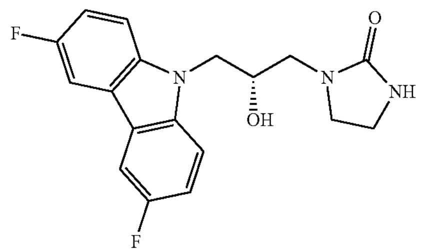 [SMILES: O=C1NCCN1C[C@H](O)Cn1c2ccc(F)cc2c2cc(F)ccc21] | (R)-1-(3-(3,6-difluoro-9H-carbazol-9-yl)-2-hydroxypropyl)imidazolidin-2-one | (300 MHz, CDCl₃): δ 7.68-7.65 (dd, 2H, J = 1.8, 9.0 Hz), 7.40-7.35 (dd, 2H, J = 4.1, 9.0 Hz), 7.25-7.17 (td, 2H, J = 2.7, 9.0 Hz), 4.43-4.30 (m, 4H), 3.43-3.14 (m, 6H); HPLC analysis: (C18, 5-95% acetonitrile in water + 0.1% trifluoroacetic acid over 20 min: retention time, % area at 254 nm): 10.8 min, 100%; Chiral HPLC analysis (Chiralcel AD-H, 30% ethanol in hexanes over 30 mins: retention time, % area at 254 nm): 13.0 min, 99.2%; 21.6 min, 0.7% (98% ee). | 346.1 (M + H) |
| 115 | 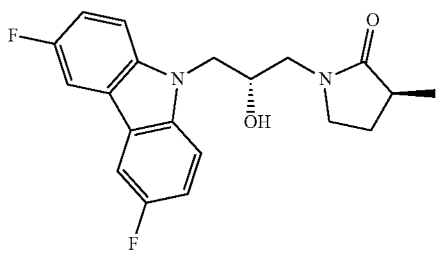 [SMILES: C[C@H]1CCN(C[C@H](O)Cn2c3ccc(F)cc3c3cc(F)ccc32)C1=O] | (S)-1-((R)-3-(3,6-difluoro-9H-carbazol-9-yl)-2-hydroxypropyl)-3-methylpyrrolidin-2-one | (300 MHz, CDCl₃): δ 7.69 (dd, 2H, J = 9.0, 2.4 Hz), 7.37 (dd, 2H, J = 9.0, 4.2 Hz), 7.23 (td, 2H, J = 9.0, 2.4 Hz), 4.45-4.25 (m, 3H), 3.96 (d, 1H, J = 4.2 Hz), 3.48 (dd, 1H, J = 14.4, 6.6 Hz), 3.38-3.15 (m, 3H), 2.54 (m, 1H), 2.25 (m, 1H), 1.66 (m, 1H), 1.23 (d, 3H, J = 6.9 Hz); HPLC analysis: (C18, 10-90% acetonitrile in water over 20 min: retention time, % area at 254 nm): 12.2 min, 100%; Chiral HPLC analysis (Phenomenex Lux 3μ cellulose-2, 15% isopropanol in hexanes over 30 mins: retention time, % area at 254 nm): 14.6 min, 96.9% de, 100% ee. | 359.1 (M + H) |
| 116 | 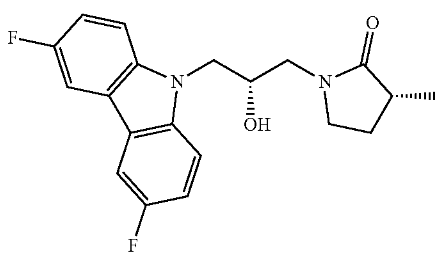 [SMILES: C[C@@H]1CCN(C[C@H](O)Cn2c3ccc(F)cc3c3cc(F)ccc32)C1=O] | (R)-1-((R)-3-(3,6-difluoro-9H-carbazol-9-yl)-2-hydroxypropyl)-3-methylpyrrolidin-2-one | (300 MHz, CDCl₃): δ 7.69 (dd, 2H, J = 9.0, 2.4 Hz), 7.37 (dd, 2H, J = 9.0, 4.2 Hz), 7.23 (td, 2H, J = 9.0, 2.4 Hz), 4.45-4.25 (m, 3H), 4.01 (d, 1H, J = 2.7 Hz), 3.53 (dd, 1H, J = 14.1, 6.9 Hz), 3.40-3.15 (m, 3H), 2.52 (m, 1H), 2.24 (m, 1H), 1.68 (m, 1H), 1.23 (d, 3H, J = 7.2 Hz); HPLC analysis: (C18, 10-90% acetonitrile in water over 20 min: retention time, % area at 254 nm): 12.2 min, 100%; Chiral HPLC analysis (Phenomenex Lux 3μ, cellulose-2, 15% isopropanol in hexanes over 30 mins: retention time, % area at 254 nm): 12.3 min, 100% de, 100% ee. | 359.2 (M + H) |
| 117 | 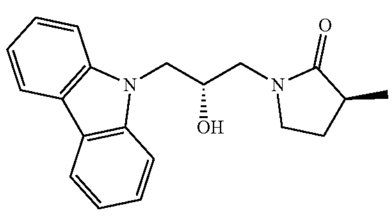 [SMILES: C[C@H]1CCN(C[C@H](O)Cn2c3ccccc3c3ccccc32)C1=O] | (S)-1-((R)-3-(9H-carbazol-9-yl)-2-hydroxypropyl)-3-methylpyrrolidin-2-one | (300 MHz, CDCl₃): δ 8.11 (d, 2H, J = 7.8 Hz), 7.53-7.42 (m, 4H), 7.32-7.22 (m, 2H), 4.50-4.30 (m, 3H), 4.01 (s, 1H), 3.51 (dd, 1H, J = 14.4, 6.9 Hz), 3.35-3.20 (m, 2H), 3.14 (td, 1H, J = 9.3, 3.3 Hz), 2.54 (m, 1H), 2.22 (m, 1H), 1.64 (m, 1H), 1.23 (d, 3H, J = 7.8 Hz); HPLC analysis: (C18, 10-90% acetonitrile in water over 20 min: retention time, % area at 254 nm): 11.6 min, 99.2%; Chiral HPLC analysis (Phenomenex Lux 3μ cellulose-2, 15% isopropanol in hexanes over 30 mins: retention time, % area at 254 nm): 13.6 min, 100% de, 100% ee. | 323.2 (M + H) |

| Cpd # | Structure | Name | ¹H NMR & HPLC | ESI (m/z) |
|---|---|---|---|---|
| 118 | 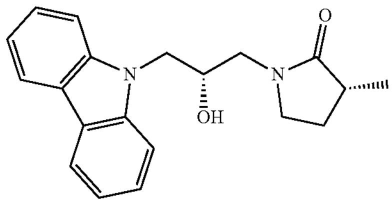 [SMILES: C[C@@H]1CCN(C[C@H](O)Cn2c3ccccc3c3ccccc32)C1=O] | (R)-1-((R)-3-(9H-carbazol-9-yl)-2-hydroxypropyl)-3-methylpyrrolidin-2-one | (300 MHz, CDCl₃): δ 8.11 (d, 2H, J = 7.8 Hz), 7.53-7.42 (m, 4H), 7.32-7.22 (m, 2H), 4.50-4.30 (m, 3H), 4.07 (s, 1H), 3.55 (dd, 1H, J = 14.1, 6.9 Hz), 3.30-3.15 (m, 3H), 2.51 (m, 1H), 2.20 (m, 1H), 1.64 (m, 1H), 1.22 (d, 3H, J = 7.5 Hz); HPLC analysis: (C18, 10-90% acetonitrile in water over 20 min: retention time, % area at 254 nm): 11.6 min, 100%; Chiral HPLC analysis (Phenomenex Lux 3µ cellulose-2, 15% isopropanol in hexanes over 30 mins: retention time, % area at 254 nm): 13.6 min, 100% de, 100% ee. | 323.1 (M + H) |
| 119 | 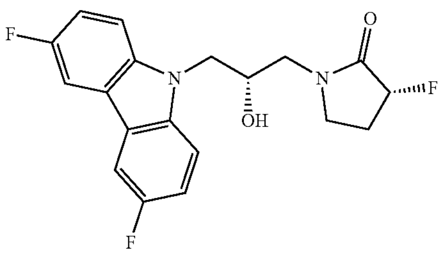 [SMILES: O=C1[C@H](F)CCN1C[C@H](O)Cn1c2ccc(F)cc2c2cc(F)ccc21] | (R)-1-((R)-3-(3,6-difluoro-9H-carbazol-9-yl)-2-hydroxypropyl)-3-fluoropyrrolidin-2-one | (300 MHz, CDCl₃): δ 7.69-7.65 (dd, 2H, J = 2.4, 8.9 Hz), 7.37-7.33 (dd, 2H, J = 8.9, 4.5 Hz), 7.24-7.18 (td, 2H, J = 9.0, 2.7 Hz), 5.20-4.98 (ddd, 1H, J = 6.0, 7.5, 52 Hz), 4.45-4.33 (m, 3H), 3.59-3.32 (m, 4H), 3.07-3.06 (d, 1H, J = 4.2 Hz), 2.60-2.10 (m, 2H); HPLC analysis: (C18, 10-90% acetonitrile in water over 20 min: retention time, % area at 254 nm): 11.6 min, 100%; Chiral HPLC analysis (Phenomenex Lux 3µ cellulose-2, 15% isopropanol in hexanes over 60 mins: retention time, % area at 254 nm): 33.0 min, 98.3%, 47.9 min, 1.6% (96.6% de). | 363.3 (M + H) |
| 120 | 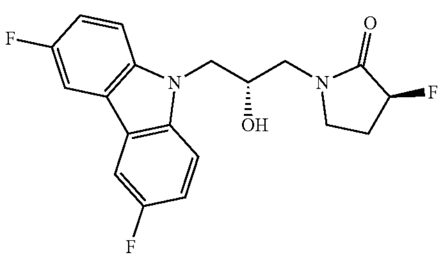 [SMILES: O=C1[C@@H](F)CCN1C[C@H](O)Cn1c2ccc(F)cc2c2cc(F)ccc21] | (S)-1-((R)-3-(3,6-difluoro-9H-carbazol-9-yl)-2-hydroxypropyl)-3-fluoropyrrolidin-2-one | (300 MHz, CDCl₃): δ 7.68-7.65 (dd, 2H, J = 2.7, 8.4 Hz), 7.37-7.33 (dd, 2H, J = 4.1, 9.5 Hz), 7.24-7.18 (td, 2H, J = 8.9, 2.5 Hz), 5.17-4.94 (ddd, 1H, J = 6.0, 7.7, 53 Hz), 4.38-4.30 (m, 3H), 3.52-3.30 (m, 5H), 2.50-2.11 (m, 2H); HPLC analysis: (C18, 10-90% acetonitrile in water over 20 min: retention time, % area at 254 nm): 11.6 min, 98.3%; Chiral HPLC analysis (Chiralcel AD-H, 30% ethanol in hexanes over 30 mins: retention time, % area at 254 nm): 7.3 min, 100% (100% de). | 363.4 (M + H) |
| 121 | 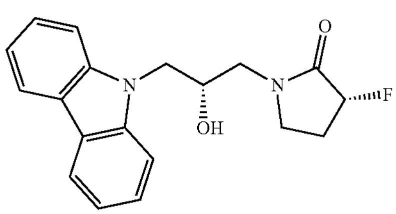 [SMILES: O=C1[C@H](F)CCN1C[C@H](O)Cn1c2ccccc2c2ccccc21] | (R)-1-((R)-3-(9H-carbazol-9-yl)-2-hydroxypropyl)-3-fluoropyrrolidin-2-one | (300 MHz, CDCl₃): δ 8.11-8.08 (d, 2H, J = 7.8 Hz), 7.50-7.42 (m, 4H), 7.28-7.23 (m, 2H), 5.19-4.97 (ddd, 1H, J = 52.8, 6.3, 7.5 Hz), 4.48-4.34 (m, 3H), 3.55-3.12 (m, 5H), 2.47-2.13 (m, 2H); HPLC analysis: (C18, 10-90% acetonitrile in water + 0.1% trifluoroacetic acid over 20 min: retention time, % area at 254 nm): 11.0 min, 100%; Chiral HPLC analysis (Phenomenex Lux 3µ cellulose-2, 15% isopropanol in hexanes over 60 mins: retention time, % area at 254 nm): 34.4 min, 98.9%, 46.8 min, 1.0% (97.9% de). | NA |

| Cpd # | Structure | Name | ¹H NMR & HPLC | ESI (m/z) |
|---|---|---|---|---|
| 122 | 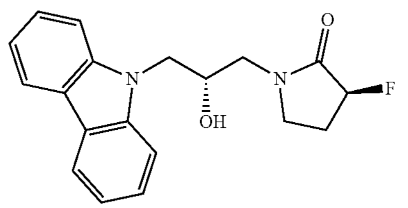 [SMILES: O=C1[C@@H](F)CCN1C[C@H](O)Cn1c2ccccc2c2ccccc21] | (S)-1-((R)-3-(9H-carbazol-9-yl)-2-hydroxypropyl)-3-fluoropyrrolidin-2-one | (300 MHz, CDCl₃): δ 8.09-8.06 (d, 2H, J = 8.1 Hz), 7.49-7.41 (m, 4H), 7.27-7.21 (m, 2H), 5.12-4.90 (ddd, 1H, J = 52.2, 6.0, 8.1 Hz), 4.39-4.32 (m, 3H), 3.48-3.25 (m, 5H), 2.45-2.33 (m, 1H), 2.22-2.06 (m, 1H); HPLC analysis: (C18, 10-90% acetonitrile + 0.1% trifluoroacetic acid in water over 20 min: retention time, % area at 254 nm): 11.0 min, 100%; Chiral HPLC analysis (Chiralcel AD-H, 15% ethanol in hexanes over 30 mins: retention time, % area at 254 nm): 19.5 min, 100% (100% de). | NA |
| 123 | 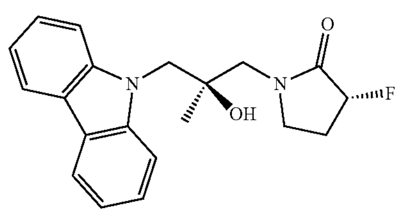 [SMILES: C[C@@](O)(CN1CC[C@@H](F)C1=O)Cn1c2ccccc2c2ccccc21] | (R)-1-((S)-3-(9H-carbazol-9-yl)-2-hydroxy-2-methylpropyl)-3-fluoropyrrolidin-2-one | (300 MHz, CDCl₃): δ 8.10-8.07 (m, 2H), 7.50-7.42 (m, 4H), 7.28-7.23 (m, 2H), 5.20-4.99 (ddd, 1H, J = 5.9, 7.4, 52.2 Hz), 4.32 (s, 2H), 3.78-3.46 (m, 4H), 2.51 (s, 1H), 2.49-2.18 (m, 2H), 1.30 (s, 3H); HPLC analysis: (C18, 10-90% acetonitrile in water over 20 min: retention time, % area at 254 nm): 11.6 min, 100%; Chiral HPLC analysis (Chiralcel AD-H, 15% isopropanol in hexanes over 60 mins: retention time, % area at 254 nm): 22.0 min, 100% (100% de). | 341.1 (M + H) |
| 124 | 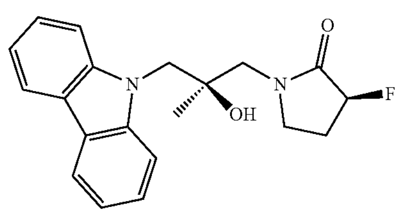 [SMILES: C[C@@](O)(CN1CC[C@H](F)C1=O)Cn1c2ccccc2c2ccccc21] | (S)-1-((S)-3-(9H-carbazol-9-yl)-2-hydroxy-2-methylpropyl)-3-fluoropyrrolidin-2-one | (300 MHz, CDCl₃): δ 8.10-8.07 (m, 2H), 7.50-7.42 (m, 4H), 7.28-7.23 (m, 2H), 5.20-4.99 (dt, 1H, J = 7.1, 52.8 Hz), 4.40-4.29 (m, 2H), 3.74-3.48 (m, 4H), 2.62 (s, 1H), 2.53-2.18 (m, 2H), 1.28 (s, 3H); HPLC analysis: (C18, 10-90% acetonitrile in water over 20 min: retention time, % area at 254 nm): 11.6 min, 100%; Chiral HPLC analysis (Chiralcel AD-H, 30% ethanol in hexanes over 60 mins: retention time, % area at 254 nm): 8.3 min, 100% (100% de). | 341.1 (M + H) |
| 125 | 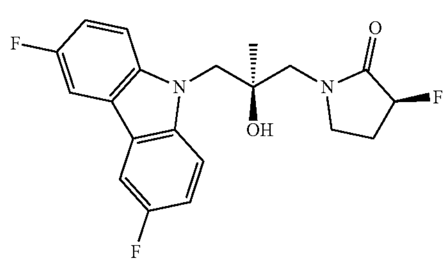 | (S)-1-((S)-3-(3,6-difluoro-9H-carbazol-9-yl)-2-hydroxy-2-methylpropyl)-3-fluoropyrrolidin-2-one | (300 MHz, CDCl₃): δ 7.68-7.64 (dd, 2H, J = 2.7, 8.4 Hz), 7.42-7.38 (dd, 2H, J = 4.2, 8.7 Hz), 7.23-7.16 (td, 2H, J = 2.6, 9.3 Hz), 5.23-5.01 (ddd, 1H, J = 52.8, 5.7, 7.5 Hz), 4.35-4.24 (m, 2H), 3.80-3.73 (m, 1H), 3.59-3.46 (m, 3H), 2.66-2.19 (m, 2H), 1.26 (s, 3H); HPLC analysis: (C18, 10-90% acetonitrile in water + 0.1% trifluoroacetic acid over 20 min: retention time, % area at 254 nm): 12.2 min, 100%; Chiral HPLC analysis (Phenomenex Lux 3μ cellulose-2, 4% ethanol + 4% methanol in hexanes over 45 mins: retention time, % area at 254 nm): 26.5 min, 97.6%, 30.9 min, 0.4%, 36.5 min, 2.0% (95.5% de, 97.1% ee). | NA |

| Cpd # | Structure | Name | ¹H NMR & HPLC | ESI (m/z) |
|---|---|---|---|---|
| 126 | 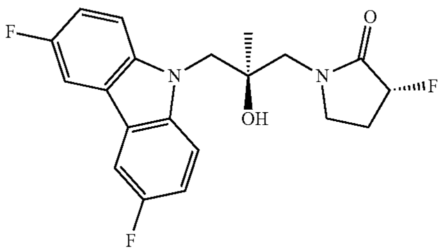 | (R)-1-((S)-3-(3,6-difluoro-9H-carbazol-9-yl)-2-hydroxy-2-methylpropyl)-3-fluoropyrrolidin-2-one | (300 MHz, CDCl$_3$): δ 7.69-7.65 (dd, 2H, J = 2.7, 8.7 Hz), 7.43-7.39 (dd, 2H, J = 4.2, 8.7 Hz), 7.24-7.20 (td, 2H, J = 2.6, 8.7 Hz), ), 5.24-4.97 (ddd, 1H, J = 52.8, 5.4, 7.5 Hz), 4.28 (s, 2H), 3.77-3.71 (m, 1H), 3.60-3.46 (m, 3H), −3.12 (m, 5H), 2.54 (s, 1H), 2.53-2.22 (m, 2H), 1.28 (s, 3H); HPLC analysis: (C18, 10-90% acetonitrile in water + 0.1% trifluoroacetic acid over 20 min: retention time, % area at 254 nm): 12.2 min, 100%; Chiral HPLC analysis (Phenomenex Lux 3μ cellulose-2, 4% ethanol + 4% methanol in hexanes over 45 mins: retention time, % area at 254 nm): 26.5 min, 3.1%, 36.6 min, 96.9% (93.7% de). | 377.0 (M + H) |
| 127 | 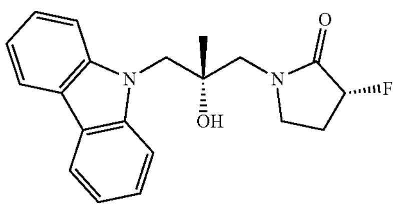 | (R)-1-((R)-3-(9H-carbazol-9-yl)-2-hydroxy-2-methylpropyl)-3-fluoropyrrolidin-2-one | (300 MHz, CDCl$_3$): δ 8.11-8.08 (d, 2H, J = 7.8 Hz), 7.52-7.43 (m, 4H), 7.28-7.23 (m, 2H), 5.24-5.02 (ddd, 1H, J = 52.8, 6.2, 7.5 Hz), 4.48-4.31 (m, 3H), 3.75-3.50 (m, 4H), 2.57 (s, 1H), 2.54-2.23 (m, 2H), 1.29 (s, 3H); HPLC analysis: (C18, 10-90% acetonitrile in water + 0.1% trifluoroacetic acid over 20 min: retention time, % area at 254 nm): 11.6 min, 100%; Chiral HPLC analysis (Chiralcel AD-H, 30% isopropanol in hexanes over 30 mins: retention time, % area at 254 nm): 9.6 min, 0.8%, 15.6 min, 98.7%, 22.0 min, 0.5% (97.3% de). | 341.0 (M + H) |
| 128 | 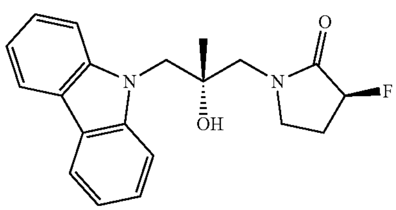 | (S)-1-((R)-3-(9H-carbazol-9-yl)-2-hydroxy-2-methylpropyl)-3-fluoropyrrolidin-2-one | (300 MHz, CDCl$_3$): δ 8.11-8.08 (d, 2H, J = 7.4 Hz), 7.51-7.43 (m, 4H), 7.28-7.22 (m, 2H), 5.23-5.02 (ddd, 1H, J = 52.2, 5.1, 7.2 Hz), 4.34 (s, 2H), 3.79-3.46 (m, 4H), 2.55-2.20 (m, 2H), 2.44 (s, 1H), 1.31 (s, 3H); HPLC analysis: (C18, 10-90% acetonitrile in water + 0.1% trifluoroacetic acid over 20 min: retention time, % area at 254 nm): 11.7 min, 100%; Chiral HPLC analysis (Chiralcel AD-H, 30% ethanol in hexanes over 30 mins: retention time, % area at 254 nm): 9.6 min, 99.6%, 15.9 min, 0.4% (99.2% de). | 341.1 (M + H) |
| 129 | 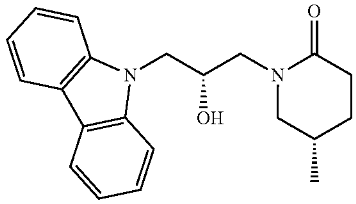 [SMILES: C[C@H]1CCC(=O)N(C[C@H](O)Cn2c3ccccc3c3ccccc32)C1] | (S)-1-((R)-3-(9H-carbazol-9-yl)-2-hydroxypropyl)-5-methylpiperidin-2-one | (300 MHz, CDCl$_3$): δ 8.10 (d, 2H, J = 8.4 Hz), 7.50-7.40 (m, 4H), 7.30-7.20 (m, 2H), 4.50-4.30 (m, 3H), 4.25 (d, 1H, J = 3.6 Hz), 3.90 (dd, 1H, J = 14.1, 8.1 Hz), 3.09 (dd, 1H, J = 14.1, 2.1 Hz), 2.98 (ddd, 1H, J = 11.7, 5.1, 1.8 Hz), 2.83 (t, 1H, J = 10.8 Hz), 2.49 (ddd, 1H, J = 18.0, 6.0, 3.0 Hz), 2.36 (ddd, 1H, J = 18.0, 11.1, 6.3 Hz), 1.95-1.75 (m, 2H), 1.43 (m, 1H), 0.88 (d, 3H, J = 6.6 Hz); Chiral HPLC analysis (Chiralcel AD-H, 8% ethanol in hexanes over 45 mins: retention time, % area at 254 nm): 25.7 min, 98.6% de, 100% ee. | 337.4 (M + H) |

| Cpd # | Structure | Name | ¹H NMR & HPLC | ESI (m/z) |
|---|---|---|---|---|
| 130 | 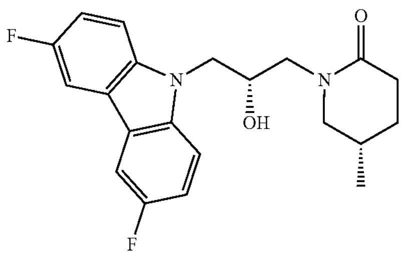 [SMILES: C[C@H]1CCC(=O)N(C[C@H](O)Cn2c3ccc(F)cc3c3cc(F)ccc32)C1] | (S)-1-((R)-3-(3,6-difluoro-9H-carbazol-9-yl)-2-hydroxypropyl)-5-methylpiperidin-2-one | (300 MHz, CDCl$_3$): δ 7.69 (dd, 2H, J = 8.7, 2.4 Hz), 7.39 (dd, 2H, J = 9.0, 4.2 Hz), 7.23 (td, 2H, J = 8.7, 2.4 Hz), 4.45-4.25 (m, 3H), 4.18 (d, 1H, J = 3.3 Hz), 3.84 (dd, 1H, J = 14.1, 8.1 Hz), 3.12 (dd, 1H, J = 14.1, 2.4 Hz), 3.07 (m, 1H), 2.89 (t, 1H, J = 11.1 Hz), 2.50 (ddd, 1H, J = 18.0, 6.3, 3.3 Hz), 2.3 (ddd, 1H, J = 18.0, 11.1, 6.3 Hz), 2.00-1.77 (m, 2H), 1.45 (m, 1H), 0.94 (d, 3H, J = 6.6 Hz); Chiral HPLC analysis (Chiralcel AD-H, 15% ethanol in hexanes over 40 mins: retention time, % area at 254 nm): 12.2 min, 100% de, 100% ee. | 373.5 (M + H) |
| 131 | 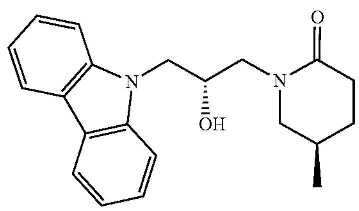 [SMILES: C[C@@H]1CCC(=O)N(C[C@H](O)Cn2c3ccccc3c3ccccc32)C1] | (R)-1-((R)-3-(9H-carbazol-9-yl)-2-hydroxypropyl)-5-methylpiperidin-2-one | (300 MHz, CDCl$_3$): δ 8.11 (d, 2H, J = 7.8 Hz), 7.50-7.40 (m, 4H), 7.30-7.20 (m, 2H), 4.66 (s, 1H), 4.50-4.30 (m, 3H), 4.00 (dd, 1H, J = 14.1, 8.7 Hz), 3.00 (dd, 1H, J = 12.0, 5.4 Hz), 2.90 (d, 1H, J = 14.1 Hz), 2.73 (t, 1H, J = 11.7 Hz), 2.49 (ddd, 1H, J = 18.0, 6.0, 3.0 Hz), 2.37 (ddd, 1H, J = 18.0, 11.1, 6.0 Hz), 1.95-1.70 (m, 2H), 1.38 (m, 1H), 0.88 (d, 3H, J = 6.6 Hz); Chiral HPLC analysis (Chiralcel AD-H, 8% ethanol in hexanes over 45 mins: retention time, % area at 254 nm): 37.2 min, 100% de, 100% ee. | 338.0 (M + H) |
| 132 | 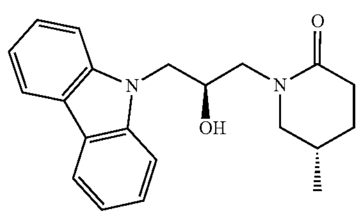 [SMILES: C[C@H]1CCC(=O)N(C[C@@H](O)Cn2c3ccccc3c3ccccc32)C1] | (S)-1-((S)-3-(9H-carbazol-9-yl)-2-hydroxypropyl)-5-methylpiperidin-2-one | (300 MHz, CDCl$_3$): δ 8.11 (d, 2H, J = 7.8 Hz), 7.55-7.43 (m, 4H), 7.32-7.22 (m, 2H), 4.64 (s, 1H), 4.50-4.30 (m, 3H), 4.00 (dd, 1H, J = 14.1, 8.7 Hz), 3.00 (ddd, 1H, J = 12.3, 4.8, 1.8 Hz), 2.90 (d, 1H, J = 14.4 Hz), 2.73 (t, 1H, J = 11.1 Hz), 2.55-2.30 (m, 2H), 1.98-1.72 (m, 2H), 1.37 (m, 1H), 0.89 (d, 3H, J = 6.6 Hz); Chiral HPLC analysis (Chiralcel AD-H, 8% ethanol in hexanes over 45 mins: retention time. % area at 254 nm): 20.3 min. 100% de, 100% ee. | 337.9 (M + H) |
| 133 | 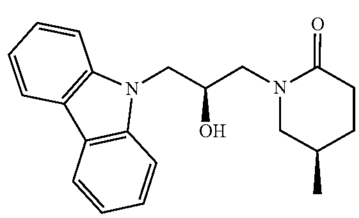 [SMILES: C[C@@H]1CCC(=O)N(C[C@@H](O)Cn2c3ccccc3c3ccccc32)C1] | (R)-1-((S)-3-(9H-carbazol-9-yl)-2-hydroxypropyl)-5-methylpiperidin-2-one | (300 MHz, CDCl$_3$): δ 8.11 (d, 2H, J = 7.8 Hz), 7.50-7.40 (m, 4H), 7.30-7.20 (m, 2H), 4.50-4.30 (m, 3H), 4.23 (d, 1H, J = 2.7 Hz), 3.90 (dd, 1H, J = 14.1, 7.8 Hz), 3.10 (dd, 1H, J = 14.1, 2.1 Hz), 2.99 (ddd, 1H, J = 11.7, 4.5, 1.8 Hz). 2.84 (t, 1H, J = 10.8 Hz), 2.49 (ddd, 1H, J = 18.0, 6.0, 3.0 Hz), 2.36 (ddd, 1H, J = 18.0, 11.1, 6.6 Hz), 1.95-1.75 (m, 2H), 1.43 (m, 1H), 0.90 (d, 3H, J = 6.6 Hz); Chiral HPLC analysis (Chiralcel AD-H, 8% ethanol in hexanes over 45 mins: retention time. % area at 254 nm): 21.6 min. 97.8% de, 100% ee. | 337.9 (M + H) |

| Cpd # | Structure | Name | ¹H NMR & HPLC | ESI (m/z) |
|---|---|---|---|---|
| 134 | 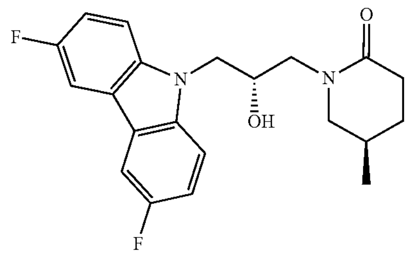 [SMILES: C[C@@H]1CCC(=O)N(C[C@H](O)Cn2c3ccc(F)cc3c3cc(F)ccc32)C1] | (R)-1-((R)-3-(3,6-difluoro-9H-carbazol-9-yl)-2-hydroxypropyl)-5-methylpiperidin-2-one | (300 MHz, CDCl₃): δ 7.69 (dd, 2H, J = 9.0, 2.4 Hz), 7.39 (dd, 2H, J = 9.3, 4.2 Hz), 7.23 (td, 2H, J = 9.3, 2.7 Hz), 4.56 (s, 1H), 4.45-4.25 (m, 3H), 3.94 (dd, 1H, J = 14.1, 9.0 Hz), 3.06 (dd, 1H, J = 12.0, 5.1 Hz), 2.90 (d, 1H, J = 14.1 Hz), 2.80 (t, 1H, J = 11.4 Hz), 2.55-2.30 (m, 2H), 2.00-1.75 (m, 2H), 1.40 (m, 1H), 0.93 (d, 3H, J = 7.2 Hz); Chiral HPLC analysis (Chiralcel AD-H, 15% ethanol in hexanes over 40 mins: retention time, % area at 254 nm): 15.7 min, 100% de, 100% ee. | 373.9 (M + H) |
| 135 | 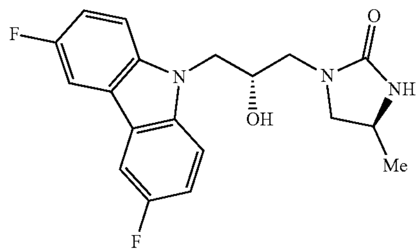 [SMILES: C[C@H]1CN(C[C@H](O)Cn2c3ccc(F)cc3c3cc(F)ccc32)C(=O)N1] | (S)-1-((R)-3-(3,6-difluoro-9H-carbazol-9-yl)-2-hydroxypropyl)-4-methylimidazolidin-2-one | (300 MHz, CDCl₃): δ 7.68 (dd, 2H, J = 9.0, 2.4 Hz), 7.39 (dd, 2H, J = 9.0, 4.2 Hz), 7.23 (td, 2H, J = 9.0, 2.7 Hz), 4.52 (s, 1H), 4.45-4.26 (m, 3H), 4.21 (brs, 1H), 3.83 (m, 1H), 3.55 (t, 1H, J = 8.7 Hz), 3.39 (dd, 1H, J = 14.7, 7.2 Hz), 3.09 (dd, 1H, J = 15.0, 2.4 Hz), 2.96 (dd, 1H, J = 9.0, 6.9 Hz), 1.24 (d, 3H, J = 5.7 Hz); Chiral HPLC analysis (Chiralcel AD-H, 15% ethanol in hexanes over 60 mins: retention time. % area at 254 nm): 29.1 min, 100% de, 100% ee. | 360.2 (M + H) |
| 136 | 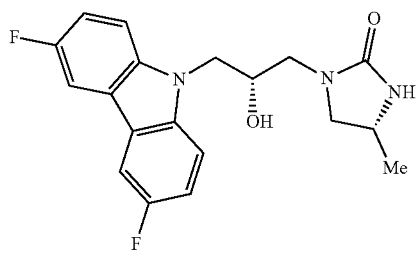 [SMILES: C[C@@H]1CN(C[C@H](O)Cn2c3ccc(F)cc3c3cc(F)ccc32)C(=O)N1] | (R)-1-((R)-3-(3,6-difluoro-9H-carbazol-9-yl)-2-hydroxypropyl)-4-methylimidazolidin-2-one | (300 MHz, CDCl₃): δ 7.68 (dd, 2H, J = 9.0, 2.4 Hz), 7.39 (dd, 2H, J = 9.0, 4.2 Hz), 7.22 (td, 2H, J = 9.0, 2.7 Hz), 4.66 (s, 1H), 4.50-4.20 (m, 4H), 3.81 (m, 1H), 3.38 (t, 1H, J = 8.7 Hz), 3.22 (s, 2H), 2.99 (dd, 1H, J = 8.4, 6.6 Hz), 1.24 (d, 3H, J = 5.7 Hz); Chiral HPLC analysis (Chiralcel AD-H, 15% ethanol in hexanes over 60 mins: retention time, % area at 254 nm): 27.0 min, 100% de, 100% ee. | 360.2 (M + H) |
| 137 | 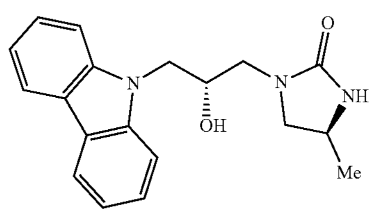 [SMILES: C[C@H]1CN(C[C@H](O)Cn2c3ccccc3c3ccccc32)C(=O)N1] | (S)-1-((R)-3-(9H-carbaxol-9-yl)-2-hydroxypropyl)-4-methylimidazolidin-2-one | (300 MHz, CDCl₃): δ 7.68 (dd, 2H, J = 9.0, 2.4 Hz), 7.39 (dd, 2H, J = 9.0, 4.2 Hz), 7.22 (td, 2H, J = 9.0, 2.7 Hz), 4.66 (s, 1H), 4.50-4.20 (m, 4H), 3.81 (m, 1H), 3.38 (t, 1H, J = 8.7 Hz), 3.22 (s, 2H), 2.99 (dd, 1H, J = 8.4, 6.6 Hz), 1.24 (d, 3H, J = 5.7 Hz); Chiral HPLC analysis (Chiralcel AD-H, 15% ethanol in hexanes over 60 mins: retention time, % area at 254 nm): 28.8 min, 100% de, 100% ee. | 324.3 (M + H) |
| 138 | 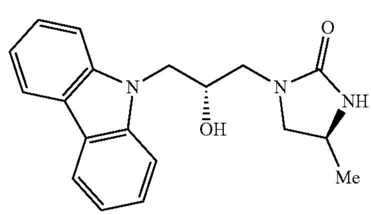 [SMILES: C[C@H]1CN(C[C@H](O)Cn2c3ccccc3c3ccccc32)C(=O)N1] | (R)-1-((R)-3-(9H-carbazol-9-yl)-2-hydroxypropyl)-4-methylimidazolidin-2-one | (300 MHz, CDCl₃): δ 8.11 (d, 2H, J = 7.8 Hz), 7.55-7.42 (m, 4H), 7.35-7.20 (m, 2H), 4.53 (brs, 1H), 4.48-4.30 (m, 4H), 3.80 (m, 1H), 3.34 (t, 1H, J = 8.7 Hz), 3.28-3.15 (m, 2H), 2.95 (dd, 1H, J = 8.7, 6.9 Hz), 1.23 (d, 3H, J = 6.6 Hz); Chiral HPLC analysis (Chiralcel AD-H, 15% ethanol in hexanes over 60 mins: retention time, % area at 254 nm): 25.1 min, 100% de, 100% ee. | 324.2 (M + H) |

Specific assays useful for evaluating the compounds of formula I include the Per2 Assay for Evaluating the Potency of Test Compounds and the Cry1 Assay for Evaluating the Target of Test Compounds, as described below.

Example 3: Per2 Assay for Evaluating the Potency of Test Compounds

Compounds were screened by using a high-throughput circadian assay system as previously described in Zhang, E. E. et al. Cell, 2009, 139, 199-210. In brief, stable U2OS reporter cells harboring Per2-dLuc were plated at a density of 30,000 cells/well in Corning 96-well, solid white, flat bottom, TC-treated microplates (Corning®), and incubated for 48 hours at 37° C. in the presence of 5% $CO_2$ in a medium of Dulbecco's Modified Eagle Medium (DMEM) supplemented with 10% fetal bovine serum (FBS) and penicillin (100 units/mL)-streptomycin (100 µg/mL). Compounds of formula I are solubilized in dimethylsulfoxide (DMSO), typically at a concentration of 2 mg/mL. DMSO stocks are then serially diluted in DMSO, typically diluting 3-fold for each dilution step. Following the 48 h period, cell culture medium is removed from plated cells and cells are synchronized with 200 µL/well of complete cell culture medium (described above), supplemented with 5 µM forskolin (Tocris®) and 1 mM beetle luciferin (Promega®). Immediately following synchronization, 1 µL of compound dilution is added to each well. Plates are sealed, shaken briefly, and gene expression was monitored by measuring luminescence (Tecan® Infinite M200 or Tecan® Infinite M200 Pro) continuously for a minimum of 3 days at 35° C. Raw luminescence data (counts) are first analyzed using Multicycle™ software (Actimetrics, Inc.) to determine the amplitude (amp), period, and phase (phz) for each compound concentration. The period length for control wells (i.e. no compound, DMSO only) should be 26-30 h. Amp data are then plotted against the logarithm compound concentration (M) and analyzed by nonlinear regression analysis to determine the $EC_{50}$.

The following table provides Per2 $EC_{50}$ data for the specified compounds. The ECsos are reported as micromolar concentration.

TABLE 1

Per2 assay data

| Compound | Per2 $EC_{50}$ (µM) | Compound | Per2 $EC_{50}$ (µM) |
|---|---|---|---|
| 1 | 0.171 | 70 | 0.061 |
| 2 | 0.736 | 71 | 0.188 |
| 3 | 0.299 | 72 | 0.389 |
| 4 | 0.192 | 73 | 1.111 |
| 5 | 0.536 | 74 | 0.284 |
| 6 | 0.719 | 75 | 0.171 |
| 7 | 0.625 | 76 | 0.609 |
| 8 | 0.527 | 77 | 0.620 |
| 9 | 0.300 | 78 | 0.440 |
| 10 | 0.487 | 79 | 0.923 |
| 11 | 0.120 | 80 | 1.105 |
| 12 | 0.909 | 81 | 0.816 |
| 13 | 0.288 | 82 | 1.192 |
| 14 | 0.541 | 83 | 0.147 |
| 15 | 0.164 | 84 | 0.325 |
| 16 | 0.463 | 85 | 0.667 |
| 17 | 0.417 | 86 | 0.497 |
| 18 | 0.338 | 87 | 0.317 |
| 19 | 0.547 | 88 | 0.310 |
| 20 | 0.379 | 89 | 0.438 |
| 21 | 1.042 | 90 | 0.605 |
| 22 | 0.261 | 91 | 0.621 |
| 23 | 0.399 | 92 | 0.527 |
| 24 | 0.332 | 93 | 0.129 |
| 25 | 0.079 | 94 | 0.833 |
| 26 | 1.051 | 95 | 0.568 |
| 27 | 0.478 | 96 | 0.493 |
| 28 | 0.824 | 97 | 0.315 |
| 29 | 0.422 | 98 | 0.269 |
| 30 | 0.895 | 99 | 0.555 |
| 31 | 0.832 | 100 | 0.721 |
| 32 | 0.539 | 101 | 0.417 |
| 33 | 0.625 | 102 | 0.455 |
| 34 | 0.286 | 103 | 0.940 |
| 35 | 0.678 | 104 | 0.115 |
| 36 | 0.760 | 105 | 0.054 |
| 37 | 0.224 | 106 | 0.220 |
| 38 | 1.216 | 107 | 0.089 |
| 39 | 0.342 | 108 | 0.750 |
| 40 | 0.484 | 109 | 0.226 |
| 41 | 0.373 | 110 | 0.830 |
| 42 | 0.420 | 111 | 0.095 |
| 43 | 1.033 | 112 | 0.470 |
| 44 | 1.060 | 113 | 0.948 |
| 45 | 0.052 | 114 | 0.287 |
| 46 | 0.618 | 115 | 0.500 |
| 47 | 0.299 | 116 | 0.311 |
| 48 | 0.120 | 117 | 0.188 |
| 49 | 0.137 | 118 | 0.120 |
| 50 | 0.204 | 119 | 0.184 |
| 51 | 0.265 | 120 | 0.302 |
| 52 | 1.355 | 121 | 0.210 |
| 53 | 1.337 | 122 | 0.263 |
| 54 | 0.808 | 123 | 0.311 |
| 55 | 0.738 | 124 | 0.309 |
| 56 | 1.057 | 125 | 0.451 |
| 57 | 0.329 | 126 | 0.958 |
| 58 | 0.716 | 127 | 0.535 |
| 59 | 0.986 | 128 | 0.172 |
| 60 | 0.331 | 129 | 0.748 |
| 61 | 0.710 | 130 | 0.895 |
| 62 | 0.370 | 131 | 0.280 |
| 63 | 0.541 | 132 | 1.133 |
| 64 | 0.462 | 133 | 0.838 |
| 65 | 1.030 | 134 | 0.397 |
| 66 | 0.523 | 135 | 1.129 |
| 67 | 0.225 | 136 | 0.826 |
| 68 | 0.288 | 137 | 0.766 |
| 69 | 0.137 | 138 | 0.520 |

One of ordinary skill in the art could readily optimize this assay to determine Per2 $EC_{50}$ data for any of the compounds described herein.

Example 4: Thermal Shift Binding Assay

Figure 21:
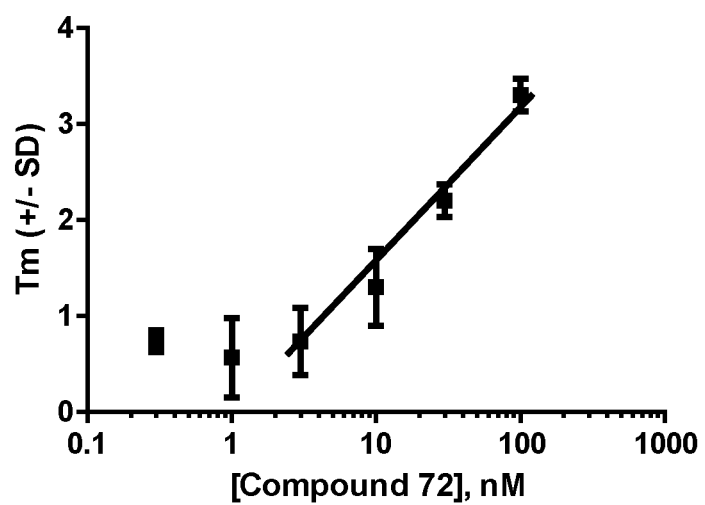
FIG. 21 is a graph showing the effect of Compound 72 on the in vitro thermal stability of the CRY1 FAD-binding domain. Treatment of purified CRY1 FAD-binding domain with Compound 72 caused a dose-dependent increase in the protein melting temperature, as determined by a differential scanning fluorimetry ('thermal shift') assay.

Binding of compounds to the isolated FAD-binding domain of human CRY1 protein (hCRY1) was determined using a differential scanning fluorimetry ('thermal shift') assay (Pantoliano et al. (2001) J Biomol Screening 6, 429; Niesen et al. (2007) Nature Protocols 2, 2212). The FAD-binding domain of hCRY1 (amino acid residues 1-494) with a C-terminal Myc-DDK tag (FADBD), was produced by transient transfection of HEK293T cells (Catalog # CRL-3216, American Type Culture Collection) and purified by anti-FLAG affinity chromatography (Catalog # A2220, Sigma-Aldrich). FADBD (0.5 µg per well) was incubated with dilutions of compounds in DMSO (5% DMSO final concentration in reaction) in 17.5 µl Tris-buffered saline (TBS) for 10 minutes on ice, then 2.5 µl of 8× Sypro-Orange Dye (Life Technologies) was added to each well. Triplicate wells were assayed for each compound concentration. The melting temperatures were measured in an ABI7500 quantitative PCR instrument using the melt curve mode with a thermal profile of 2 minutes at 25° C., followed by a ramp rate of 1° C./minute up to 99° C. The melting temperature for each well was determined from the first derivative of the melt curve. The change in melting temperature (ΔTm) was obtained by subtraction of the melting temperature of the FADBD in 5% DMSO alone. As shown in FIG. 21, a dose-dependent increase in ΔTm was observed for Compound 72, indicating that the compound physically associates with the hCRY1 FADBD protein.

Example 5: In Vivo Effect on Clock Gene and Gluconeogenic Gene Expression

In this example, the effect of carbazole-containing amids, carbamates, and ureas on clock and gluconeogenic gene expression in various mouse models were examined. Specifically, four different mouse models were used: ICR mice, Balb/c mice, C57Bl/6J DIO (diet-induced obesity) mice, and db/db mice. Both the C57Bl/6J DIO and db/db mice are art-recognized models of diabetes, obesity, and dyslipidemia. Diet induced obese (DIO) mice, which exhibit a type II diabetic phenotype in response to high fat feeding develop obesity, hyperinsulinemia, insulin resistance and glucose intolerance (Srinivasan and Ramarao, 2007). The db/db mouse ($lepr^{db}$ mouse) has a mutation in the db gene, which encodes the leptin receptor. Db/db mice are spontaneously hyperphagic and become obese, hyperglycemic, hyperinsulinemic and insulin resistant.

The in vivo studies examining the effect of Cry modulator compounds on gene expression were performed using the various experimental methods described below.

Four Day Study.

Male ICR mice (weighing 30-35 g), obtained from Charles River Laboratories (Hollister, CA), were used for the experiment following at least 3 days of acclimation. Mice were dosed with vehicle (WFI or 10% Kolliphor) or compound (50 mg/kg, dose volume 5 mL/kg, PO) for 4 days BID (twice a day), beginning in the afternoon of the first day. The last dose of compound or vehicle was administered on the morning of harvest. On the day of harvest (6 hours following the final dose), mice were euthanized by $CO_2$ asphyxiation and 50 mg of liver tissue was excised and placed in a tube containing 500 µl of RNA later.

24 Hour Gene Expression Studies.

Male C57Bl/6J DIO mice were purchased at 17 weeks of age (The Jackson Laboratory, Sacramento, Calif.) and acclimated for a 2 week period before being used for the experiment. Overall group size was 15 per treatment, divided into 5 time-points to give a final group size of 3 mice. Mice were dosed with vehicle (water for injection (WFI) or the Cry Modulator compound Compound 72 (50 mg/kg in WFI) at a dose volume of 5 ml/kg, BID, via oral gavage for 2 days, with a final fifth dose administered 12 hours prior to harvest.

In total, each mouse received 5 doses of compound over the course of the experiment. Mice were weighed and randomly assigned to each treatment based on weight the evening before the commencement of the study. Beginning on Day 3 at 3:00 PM, a group of animals from the vehicle and Compound 72-treated groups were euthanized using $CO_2$ asphyxiation, 50 mg of liver, epididymal fat, and skeletal muscle, respectively, were excised and placed in tube containing 500 µl of RNALater. This procedure took place for the remainder of the time-point groups at their given harvest times. Plasma samples were also taken for each animal and frozen, to be used for later measurement of compound levels.

Mouse Liver Total RNA Preparation.

E.Z.N.A.® HP Total RNA Isolation Kits (R6812-01 and the protocol described in the Manual, Revised 2010) were utilized to prepare and isolate RNA from the liver samples. To prepare the RNA samples, 10-30 mg of sample was removed from RNA-Later and placed in a 1.5 ml microfuge tube. GTC lysis buffer (700 µl) was added to the tissue, which was homogenized with a rotor-stator homogenizer (e.g. Tissue-Tearor, Model #985370 BioSpec Products with 4.5 mm probe, Cat. #985370-04), and then centrifuged at full speed (>13,000×g) for 5 minutes. The cleared supernatant was transferred by pipetting to a DNA Clearance Column Pre-inserted in a 2 mL Collection Tube. The assembled column was centrifuged at 13,000×g for 1 minute, and the flow-through was saved. An equal volume (700 µl) of 70% ethanol was added to the lysate and mixed. The sample was then applied to a HiBind RNA spin column placed into a 2 ml collection tube, which was centrifuged at 10,000×g for 60 seconds at room temperature. RNA Wash Buffer I (250 µl) was added by pipetting directly onto a new HiBind RNA column inserted in a 2 ml collection tube. The assembled column was centrifuged at 10,000×g for 60 seconds. The RNA column was placed into a new 2 ml collection tube. DNase I stock solution is pipetted (75 µl) directly onto the surface of the HiBind RNA resin in each column (Using DNAse Digestion with RNase Free DNase Set (E1091): for each HiBind RNA column, the DNase I stock solution was prepared as followed: E.Z.N.A.® DNase I Digestion Buffer 73.5µl, RNase Free DNase I (20 Kunitz/µl) 1.5 µl=Total Volume 75 µl.). The column with bound RNA was incubated at room temperature (25-30° C.) for 15 minutes. RNA Wash Buffer I (500 µl) was added to the column and placed on a bench top for 2 minutes. After centrifuging at 10,000×g for 60 seconds, discarding the flow-through, 500 µl of RNA Wash Buffer II was added and centrifuged at 10,000×g for 60 seconds. Another 500 µl of RNA Wash Buffer II was added and the column assembly was centrifuged at 10,000×g for 60 seconds. The column was centrifuged for 2 minutes at maximum speed to completely dry the HiBind matrix. The column was placed in a clean 1.5 ml microcentrifuge tube and 40-70 µl of molecular biology grade water is added. After sitting for 1 minute, the column was centrifuged for 2 minutes at maximum speed to elute the RNA. The isolated RNA was collected into the collection tube.

Mouse Blood Total RNA Preparation.

For whole blood RNA studies, male db/db mice (9 weeks of age, The Jackson Laboratory, Bar Harbor, Me.) were used for the experiment with n=8 mice for each experimental group. Mice were dosed with Compound 72 (100 mg/kg, P.O; dose volume 5 ml/kg, in 10% Kolliphor), or 10% Kolliphor, once daily for three days at ZT0 (7:00 am) (ZT refers to Zeitgeber Time, and indicates the time at which the lights were turned on to stimulate day in the mouse facility). On the final day at ZT7.5 (2:30 pm), animals were euthanized using $CO_2$ asphyxiation, and the blood collected from the heart via cardiac puncture. The blood was placed in RNALater solution to 1.5 ml total volume. Total RNA was prepared using an Ambion Mouse RiboPure Blood RNA Isolation Kit AM1951 as follows. Samples were centrifuged for 3 minutes, discarding the supernatant. Two ml of lysis solution was added and vortexed, transferred to a 15 ml tube followed by the addition of microliters 3M Sodium Acetate. Lysis buffer was added to a total volume of 3.8 ml and vortexed. The sample mixture was extracted with 1.5 ml Acid Phenol: Chloroform and the aqueous phase was recovered. After adding 0.5 volumes of 100% ethanol and vortexing, the samples were passed through a filter column provided in the kit and washed with 750 microliters of wash buffer 1. The filter was washed with 2 passes of 750 microliters wash buffer 2/3 and dried. RNA was eluted in 200 microliters of molecular biology grade water (RNase-free).

Quantitation of Total RNA.

RediPlate 96 RiboGreen RNA Quantification Kit (Invitrogen) RediPlate standard curve was prepared by transferring 20 µl reconstituted RNA standard to a RediPlate well reconstituted in 180 µl RediPlate TE buffer. For liver RNAs prepared from 30-100 mg of tissue using a kit similar to the Omega Bio-Tek HP Total RNA Kit and eluted in RNAse-free water in a volume of 50 µl (microliters), 5 µl of the total RNA is diluted in 195 µl of RediPlate TE buffer (1:40 dilution of RNA), mix. After transferring 5 µl to RediPlate well reconstituted in 195 µl TE buffer and incubating 10 min. at RT, Fluorescence Intensity of wells with standards and samples were read in a Tecan M200 with Excitation set at 480 nm and Emission set at 520 nm with the gain set to −70%. Alternatively, one can use the FlexStation 3 with Ex 488 nm and Em 525 nm and a Cutoff of 515 nm. A standard curve was generated in GraphPad Prism and sample readings (unknowns) are interpolated via linear regression analysis, and the RNA sample concentrations were calculated.

Preparation of cDNA.

High-Capacity cDNA Reverse Transcription Kit (Invitrogen)10×RT Buffer (40-70 µl), dNTPs and random primers were thawed on ice. Using the same amount of input RNA for each sample (usually 0.5-4.0 µg) reactions were set up in a total volume of 40 µl. Appropriate amounts of total RNA and Nuclease-Free $H_2O$ were mixed to obtain total volume of 20 µl. A master mix was created with 4.2 µl RNAse-Free $H_2O$, 2 µl 10×RT Buffer, 0.8 µl 25×dNTPs, and 2 µl Random Primers for each reaction (optionally, 10% more can be added to the total number of reactions to be performed to ensure sufficient volume). Reverse Transcriptase (1 µl) was added for each reaction and mixed carefully without vortexing. Some duplicate samples (~10% of total) were assigned to an RT(−) set and enough master mix lacking Reverse Transcriptase was prepared to include these controls. Master mix (20 µl) was added (or RT(−) master mix) to 20 µl of fixed-input RNA sample. The reactions were incubated at 37° C. for 2 hours, heated to 85° C. for 5 min., and placed on ice. Samples of cDNA were stored at 4° C. if used by the next day or stored at −20° C. for longer periods.

RT-PCR.

For PCR analysis, the kit utilized was TaqMan® Fast Universal Master Mix (2×), No AmpErase® UNG. For reactions to be run on ABI 7500, 2 µl of cDNA template or RT(−) control template was placed in each well. A master mix was made including 1.0 µl TaqMan Expression Assay (primers/probes) and 7 µl Nuclease-Free $H_2O$ for each sample to be run, and 18 µl of master mix+Expression Assay+Nuclease-Free $H_2O$ was added to each 2 µl sample, mix by pipetting. The plate was sealed, spun down and loaded in an ABI7500. At least one housekeeping mRNA Expression Assay (e.g. GAPDH; Mm03302249_g1 or Hs02758991_g1) was included in each set of RNA samples to be assessed.

The effect of Cry modulator Compound 72 on core clock function was examined in diabetic mice and non-diabetic mice. Male C57Bl/6J DIO mice at 17 weeks of age (The Jackson Laboratory, Sacramento, Calif.) were maintained on a high fat diet (HFD) and acclimated for a 2 week period before treatment to recapitulate diabetes and obesity. Three mice were treated with compound or vehicle for each of the 5 time points. Mice were dosed with vehicle (water for injection (WFI) or the Compound 72 (50 mg/kg in WFI) at a dose volume of 5 ml/kg, BID (twice daily), via oral gavage. In total, each mouse received 5 doses of compound over the course of the experiment. Mice were weighed and randomly assigned to each treatment based on weight the evening before the commencement of the study. Beginning on Day 3 at 3:00 PM, a group of animals from the vehicle and Compound 72-treated groups were euthanized using $CO_2$ asphyxiation, 50 mg of liver, epididymal white fat, and skeletal muscle, were excised for RNA preparation.

The effect of Compound 72 was also examined in normal Balb/c mice on circadian mRNAs over 24 hours. The mice were 8 weeks old, obtained from Charles River, and allowed to acclimate for 2 weeks. Mice were dosed BID for 3 days, with a total of 7 doses for each animal, with the last dose 12 hours before obtaining tissues. Mice were dosed with vehicle (WFI) or Compound 72 (50 mg/kg in WFI) at a dose volume of 5 ml/kg, BID, via oral gavage. Beginning on Day 3 at 3:00 PM, a group of animals from the vehicle and Compound 72 groups were sacrificed, and approximately 50 mg of liver, lung, kidney, adrenal gland, spleen, epididymal fat, and brown adipose tissue were excised and placed in RNALater.

Figure 1B:
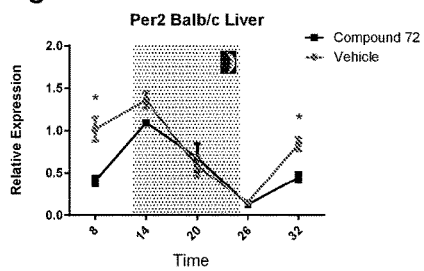
Figure 1C:
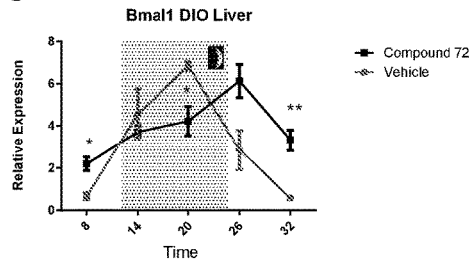
Figure 1D:
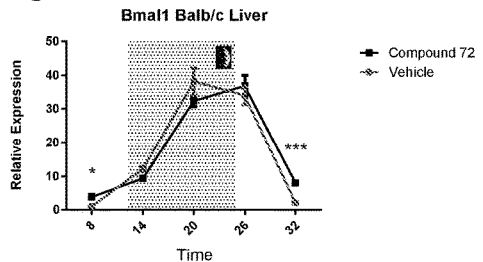
Figure 1E:
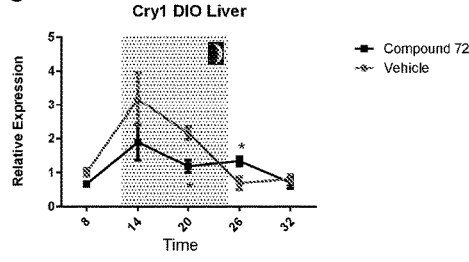
Figure 1F:
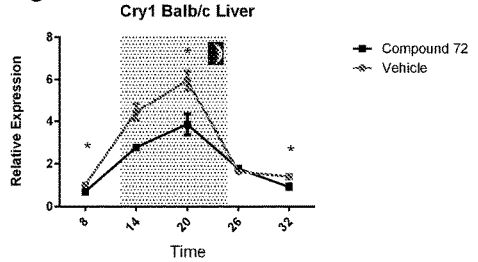
Figure 1G:
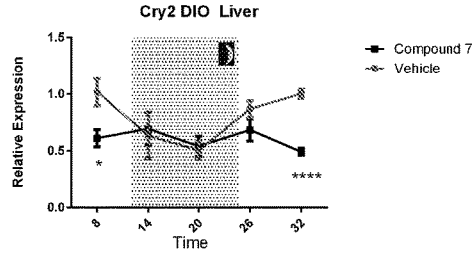
Figure 1H:
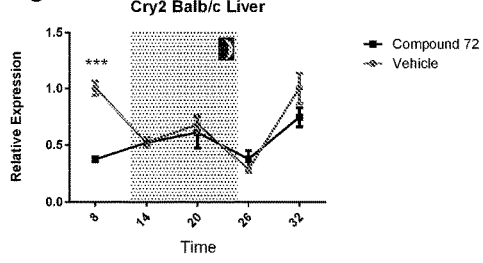

The core clock mRNAs from vehicle-treated C57Bl/6J DIO mice displayed the characteristic circadian expression pattern (FIG. 1A-1H). With Compound 72 treatment, however, Per2 mRNA was suppressed in both C57Bl/6J DIO and Balb/c mice over 24 hours, and these were most reduced at ZT8 and again at ZT8 24 hours later (FIG. 1A & FIG. 1B). Bmal1 mRNAs were substantially increased by Compound 72 treatment at ZT8 and 32 hours after the original ZT0 in both strains of mice. Bmal1 transcripts also displayed a prominent phase delay in C57Bl/6J DIO mice and to a lesser extent in Balb/c mice (FIG. 1C & FIG. 1D). The mRNA for Cry1 was suppressed during its peak of expression during the dark period (FIG. 1E & FIG. 1F, shaded regions). The phase advance in vehicle-treated Cry1 transcripts observed in DIO mice relative to vehicle-treated Balb/c mice may be in part due to the known effects of high fat diet on many diurnal patterns (Eckel-Mahan et al. (2013) *Cell*). In contrast with Cry1 mRNA, the mRNA for Cry2 peaked in the daytime hours in vehicle-treated mice, but this was strongly attenuated by treatment with Compound 72 in both C57Bl/6J DIO and Balb/c mice (FIG. 1G & FIG. 1H).

Figure 2A:
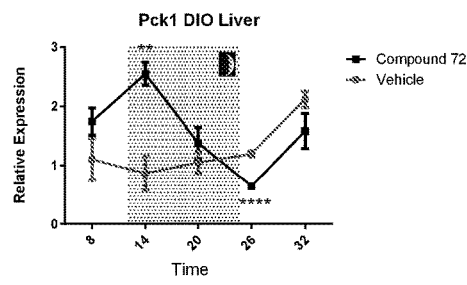
FIGS. 2A-D are a series of graphs showing gluconeogenic gene expression in mice after administration of Compound 72. mRNA expression of gluconeogenic genes Pck1 (PEPCK.
Figure 2B:
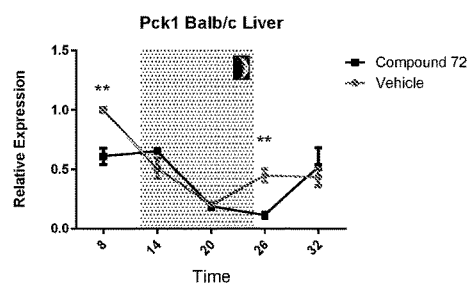
Figure 2C:
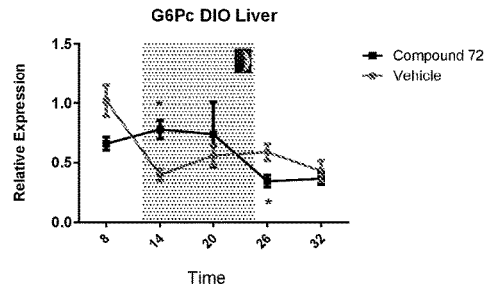
Figure 2D:
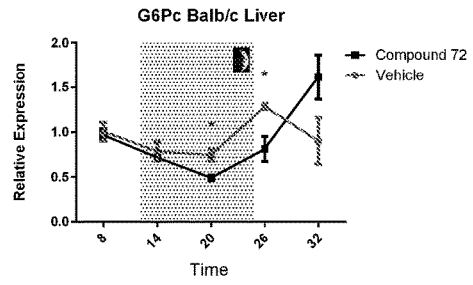

In the same 24 hour studies described above, the circadian pattern of mRNAs for the gluconeogenic genes Pck1 (PEPCK) and G6Pc (Glucose 6-phosphatase catalytic subunit) were substantially altered by Compound 72 relative to vehicle in C57Bl/6J DIO mice (FIG. 2A & FIG. 2C). The vehicle-treated mice displayed a pattern that was flattened and phase-advanced over that observed for chow-fed C57Bl/6J mice in other studies (Hughes et al. (2009)). The Compound 72-treated C57Bl/6J DIO mice displayed a peak of expression for both of these gluconeogenic genes in the early evening (ZT14), which is closer to the peak time of their expression observed in chow-fed mice (Hughes et al. (2009)). The diurnal patterns of expression for Pck1 and G6Pc were altered more by Compound 72 in the C57Bl/6J DIO mice relative to vehicle than they were in the Balb/c mice (FIG. 2B & FIG. 2D).

Figure 3A:
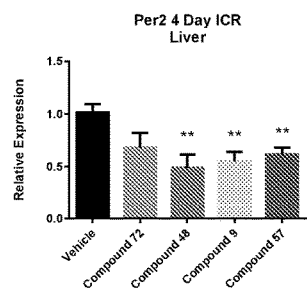
FIGS. 3A-C are a series of graphs showing core clock gene expression in the livers of ICR mice after administration of Compound 72, Compound 48, Compound 9, or Compound 57. mRNA expression of core clock genes Per2 (FIG. 3A), Bmal1 (FIG. 3B), and Cry2 (FIG. 3C) was measured in the livers of ICR mice treated for 4 days BID with Compound 72, Compound 48, Compound 9, Compound 57 or vehicle. Levels of the mRNAs were determined by RT-qPCR on samples taken at ZT6 after the final ZT0 dose. The mRNA levels from Compound 72-treated for each time point was compared to vehicle by T-test: * <0.05,  <0.01, * <0.001, **** <0.0001.
Figure 3B:
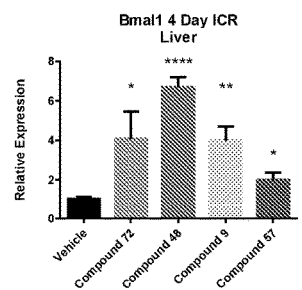
Figure 3C:
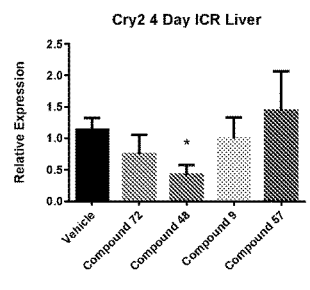

The effects of multiple Cry modulator compounds, Compound 72, Compound 48 Compound 9 and Compound 57 were examined in ICR mice. The mice were treated with 50 mg/kg of each compound (Compound 72, Compound 48, Compound 9, and Compound 57), PO (oral administration) at a dose volume of 5 ml/kg for 4 days, BID or vehicle control. Each compound caused a suppression of liver Per2 expression (FIG. 3A). Compound 48 treatment resulted in an 8-fold increase in Bmal1 mRNA at ZT6, Compound 72 and Compound 9 treated mice displayed a 4 fold increase, and Compound 57 treated mice displayed at least a 2 fold increase (FIG. 3B). Compound 72, Compound 48 and Compound 9 also caused a decrease in Cry2 transcripts (FIG. 3C).

The levels of core clock gene mRNAs in whole blood may provide a non-invasive method of determining effects of compounds in treated subjects. Male db/db mice (9 weeks of age, The Jackson Laboratory, Bar Harbor, Me.) were used with n=8 for each experimental group. Mice were dosed with Compound 72 (100 mg/kg, P.O; dose volume 5 ml/kg, in 10% Kolliphor), or 10% Kolliphor, once daily for three days at ZT0 (7:00 am) (ZT refers to Zeitgeber Time, and indicates the time at which the lights were turned on to stimulate day in the mouse facility). On the final day at ZT7.5 (2:30 pm), animals were euthanized using $CO_2$ asphyxiation, and the blood collected from the heart via cardiac puncture. Whole blood was transferred to a tube containing RNALater for assay by RT-qPCR.

Figure 4:
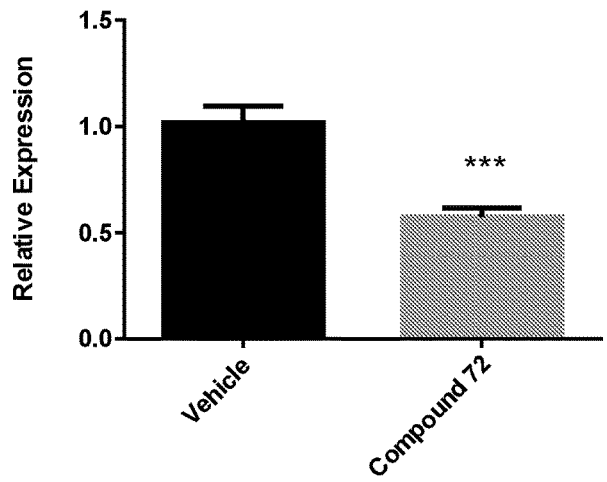
FIG. 4 is a graph showing Dbp gene expression after three daily doses of Compound 72 at the peak of Cry1 expression. Expression of Dbp mRNA was measured at ZT7.5 in whole blood from db/db mice after three daily doses of 100 mg/kg Compound 72. Transcript levels were determined by RT-qPCR and compared to blood from vehicle (10% kolliphor)-treated mice at ZT7.5. The mRNA levels from each compound treatment was compared to vehicle by T-test (***; p<0.001).
Figure 5A:
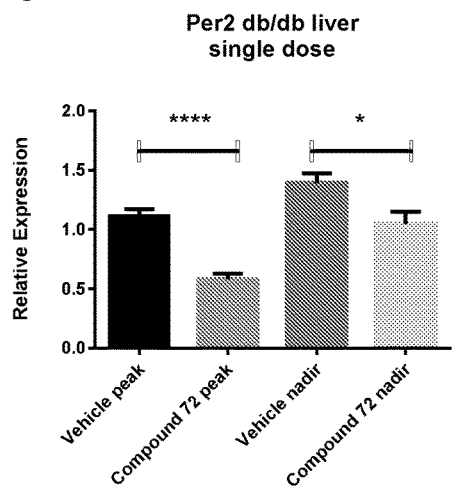
FIGS. 5A-D are a series of graphs showing core clock gene expression after a single dose of Compound 72 at the peak or nadir of Cry1 expression. mRNA expression of core clock genes Per2 (FIG. 5A), Bmal1 (FIG. 5B), Cry1 (FIG. 5C) and Cry2 (FIG. 5D) was measured at ZT7.5 (Peak of Cry1 expression) or ZT17.5 (nadir of Cry1 expression) in liver from C57Bl/6J DIO mice after a single dose of 100 mg/kg Compound 72. Transcript levels were determined by RT-qPCR and compared to liver from vehicle (10% kolliphor)-treated. The mRNA levels from Compound 72-treated for each time point was compared to vehicle by T-test: * <0.05,  <0.01, * <0.001, **** <0.0001.
Figure 5B:
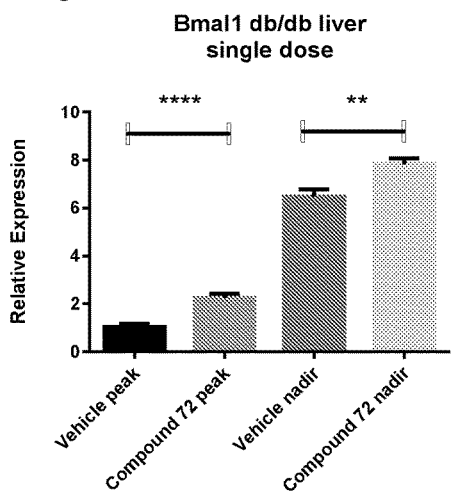
Figure 5C:
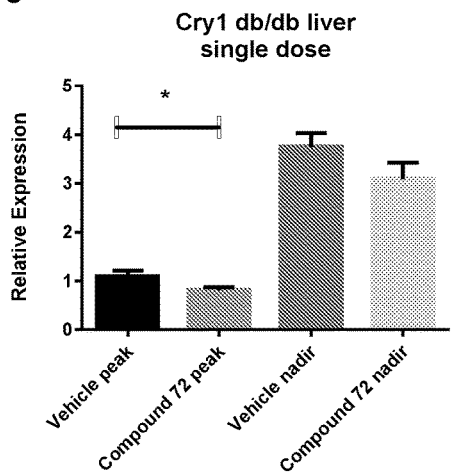
Figure 5D:
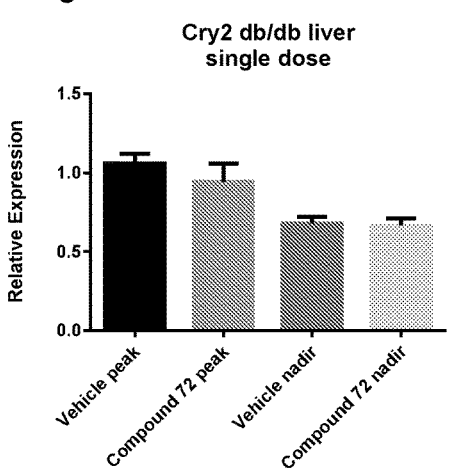

The D-box binding protein Dbp is regulated in a strongly circadian manner. Compound 72 caused a statistically significant suppression of Dbp gene expression in this study (FIG. 4), demonstrating that white blood cells in mice treated with such compounds can provide information about the effects of compounds on the core clock mechanism in the whole organism. Such information may be used as a diagnostic marker, or as a biomarker to assess the effects of Cry modulators and other therapeutic agents that impact the core circadian mechanism.

For compounds that interact directly with the core clock mechanism, the time of dosing may be critical for maximizing their effects. Db/db mice were treated with a single dose of Compound 72 (50 mg/kg) given at either ZT0 or ZT10. The former (ZT0) is coincident with the peak of Cry1 and Bmal1 protein in mouse liver and the latter (ZT10) corresponds to the approximate nadir of Cry1 and Bmal1. Liver tissue was taken 7.5 hours later for each, and the samples were examined for core clock gene mRNAs by RT-qPCR. Since Compound 72 had a greater relative impact on the clock mRNAs at the peak compared to the nadir (FIGS. 5A-D), dosing around the time of the former provides for greater effects on the clock mechanism, and this may further lead to a greater effect on the metabolic outputs of the clock.

Example 6: Effect of Single Dose of Compound 72 Administered at Peak or Nadir of Clock Gene Expression in a Diabetes Mouse Model The effect of Compound 72 on glucose metabolism was assessed when administered as a single dose administered either at peak or nadir of core clock genes Cry1/Bmal1 expression in a db/db mouse model of type II diabetes.

Male db/db mice homozygous for Lepr$^{db}$ (6 weeks of age), were obtained from The Jackson Laboratory (Bar Harbor, Me.). Mice were group housed on a normal light/dark cycle (lights on: 07:00-19:00 h) with ad libitum access to a standard pelleted mouse diet and water. Animals were accustomed to these conditions for 2 weeks before experimentation. Mice were split into two study arms, to be dosed at either the peak or nadir of Cry1 and Bmal1 gene expression. Mice were dosed once with vehicle (10% Kolliphor, Sigma-Aldrich) or Compound 72 (50 mg/kg in 10% Kolliphor in water) at a dose volume of 5 ml/kg, QD, via oral gavage, at ZT0 (peak, 7:00 am) or ZT10 (nadir, 5:00 pm). Animals were weighed on day 0 and randomly assigned to treatment groups so that each group had similar average starting weights. Mice dosed at ZT0 were fasted overnight beginning at 10:30 pm, when they were transferred to a clean cage and given free access to water, but not food, for a period of 12 hours. Mice dosed at ZT10 were fasted beginning at 8:30 am in the same manner. On the day of the study, after dosing, mice underwent a tail cut injury 2 hours prior to measurement of fasting blood glucose, to allow recovery from any stress the procedure might cause. Fasting blood glucose (FBG) was assessed from the animals at 10:30 am or 8:30 pm using an AlphaTRAK glucometer (Abbott Laboratories, USA). At 11:30 am (peak dosed mice) or 9:30 pm (nadir dosed mice) each animal was dosed with 0.5 g/kg of glucose, then blood glucose was measured at t=15, 30, 60, 90 and 120 minutes after glucose load. Animals were terminated following the last blood collection and tissues and blood harvested for other endpoint determinations.

Fasting blood glucose values and glucose measurements taken during the OGTT were averaged and graphed (GraphPad Prism, GraphPad Software, La Jolla, Calif.). The area under the curve (AUC) was calculated for each individual animal. Statistical analysis was performed using one-way ANOVA followed by the appropriate post-test. Significance was accepted when $p<0.05$. Data are presented as mean and S.E.M.

Figure 6A:
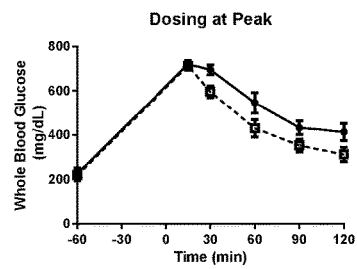
FIGS. 6A-B are a series of graphs showing the effect of Compound 72 on oral glucose tolerance test (OGTT) in db/db mice. Compound 72 (50 mg/kg, PO) or 10% kolliphor (control) was administered as a single dose either at the peak (ZTO) (FIG. 6A) or nadir (ZT10) (FIG. 6B) of Cry1 and Bmal1 gene expression.
Figure 6B:
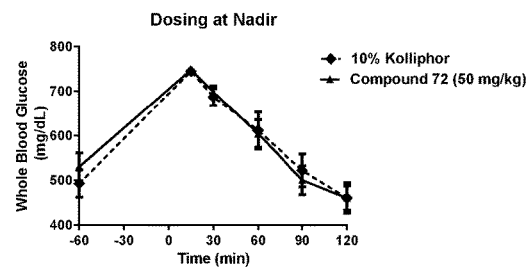
Figure 7:
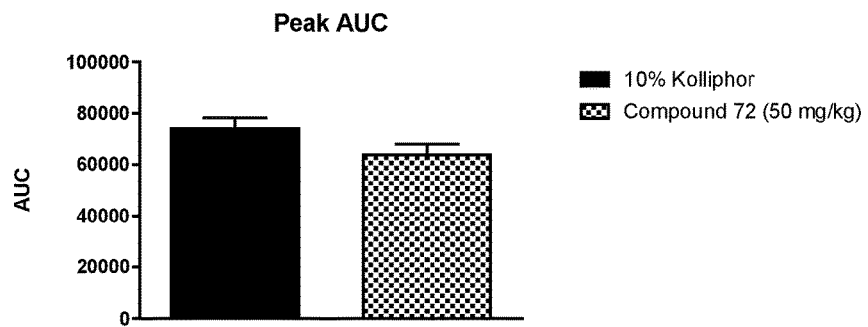
FIG. 7 is a graph showing the effect of Compound 72 on glucose area under the curve (AUC) in db/db mice. Compound 72 (50 mg/kg, PO) or 10% kolliphor (control) was administered as a single dose at the peak (ZTO) of Cry1 and Bmal1 gene expression.

Administration of Compound 72 (50 mg/kg, PO) at a single dose, administered at the peak of Cry1 and Bmal1 gene expression, to db/db mice resulted in an apparent effect on the OGTT measurement (FIG. 6A) compared to the vehicle control, but no effect when dosed at the nadir (FIG. 6B). The AUC calculated from the OGTT of animals dosed at the peak of gene expression showed that Compound 72 treatment resulted in a reduction in glucose excursion of 14% (74098+/−4194 to 63842+/−4318; FIG. 7).

Example 7: Effect of a Single Dose of Compound 72 Administered Over 7 Days in a Diabetes Mouse Model The effect of Compound 72 on glucose metabolism and insulin levels was assessed when administered as a single dose administered over 7 days in a db/db mouse model of type II diabetes.

Male db/db mice homozygous for Lepr$^{db}$ (6 weeks of age), were obtained from The Jackson Laboratory (Bar Harbor, Me.). Mice were group housed on a normal light/dark cycle (lights on: 07:00-19:00 h) with ad libitum access to a standard pelleted mouse diet and water. Animals were accustomed to these conditions for 2 weeks before experimentation. Mice were dosed with vehicle (10% Kolliphor, Sigma-Aldrich) or Compound 72 (50 mg/kg in 10% Kolliphor in water) at a dose volume of 5 ml/kg, QD, via oral gavage, at ZT0 (7:00 am) for seven days. Mice were weighed on Day 0 and randomly assigned to either treatment group so that each group had similar average starting weights. At 10:30 pm on the evening prior to endpoint measurement, mice were placed into clean cages and given free access to water, but not food for a period of 12 hours before the fasting blood glucose measurement. On the final day of the study, animals were dosed as normal, and then underwent a tail cut injury 2 hours prior to measurement of fasting blood glucose, to allow recovery from any stress the procedure might cause. Fasting blood glucose (FBG) was assessed from the animals at 10:30 am using an AlphaTRAK glucometer (Abbott Laboratories, USA). Following the FBG measurement blood was collected from each mouse, using a tail milking technique, into a capillary tube. Capillary tubes were centrifuged in a hematocrit (BD Triac 0200) and the resultant plasma transferred to an eppendorff. This sample, labelled as t=0hr, was frozen at −80° C. to allow later measurement of insulin. At 11:30 am each animal was dosed with 0.5 g/kg of glucose, then blood glucose was measured at t=15, 30, 60, 90 and 120 minutes after glucose load. At the end of the OGTT blood was collected for a t=2 hr insulin determination as described above. Animals were terminated following the last blood collection and tissues and blood harvested for other endpoint determinations (detailed elsewhere). Plasma and liver tissue from Compound 72 treated animals were submitted to a CRO for measurement of compound levels, using LC/MS/MS and comparing to a standard curve of known compound amounts.

Fasting blood glucose values and glucose measurements taken during the OGTT were averaged and graphed (GraphPad Prism, GraphPad Software, La Jolla, Calif.). The area under the curve (AUC) was calculated for each individual animal. Plasma insulin levels were determined using an Ultrasensitive Insulin ELISA (ALPCO, Salem, N.H.). The HOMA-IR (homeostatic model assessment-insulin resistance) was calculated using the following formula: (FPI (µU/L)×FPG (mmol/L))/22.5, where FPI and FPG denote Fasting Plasma Insulin and Fasting Plasma Glucose, respectively. Insulin data was also represented in GraphPad Prism format. Statistical analysis was performed using one-way ANOVA followed by the appropriate post-test. Significance was accepted when p<0.05. Data are presented as mean and S.E.M.

Figure 8A:
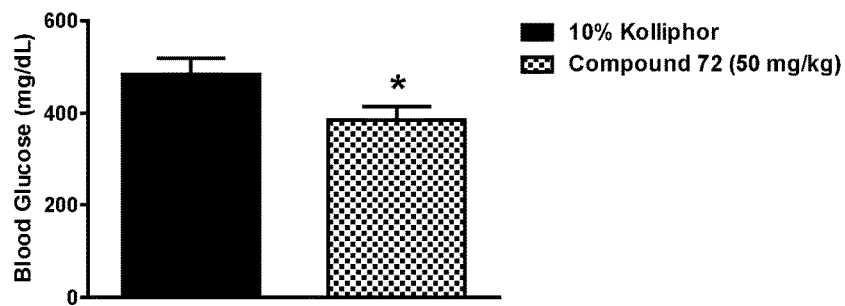
FIGS. 8A-C are a series of graphs showing the effect of Compound 72 administered for 7 days on glucose metabolism in db/db mice. Compound 72 (50 mg/kg, PO) or 10% kolliphor (control) was administered for 7 days.
Figure 8B:
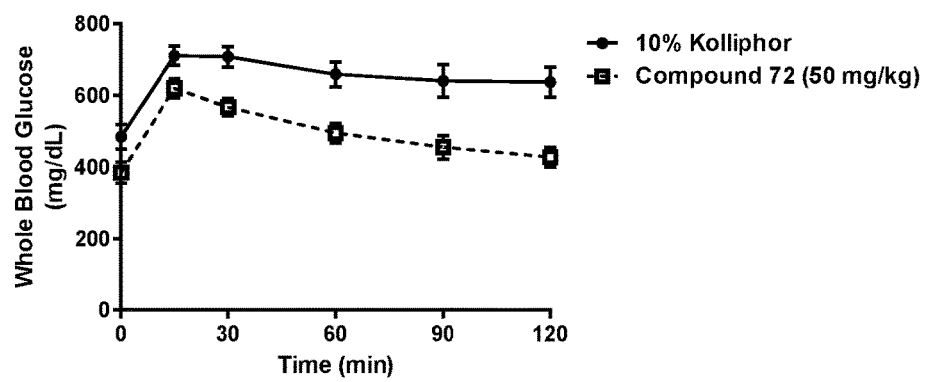
Figure 8C:
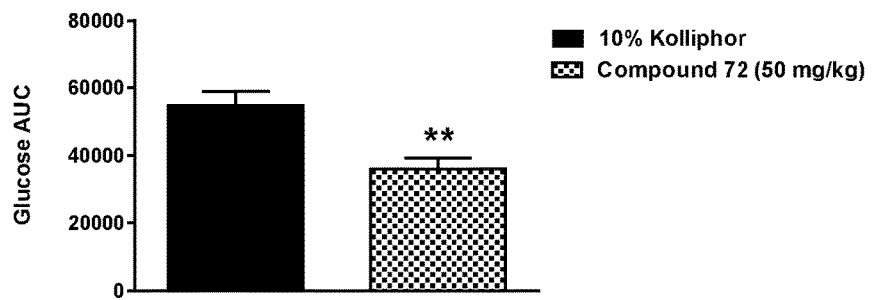

Administration of Compound 72 (50 mg/kg, PO) for 7 days to db/db mice resulted in a significant reduction in FBG compared to vehicle control (484.9+/−34.37 mg/dL to 385.0+/−29.69 mg/dL; FIG. 8A). During the course of the OGTT measurement, Compound 72 treated animals were lower than the vehicle control group (FIG. 8B). The AUC calculated from the OGTT showed that Compound 72 administration resulted in a significant reduction in glucose excursion (54845+/−4112 to 35942+/−3192; FIG. 8C).

Figure 9A:
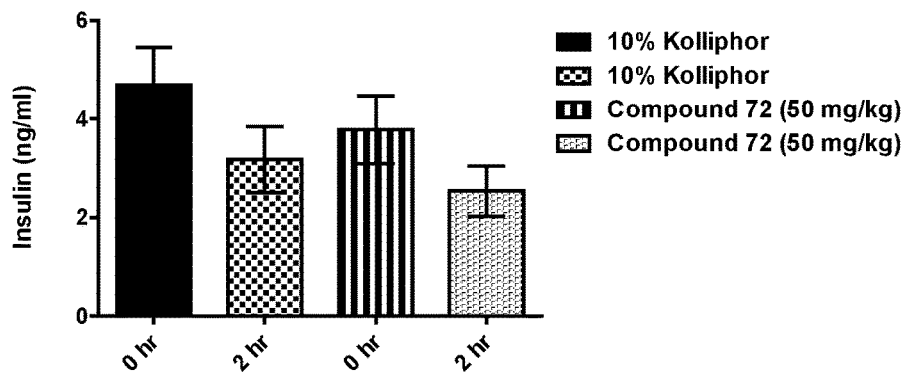
FIGS. 9A-B are a series of graphs showing the effect of Compound 72 administered for 7 days on insulin levels in db/db mice. Compound 72 (50 mg/kg, PO) or 10% kolliphor (control) was administered.
Figure 9B:
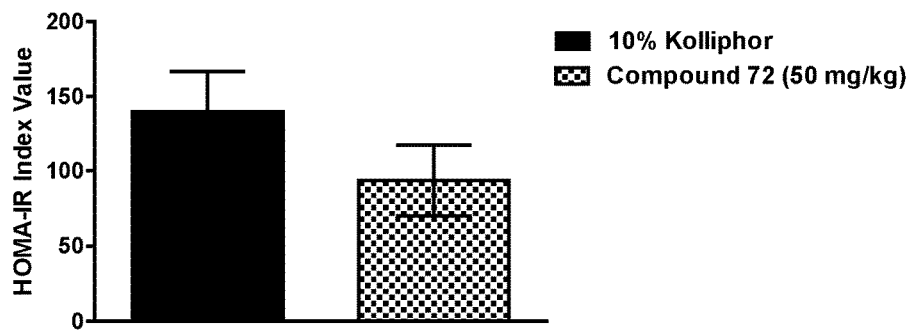

Plasma insulin measurements were made from the samples taken at t=0 and t=2 hr, and are shown in FIG. 9A. Insulin was reduced by treatment with Compound 72 at both t=0 and t=2 hr time-points by 20% and 21%, respectively (4.70+/−0.76 to 3.78+/−0.69 ng/mL and 3.17+/−0.67 to 2.53+/−0.50 ng/mL, respectively). The HOMA-IR (an indication of re-sensitization to insulin) was reduced by 33% from 139.91+/−26.57 to 93.69+/−23.60 units (FIG. 9B).

Figure 10:
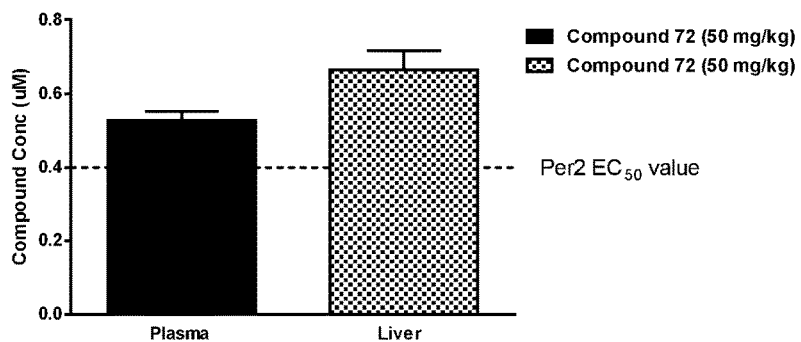
FIG. 10 is a graph showing the compound levels of Compound 72 measured in plasma and liver around 8 hours after administration of the last dose (50 mg/kg, PO). The $EC_{50}$ concentration for Compound 72 in the Per2 assay is designated on the graph by the dashed line.

Compound 72 compound levels were assessed from the samples taken at study termination, and are shown in FIG. 10, along with the $EC_{50}$ value determined from the Per2 assay as described in Example 3, for comparison purposes. Compound 72 was found in both the plasma and liver at around 8 hours after administration of the last dose (plasma: 0.53+/−0.03 µM; liver: 0.67+/−0.05 µM, shown as Mean and S.E.M). In both cases compounds levels were slightly higher than the Per2 $EC_{50}$ value determined for Compound 72 (0.4 µM; 1.3 fold and 1.7 fold higher than the $EC_{50}$ value in plasma and liver, respectively).

Example 8: Effect of Increasing Dosages of Compound 72 in a Diabetes Mouse Model The effect of Compound 72 was assessed over increasing doses administered over 7 days on glucose metabolism and insulin levels in a db/db mouse model of type II diabetes.

Male db/db mice homozygous for $Lepr^{db}$ (5 weeks of age), were obtained from The Jackson Laboratory (Bar Harbor, Me.). Mice were group housed on a normal light/dark cycle (lights on: 07:00-19:00 h) with ad libitum access to a standard pelleted mouse diet and water. Animals were accustomed to these conditions for 2 weeks before experimentation. Mice were dosed with vehicle (10% Kolliphor, Sigma-Aldrich) or Compound 72 at 10, 50 or 100 mg/kg (in 10% Kolliphor in water) at a dose volume of 5 ml/kg, QD, via oral gavage, at ZT0 (7:00 am) for seven days. The experimental methods performed were the same as those detailed in Example 11. The compound levels in plasma and liver tissue from Compound 72 treated animals were measured using LC/MS/MS and compared to a standard curve of known compound amounts.

Figure 11A:
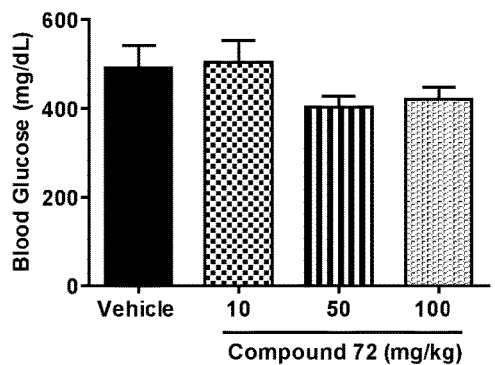
FIGS. 11A-C are a series of graphs showing the effect of increasing dosages of Compound 72 (10 mg/kg, 50 mg/kg, and 100 mg/kg) on glucose metabolism in db/db mice. 10% kolliphor was used as vehicle control.
Figure 11B:
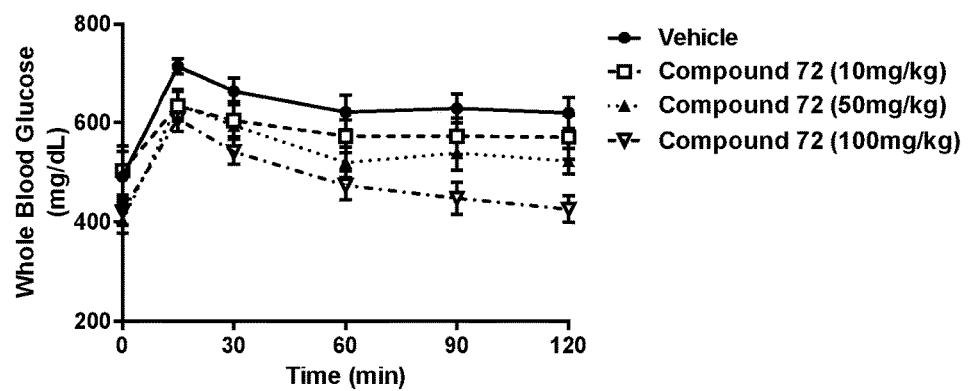
Figure 11C:
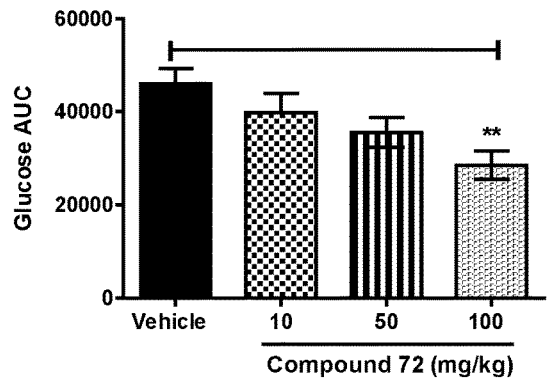

Administration of Compound 72, at ascending doses, for 7 days to db/db mice resulted in a reduction in fasting blood glucose levels compared to the vehicle control group at 50 and 100 mg/kg, though this did not reach statistical significance (vehicle control: 491.0+/−51.30 mg/dL, 50 mg/kg: 402.8+/−25.25 mg/dL, 100 mg/kg: 420.7+/−26.44 mg/dL; FIG. 11A). Compound 72, administered at a dose of 10 mg/kg, demonstrated no reduction in fasting blood glucose levels (503.5+/−49.68 mg/dL). During the course of the OGTT measurement, Compound 72 treated animals demonstrated a dose dependent effect on glucose excursion from the animals following a glucose load (FIG. 11B). The area under the curve calculated from the OGTT showed that Compound 72 administration reduced the glucose AUC in a dose dependent manner which was significant at 100 mg/kg (vehicle: 46088+/−3303, 10 mg/kg: 39771+/−4244, 50 mg/kg: 35527+/−3215, 100 mg/kg: 28499+/−3079; FIG. 11C).

Figure 12A:
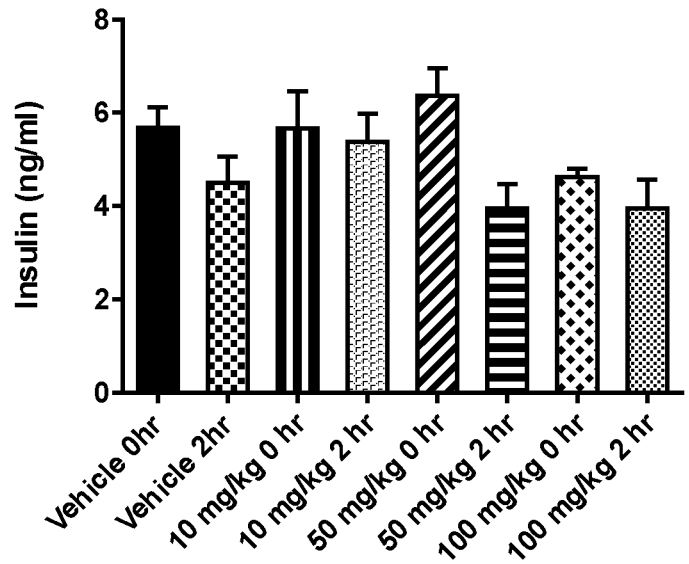
FIGS. 12A-B are a series of graphs showing the effect of increasing dosages of Compound 72 (10 mg/kg, 50 mg/kg, and 100 mg/kg) on insulin levels in db/db mice. 10% kolliphor was used as vehicle control.
Figure 12B:
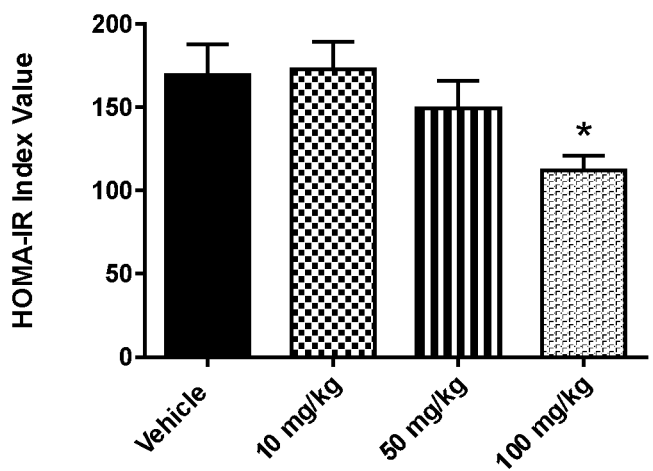

Plasma insulin measurements were made from the samples taken at t=0 and t=2 hr, and are shown in FIG. 12A. Insulin was reduced, at t=0, by treatment with Compound 72 when dosed at 100 mg/kg (from 5.68+/−0.43 to 4.63+/−0.17 ng/mL (vehicle and 100 mg/kg group, respectively)). The HOMA-IR was reduced in a dose dependent manner following Compound 72 administration (vehicle: 169.3+/−18.41, 10 mg/kg: 172.7+/−16.61, 50 mg/kg: 149.2+/−16.49, 100 mg/kg: 111.9+/−9.02 units; FIG. 12B). At 100 mg/kg, the effect of Compound 72 was significant (34% reduction compared to the vehicle control group).

Figure 13:
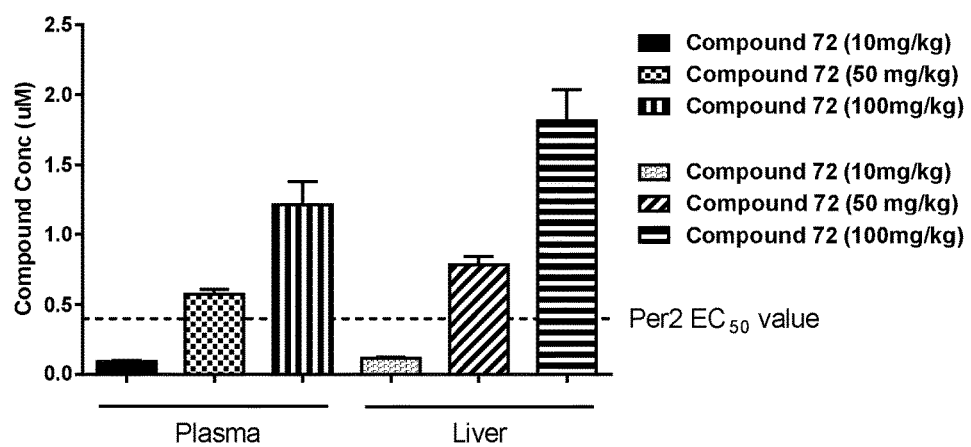
FIG. 13 is a graph showing the compound levels of Compound 72 measured in plasma and liver around 8 hours after administration of the last dose at increasing dosages (10 mg/kg, 50 mg/kg, and 100 mg/kg). The $EC_{50}$ concentration for Compound 72 in the Per2 assay is designated on the graph by the dashed line.

Compound 72 compound levels were assessed from the samples taken at study termination, and are shown in FIG. 13, along with the Per2 $EC_{50}$ value (as described in Example 3), for comparison purposes. Compound 72 was found in both the plasma and liver at around 8 hours after administration of the last dose, with exposure levels which were increased relative to the increase in dose administered (plasma, 10 mg/kg: 0.09+/−0.01 µM; 50 mg/kg: 0.57+/−0.03 µM; 100 mg/kg: 1.22+/−0.17 µM; liver, 10 mg/kg: 0.12+/−0.01 µM; 50 mg/kg: 0.78+/−0.06 µM; 100 mg/kg: 1.81+/−0.22 µM). In both plasma and liver exposure levels were 1.4 fold and 1.95 fold higher at 50 mg/kg, and 3 fold and 4.5 fold higher at 100 mg/kg, than the Per2 $EC_{50}$ value in the plasma and liver respectively.

Example 9: Effect of Increasing Dosages of Compound 9 in a Diabetes Mouse Model

The effect of Compound 9 was assessed over increasing doses administered over 7 days on glucose metabolism and insulin levels in a db/db mouse model of type II diabetes.

Male db/db mice homozygous for $Lepr^{db}$ (5 weeks of age), were obtained from The Jackson Laboratory (Bar Harbor, Me.). Mice were group housed on a normal light/dark cycle (lights on: 07:00-19:00 h) with ad libitum access to a standard pelleted mouse diet and water. Animals were accustomed to these conditions for 2 weeks before experimentation. Mice were dosed with vehicle (10% Kolliphor, Sigma-Aldrich) or compound Compound 9 at 30, 100 or 300 mg/kg, or Rosiglitazone at 30 mg/kg (in 10% Kolliphor in water) at a dose volume of 5 ml/kg, QD, via oral gavage, at ZTO (7:00 am) for seven days. Rosiglitazone is an antidiabetic therapeutic agent that was used for positive control. The experimental methods performed were the same as those detailed in Example 11. The compound levels in plasma and liver tissue from Compound 9 treated animals were measured using LC/MS/MS and compared to a standard curve of known compound amounts.

Figure 14A:
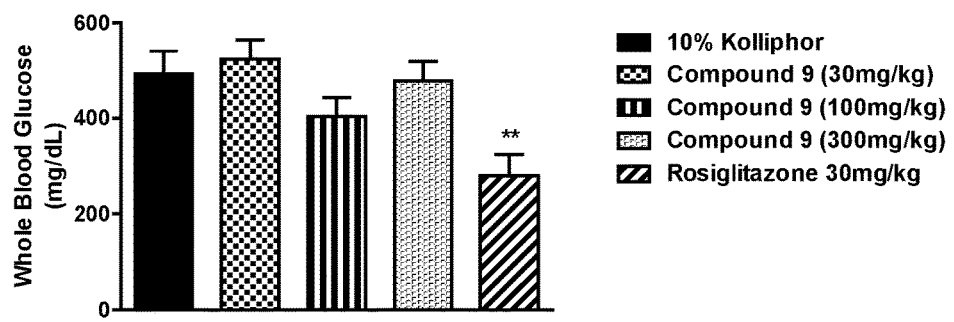
FIGS. 14A-C are a series of graphs showing the effect of increasing dosages of Compound 9 (30 mg/kg, 100 mg/kg, and 300 mg/kg) on glucose metabolism in db/db mice. 10% kolliphor was used as control.
Figure 14B:
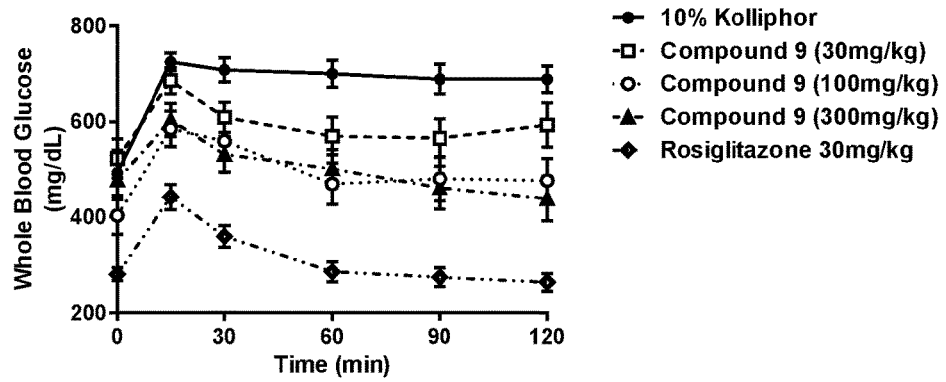
Figure 14C:
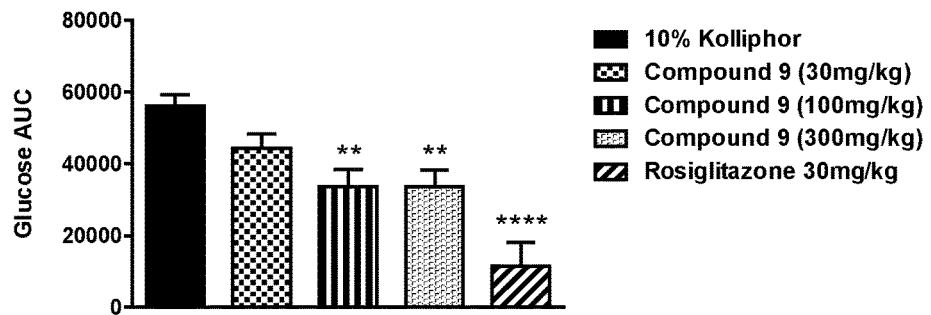

Administration of Compound 9, at ascending doses, for 7 days to db/db mice resulted in a reduction in fasting blood glucose levels at 100 mg/kg compared to the vehicle control group (from 492.8+/−48.07 to 403.1+/−39.73 mg/dL; FIG. 14A) but no statistically significant effect overall. Compound 9, administered at a dose of 30 and 100 mg/kg, demonstrated a dose dependent reduction in glucose levels measurement during the OGTT, with no increased effect observed at the highest dose tested of 300 mg/kg (FIG. 14B). The area under the curve calculated from the OGTT showed that administration of Compound 9 reduced the glucose AUC in a dose dependent manner which was significant at both 100 and 300 mg/kg (vehicle: 56046+/−3204, 30 mg/kg: 44442+/−3895, 100 mg/kg: 33643+/−4822, 300 mg/kg: 33650+/−4688; FIG. 8C). The glucose AUC was reduced by 21%, 40% and 40% at 30, 100 and 300 mg/kg, respectively, from the vehicle control group. Rosiglitazone, used as a positive control for the animal model, significantly inhibited fasting blood glucose (from 492.8+/−48.07 to 280.4+/−13.66 mg/dL; FIG. 14A), and glucose AUC (from 56046+/−3204 to 11502+/−2118 units; FIG. 14C).

Figure 15A:
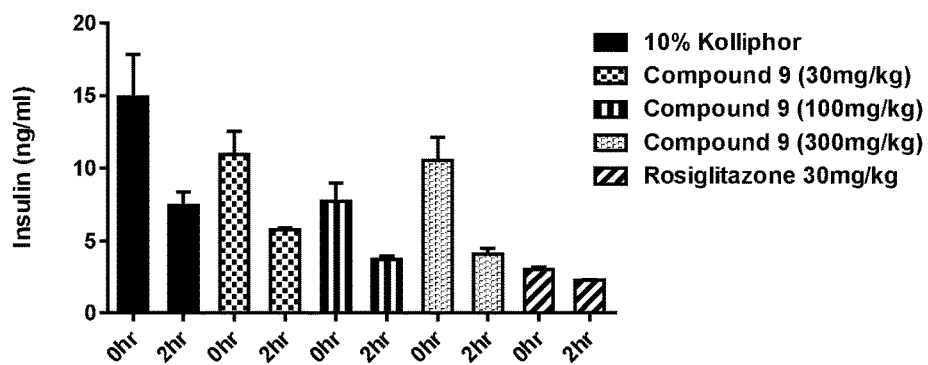
FIGS. 15A-B are a series of graphs showing the effect of varying dosages of Compound 9 (30 mg/kg, 100 mg/kg, and 300 mg/kg) on insulin levels in db/db mice. 10% kolliphor was used as control.
Figure 15B:
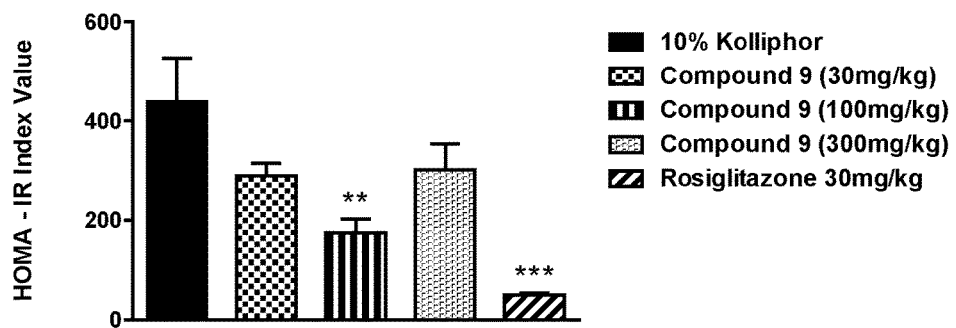

Plasma insulin measurements were made from the samples taken at t=0 and t=2 hr, and are shown in FIG. 15A. Insulin was reduced following treatment with Compound 9 at both t=0 (vehicle: 14.89+/−2.93, 30 mg/kg: 10.94+/−1.62, 100 mg/kg: 7.71+/−1.26, 300 mg/kg: 10.54+/−1.6 ng/mL) and t=2 hr (vehicle: 7.44+/−0.92, 30 mg/kg: 5.76+/−0.11, 100 mg/kg: 3.70+/−0.29, 300 mg/kg: 4.01+/−0.44 ng/mL). The HOMA-IR was reduced in a dose dependent manner following administration of Compound 9, though there was a lesser effect of the compound at 300 mg/kg on this endpoint (vehicle: 438.8+/−87.88, 30 mg/kg: 289.9+/−24.40, 100 mg/kg: 175.3+/−27.52, 300 mg/kg: 301.4+/−52.66 units; FIG. 15B). At 100 mg/kg, the effect of Compound 9 was significant (60% reduction compared to the vehicle control group). Rosiglitazone reduced insulin levels at t=0 and t=2 hr (to 3.05+/−0.14 and 2.28+/−0.08 ng/mL, respectively; FIG. 15A), as well as significantly reducing the HOMA-IR (to 50.58+/−3.52 units, FIG. 15B).

Figure 16:
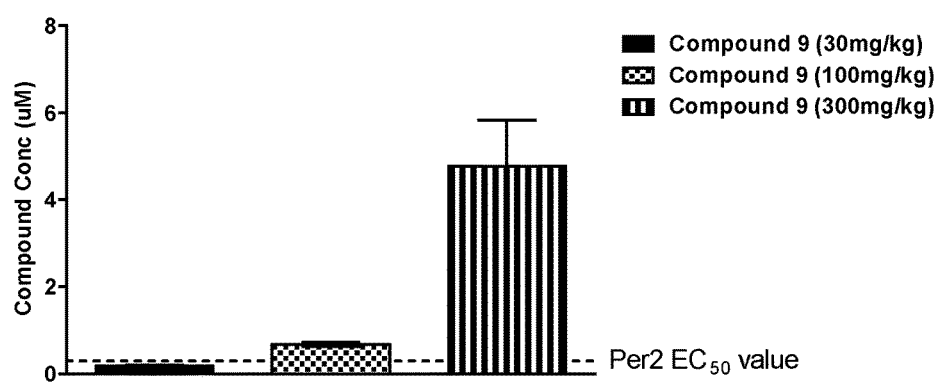
FIG. 16 is a graph showing the compound levels of Compound 9 in plasma and liver around 8 hours after administration of the last dose at increasing dosages (30 mg/kg, 100 mg/kg, and 300 mg/kg). The $EC_{50}$ concentration for Compound 9 in the Per2 assay is designated on the graph by the dashed line.

Compound 9 tissue levels were assessed from the liver samples taken at study termination, and are shown in FIG. 16, along with the Per2 $EC_{50}$ value, for comparison purposes. Compound 9 was found in the plasma liver at around 8 hours after administration of the last dose, with exposure levels which were increased relative to the increase in dose administered between the 30 mg/kg and 100 mg/kg doses. Exposure levels at 300 mg/kg indicated an accumulation of drug (7.1 fold increase rather than 3 fold as expected). Compound levels in the liver samples of animals administered 30, 100 or 300 mg/kg of Compound 9 were 0.19+/−0.02 µM, 0.67+/−0.05 µM and 4.77+/−1.06 µM, respectively. Liver exposure levels following administration of 30 mg/kg Compound 9 were around 1.6 fold below the Per2 $EC_{50}$ value (0.3 µM), while levels were 2.2 fold and 15.9 fold higher at 100 mg/kg and 300 mg/kg, respectively.

Example 10: Effect of Compound 72 in a Diet-Induced Obesity Mouse Model

The effect of Compound 72 was examined in a diet-induced obesity (DIO) mouse model of type II diabetes.

Male C57/Bl6J DIO mice were obtained from The Jackson Laboratory (Sacramento, Calif.). Mice were group housed on a normal light/dark cycle (lights on: 07:00-19:00 h) with ad libitum access to high fat diet (D12492 (60 kcal % fat), Research Diets, Inc.) and water. Animals were accustomed to these conditions for at least 2 weeks before experimentation and used at approximately 24 weeks of age. Mice were dosed with vehicle (10% Kolliphor, Sigma-Aldrich), Compound 72 (100 mg/kg in 10% Kolliphor in water) or Rosiglitazone (30 mg/kg in 10% Kolliphor in water) at a dose volume of 5 ml/kg, QD, via oral gavage, at ZTO (7:00 am) for seven days. Rosiglitazone is an antidiabetic therapeutic agent that was used for positive control. Mice were weighed on Day 0 and randomly assigned to either treatment group so that each group had similar average starting weights. At 10:30 pm on the evening prior to endpoint measurement, mice were placed into clean cages and given free access to water, but not food for a period of 12 hours before the fasting blood glucose measurement. On the final day of the study, animals were dosed as normal, and then underwent a tail cut injury 2 hours prior to measurement of fasting blood glucose, to allow recovery from any stress the procedure might cause. Fasting blood glucose (FBG) was assessed from the animals at 10:30 am using an AlphaTRAK glucometer (Abbott Laboratories, USA). Following the FBG measurement blood was collected from each mouse, using a tail milking technique, into a capillary tube. Capillary tubes were centrifuged in a hematocrit (BD Triac 0200) and the resultant plasma transferred to an eppendorff. This sample, labelled as t=0hr, was frozen at −80 to allow later measurement of insulin. At 11:30 am each animal was dosed with 1.5 g/kg of glucose, then blood glucose was measured at t=15, 30, 60, 90 and 120 minutes after glucose load. At the end of the OGTT blood was collected for a t=2 hr insulin determination as described above. Animals were terminated following the last blood collection and tissues and blood harvested for other endpoint determinations.

Fasting blood glucose values and glucose measurements taken during the OGTT were averaged and graphed (GraphPad Prism, GraphPad Software, LA Jolla, Calif.). The area under the curve (AUC) was calculated for each individual animal. Plasma insulin levels were determined using an Ultrasensitive Insulin ELISA (ALPCO, Salem, N.H.). The HOMA-IR (homeostatic model assessment-insulin resistance) was calculated using the following formula: (FPI (µU/L)×FPG (mmol/L))/22.5, where FPI and FPG denote Fasting Plasma Insulin and Fasting Plasma Glucose, respectively. Insulin data was also represented in GraphPad Prism format. Statistical analysis was performed using one-way ANOVA followed by the appropriate post-test. Significance was accepted when $p<0.05$. Data are presented as mean and S.E.M.

Figure 17A:
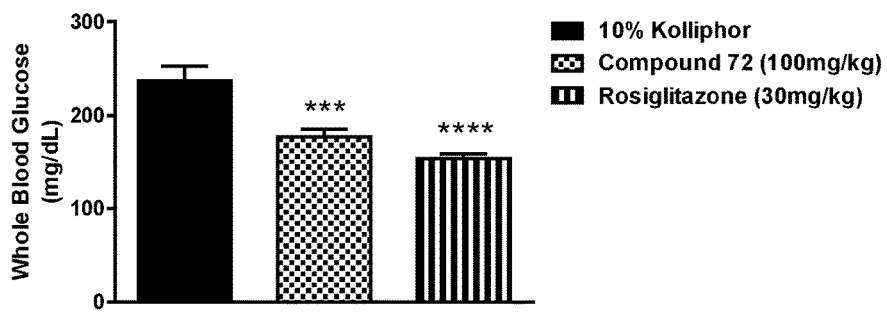
FIGS. 17A-C are a series of graphs showing the effect of Compound 72 on glucose metabolism in C57/Bl6J DIO mice. Compound 72 (100 mg/kg, PO), 10% kolliphor (control), or rosiglitazone (30 mg/kg) was administered for 7 days.
Figure 17B:
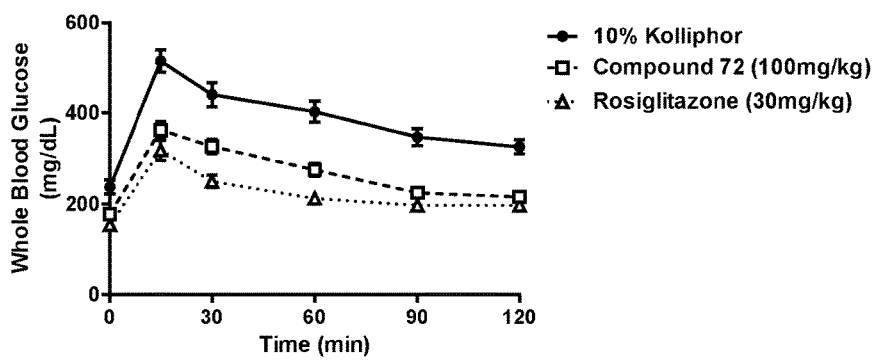
Figure 17C:
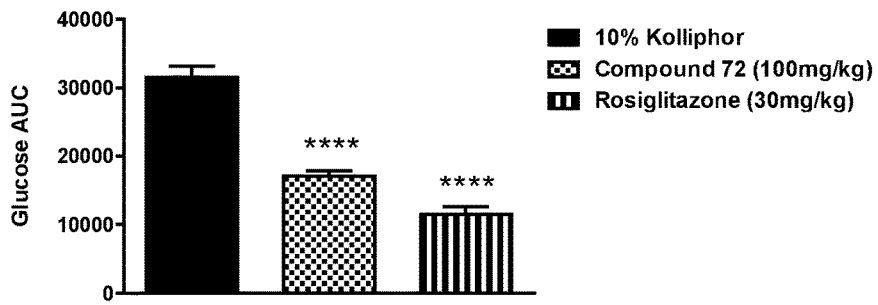

Administration of Compound 72 (100 mg/kg, PO) for 7 days to C57/Bl6J DIO mice resulted in a significant reduction in fasting blood glucose levels compared to vehicle control (237.2+/−15.29 mg/dL to 177.1+/−8.28 mg/dL; FIG. 17A). During the course of the OGTT measurement, Compound 72 treated animals were much lower than the vehicle control group (FIG. 17B). The AUC calculated from the OGTT showed that Compound 72 administration resulted in a significant reduction in glucose excursion (31511+/−1670 to 17055+/−769.1; FIG. 17C). Rosiglitazone, used as a positive control for the animal model, reduced fasting blood glucose to 153.9+/−5.05 mg/dL and the glucose AUC to 11500+/−1104 units.

Figure 18A:
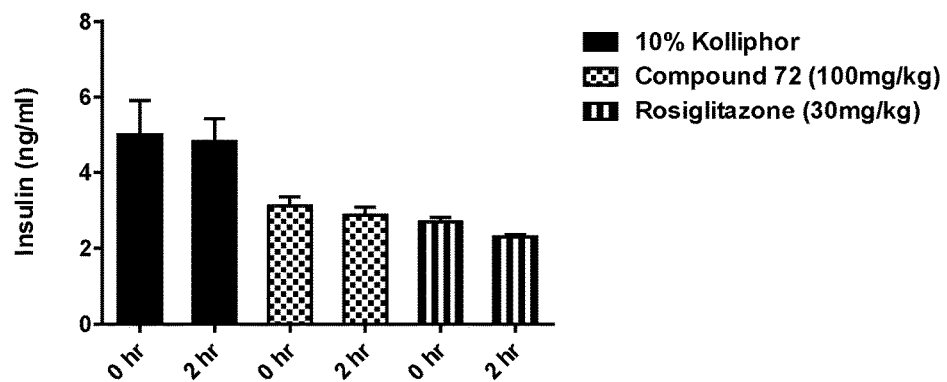
FIGS. 18A-B are a series of graphs showing the effect of Compound 72 on insulin levels in C57/Bl6J DIO mice. Compound 72 (100 mg/kg, PO), 10% kolliphor (control), or rosiglitazone (30 mg/kg) was administered for 7 days.
Figure 18B:
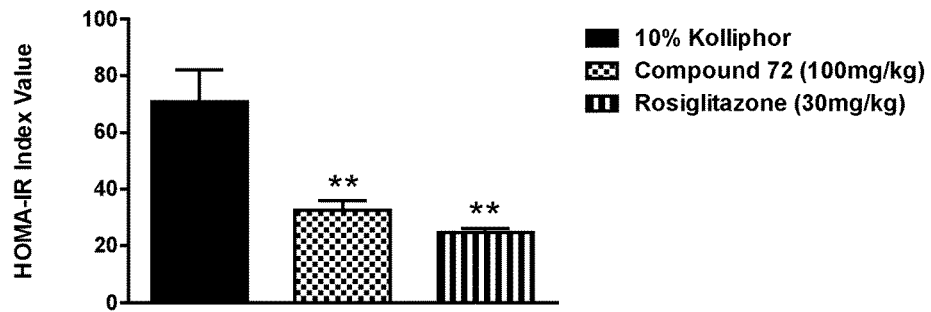

Plasma insulin measurements were made from the samples taken at t=0 and t=2 hr, and are shown in FIG. 18A. Insulin was reduced following treatment with Compound 72 at both t=0 (vehicle: 5.00+/−0.92, 100 mg/kg: 3.12+/−0.24, ng/mL) and t=2 hr (vehicle: 4.82+/−0.60, 100 mg/kg: 2.88+/−0.21 ng/mL). The HOMA-IR was significantly reduced following Compound 72 administration (vehicle: 70.76+/−11.30, 100 mg/kg: 32.54+/−3.37 units; FIG. 18B). Rosiglitazone (30 mg/kg) reduced insulin at t=0 and t=2 hr (to 2.70+/−0.12 and 2.30+/−0.06 ng/mL, respectively) and significantly reduced HOMA-IR (to 24.60+/−1.42 units).

Example 11: Effect of Compound 72 on the Development of Cortisone Induced Insulin Resistance in Rats Repeated administration of cortisone to rats for 6 days induces a significant decrease in body weight which is associated with a significant rise in plasma insulin and glucose. These effects are mediated via cortisol generated by 11-βHSD1 activity. Glucocorticoid receptor antagonists such as mifepristone ameliorate the effects of cortisol on insulin resistance. The aim of these experiments was to determine the effect of Compound 72 on the development of cortisone-induced insulin resistance in the rat.

Animals were dosed with cortisone (30 mg/kg sc qd) in combination with test compounds for 6 days and then terminated 27 hours after the final dose of cortisone. A reference standard (Mifepristone) was also included. Cortisone 21-acetate (Sigma C-3130) was supplied by RenaSci and administered using a dose volume of 5 ml/kg via the subcutaneous route as a fine suspension in 1% methylcellulose. Compound 72 (50 mg/kg in 10% Kolliphor in water) was dosed QD using a dose volume of 5 ml/kg via oral gavage. Mifepristone (Sigma M8046) was provided by RenaSci.

Glucose and insulin determinations were performed on plasma samples obtained from a tail vein bleed taken after a 12 h fast, approximately 27 h after the last cortisone dose. Animals were then terminated and a terminal (cardiac) blood sample taken from which plasma was prepared.

Thirty four male Sprague Dawley rats (weight range 200-250 g) were ordered from Charles River, Margate, Kent, UK. Rats were group housed on a normal light/dark cycle (lights on: 07:00-19:00 h) with free access to a standard pelleted rat diet and tap water at all times. Animals were accustomed to these conditions for 2 weeks before experimentation. Subsequently, animals underwent a 3 day baseline period during which they were dosed once daily with vehicle at t=0 h (07:00). This procedure has been found to reduce the incidence of stress-related effects in studies. All drugs were administered for 6 days as shown in Table 2 below. Body weight was recorded immediately before dosing began at 07:00 (t=0 h). Cortisone was administered via the subcutaneous route (sc) whilst Compound 72 and mifepristone were administered orally, via gavage, immediately after cortisone administration at t=0 h.

TABLE 2

| Group | Treatment(t = 0 h; 07:00) | | n |
|---|---|---|---|
| A | Vehicle (1% methylcellulose; 5 ml/kg sc) | Vehicle (5 ml/kg po) | 8 |
| B | Cortisone (30 mg/kg sc) | Vehicle (5 ml/kg po) | 8 |
| C | Cortisone (30 mg/kg sc) | Compound72 (50 mg/kg po) | 8 |
| D | Cortisone (30 mg/kg sc) | Mifepristone (30 mg/kg po) | 8 |

On Day 6 of dosing rats were fasted for 12 h beginning at 22:30 (timed to coincide with the Day 7 termination). On Day 7 rats were administered vehicle but not cortisone (sc) followed by oral administration of vehicle/Compound 72/mifepristone as usual at 07:00. At 10:30 on Day 7, 27 h after the final dose of cortisone, a blood sample (300 μl) was taken from the lateral tail vein into tubes containing EDTA (Sarstedt 16.444). The blood was centrifuged and resultant plasma aliquot stored at −75° C. The animals were euthanized by $CO_2$ asphyxiation followed by cervical dislocation. Terminal blood (approximately 10 ml) was collected by cardiac puncture into tubes containing EDTA (Sarstedt 5 ml 32.332) and then centrifuged and plasma stored at −75° C. The tail vein plasma was analyzed for glucose (n=2) using a commercial clinical reagent (Thermoelectron Infinity glucose reagent (TR15421) and for insulin (n=1) using the Mercodia ultrasensitive rat insulin rat ELISA (10-1251-10).

Plasma glucose and insulin were analyzed by robust regression or general linear model with treatment as a factor and bleeding order and baseline body weight as covariates. A log transformation was used if appropriate. Appropriate multiple comparison tests (two-tailed) were used to determine significant differences from the vehicle group and from the Cortisone group. P<0.05 was considered to be statistically significant.

Figure 19A:
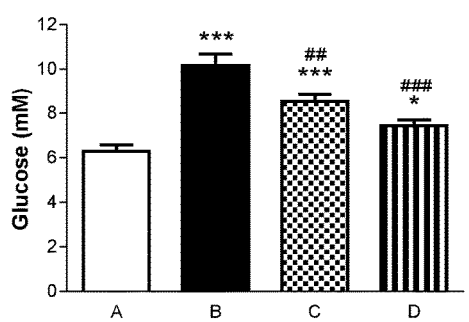
FIGS. 19A-B are a series of graphs showing the effect of Compound 72 on a rat model of cortisone-induced insulin resistance. Cortisone (30 mg/kg, SC) was administered with either vehicle, Compound 72 (50 mg/kg, PO) or mifepristone (30 mg/kg, PO) for 7 days.
Figure 19B:
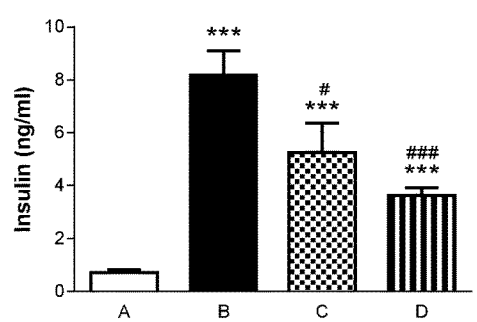

Administration of Compound 72 to rats significantly reduced the increase in plasma glucose and insulin caused by cortisone administration treatment. Plasma glucose levels were increased from 6.28+/−0.30 mM to 10.17+/−0.51 mM following treatment with cortisone, which was significantly reduced by Compound 72 (50 mg/kg) to 8.55+/−0.3 mM (p<0.01; Mean and S.E.M; FIG. 19A). Plasma insulin levels were increased from 0.70+/−0.11 ng/mL to 8.19+/−0.91 ng/mL upon cortisone treatment, which was reduced by Compound 72 (50 mg/kg) to 5.24+/−1.1 llng/mL (p<0.05; data represented as Mean and S.E.M; FIG. 19B). Mifepristone, used as a positive control for the animal model, significantly reduced plasma glucose (FIG. 19A) and plasma insulin (FIG. 19B) to 7.43+/−0.27 ng/mL and 3.62+/−0.29 ng/mL, respectively.

Figure 20:
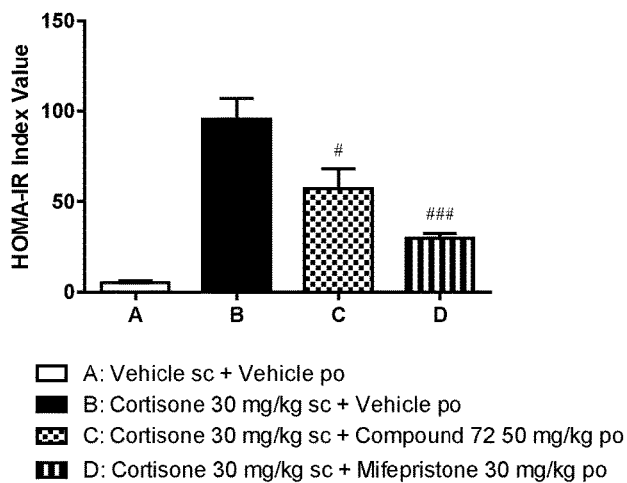
FIG. 20 is a graph showing the effect of Compound 72 (50 mg/kg, PO), administered for 7 days on HOMA-IR in a rat model of cortisone-induced insulin resistance. Cortisone (30 mg/kg, SC) was administered with either vehicle, Compound 72 (50 mg/kg, PO) or mifepristone (30 mg/kg, PO) for 7 days.

HOMA-IR values were calculated as described in Compound 9, and the data is shown in FIG. 20. Cortisone treatment increased HOMA-IR to 95.57+/−11.4 units compared with the vehicle: vehicle control group (5.27+/−1.04 units). Administration of Compound 72 (50 mg/kg) and mifepristone significantly reduced the HOMA-IR value in insulin resistant rats to 56.94+/−11.18 units and 29.99+/−2.54 units, respectively.

Example 12: Pharmacokinetic (PK) Analysis of Compound 9 and Compound 72

Male ICR mice (weighing 30-40 g, Charles River Laboratories) were used for the experiment with n=3 mice for each experimental group (27 mice total for the study). Mice were dosed with Cry Modulator Compound 9 or Compound 72 (50 mg/kg, P.O; dose volume 5 ml/kg, in 10% Kolliphor). Blood and liver tissue were collected at the following time points after administration: 15, 30, 60, 90 minutes, 3, 6, 12 and 24 hours. A control group of animals (TO) was also sampled. Animals were euthanized with $CO_2$ and the blood collected from the heart using cardiac puncture, transferred to an EDTA tube, and then centrifuged at 5400 rpm for 5 minutes at 4° C. The resultant plasma was frozen using dry ice and then stored at −80° C. until ready for assay. Liver tissue was removed from each animal, 0.5 g was collected in an eppendorff, frozen and submitted for pharmacokinetic measurement. Plasma and liver tissue from each animal was submitted to a CRO for measurement of compound levels, using LC/MS/MS and comparing to a standard curve of known compound amounts in both plasma and liver. Raw data was analyzed using WinNonLin for PK parameters (Cmax, Tmax, elimination $t^{1/2}$, MRT (mean residence time), AUC (area under the curve)–(0-last and % extrapolated).

Male SD rats (weighing 250-300 g, Charles River Laboratories) were used for the experiment with n=4 rats for each experimental group. Rats were dosed with Compound 72 (50 mg/kg, P.O; dose volume 5 ml/kg, in 10% Kolliphor). Blood was collected at the following time points after administration: 15, 30, 60, 90 minutes, 3, 6, 12 and 24 hours. A pre-dose sample was also collected. Animals were cannulated by technical staff at Charles River, prior to delivery at Reset. Whole blood (0.3 ml) was collected from a cannula in the right common jugular vein at each time-point. The whole blood was transferred to an EDTA tube, and then centrifuged at 5400 rpm for 5 minutes at 4° C. The resultant plasma was frozen using dry ice and then stored at −80° C. until ready for assay. 0.9% Sodium Chloride (0.3 ml) was administered for fluid replenishment after each blood draw. 0.1 ml of Sodium Heparin (500 IU/ml) was used as a lock solution after the 12 hr time-point. Samples were assayed as described above. Tables 3 and 4 summarize the results from the analyses.

Example 13: Effect of Increasing Dosages of Compound 72 in a Diet-Induced Obesity Mouse Model The effect of Compound 72 was assessed over increasing doses in a diet-induced obesity (DIO) mouse model of type II diabetes.

Male C57/Bl6J DIO mice were obtained from The Jackson Laboratory (Sacramento, Calif.). Mice were group housed on a normal light/dark cycle (lights on: 07:00-19:00 h) with ad libitum access to high fat diet (D12492 (60 kcal % fat), Research Diets, Inc.) and water. Animals were accustomed to these conditions for at least 2 weeks before experimentation and used at approximately 26 weeks of age. Mice were dosed with vehicle (10% Kolliphor, Sigma-Aldrich), Compound 72 (10, 30 or 100 mg/kg in 10% Kolliphor in water) or Rosiglitazone (30 mg/kg in 10% Kolliphor in water) at a dose volume of 5 ml/kg, QD, via oral gavage, at ZTO (7:00 am) for seven days. The experimental methods performed were the same as those detailed in Example 10.

Figure 22A:
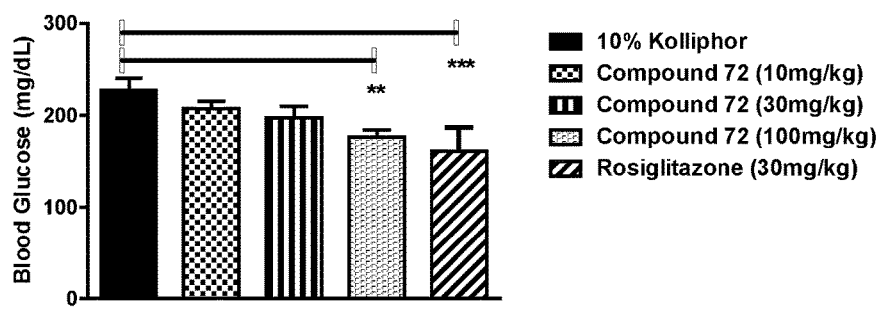
FIGS. 22A-C are a series of graphs showing the effect of increasing dosages of Compound 72 (10 mg/kg, 30 mg/kg, and 100 mg/kg) on glucose metabolism in DIO mice. Compound 72 (100 mg/kg, PO), 10% kolliphor (control), or Rosiglitazone (30 mg/kg) was administered for 7 days.
Figure 22B:
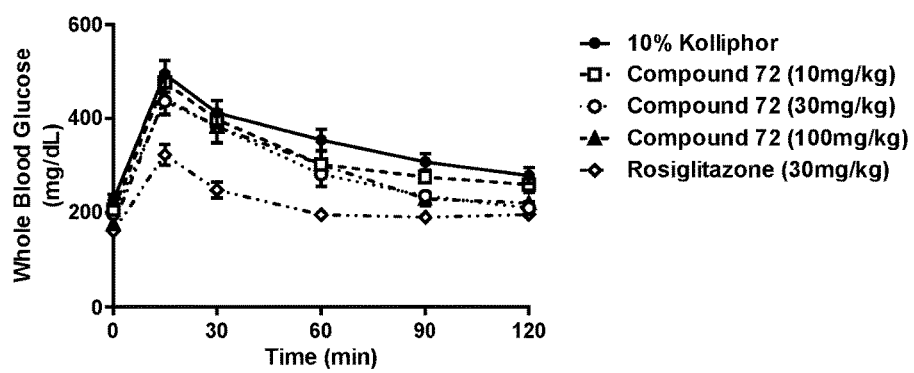

Administration of Compound 72, at ascending doses, for 7 days to C57/Bl6J DIO mice resulted in a reduction in fasting blood glucose levels compared to vehicle control which reached significance at 100 mg/kg (vehicle control: 226.9+/−13.11 mg/dL, 10 mg/kg: 206.8+/−8.36 mg/dL, 30 mg/kg: 197.5+/−12.06 mg/dL, 100 mg/kg: 176.3+/−7.83 mg/dL, FIG. 22A. During the course of the OGTT measurement, Compound 72 treated animals demonstrated a reduction in glucose excursion following a glucose load (FIG. 22B. The area under the curve calculated from the OGTT showed that Compound 72 administration reduced the glucose AUC, demonstrating significance at 30 and 100 mg/kg (vehicle: 26090+/−1917, 10 mg/kg: 22563+/−1224, 30 mg/kg: 19033+/−1934, 100 mg/kg: 19502+/−2404 units;

TABLE 3

PK Parameters of Compound 9 and Compound 72

| Compound | | | Cmax (ng/ml) | Tmax (hr) | Elimination T1/2 (hr) | MRT (0-last, hr) | MRT (0-last; ng · hr/mL) | AUC (total; ng · hr/mL) | % AUC extrapolated |
|---|---|---|---|---|---|---|---|---|---|
| Compound 9 | Plasma | Mouse | 893 | 0.25 | 3.18 | 3.92 | 1920 | 1930 | 0.564 |
| Compound 9 | Liver | Mouse | 33000 | 0.25 | 3.12 | 1.50 | 26800 | 26800 | 0.142 |
| Compound 72* | Plasma | Mouse | 1149 +/− 108.7 | 0.25-0.5 | 3.13 +/− 0.24 | 5.30 +/− 0.39 | 4158 +/− 249.7 | 4236 +/− 264.1 | 1.74 +/− 1.20 |
| Compound 72* | Liver | Mouse | 7890 +/− 972.6 | 0.25-0.5 | 3.40 +/− 0.28 | 4.74 +/− 0.51 | 17822 +/− 2187 | 17961 +/− 2184 | 0.85 +/− 0.24 |
| Compound 72 | Plasma | Rat | 7098 | 1.7 | 1.87 | 4.94 | 57933 | 57952 | 3.3 |

*Denotes data from 4 experiments, shown as Mean and S.E.M.

TABLE 4

Unbound Exposure Data

| Compound | Cmax (plasma) (ng/ml) | Cmax UB (plasma) (ng/ml) | Cmax (liver) (ng/ml) | Cmax UB (liver) (ng/ml) | Total Plasma AUC (0-last) | Unbound Plasma AUC (0-last) | Total Liver AUC (0-last) | Unbound Liver AUC (0-last) |
|---|---|---|---|---|---|---|---|---|
| Compound 9 | 893 | 26.8 | 33000 | 990 | 1910 | 57 | 26800 | 804 |
| Compound 72 (m)* | 1149 +/− 108.7 | 41.93 +/− 3.97 | 7890 +/− 972.6 | 288.0 +/− 35.51 | 4158 +/− 249.7 | 151.5 +/− 9.11 | 17822 +/− 2187 | 650.5 +/− 79.81 |
| Compound 72 (r) | 7098 | 277 | | | 57933 | 2259 | | |

*denotes data from 4 experiments, shown as Mean and S.E.M.

Figure 22C:
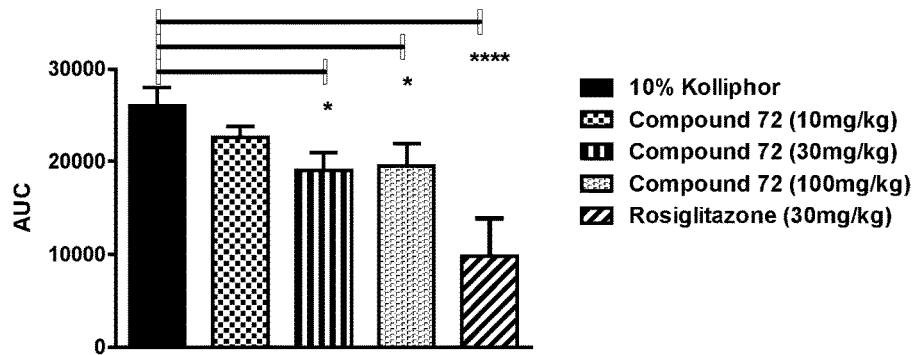

FIG. 22C). Rosiglitazone, used as a positive control for the animal model, significantly inhibited fasting blood glucose (from 226.9+/−13.11 to 161.1+/−8.06 mg/dL; FIG. 22A), and glucose AUC (from 26090+/−1917 to 9858+/−1281 units; FIG. 22C.

The invention claimed is:
1. A compound of formula I

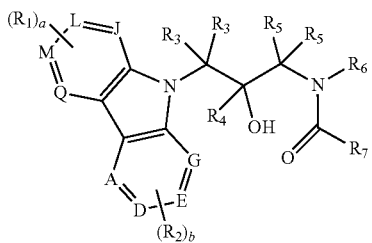

I or a pharmaceutically acceptable salt or hydrate thereof, wherein each of A, D, E, G, J, L, M, and Q is carbon;

each of $R_1$ and $R_2$ is independently selected from the group consisting of hydrogen, halo, cyano, nitro, —$CF_3$, —$CHF_2$, —$CH_2F$, trifluoromethoxy, azido, hydroxyl, ($C_1$-$C_6$)alkoxy, ($C_1$-$C_6$)alkyl, ($C_2$-$C_6$)alkenyl, ($C_2$-$C_6$)alkynyl, —(C=O)—$R_8$, —(C=O)—O—$R_8$, —O—(C=O)—$R_8$, —$NR_8$(C=O)—$R_{10}$, —(C=O)—$NR_8R_9$, —$NR_8R_9$, —$NR_8OR_9$, —S(O)$_c$$NR_8R_9$, —S(O)$_d$($C_1$-$C_6$)alkyl, —O—SO$_2$—$R_8$, $NR_8$—S(O)$_c$, —(CR$_8$R$_9$)$_d$(3-10)-membered cycloalkyl, —(CR$_8$R$_9$)$_e$($C_6$-$C_{10}$)aryl, —(CR$_8$R$_9$)$_e$(4-10)-membered heterocyclyl, —(CR$_8$R$_9$)$_f$(C=O)(CR$_8$R$_9$)$_e$($C_6$-$C_{10}$)aryl, —(CR$_8$R$_9$)$_f$(C=O)(CR$_8$R$_9$)$_e$(4-10)-membered heterocyclyl, —(CR$_8$R$_9$)$_e$O(CR$_8$R$_9$)$_f$($C_6$-$C_{10}$)aryl, —(CR$_8$R$_9$)$_e$O(CR$_8$R$_9$)$_f$(4-10)-membered heterocyclyl, —(CR$_8$R$_9$)$_f$S(O)$_d$(CR$_8$R$_9$)$_e$($C_6$-$C_{10}$)aryl, and —(CR$_8$R$_9$)$_f$S(O)$_d$(CR$_8$R$_9$)$_e$(4-10)-membered heterocyclyl;

each of $R_3$ and $R_5$ is independently selected from the group consisting of hydrogen, cyano, —$CF_3$, —$CHF_2$, —$CH_2F$, ($C_1$-$C_6$)alkyl, ($C_2$-$C_6$)alkenyl, ($C_2$-$C_6$)alkynyl, —(C=O)—$R_8$, —(C=O)—O-$R_8$, —(C=O)—$NR_8R_9$, —S(O)$_c$$NR_8R_9$, —S(O)$_d$($C_1$-$C_8$)alkyl, —(CR$_8$R$_9$)$_d$(3-10)-membered cycloalkyl, —(CR$_8$R$_9$)$_e$($C_6$-$C_{10}$)aryl, —(CR$_8$R$_9$)$_e$(4-10)-membered heterocyclyl, —(CR$_8$R$_9$)$_f$(C=O)(CR$_8$R$_9$)$_e$($C_6$-$C_{10}$)aryl, —(CR$_8$R$_9$)$_f$(C=O)(CR$_8$R$_9$)$_e$(4-10)-membered heterocyclyl, —(CR$_8$R$_9$)$_e$O(CR$_8$R$_9$)$_f$($C_6$-$C_{10}$)aryl, —(CR$_8$R$_9$)$_e$O(CR$_8$R$_9$)$_f$(4-10)-membered heterocyclyl, —(CR$_8$R$_9$)$_f$S(O)$_d$(CR$_8$R$_9$)$_e$($C_6$-$C_{10}$)aryl, and —(CR$_8$R$_9$)$_f$S(O)$_d$(CR$_8$R$_9$)$_e$(4-10)-membered heterocyclyl;

wherein each of the $R_3$ groups are optionally linked to each other as a 4-12 membered mono- or bicyclic ring;

wherein each of the $R_5$ groups are optionally linked to each other as a 4-12 membered mono- or bicyclic ring;

$R_4$ is selected from the group consisting of hydrogen, —$CF_3$, —$CHF_2$, —$CH_2F$, ($C_1$-$C_6$)alkyl, ($C_2$-$C_6$)alkenyl, ($C_2$-$C_6$)alkynyl, —(C=O)—$R_8$, —(C=O)—O—$R_8$, —(C=O)—$NR_8R_9$, —(CR$_8$R$_9$)$_d$(3-10)-membered cycloalkyl, —(CR$_8$R$_9$)$_e$($C_6$-$C_{10}$)aryl, —(CR$_8$R$_9$)$_e$(4-10)-membered heterocyclyl, —(CR$_8$R$_9$)$_f$(C=O)(CR$_8$R$_9$)$_e$($C_6$-$C_{10}$)aryl, —(CR$_8$R$_9$)$_f$(C=O)(CR$_8$R$_9$)$_e$(4-10)-membered heterocyclyl, —(CR$_8$R$_9$)$_e$O(CR$_8$R$_9$)$_f$($C_6$-$C_{10}$)aryl, —(CR$_8$R$_9$)$_e$O(CR$_8$R$_9$)$_f$(4-10)-membered heterocyclyl, —(CR$_8$R$_9$)$_f$S(O)$_d$(CR$_8$R$_9$)$_e$($C_6$-$C_{10}$)aryl, and —(CR$_8$R$_9$)$_f$S(O)$_d$(CR$_8$R$_9$)$_e$(4-10)-membered heterocyclyl;

wherein $R_6$ and $R_7$ are linked to each other as a piperidinone ring, optionally substituted with one or more halo, ($C_1$-$C_6$)alkyl, ($C_3$-$C_{10}$)cycloalkyl, or ($C_6$-$C_{10}$)aryl;

each of $R_8$, $R_9$ and $R_{10}$ are independently selected from the group consisting of hydrogen, ($C_1$-$C_6$)alkyl, —(CR$_{11}$R$_{12}$)$_e$(3-10)-membered cycloalkyl, —(CR$_{11}$R$_{12}$)$_g$($C_6$-$C_{10}$)aryl, and —(CR$_{11}$R$_{12}$)$_g$(4-10)-membered heterocyclyl;

any carbon atoms of the ($C_1$-$C_6$)alkyl, the (3-10)-membered cycloalkyl, the ($C_6$-$C_{10}$)aryl and the (4-10)-membered heterocyclyl of the foregoing $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{15}$, and $R_{16}$ are independently optionally substituted with 1 to 3 $R_{14}$ substituents each independently selected from the group consisting of halo, cyano, nitro, —$CF_3$, —$CHF_2$, —$CH_2F$, trifluoromethoxy, azido, hydroxyl, —O—$R_{15}$, ($C_1$-$C_6$)alkoxy, ($C_1$-$C_6$)alkyl, ($C_2$-$C_6$)alkenyl, ($C_2$-$C_6$)alkynyl, —(C=O)—$R_{11}$, —(C=O)—$R_{15}$, —(C=O)—O—$R_{11}$, —(C=O)—O—$R_{15}$, —O—(C=O)—$R_{11}$, —O—(C=O)—$R_{15}$, —$NR_{11}$(C=O)—$R_{13}$, —(C=O)—$NR_{11}R_{12}$, —(C=O)—$NR_{11}R_{15}$, —$NR_{11}R_{12}$, —$NR_{11}R_{15}$, —$NR_{11}OR_{12}$, —$NR_{11}OR_{15}$, —S(O)$_c$$NR_{11}R_{12}$, —S(O)$_c$$NR_{11}R_{15}$, —S(O)$_d$($C_1$-$C_6$)alkyl, —S(O)$_d$$R_{15}$, —O—SO$_2$—$R_{11}$, —O—SO$_2$—$R_{15}$, —$NR_{11}$—S(O)$_c$, —$NR_{15}$—S(O)$_c$, —(CR$_{11}$R$_{12}$)$_e$(3-10)-membered cycloalkyl, —(CR$_{11}$R$_{12}$)$_e$($C_6$-$C_{10}$)aryl, —(CR$_{11}$R$_{12}$)$_e$(4-10)-membered heterocyclyl, —(CR$_{11}$R$_{12}$)$_f$(C=O)(CR$_{11}$R$_{12}$)$_e$($C_6$-$C_{10}$)aryl, —(CR$_{11}$R$_{12}$)$_f$(C=O)(CR$_{11}$R$_{12}$)$_e$(4-10)-membered heterocyclyl, —(CR$_{11}$R$_{12}$)$_e$O(CR$_{11}$R$_{12}$)$_f$($C_6$-$C_{10}$)aryl, —(CR$_{11}$R$_{12}$)$_e$O(CR$_{11}$R$_{12}$)$_f$(4-10)-membered heterocyclyl, —(CR$_{11}$R$_{12}$)$_f$S(O)$_d$(CR$_{11}$R$_{12}$)$_e$($C_6$-$C_{10}$)aryl, and —(CR$_{11}$R$_{12}$)$_f$S(O)$_d$(CR$_{11}$R$_{12}$)$_e$(4-10)-membered heterocyclyl;

any carbon atoms of the ($C_1$-$C_6$)alkyl, the (3-10)-membered cycloalkyl, the ($C_6$-$C_{10}$)aryl and the (4-10)-membered heterocyclyl of the foregoing $R_{14}$ are independently optionally substituted with 1 to 3 $R_{16}$ substituents each independently selected from the group consisting of halo, cyano, nitro, —$CF_3$, —$CHF_2$, —$CH_2F$, trifluoromethoxy, azido, (CH$_2$)$_e$OH, ($C_1$-$C_6$)alkoxy, ($C_1$-$C_6$)alkyl, ($C_2$-$C_6$)alkenyl, ($C_2$-$C_6$)alkynyl, —(C=O)—$R_{11}$, —(C=O)—$R_{15}$, —(C=O)—O—$R_{11}$, —(C=O)—O—$R_{15}$, —O—(C=O)—$R_{11}$, —O—(C=O)—$R_{15}$, —$NR_{11}$(C=O)—$R_{13}$, —(C=O)—$NR_{11}R_{12}$, —$NR_{11}R_{12}$, and —$NR_{11}R_{15}$; any nitrogen atoms of the (4-10)-membered heterocyclyl of the foregoing $R_1$, $R_2$, $R_3$, $R_4$, $R_8$, $R_6$, $R_7$, $R_8$, $R_9$, $R_{10}$, $R_{14}$, and $R_{15}$ are independently optionally substituted with ($C_1$-$C_6$)alkyl, ($C_2$-$C_6$)alkenyl, ($C_2$-$C_6$)alkynyl, —(C=O)—$R_{11}$, —(C=O)—O—$R_{11}$, —(C=O)—$NR_{11}R_{12}$, —(CR$_{11}$R$_{12}$)$_e$(3-10)-membered cycloalkyl, —(CR$_{11}$R$_{12}$)$_e$($C_6$-$C_{10}$)aryl, —(CR$_{11}$R$_{12}$)$_e$(4-10)-membered heterocyclyl, —(CR$_{11}$R$_{12}$)$_f$(C=O)(CR$_{11}$R$_{12}$)$_e$($C_6$-$C_{10}$)aryl, or —(CR$_{11}$R$_{12}$)$_f$(C=O)(CR$_{11}$R$_{12}$)$_e$(4-10)-membered heterocyclyl;

each $R_{11}$, $R_{12}$, and $R_{13}$ are independently hydrogen or ($C_1$-$C_6$)alkyl;

$R_{15}$ is —(CR$_{11}$R$_{12}$)$_e$(3-10)-membered cycloalkyl, —(CR$_{11}$R$_{12}$)$_e$($C_6$-$C_{10}$)aryl, or —(CR$_{11}$R$_{12}$)$_e$(4-10)-membered heterocyclyl;

a and b are each independently 1, 2, 3, or 4;
c is 1 or 2;

d is 0, 1, or 2; and e, f, and g are each independently 0, 1, 2, 3, 4, or 5.

2. The compound of claim 1, wherein each of $R_1$ and $R_2$ is hydrogen or halo.

3. The compound of claim 1, wherein each of $R_3$ and $R_5$ is independently selected from the group consisting of hydrogen or methyl.

4. The compound of claim 1, wherein $R_4$ is hydrogen or methyl.

5. The compound of claim 1, wherein the compound is selected from the group consisting of:
- 1-(3-(9H-carbazol-9-yl)-2-hydroxypropyl)piperidin-2-one (1);
- 1-(3-(3,6-difluoro-9H-carbazol-9-yl)-2-hydroxypropyl)piperidin-2-one (4);
- 1-(3-(3,6-difluoro-9H-carbazol-9-yl)-2-hydroxy-2-methylpropyl)piperidin-2-one (5);
- 1-(3-(3,6-difluoro-9H-carbazol-9-yl)-2-hydroxypropyl)-3-fluoropiperidin-2-one (11);
- 1-(3-(3,6-difluoro-9H-carbazol-9-yl)-2-hydroxy-2-methylpropyl)-3-fluoropiperidin-2-one (12);
- 1-(3-(3,6-difluoro-9H-carbazol-9-yl)-2-hydroxypropyl)-3,3-difluoropiperidin-2-one (13);
- 1-(3-(3,6-difluoro-9H-carbazol-9-yl)-2-hydroxy-2-methylpropyl)-3,3-difluoropiperidin-2-one (14);
- 1-(3-(3,6-difluoro-9H-carbazol-9-yl)-2-hydroxypropyl)-3,3-dimethylpiperidin-2-one (16);
- 1-(3-(3,6-difluoro-9H-carbazol-9-yl)-2-hydroxypropyl)-3-phenylpiperidin-2-one (19);
- 3-cyclohexyl-1-(3-(3,6-difluoro-9H-carbazol-9-yl)-2-hydroxypropyl)piperidin-2-one (20);
- 3-cyclohexyl-1-(3-(3,6-difluoro-9H-carbazol-9-yl)-2-hydroxy-2-methylpropyl)piperidin-2-one (21);
- 3-cyclopentyl-1-(3-(3,6-difluoro-9H-carbazol-9-yl)-2-hydroxypropyl)piperidin-2-one (23);
- 1-(3-(3,6-difluoro-9H-carbazol-9-yl)-2-hydroxypropyl)-3-ethylpiperidin-2-one (24);
- 1-(3-(3,6-difluoro-9H-carbazol-9-yl)-2-hydroxypropyl)-3-isopropylpiperidin-2-one (25);
- 1-(3-(3,6-difluoro-9H-carbazol-9-yl)-2-hydroxy-2-methylpropyl)-3-isopropylpiperidin-2-one (26);
- 1-(3-(3,6-difluoro-9H-carbazol-9-yl)-2-hydroxypropyl)-3-methylpiperidin-2-one (27);
- 1-(3-(3,6-difluoro-9H-carbazol-9-yl)-2-hydroxy-2-methylpropyl)-3-methylpiperidin-2-one (28);
- 1-(3-(3,6-difluoro-9H-carbazol-9-yl)-2-hydroxy-2-methylpropyl)-4-methylpiperidin-2-one (36);
- 1-(3-(3,6-difluoro-9H-carbazol-9-yl)-2-hydroxypropyl)-5-methylpiperidin-2-one (37);
- 1-(3-(3,6-difluoro-9H-carbazol-9-yl)-2-hydroxy-2-methylpropyl)-5-methylpiperidin-2-one (38);
- 1-(3-(3,6-difluoro-9H-carbazol-9-yl)-2-hydroxypropyl)-6-methylpiperidin-2-one (39);
- 1-(3-(3,6-difluoro-9H-carbazol-9-yl)-2-hydroxy-2-methylpropyl)-6-methylpiperidin-2-one (40);
- 1-(3-(3,6-difluoro-9H-carbazol-9-yl)-2-hydroxypropyl)-4-methylpiperidin-2-one (49);
- 3-cyclobutyl-1-(3-(3,6-difluoro-9H-carbazol-9-yl)-2-hydroxypropyl)piperidin-2-one (51);
- 3-cyclobutyl-1-(3-(3,6-difluoro-9H-carbazol-9-yl)-2-hydroxy-2-methylpropyl)piperidin-2-one (52);
- 1-(3-(3,6-difluoro-9H-carbazol-9-yl)-2-hydroxypropyl)-3-methoxypiperidin-2-one (57);
- 1-(3-(9H-carbazol-9-yl)-2-hydroxypropyl)-3-methoxypiperidin-2-one (60);
- 1-(3-(9H-carbazol-9-yl)-2-hydroxypropyl)-4-methylpiperidin-2-one (61);
- 1-(3-(9H-carbazol-9-yl)-2-hydroxypropyl)-5-methylpiperidin-2-one (62);
- 1-(3-(9H-carbazol-9-yl)-2-hydroxypropyl)-6-methylpiperidin-2-one (63);
- 1-(3-(9H-carbazol-9-yl)-2-hydroxypropyl)-3-methylpiperidin-2-one (64);
- 1-(3-(9H-carbazol-9-yl)-2-hydroxy-2-methylpropyl)piperidin-2-one (66);
- 1-(3-(9H-carbazol-9-yl)-2-hydroxypropyl)-3,3-difluoropiperidin-2-one (69);
- 1-(3-(9H-carbazol-9-yl)-2-hydroxypropyl)-3-fluoropiperidin-2-one (70);
- (S)-1-((R)-3-(9H-carbazol-9-yl)-2-hydroxypropyl)-5-methylpiperidin-2-one (129);
- (S)-1-((R)-3-(3,6-difluoro-9H-carbazol-9-yl)-2-hydroxypropyl)-5-methylpiperidin-2-one (130);
- (R)-1-((R)-3-(9H-carbazol-9-yl)-2-hydroxypropyl)-5-methylpiperidin-2-one (131);
- (S)-1-((S)-3-(9H-carbazol-9-yl)-2-hydroxypropyl)-5-methylpiperidin-2-one (132);
- (R)-1-((S)-3-(9H-carbazol-9-yl)-2-hydroxypropyl)-5-methylpiperidin-2-one (133); and
- (R)-1-((R)-3-(3,6-difluoro-9H-carbazol-9-yl)-2-hydroxypropyl)-5-methylpiperidin-2-one (134); or a pharmaceutically acceptable salt or hydrate thereof.

6. A compound of formula I or a pharmaceutically acceptable salt or hydrate thereof, wherein each of A, D, E, G, J, L, M, and Q is carbon;

each of $R_1$ and $R_2$ is fluoro;

each of $R_3$ and $R_5$ is independently selected from the group consisting of hydrogen, cyano, —CF$_3$, —CHF$_2$, —CH$_2$F, (C$_1$-C$_6$)alkyl, (C$_2$-C$_6$)alkenyl, (C$_2$-C$_6$)alkynyl, —(C═O)—R$_8$, —(C═O)—O—R$_8$, —(C═O)—NR$_8$R$_9$, —S(O)$_c$NR$_8$R$_9$, —S(O)$_d$(C$_1$-C$_8$)alkyl, —(CR$_8$R$_9$)$_d$(3-10)-membered cycloalkyl, —(CR$_8$R$_9$)$_e$(C$_6$-C$_{10}$)aryl, —(CR$_8$R$_9$)$_e$(4-10)-membered heterocyclyl, —(CR$_8$R$_9$)$_f$(C═O)(CR$_8$R$_9$)$_e$(C$_6$-C$_{10}$)aryl, —(CR$_8$R$_9$)$_f$(C═O)(CR$_8$R$_9$)$_e$(4-10)-membered heterocyclyl, —(CR$_8$R$_9$)$_e$O(CR$_8$R$_9$)$_f$(C$_6$-C$_{10}$)aryl, —(CR$_8$R$_9$)$_e$O(CR$_8$R$_9$)$_f$(4-10)-membered heterocyclyl, —(CR$_8$R$_9$)$_f$S(O)$_d$(CR$_8$R$_9$)$_e$(C$_6$-C$_{10}$)aryl, and —(CR$_8$R$_9$)$_f$S(O)$_d$(CR$_8$R$_9$)$_e$(4-10)-membered heterocyclyl;

wherein each of the $R_3$ groups are optionally linked to each other as a 4-12 membered mono- or bicyclic ring;

wherein each of the $R_5$ groups are optionally linked to each other as a 4-12 membered mono- or bicyclic ring;

$R_4$ is selected from the group consisting of hydrogen, —CF$_3$, —CHF$_2$, —CH$_2$F, (C$_1$-C$_6$)alkyl, (C$_2$-C$_6$)alkenyl, (C$_2$-C$_6$)alkynyl, —(C═O)—R$_8$, —(C═O)—O—R$_8$, —(C═O)—NR$_8$R$_9$, —(CR$_8$R$_9$)$_d$(3-10)-membered cycloalkyl, —(CR$_8$R$_9$)$_e$(C$_6$-C$_{10}$)aryl, —$(CR_8R_9)_e$(4-10)-membered heterocyclyl, —$(CR_8R_9)_f(C=O)(CR_8R_9)_e(C_6$-$C_{10})$aryl, —$(CR_8R_9)_f$ $(C=O)(CR_8R_9)_e$(4-10)-membered heterocyclyl, —$(CR_8R_9)_e O(CR_8R_9)_f(C_6$-$C_{10})$aryl, —$(CR_8R_9)_e O$ $(CR_8R_9)_f$(4-10)-membered heterocyclyl, —$(CR_8R_9)_f$ $S(O)_d(CR_8R_9)_e(C_6$-$C_{10})$aryl, and —$(CR_8R_9)_f S(O)_d$ $(CR_8R_9)_e$(4-10)-membered heterocyclyl;

a wherein $R_6$ and $R_7$ are linked to each other as saturated pyrimidinone ring, optionally substituted with one or more halo, $(C_1$-$C_6)$alkyl, $(C_3$-$C_{10})$cycloalkyl, or $(C_6$-$C_{10})$aryl;

each of $R_8$, $R_9$ and $R_{10}$ are independently selected from the group consisting of hydrogen, $(C_1$-$C_6)$alkyl, —$(CR_{11}R_{12})_e$(3-10)-membered cycloalkyl, —$(CR_{11}R_{12})_g(C_6$-$C_{10})$aryl, and —$(CR_{11}R_{12})_g$(4-10)-membered heterocyclyl;

any carbon atoms of the $(C_1$-$C_6)$alkyl, the (3-10)-membered cycloalkyl, the $(C_6$-$C_{10})$aryl and the (4-10)-membered heterocyclyl of the foregoing $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{15}$, and $R_{16}$ are independently optionally substituted with 1 to 3 $R_{14}$ substituents each independently selected from the group consisting of halo, cyano, nitro, —$CF_3$, —$CHF_2$, —$CH_2F$, trifluoromethoxy, azido, hydroxyl, —O—$R_{15}$, $(C_1$-$C_6)$alkoxy, $(C_1$-$C_6)$alkyl, $(C_2$-$C_6)$alkenyl, $(C_2$-$C_6)$ alkynyl, —(C=O)—$R_{11}$, —(C=O)—$R_{15}$, —(C=O)—O—$R_{11}$, —(C=O)—O—$R_{15}$, —O—(C=O)—$R_{11}$, —O—(C=O)—$R_{15}$, —$NR_{11}$(C=O)—$R_{13}$, —(C=O)—$NR_{11}R_{12}$, —(C=O)—$NR_{11}R_{15}$, —$NR_{11}R_{12}$, —$NR_{11}R_{15}$, —$NR_{11}OR_{12}$, —$NR_{11}OR_{15}$, —$S(O)_c NR_{11}R_{12}$, —$S(O)_c NR_{11}R_{15}$, —$S(O)_d(C_1$-$C_6)$ alkyl, —$S(O)_d R_{15}$, —O—$SO_2$—$R_{11}$, —O—$SO_2$—$R_{15}$, —$NR_{11}$—$S(O)_c$—, —$NR_{15}$—$S(O)_c$—, —$(CR_{11}R_{12})_e$ (3-10)-membered cycloalkyl, —$(CR_{11}R_{12})_e(C_6$-$C_{10})$ aryl, —$(CR_{11}R_{12})_e$(4-10)-membered heterocyclyl, —$(CR_{11}R_{12})_f(C=O)(CR_{11}R_{12})_e(C_6$-$C_{10})$aryl, —$(CR_{11}R_{12})_f(C=O)(CR_{11}R_{12})_e$(4-10)-membered heterocyclyl, —$(CR_{11}R_{12})_e O(CR_{11}R_{12})_f(C_6$-$C_{10})$aryl, —$(CR_{11}R_{12})_e O(CR_{11}R_{12})_f$(4-10)-membered heterocyclyl, —$(CR_{11}R_{12})_f S(O)_d(CR_{11}R_{12})_e(C_6$-$C_{10})$aryl, and —$(CR_{11}R_{12})_f S(O)_d(CR_{11}R_{12})_e$(4-10)-membered heterocyclyl;

any carbon atoms of the $(C_1$-$C_6)$alkyl, the (3-10)-membered cycloalkyl, the $(C_6$-$C_{10})$aryl and the (4-10)-membered heterocyclyl of the foregoing $R_{14}$ are independently optionally substituted with 1 to 3 $R_{16}$ substituents each independently selected from the group consisting of halo, cyano, nitro, —$CF_3$, —$CHF_2$, —$CH_2F$, trifluoromethoxy, azido, $(CH_2)_e$OH, $(C_1$-$C_6)$ alkoxy, $(C_1$-$C_6)$alkyl, $(C_2$-$C_6)$alkenyl, $(C_2$-$C_6)$alkynyl, —(C=O)—$R_{11}$, —(C=O)—$R_{15}$, —(C=O)—O—$R_{11}$, —(C=O)—O—$R_{15}$, —O—(C=O)—$R_{11}$, —O—(C=O)—$R_{15}$, —$NR_{11}$(C=O)—$R_{13}$, —(C=O)—$NR_{11}R_{12}$, —$NR_{11}R_{12}$, and —$NR_{11}R_{15}$;

any nitrogen atoms of the (4-10)-membered heterocyclyl of the foregoing $R_1$, $R_2$, $R_3$, $R_4$, $R_8$, $R_6$, $R_7$, $R_8$, $R_9$, $R_{10}$, $R_{14}$, and $R_{15}$ are independently optionally substituted with $(C_1$-$C_6)$alkyl, $(C_2$-$C_6)$alkenyl, $(C_2$-$C_6)$alkynyl, —(C=O)—$R_{11}$, —(C=O)—O—$R_{11}$, —(C=O)—$NR_{11}R_{12}$, —$(CR_{11}R_{12})_e$(3-10)-membered cycloalkyl, —$(CR_{11}R_{12})_e(C_6$-$C_{10})$aryl, —$(CR_{11}R_{12})_e$(4-10)-membered heterocyclyl, —$(CR_{11}R_{12})_f(C=O)(CR_{11}R_{12})_e$ $(C_6$-$C_{10})$aryl, or —$(CR_{11}R_{12})_f(C=O)(CR_{11}R_{12})_e$(4-10)-membered heterocyclyl;

each $R_{11}$, $R_{12}$, and $R_{13}$ are independently hydrogen or $(C_1$-$C_6)$alkyl;

$R_{15}$ is —$(CR_{11}R_{12})_e$(3-10)-membered cycloalkyl, —$(CR_{11}R_{12})_e(C_6$-$C_{10})$aryl, or —$(CR_{11}R_{12})_e$(4-10)-membered heterocyclyl;

a and b are each independently 1, 2, 3, or 4;

c is 1 or 2;

d is 0, 1, or 2; and e, f, and g are each independently 0, 1, 2, 3, 4, or 5.

7. The compound of claim 6, wherein each of $R_3$ and $R_5$ is independently selected from the group consisting of hydrogen and methyl.

8. The compound of claim 6, wherein $R_4$ is hydrogen or methyl.

9. The compound of claim 6, wherein the compound is selected from the group consisting of:
  1-(3-(3,6-difluoro-9H-carbazol-9-yl)-2-hydroxypropyl)-3-methyltetrahydropyrimidin-2(1H)-one (6);
  1-(3-(3,6-difluoro-9H-carbazol-9-yl)-2-hydroxypropyl) tetrahydropyrimidin-2(1H)-one (71);
  1-cyclohexyl-3-(3-(3,6-difluoro-9H-carbazol-9-yl)-2-hydroxypropyl)tetrahydropyrimidin-2(1H)-one (74);
  1-(3-(3,6-difluoro-9H-carbazol-9-yl)-2-hydroxypropyl)-3-phenyltetrahydropyrimidin-2(1H)-one (75);
  1-cyclopentyl-3-(3-(3,6-difluoro-9H-carbazol-9-yl)-2-hydroxypropyl)tetrahydropyrimidin-2(1H)-one (76);
  1-(3-(3,6-difluoro-9H-carbazol-9-yl)-2-hydroxypropyl)-3-isopropyltetrahydropyrimidin-2(1H)-one (77);
  1-cyclobutyl-3-(3-(3,6-difluoro-9H-carbazol-9-yl)-2-hydroxypropyl)tetrahydropyrimidin-2(1H)-one (78);
  1-(3-(3,6-difluoro-9H-carbazol-9-yl)-2-hydroxy-2-methylpropyl)-3-phenyltetrahydropyrimidin-2(1H)-one (79);
  1-(3-(3,6-difluoro-9H-carbazol-9-yl)-2-hydroxy-2-methylpropyl)-3-isopropyltetrahydropyrimidin-2(1H)-one (80);
  1-cyclobutyl-3-(3-(3,6-difluoro-9H-carbazol-9-yl)-2-hydroxy-2-methylpropyl)tetrahydropyrimidin-2(1H)-one (81);
  1-cyclohexyl-3-(3-(3,6-difluoro-9H-carbazol-9-yl)-2-hydroxy-2-methylpropyl)tetrahydropyrimidin-2(1H)-one (82);
  1-cyclopropyl-3-(3-(3,6-difluoro-9H-carbazol-9-yl)-2-hydroxypropyl)tetrahydropyrimidin-2(1H)-one (83);
  1-(3-(3,6-difluoro-9H-carbazol-9-yl)-2-hydroxypropyl)-3-ethyltetrahydropyrimidin-2(1H)-one (86);
  1-(3-(3,6-difluoro-9H-carbazol-9-yl)-2-hydroxy-2-methylpropyl)-3-ethyltetrahydropyrimidin-2(1H)-one (87);
  1-(3-(3,6-difluoro-9H-carbazol-9-yl)-2-hydroxypropyl)-3,5-dimethyltetrahydropyrimidin-2(1H)-one (94); and
  1-(3-(3,6-difluoro-9H-carbazol-9-yl)-2-hydroxypropyl)-3,4-dimethyltetrahydropyrimidin-2(1H)-one (101); or a pharmaceutically acceptable salt or hydrate thereof.

10. A compound selected from the group consisting of:
  1-(3-(9H-carbazol-9-yl)-2-hydroxypropyl)-3-methyltetrahydropyrimidin-2(1H)-one (2);
  1-(3-(9H-carbazol-9-yl)-2-hydroxypropyl)tetrahydropyrimidin-2(1H)-one (3);
  4-(3-(3,6-difluoro-9H-carbazol-9-yl)-2-hydroxypropyl) morpholin-3-one (55);
  4-(3-(3,6-difluoro-9H-carbazol-9-yl)-2-hydroxy-2-methylpropyl)morpholin-3-one (56);
  1-(3-(9H-carbazol-9-yl)-2-hydroxypropyl)-3-ethyltetrahydropyrimidin-2(1H)-one (95);
  1-(3-(9H-carbazol-9-yl)-2-hydroxypropyl)-3-cyclopropyltetrahydropyrimidin-2(1H)-one (99); and
  1-(3-(9H-carbazol-9-yl)-2-hydroxypropyl)-3-cyclobutyltetrahydropyrimidin-2(1H)-one (100); or a pharmaceutically acceptable salt or hydrate thereof.

11. A pharmaceutical composition comprising a compound according to claim 5, or a pharmaceutically acceptable salt or hydrate thereof, and a pharmaceutically acceptable carrier, adjuvant, or diluent.

12. The pharmaceutical composition according to claim 11, further comprising one or more additional therapeutic agents selected from the group consisting of DPP-IV inhibitors, SGLT2 inhibitors, metformin, sulfonylureas, Signifor®, ketoconazole, metyrapone, mitotane, etomidate, Korlym®, epidermal growth factor receptor inhibitors, the aldosterone synthase/11β-hydroxylase inhibitor LCI699, and levoketoconazole (COR-003).

13. A method of treating or alleviating a subject suffering from a Cry-mediated disease or disorder, comprising administering to the subject a therapeutically effective amount of the pharmaceutical composition according to claim 11, wherein the Cry-mediated disease or disorder is selected from the group consisting of diabetes, a diabetic complication, nonalcoholic steatohepatitis (NASH); non-alcoholic fatty liver disease (NAFLD); asthma; chronic obstructive pulmonary disease (COPD); metabolic syndrome; insulin resistance syndrome; obesity; glaucoma; Cushing's syndrome; psychotic depression; Alzheimer's disease; neuropathic pain; drug abuse; osteoporosis; cancer; macular degeneration; and myopathy, wherein the subject suffers from a Cry-mediated disease or disorder.

14. The method of claim 13, wherein the diabetic complication is selected from the group consisting of diabetic neuropathy, diabetic retinopathy, diabetic nephropathy, cataract formation, glaucoma, diabetic angiopathy, and atherosclerosis.

15. A pharmaceutical composition comprising a compound according to claim 6, or a pharmaceutically acceptable salt or hydrate thereof, and a pharmaceutically acceptable carrier, adjuvant, or diluent.

16. The pharmaceutical composition according to claim 15, further comprising one or more additional therapeutic agents selected from the group consisting of DPP-IV inhibitors, SGLT2 inhibitors, metformin, sulfonylureas, Signifor®, ketoconazole, metyrapone, mitotane, etomidate, Korlym®, epidermal growth factor receptor inhibitors, the aldosterone synthase/11β-hydroxylase inhibitor LCI699, and levoketoconazole (COR-003).

17. A method of treating or alleviating a subject suffering from a Cry-mediated disease or disorder, comprising administering to the subject a therapeutically effective amount of the pharmaceutical composition according to claim 15, wherein the Cry-mediated disease or disorder is selected from the group consisting of diabetes, a diabetic complication, nonalcoholic steatohepatitis (NASH); non-alcoholic fatty liver disease (NAFLD); asthma; chronic obstructive pulmonary disease (COPD); metabolic syndrome; insulin resistance syndrome; obesity; glaucoma; Cushing's syndrome; psychotic depression; Alzheimer's disease; neuropathic pain; drug abuse; osteoporosis; cancer; macular degeneration; and myopathy, wherein the subject suffers from a Cry-mediated disease or disorder.

18. The method of claim 17, wherein the diabetic complication is selected from the group consisting of diabetic neuropathy, diabetic retinopathy, diabetic nephropathy, cataract formation, glaucoma, diabetic angiopathy, and atherosclerosis.

19. A pharmaceutical composition comprising a compound according to claim 10, or a pharmaceutically acceptable salt or hydrate thereof, and a pharmaceutically acceptable carrier, adjuvant, or diluent.

20. The pharmaceutical composition according to claim 19, further comprising one or more additional therapeutic agents selected from the group consisting of DPP-IV inhibitors, SGLT2 inhibitors, metformin, sulfonylureas, Signifor®, ketoconazole, metyrapone, mitotane, etomidate, Korlym®, epidermal growth factor receptor inhibitors, the aldosterone synthase/11β-hydroxylase inhibitor LCI699, and levoketoconazole (COR-003).

21. A method of treating or alleviating a subject suffering from a Cry-mediated disease or disorder, comprising administering to the subject a therapeutically effective amount of the pharmaceutical composition according to claim 19, wherein the Cry-mediated disease or disorder is selected from the group consisting of diabetes, a diabetic complication, nonalcoholic steatohepatitis (NASH); non-alcoholic fatty liver disease (NAFLD); asthma; chronic obstructive pulmonary disease (COPD); metabolic syndrome; insulin resistance syndrome; obesity; glaucoma; Cushing's syndrome; psychotic depression; Alzheimer's disease; neuropathic pain; drug abuse; osteoporosis; cancer; macular degeneration; and myopathy, wherein the subject suffers from a Cry-mediated disease or disorder.

22. The method of claim 21, wherein the diabetic complication is selected from the group consisting of diabetic neuropathy, diabetic retinopathy, diabetic nephropathy, cataract formation, glaucoma, diabetic angiopathy, and atherosclerosis.

* * * * *

UNITED STATES PATENT AND TRADEMARK OFFICE
CERTIFICATE OF CORRECTION

PATENT NO. : 10,214,507 B2
APPLICATION NO. : 15/985168
DATED : February 26, 2019
INVENTOR(S) : Ross Bersot et al.

It is certified that error appears in the above-identified patent and that said Letters Patent is hereby corrected as shown below:

On the Title Page

Page 2, item (56) Other Publications:
"de Filippis, A. et al., "Palladium-catalyzed a-arylation of N-protected 2-piperidinones", *Tetrahedron* (2004), 60(43): 9757-9767."
Should read:
-- de Filippis, A. et al., "Palladium-catalyzed α-arylation of N-protected 2-piperidinones", *Tetrahedron* (2004), 60(43): 9757-9767. --

In the Claims

At Column 185, Claim number 1, Line number 31:
"-S(O)$_c$NR$_8$R$_9$, -S(O)$_d$(C$_1$-C$_6$)alkyl, -O-SO$_2$-"
Should read:
-- "-S(O)$_c$NR$_8$R$_9$, -S(O)$_d$(C$_1$-C$_8$)alkyl, -O-SO$_2$- --

At Column 186, Claim number 1, Line number 52:
"foregoing R$_1$, R$_2$, R$_3$, R$_4$, R$_8$, R$_6$, R$_7$, R$_8$, R$_9$, R$_{10}$, R$_{14}$,"
Should read:
-- foregoing R$_1$, R$_2$, R$_3$, R$_4$, R$_5$, R$_6$, R$_7$, R$_8$, R$_9$, R$_{10}$, R$_{14}$, --

At Column 189, Claim number 6, Line number 8:
"a wherein R$_6$ and R$_7$ are linked to each other as saturated"
Should read:
-- wherein R$_6$ and R$_7$ are linked to each other as a saturated --

At Column 189, Claim number 6, Line number 57:
"of the foregoing R$_1$, R$_2$, R$_3$, R$_4$, R$_8$, R$_6$, R$_7$, R$_8$, R$_9$, R$_{10}$,"
Should read:
-- of the foregoing R$_1$, R$_2$, R$_3$, R$_4$, R$_5$, R$_6$, R$_7$, R$_8$, R$_9$, R$_{10}$, --

Signed and Sealed this
Fourth Day of June, 2019

Andrei Iancu
*Director of the United States Patent and Trademark Office*

At Column 191, Claim number 11, Line number 2:
"pound according to claim 5, or a pharmaceutically accept-"
Should read:
-- pound according to claim 1, or a pharmaceutically accept- --